(12) United States Patent
Bonvini et al.

(10) Patent No.: US 10,787,521 B2
(45) Date of Patent: *Sep. 29, 2020

(54) BI-SPECIFIC MONOVALENT DIABODIES THAT ARE CAPABLE OF BINDING CD123 AND CD3, AND USES THEREOF

(71) Applicant: MacroGenics, Inc., Rockville, MD (US)

(72) Inventors: Ezio Bonvini, Potomac, MD (US); Leslie S. Johnson, Darnestown, MD (US); Ling Huang, Bethesda, MD (US); Paul A. Moore, Bethesda, MD (US); Gurunadh Reddy Chichili, Germantown, MD (US); Ralph Froman Alderson, North Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/730,868

(22) Filed: Oct. 12, 2017

(65) Prior Publication Data

US 2018/0094072 A1 Apr. 5, 2018

Related U.S. Application Data

(63) Continuation of application No. 14/913,632, filed as application No. PCT/US2014/051790 on Aug. 20, 2014, now Pat. No. 9,822,181.

(60) Provisional application No. 61/990,475, filed on May 8, 2014, provisional application No. 61/907,749, filed on Nov. 22, 2013, provisional application No. 61/869,510, filed on Aug. 23, 2013.

(30) Foreign Application Priority Data

Dec. 20, 2013 (EP) .................................... 13198784

(51) Int. Cl.
C07K 16/28 (2006.01)
A61K 39/00 (2006.01)

(52) U.S. Cl.
CPC ...... *C07K 16/2896* (2013.01); *C07K 16/2809* (2013.01); *C07K 16/2866* (2013.01); *A61K 2039/505* (2013.01); *C07K 2317/31* (2013.01); *C07K 2317/33* (2013.01); *C07K 2317/56* (2013.01); *C07K 2317/626* (2013.01); *C07K 2317/73* (2013.01); *C07K 2317/92* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,752,601 A | 6/1988 | Hahn |
| 4,980,286 A | 12/1990 | Morgan et al. |
| 5,116,964 A | 5/1992 | Capon et al. |
| 5,128,326 A | 7/1992 | Balazs et al. |
| 5,169,933 A | 12/1992 | Anderson et al. |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,679,377 A | 10/1997 | Bernstein et al. |
| 5,698,449 A | 12/1997 | Baumann et al. |
| 5,723,584 A | 3/1998 | Schatz |
| 5,736,135 A | 4/1998 | Goeddel et al. |
| 5,736,137 A | 4/1998 | Anderson et al. |
| 5,874,239 A | 2/1999 | Schatz |
| 5,888,533 A | 3/1999 | Dunn |
| 5,912,015 A | 6/1999 | Bernstein et al. |
| 5,916,597 A | 6/1999 | Lee et al. |
| 5,932,433 A | 8/1999 | Schatz |
| 5,945,115 A | 8/1999 | Dunn et al. |
| 5,985,599 A | 11/1999 | Mckenzie et al. |
| 5,989,463 A | 11/1999 | Tracy et al. |
| 6,025,485 A | 2/2000 | Kamb et al. |
| 6,114,147 A | 9/2000 | Frenken et al. |
| 6,165,745 A | 12/2000 | Ward et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,300,065 B1 | 10/2001 | Kieke et al. |
| 6,423,538 B1 | 7/2002 | Wittrup et al. |

(Continued)

FOREIGN PATENT DOCUMENTS

| | | |
|---|---|---|
| EP | 0327378 | 8/1989 |
| EP | 1354600 | 10/2003 |

(Continued)

OTHER PUBLICATIONS

US 6,331,391 B1, 12/2001, Wittrup et al. (withdrawn)

(Continued)

*Primary Examiner* — Nelson B Moseley, II

(74) *Attorney, Agent, or Firm* — William C. Schrot; Jeffrey I. Auerbach; AuerbachSchrot LLC

(57) ABSTRACT

The present invention is directed to sequence-optimized CD123×CD3 bi-specific monovalent diabodies that are capable of simultaneous binding to CD123 and CD3, and to the uses of such diabodies in the treatment of hematologic malignancies.

18 Claims, 66 Drawing Sheets

Specification includes a Sequence Listing.

(56) References Cited

U.S. PATENT DOCUMENTS

| | | |
|---|---|---|
| 6,455,263 B2 | 9/2002 | Payan |
| 6,492,123 B1 | 12/2002 | Holliger et al. |
| 6,528,624 B1 | 3/2003 | Idusogie et al. |
| 6,538,124 B1 | 3/2003 | Idusogie et al. |
| 6,613,884 B1 | 9/2003 | Johansson et al. |
| 6,623,940 B1 | 9/2003 | Ledbetter et al. |
| 6,737,056 B1 | 5/2004 | Presta |
| 6,821,505 B2 | 11/2004 | Ward |
| 7,122,646 B2 | 10/2006 | Holliger et al. |
| 7,315,786 B2 | 1/2008 | Dahiyat et al. |
| 7,317,091 B2 | 1/2008 | Lazar et al. |
| 7,425,619 B2 | 9/2008 | Koenig et al. |
| 7,521,542 B2 | 4/2009 | Johnson et al. |
| 7,632,497 B2 | 12/2009 | Stavenhagen |
| 7,700,100 B2 | 4/2010 | Johnson et al. |
| 7,960,512 B2 | 6/2011 | Stavenhagen et al. |
| 8,003,774 B2 | 8/2011 | Stavenhagen et al. |
| 8,044,180 B2 | 10/2011 | Koenig et al. |
| 8,133,982 B2 | 3/2012 | Johnson et al. |
| 8,187,593 B2 | 5/2012 | Koenig et al. |
| 8,192,737 B2 | 6/2012 | Stavenhagen et al. |
| 8,193,318 B2 | 6/2012 | Koenig et al. |
| 8,216,574 B2 | 7/2012 | Stavenhagen et al. |
| 8,216,579 B2 | 7/2012 | Johnson et al. |
| 8,217,147 B2 | 7/2012 | Stavenhagen et al. |
| 8,586,713 B2 | 11/2013 | Davis et al. |
| 8,642,743 B2 | 2/2014 | Herne |
| 2003/0077282 A1 | 4/2003 | Bigler et al. |
| 2003/0158389 A1 | 8/2003 | Idusogie et al. |
| 2004/0002587 A1 | 1/2004 | Watkins et al. |
| 2004/0038339 A1 | 2/2004 | Kuffer et al. |
| 2004/0058400 A1 | 3/2004 | Holliger et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0220388 A1 | 11/2004 | Mertens et al. |
| 2004/0259075 A1 | 12/2004 | Dimitrov et al. |
| 2005/0037000 A1 | 2/2005 | Stavenhagen et al. |
| 2005/0054832 A1 | 3/2005 | Lazar et al. |
| 2005/0100543 A1 | 5/2005 | Hansen et al. |
| 2005/0142539 A1 | 6/2005 | Herman |
| 2005/0257285 A1 | 11/2005 | Gupta et al. |
| 2005/0260213 A1 | 11/2005 | Koenig et al. |
| 2006/0099216 A1 | 5/2006 | Cardy et al. |
| 2006/0193849 A1 | 8/2006 | Krauss et al. |
| 2007/0004909 A1 | 1/2007 | Johnson et al. |
| 2007/0036799 A1 | 2/2007 | Stavenhagen et al. |
| 2007/0135338 A1 | 6/2007 | O'Neil et al. |
| 2007/0140966 A1 | 6/2007 | Chang et al. |
| 2007/0274998 A1 | 11/2007 | Utku |
| 2008/0085277 A1 | 4/2008 | Cho et al. |
| 2008/0187517 A1 | 8/2008 | Herne |
| 2010/0174053 A1 | 7/2010 | Johnson et al. |
| 2010/0178298 A1 | 7/2010 | Lindhofer |
| 2010/0196362 A1 | 8/2010 | Stavenhagen et al. |
| 2010/0196372 A1 | 8/2010 | Johnson et al. |
| 2010/0291112 A1 | 11/2010 | Kellner et al. |
| 2010/0322924 A1 | 12/2010 | Johnson et al. |
| 2011/0243941 A1 | 10/2011 | Stavenhagen et al. |
| 2011/0305714 A1 | 12/2011 | Stavenhagen et al. |
| 2012/0009186 A1 | 1/2012 | Koenig et al. |
| 2012/0141476 A1 | 6/2012 | Johnson et al. |
| 2012/0189540 A1 | 7/2012 | Bergstein |
| 2012/0219551 A1 | 8/2012 | Johnson et al. |
| 2012/0263711 A1 | 10/2012 | Stavenhagen et al. |
| 2012/0269811 A1 | 10/2012 | Johnson et al. |
| 2012/0276094 A1 | 11/2012 | Stavenhagen et al. |
| 2013/0137855 A1 | 5/2013 | Panousis |
| 2013/0280220 A1 | 10/2013 | Ahmed et al. |

FOREIGN PATENT DOCUMENTS

| | | |
|---|---|---|
| JP | 2007-531788 | 10/2005 |
| WO | WO 1988/007089 | 9/1988 |
| WO | WO 1989/007142 | 8/1989 |
| WO | WO 1991/005548 | 5/1991 |
| WO | WO 1992/016562 | 10/1992 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1996/020698 | 7/1996 |
| WO | WO 1997/028267 | 8/1997 |
| WO | WO 1997/034631 | 9/1997 |
| WO | WO 1997/044362 | 11/1997 |
| WO | WO 1998/005787 | 2/1998 |
| WO | WO 1998/023289 | 6/1998 |
| WO | WO 1998/052975 | 11/1998 |
| WO | WO 1999/015154 | 4/1999 |
| WO | WO 1999/020253 | 4/1999 |
| WO | WO 1999/043713 | 9/1999 |
| WO | WO 1999/051642 | 10/1999 |
| WO | WO 1999/058572 | 11/1999 |
| WO | WO 2000/009560 | 2/2000 |
| WO | WO 2000/042072 | 7/2000 |
| WO | WO 2001/011059 | 2/2001 |
| WO | WO 2002/002781 | 1/2002 |
| WO | WO 2002/060919 | 8/2002 |
| WO | WO 2002/086070 | 10/2002 |
| WO | WO 2003/074679 | 9/2003 |
| WO | WO 2003/101485 | 12/2003 |
| WO | WO 2004/001064 | 12/2003 |
| WO | WO 2004/016750 | 2/2004 |
| WO | WO 2004/029207 | 4/2004 |
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/097202 | 10/2005 |
| WO | WO 2006/020114 | 2/2006 |
| WO | WO 2006/113665 | 10/2006 |
| WO | WO 2008/157379 | 12/2008 |
| WO | WO 2010/080538 | 7/2010 |
| WO | WO 2011/100786 | 8/2011 |
| WO | WO 2012/018687 | 2/2012 |
| WO | WO 2012/021934 | 2/2012 |
| WO | WO 2012/162067 | 11/2012 |
| WO | WO 2012/162068 | 11/2012 |
| WO | WO 2013/092001 | 6/2013 |
| WO | WO 2013/173820 | 11/2013 |

OTHER PUBLICATIONS

Mariuzza (Annu. Rev. Biophys. Biophys. Chem., 16: 139-159, 1987).*

Alt et al., "Novel Tetravalent and Bispecific IgG-Like Antibody Molecules Combining Single-Chain Diabodies with the Immunoglobin Gamma 1 Fc or CH3 Region," FEBS Letters 454: 90-94, 1999.

Altman et al., "Phenotypic Analysis of Antigen-Specific T Lymphocytes", Science 274:94-96, 1996.

Angal et al., "A single amino acid substitution abolishes the heterogeneity (IgG4) antibody," Mol Immunol 30 :105-108, 1993.

Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.

Anonymous, "MacroGenics Enters Global Research Collaboration and License Agreement with Pfizer;" Press Release of MacroGenics, Inc.; Oct. 26, 2010; 2 pages.

Apostolovic, B. et al. (2008) "pH-Sensitivity of the E3/K3 Heterodimeric Coiled Coil," Biomacromolecules 9:3173-3180.

Armour et al., "Differential binding to human FcgammaRIIa and FcgammaRIIb receptors by human IgG wildtype and mutant antibodies," Mol Immunol 40 :585-593, 2003.

Armour et al., "Recombinant human IgG molecules lacking Fcgamma receptor I binding and monocyte triggering activities," Eur J Immunol 29:2613-2624, 1999.

Armour et al., "The contrasting IgG-binding interactions of human and herpes simplex virus Fc receptors," Biochemical Society Transactions 30:495-50, 2002.

(56) References Cited

OTHER PUBLICATIONS

Armstrong, S. et al. "Heterogeneity of IgG1 monoclonal anti-Rh(D): an investigation using ADCC and macrophage binding assays," Brit. J. Haematol. 66:257-262 (1987).
Arndt, K.M. et al. (2001) "Helix-stabilized Fv (hsFv) Antibody Fragments: Substituting the Constant Domains of a Fab Fragment for a Heterodimeric Coiled-coil Domain," J. Molec. Biol. 312:221-228.
Arndt, K.M. et al.(2002) "Comparison of in Vivo Selection and Rational Design of Heterodimeric Coiled Coils," Structure 10:1235-1248.
Asano, R. et al. (2004) "A Diabody for Cancer Immunotherapy and Its Functional Enhancement by Fusion of Human Fc Region," Abstract 3P-683, J. Biochem. 76(8):992.
Atwell et al. (1997) "Stable Heterodimers from Remodeling the Domain Interface of a Homodimer Using a Phage Display Library," J. Mol. Biol. 270: 26-35.
Baeuerle, P.A. et al. (2009) "Bispecific T-Cell Engaging Antibodies for Cancer Therapy," Cancer Res. 69(12):4941-4944.
Baggiolini M, Dewald B. "Cellular models for the detection and evaluation of drugs that modulate human phagocyte activity," Experientia. Oct. 15;44(10):841-848, 1988.
Bargou, R. et al. (2008) "Tumor Regression in Cancer Patients by Very Low Doses of a T Cell-Engaging Antibody," Science 321:974-977.
Bedzyk et al. (1989) "Comparison of Variable Region Primary Structures Within an Anti-Fluorescein Idiotype Family," J. Biol. Chem, 264(3):1565-1569.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder and Wittrup, 1997, "Yeast surface display for screening combinatorial polypeptide libraries", Nature Biotechnology 15:553-557.
Boder et al., "Directed evolution of antibody fragments with monovalent femtomolar antigen-binding affinity," Proc. Natl. Acad. Sci. USA 97:10701-10705, 2000.
Boucher, C. et al. (2010) "Protein Detection by Western Blot via Coiled-Coil Interactions," Analytical Biochemistry 399:138-140.
Bredius et al., "Role of neutrophil Fc gamma RIIa (CD32) and Fc gamma RIIIb (CD16) polymorphic forms in phagocytosis of human IgG1- and IgG3-opsonized bacteria erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brown EJ., "In Vitro Assays of Phagocytic Function of Human Peripheral Blood Leukocytes: Receptor Modulation and Signal Transduction," vol. 45 (Microbes as Tools for Cell Biology) in Methods in Cell Biololgy, Russell ed. Academic Press Inc. pp. 147-164, 1994.
Buchwald et al. "Long-Term, Continuous Intravenous Heparin Administration by an Implantable Infusion Pump in Ambulatory Patients with Recurrent Venous Thrombosis," Surgery 88:507-516.
Burlmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Cachia, P.J. et al. (2004) "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit. 17:540-557.
Canfield and Morrison, "The binding affinity of human IgG for its high affinity Fc receptor is determined by multiple amino acids in CH2 domain and is modulated the by the hinge region," J Exp Med 173:1483-1491, 1991.
Cao et al (2003) "Bispecific Antibody Conjugates in Therapeutics," Adv. Drug Deliv. Rev. 55:171-197.
Caron et al., "Engineered humanized dimeric forms of IgG are more effective antibodies," J Exp Med 176 :1191-5, 1992.
Carter et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99:754-758, 2002.
Chappel et al., "Identification of a secondary Fc gamma RI binding site within a gentetically engineered human IgG antibody," J Biol. Chem 268:25124-25131, 1993.
Chappel et al., "Identification of he Fc gamma receptor class I binding site in human IgG through the use of recombinant IgG1-IgG2 hybrid and point-mutated antibodies," Proc. Natl. Acad. Sci USA 88:9036-9040, 1991.
Chu, P. G. et al. (2001) "CD79: A Review," Appl. Immunohistochem. Molec. Morphol. 9(2):97-106.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Fc receptors are required in passive and active immunity to melanoma," Proc. Natl. Acad. Sci USA 95:652-656, 1998.
Clynes et al., "Inhibitory Fc receptors modulate in vivo cytoxicity against tumor targets," Nature Medicine 6 :443-446, 2000.
Clynes et al., "Modulation of immune complex-induced inflammation in vivo by the coordinate expression of activation and inhibitory Fc receptors," J Exp Med 189:179-185, 1999.
Clynes et al., "Uncoupling of immune complex formation and kidney damage in autoimmune glomerulonephritis," Science 279:1052-1054, 1998.
Colonna, M. et al. (1997) "Specificity and Function of Immunoglobulin Superfamily NK Cell Inhibitory and Stimulatory Receptors," Immunol. Rev. 155:127-133.
Corbett et al. (2004) "In Vivo Methods for Screening and Preclinical Testing," Cancer Drug Discovery and Development: Anticancer Drug Development Guide: Preclinical Screening, Clinical Trials, and Approval, $2^{nd}$ Ed. 99-123.
Cuesta, A.M. et al. (2010) "Multivalent Antibodies: When Design Surpasses Evolution," Trends in Biotechnol., 28(7):355-362.
De Crescenzo, G.D. et al. (2003) "Real-Time Monitoring of the Interactions of Two-Stranded de novo Designed Coiled-Coils: Effect of Chain Length on the Kinetic and Thermodynamic Constants of Binding," Biochemistry 42:1754-1763.
De Haas, Wien Kin "IgG-Fc receptors and the clinical relevance of their polymorphisms," Wien Klin Wochenscha 113:825-831, 2001.
De Kruif, J. et al. (1996) "Leucine Zipper Dimerized Bivalent and Bispecific scFv Antibodies from a Semi-Synthetic Antibody Phage Display Library," J. Biol. Cherm. 271(13):7630-7634.
Deisenhofer, "Crystallographic refinement and atomic models of a human Fc fragment and its complex with fragment B of protein A from *Staphylococcus aureus* at 2.9- and 2.8-A resolution," Biochem. 20:2361-2370, 1981.
Deo et al., "Clinical significance of IgG Fc receptors and Fc gamma R-directed immunotherapies," Immunology Today 18:127-135, 1997.
Duncan and Winter, "Localization of the binding site for the human high-affinity Fc receptor on IgG," Nature 332:563-564, 1988.
Duncan and Winter, "The binding site for C1q on IgG," Nature 332 :738-740, 1988.
During et al. (1989) "Controlled Release of Dopamine from a Polymeric Brain Implant: In Vivo Characterization," Ann. Neurol. 25:351-356.
Edberg et al., "Modulation of Fcgamma and Complement Receptor Function by the Glycosyl-Phosphatidylinositol-Anchored Form of FcgammaRIII," Journal of Immunology 152: 5826-5835, 1994.

(56) References Cited

OTHER PUBLICATIONS

European Search Report (EP 06750508) dated Nov. 2, 2010 (19 pages).
European Search Report (EP 08771050) dated Nov. 2, 2010 (13 pages).
Fernandez-Rodriguez, J. et al. (2012) "Induced Heterodimerization and Purification of Two Target Proteins by a Synthetic Coiled-Coil Tag," Protein Sci. 21:511-519.
FitzGerald, et al., "Improved tumor targeting by disulphide stabilized diabodies expressed in Pichia pastoris," Protein Engineering 10(10): 1221-1225, 1997.
Flesch and Neppert, "Functions of the Fc receptors for immunoglobulin G," J Clin Lab Anal 14:141-156, 2000.
Florian, S. et al.(2006) "Detection of Molecular Targets on the Surface of CD34+/CD38—Stem Cells in Various Myeloid Malignancies,"Leuk. Lymphoma 47:207-222.
Frankel, A. et al.(2008) "Phase I Clinical Study of Diphtheria Toxin-Interleukin 3 Fusion Protein in Patients with Acute Myeloid Leukemia and Myelodysplasia," Leuk. Lymphoma 49:543-553.
Fromm, J.R. (2011) "Flow Cytometric Analysis of CD123 is Useful for Immunophenotyping Classical Hodgkin Lymphoma," Cytometry B Clin. Cytom. 80:91-99.
Gao, Y. et al.(2004) "Efficient Inhibition of Multidrug-Resistant Human Tumors with a Recombinant Bispecific Anti-P-Glycoprotein X Anti-CD3 Diabody," Leukemia 18(3):513-520.
Gebel, H.M. et al. (1989) "T Cells from Patients Successfully Treated with OKT3 Do Not React with the T-Cell Receptor Antibody," Hum. Immunol. 26:123-129.
Gergely et al., "Fc receptors on lymphocytes and K cells," Biochemical Society Transactions 12:739-743, 1984.
Gergely and Sarmay, "The two binding-site models of human IgG Binding Fc gamma receptors," FASEB J 4:3275-3283, 1990.
Ghosh, T.S. et al. (2009) "End-To-End and End-To-Middle Interhelical Interactions: New Classes of Interacting Helix Pairs in Protein Structures," Acta Cryst. D65:1032-1041.
Gill, S. et al. (2014) "Efficacy Against Human Acute Myeloid Leukemia and Myeloablation of Normal Hematopoiesis in a Mouse Model Using Chimeric Antigen Receptor-Modified T Cells," Blood 123(15):2343-2354.
Greenwood and Clark, "Effector functions of matched sets of recombinant human IgG subclass antibodies". (final version edited Feb. 11, 1993).
Greenwood et al., "Engineering multiple-domain forms of the therapeutic antibody CAMPATH-1H: effects on complement lysis," Therapeutic Immunology 1:247-255, 1994.
Greenwood et al., "Structural motifs involved in human IgG antibody effector functions," Eur J Immunol 23:1098-1104, 1993.
Grigoryan, G. et al. (2008) "Structural Specificity in Coiled-Coil Interactions," Curr. Opin. Struc. Biol. 18:477-483.
Grosjean, H. et al. (1982) "Preferential Codon Usage in Prokaryotic Genes: The Optimal Codon-Anticodon Interaction Energy and the Selective Codon Usage in Efficiently Expressed Genes" Gene 18(3):199-209.
Guo, J. et al. (2003) "[New Type Recombinant Antibody Fragment Scfv Multimer and Cancer Targeting]," Sheng Wu Yi Xue Gong Cheng Xue Za Zhi 20(2):361-365 (Abstract Only; Article in Chinese).
Guo, N. et al. (2005) "The Development of New Formats of Engineered Bispecific Antibodies," in Trends in Immunology Research, Veskler, Ed. Nova Science Publishers. Chapter 3:33-47.
Hadley et al., "The functional activity of Fc gamma RII and Fc gamma RIII on subsets of human lymphocytes," Immunology 76:446-451, 1992.
Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide-MHC," Proc. Natl. Acad. Sci. U.S.A. 97 :5387-92, 2000.
Holliger at al. (1996) "Specific Killing of Lymphoma Cells by Cytotoxic T-Cells Mediated by a Bispecific Diabody," Protein Eng. 9:299-305.
Holliger et al. (1993) "'Diabodies': Small Bivalent and Bispecific Antibody Fragments," Proc. Natl. Acad. Sci. (U.S.A.) 90:6444-6448.
Holliger et al. (1999) "Carcinoembryonic Antigen (CEA)-Specific T-cell Activation in Colon Carcinoma Induces by Anti-CD3 x Anti-CEA Bispecific Diabodies and B7 x Anti-CEA Bispecific Fusion Proteins," Cancers Res. 59:2909-2916.
Holliger, et al., "Engineered antibody fragments and the rise of single domains," Nature Biotechnoloy 23(9): 1126-1135, Sep. 2005.
Honda, T. et al. (2014) "Tuning of Antigen Sensitivity by T Cell Receptor-Dependent Negative Feedback Controls T Cell Effector Function in Inflamed Tissues," Immunity 40:235-247.
Howard et al. (1989) "Intracerebral Drug Delivery in Rats with Lesion-Induces Memory Deficits," J. Neurosurg. 7(1):105-112.
Hudson, P.J. et al. (1999) "High avidity scFv multimers; diabodies and triabodies," J. Immunol. Methods 231(1-2):177-189.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
International Search Report and Written Opinion PCT/US2009/068577 (2010) (14 pages).
International Search Report and Written Opinion PCT/US2011/045922 (2011) (13 pages).
International Search Report and Written Opinion PCT/US2014/051790 (2014) (61 pages).
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148:3062-3071, 1992.
Isaacs et al., "Therapy with monoclonal antibodies. II. The contribution of Fc gamma receptor binding and the influence of C(H)1 and C(H)3 domains on in vivo effector function," J Immunol 161:3862-3869, 1998.
Jassal et al., "Remodeling glycans on IgG by genetic re-engineering," Biochem Soc Trans 26: S113, 1998.
Jefferis and Lund, "Interaction sites on human IgG-Fc for FcgammaR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jefferis et al., "Recognition sites on human IgG for Fc gamma receptors: the role of glycosylation," Immunol Lett 44 :111-7, 1995.

(56) References Cited

OTHER PUBLICATIONS

Jendeberg et al., "Engineering of Fc(1) and Fc(3) from human immunoglobulin G to analyse subclass specificity for staphylococcal protein A," J Immunological Methods 201:25-34, 1997.
Jin, L. et al.(2009) "Monoclonal Antibody-Mediated Targeting of CD123, IL-3 Receptor Alpha Chain, Eliminates Human Acute Myeloid Leukemic Stem Cells," Cell Stem Cell 5:31-42.
Jin, W. et al.(2009) "Regulation of Th17 Cell Differentiation and EAE Induction by MAP3K NIK," Blood 113:6603-6610.
Johansson, M.U. et al. (2002) "Structure, Specificity, and Mode of Interaction for Bacterial Albumin-Binding Modules," J. Biol. Chem. 277(10):8114-8120.
Johnson et al., (2010) "Effector Cell Recruitment with Novel Fv-based Dual-affinity Re-targeting Protein Leads to Potent Tumor Cytolysis and in Vivo B-cell Depletion," J. Mol. Biol (399) pp. 436-449.
Joliot et al. (1991) "Antennapedia Homeobox Peptide Regulates Neural Morphogenesis," Proc. Natl. Acad. Sci. (U.S.A.) 88:1864-1868.
Jordan, C.T. et al. (2000) "The Interleukin-3 Receptor Alpha Chain is a Unique Marker for Human Acute Myelogenous Leukemia Stem Cells," Leukemia 14:1777-1784.
Kadar et al., "Modulatory effect of synthetic human IgG Fc peptides on the in vitro immune response of murine spleen cells," Int. J Immunpharmacol 13:1147-55, 1991.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kato et al., "Structural basis of the interaction between IgG and Fcγ receptors," J Mol Biol 295:213-224, 2000.
Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.
Kharfan-Dabaja, M.A. et al. (2013) "Diagnostic and Therapeutic Advances in Blastic Plasmacytoid Dendritic Cell Neoplasm: A Focus on Hematopoietic Cell Transplantation," Biol. Blood Marrow Transplant, 19:1006-1012.
Kieke et al., "Selection of functional T cell receptor mutants from a yeast surface-display library," Proc. Natl. Acad. Sci. U.S.A. 96:5651-56, 1999.
Kim et al., "Analysis of FcγRIII and IgG Fc polymorphism reveals functional and evolutionary implications of protein-protein interaction," J Mol Evol 53:1-9, 2001.
Klein et al., "Expression of biological effector functions by immunoglobulin G molecules lacking the hinge region," Proc. Natl. Acad. Sci. U.S.A. 78:524-528, 1981.
Klinger et al. (2012) "Immunopharmacologic Response of Patients with B-Lineage Acute Lymphoblastic Leukemia to Continuous Infusion of T Cell-Engaging CD19/CD3-Bispecific BiTE Antibody Blinatumomab," Blood 119:6226-6233.
Koene et al., "Fc gammaRIIIa-158V-F polymorphism influences the binding of IgG by natural killer cell Fc gammaRIIIa, independently of the Fc gammaRIIIa-48L-R-H phenotype," Blood 90:1109-1114, 1997.
Kontermann, R.E. (2005) "Recombinant Bispecific Antibodies for Cancer Therapy," Acta. Pharmacol. Sin. (2005) 26(1):1-9.
Korpelainen, E.I. et al. (1995) "Interferon-Gamma Upregulates Interleukin-3 (IL-3) Receptor Expression in Human Endothelial Cells and Synergizes with IL-3 in Stimulating Major Histocompatibility Complex Class II Expression and Cytokine Production," Blood 86:176-182.
Korpelainen, E.I. et al. (1996) "IL-3 Receptor Expression, Regulation and Function in Cells of the Vasculature," Immunol. Cell Biol. 74:1-7.
Kortt, A.A. et al. (2001) "Dimeric and Trimeric Antibodies: High Avidity Scfvs for Cancer Targeting," Biomol. Eng. 18(3):95-108.
Kranz et al., "Mechanisms of ligand binding by monoclonal anti-fluorescyl antibodies," J. Biol. Chem. 257:6987-6995, 1982.
Kuhns, M.S. et al. (2006) "Deconstructing the Form and Function of the TCR/CD3 Complex," Immunity Feb. 2006;24(2):133-139.
Kumpel, B.M. Brit. "Human monoclonal anti-D antibodies," J. Haematol. 71:415-420 (1989).
Kuo, S. R. et al. (2012) "Engineering a CD123xCD3 Bispecific scFv Immunofusion for the Treatment of Leukemia and Elimination of Leukemia Stem Cells," Protein Eng. Des. Sel. 35:561-569.
Langer (1990) "New Methods of Drug Delivery," Science 249:1527-1533.
Le Gall, F. et al. (Epub May 4, 2004) "Effect of Linker Sequences Between the Antibody Variable Domains on the Formation, Stability and Biological Activity of a Bispecific Tandem Diabody," Protein Eng des Sel. 17(4):357-366.
Le, P.U. et al.(2009) "*Escherichia coli* Expression and Refolding of E-K-Coil-Tagged EGF Generates Fully bioactive EGF for Diverse Applications," Protein Expression and Purification 64:108-117.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Levy et al. (1985) "Inhibition of Calcification of Bioprosthetic Heart Valves by Local Controlled-Release Diphosphonate," Science 228:190-192.
Li et al., "Reconstitution of human Fc gamma RIII cell type specificity in transgenic mice," J Exp Med 183:1259-1263, 1996.
Litowski, J.R. et al. (2002) "Designing Heterodimeric Two-Stranded α-Helical Coiled-Coils: The Effects of Hydrophobicity and α-Helical Propensity on Protein Folding, Stability, and Specificity," J. Biol. Chem. 277:37272-37279.
Liu et al., "Production of a mouse-human chimeric monoclonal antibody to CD20 with potent Fc-dependent biologic activity," J. Immunol. 139:3521-3526, 1987.
Lopez, A.F. et al. (1989) "Reciprocal Inhibition Binding Between Interleukin 3 and Granulocyte-Macrophage Colony-Stimulating Factor to Human Eosinophils," Proc. Natl. Acad. Sci. (U.S.A.) 86:7022-7026.
Lu, D. et al., (2003) "Di-diabody: a novel tetravalent bispecific antibody molecule by design," J. Immunol. Meth. 279:219-232.
Lu, D. et al., (2004) "The effect of variable domain orientation and arrangement on the antigen-binding activity of a recombinant human bispecific diabody," BBRC 318:507-513.
Lu, et al., (2005) "A Fully Human Recombinant IgG-like Bispecific Antibody to Both the Epidermal Growth Factor Receptor and the Insulin-like Growth Factor Receptor for Enhanced Antitumor Activity," The Journal of Biological Chemistry, vol. 280(20) pp. 19665-19672.
Lund et al., "Expression and characterization of truncated forms of humanized L243 IgG1. Architectural features can influence synthesis of its oligosaccharide chains and affect superoxide production triggered through human Fcgamma receptor I," Eur J Biochem 267:7246-57, 2000.
Lund et al., "Human Fc gamma RI and Fc gamma RII interact with distinct but overlapping sites on human IgG," J Immunol 147:2657-62, 1991.
Lund et al., "Multiple binding sites on the CH2 domain of IgG for mouse Fc gamma R11," Molecular Immunology 29:53-59, 1992.
Lund et al., "Multiple interactions of IgG with its core oligosaccharide can modulate recognition by complement and human Fc gamma receptor I and influence the synthesis of its oligosaccharide chains," J Immunol 157:4963-4969, 1996.
Lund et al., "Oligosaccharide-protein interactions in IgG can modulate recognition by Fc gamma receptors," FASEB J 9:115-119, 1995.
Luo et al. (1995) "VL-Linker-VH Orientation-Dependent Expression of Single Chain Fv Containing an Engineered Disulfide-Stabilized Bond in the Framework Regions," J. Biochem. 4(118):825-831.
Maenaka et al., "The human low affinity Fcgamma receptors IIa, IIb, and III bind IgG with fast kinetics and distinct thermodynamic properties," J Biol Chem 48:44898-904, 2001.

(56) References Cited

OTHER PUBLICATIONS

Mardiros, A. et al. (2013) "T Cells Expressing CD123-Specific Chimeric Antigen Receptors Exhibit Specific Cytolytic Effector Functions and Antitumor Effects Against Human Acute Myeloid Leukemia," Blood 122:3138-3148.
Marelli-Berg, F.M. et al. (2010) "Memory T-Cell Trafficking: New Directions for Busy Commuters," Immunology 130:158-165.
Mariuzza et al., (1987) "The Structural Basis of Antigen-Antibody Recognition," Annual Review of Biophysics and Biophysical Chemistry 16:139-159.
Marvin et al., "Recombinant approaches to IgG-like bispecific antibodies," Acta Pharmacologica Simca, 26(6): 649-658, Jun. 2005.
Masten, B.J. et al. (2006) "Characterization of Myeloid and Plasmacytoid Dendritic Cells in Human Lung," J. Immunol. 177:7784-7793.
Mertens, N. et al., "New Recombinant BI- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands (2001) 195-208.
Michaelsen et al., "One disulfide bond in front of the second heavy chain constant region is necessary and sufficient for effector functions of human IgG3 without a genetic hinge," Immunology 91:9243-9247, 1994.
Mirenda, V. et al. (2007) "Physiologic and Aberrant Regulation of Memory T-Cell Trafficking by the Costimulatory Molecule CD28," Blood 109:2968-2977.
Moore, P.A. et al., (2011) "Application of Dual Affinity Retargeting Molecules to Achieve Optimal Redirected T-Cell Killing of B-Cell Lymphoma," Blood 117:4542-4551.
Morgan et al., "The N-terminal end of the CH2 domain of chimeric human IgG1 anti-HLA-DR is necessary for C1q, Fc gamma RI and Fc gamma RIII binding," Immunology 86 :319-324, 1995.
Morrison et al., "Structural determinants of IgG structure," Immunologist 2 :119-124, 1994.
Munn et al., "Phagocytosis of tumor cells by human monocytes cultured in recombinant macrophage colony-stimulating factor," J Exp Med. 172(1):231-7, 1990.
Muñoz, L. et al. (2001) "Interleukin-3 Receptor Alpha Chain (CD123) is Widely Expressed in Hematologic Malignancies," Haematologica 86(12):1261-1269.
Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.
Nakamura, T. et al. (1992) "Heterogeneity of Immunoglobulin-Associated Molecules on Human B Cells Identified by Monoclonal Antibodies," Proc. Natl. Acad. Sci. (USA) 89:8522-8526).
Neuberger et al., "Recombinant antibodies possessing novel effector functions," Nature 312 :604-608, 1984.
Ning et al. (1996) "Intratumoral Radioimmunotherapy of a Human Colon Cancer Xenograft Using a Sustained-Release Gel," Radiotherapy & Oncology 39:179-189.
Norderhaug et al., "Chimeric mouse human IgG3 antibodies with an IgG4-like hinge region induce complement-mediated lysis more efficiently than IgG3 with normal hinge," Eur J Immunol 21:2379-84, 1991.
Nose and Leanderson, "Substitution of asparagine324 with aspartic acid in the Fc portion of mouse antibodies reduces their capacity for C1q binding," Eur J Immunol 19 :2179-81, 1989.
Okazaki et al., "Fucose depletion IgG1 from human IgG1 oligosaccharide enhances binding enthalpy and association rate between and FcgammaRIIIa," J Mol Biol 336 :1239-1249, 2004.
Olafsen et al., "Covalent disulfide-linked anti-CEA diabody allows site-specific conjugation and radiolabeling for tumor targeting applications," Protein Engineering, Design & Selection, 17(1): 21-27, 2004.
Orfao and Ruiz-Arguelles, "General concepts about cell sorting techniques," Clinical Biochem. 29:5-9, 1996.

Pack, P. et al. (1992) "Miniantibodies: Use of Amphipathic Helices to Produce Functional, Flexibly Linked Dimeric Fv Fragments with High Avidity in *Escherichia coli*," 31(6):1579-1584.
Pang, W.W. et al. (2011) "Human Bone Marrow Hematopoietic Stem Cells Are Increased in Frequency and Myeloid-Biased with Age," Proc. Natl. Acad. Sci. (U.S.A.) 108:20012-20017.
Partridge et al., "The use of anti-IgG monoclonal antibodies in mapping the monocyte receptor site on IgG," Mol Immunol. 23(12):1365-72, 1986.
Perussia "Human Natural Killer Cell Protocols" in Methods Molecular Biology. vol. 121 (Campbell et al. eds.) Humana Press Inc., Totowa, NJ. 179-92, 2000.
Pizzitola, I. et al. (2014) "Chimeric Antigen Receptors Against CD33/CD123 Antigens Efficiently Target Primary Acute Myeloid Leukemia Cells in vivo," Leukemia doi:10.1038/leu.2014.62.
Radaev and Sun, "Recognition of immunoglobulins by Fcgamma receptors," Molecular Immunology 38 :1073-1083, 2001.
Rankin et al. "CD32B, The Human Inhibitory Fc-γ Receptor IIB, as a Target for Monoclonal Antibody Therapy of B-Cell Lymphoma," (2006) Blood 108(7):2384-2391.
Ravetch (1994) "Fc Receptors: Rubor Redux," Cell 78:553-560.
Ravetch and Bolland, "IgG Fc receptors," Annu Rev Immunol 19:275-90, 2001.
Ravetch and Clynes, "Divergent roles for Fc receptors and complement in vivo," Annu Rev Immunol 16:421-432, 1998.
Ravetch and Kinet, "Fc receptors," Annu Rev Immunol 9:457-492, 1991.
Ravetech and Lanier, "Immune inhibitory receptors," Science 290:84-89, 2000.
Redpath et al., "The influence of the hinge region length in binding of human IgG to human Fcgamma receptors," Hum Immunol 59:720-727, 1998.
Reff et al., "Depletion of B cells in vivo by a chimeric mouse human monoclonal antibody to CD20," Blood 83:435-445, 1994.
Ridgway et al. (1996) "Knobs-Into-Holes' Engineering of Antibody CH3 Domains for Heavy Chain Heterodimerization," Protein Engr. 9:617-621.
Riechmann et al., "Reshaping human antibodies for therapy," Nature. 332(6162):323-7, 1988.
Rieger, M.A. et al. (2012) "Hematopoiesis," Cold Spring Harb. Perspect. Biol. 4: a008250.
Robak, T. et al. (2009) "Current and Emerging Therapies for Acute Myeloid Leukemia," Clin. Ther. 2:2349-2370.
Roberts, A.W. et al. (2010) "A Phase I Study of Anti-CD123 Monoclonal Antibody (mAb) CSL360 Targeting Leukemia Stem Cells (LSC) in AML," J. Clin. Oncol. 28(Suppl): e13012.
Roboz, G.J. (2012) "Current Treatment of Acute Myeloid Leukemia," Curr. Opin. Oncol. 24:711-719.
Rothlisberger, D. et al. (2005) "Domain Interactions in the Fab Fragment: A Comparative Evaluation of the Single-chain Fv and Fab Format Engineered with Variable Domains of Different Stability," J. Molec. Biol. 347:773-789.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sarmay et al., "The effect of synthetic peptides corresponding to Fc sequences in human IgG1 on various steps in the B cell activation pathway," Eur J Immunol 18 :289-294, 1988.
Saudek et al. (1989) "A Preliminary Trial of the Programmable Implantable Medication System for Insulin Delivery," N. Engl. J. Med. 321:574-579.
Sautes-Fridman et al., "Fc gamma receptors: a magic link with the outside world," ASHI Quarterley, 4th Quarter:148-151, 2003.
Sawant, A. et al. (2012) "Depletion of Plasmacytoid Dendritic Cells Inhibits Tumor Growth and Prevents Bone Metastasis of Breast Cancer Cells," J. Immunol. 189:4258-4265.
Schaffner et al., "Chimeric interleukin 2 receptor alpha chain antibody derivatives with fused mu and gamma chains permit

(56) References Cited

OTHER PUBLICATIONS improved recruitment of effector functions," Mol Immunol 32 :9-20, 1995 (Erratum in 32:1299, 1995).
Schatz et al., "Use of peptide libraries to map the substrate specificity of a peptide-modifying enzyme: a 13 residue consensus peptide specifies biotinylation in *Escherichia coli*," Bio-Technology 11:1138-1143, 2000.
Sensel et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RII, and Fc gamma RIII, and FcRn and design of IgG1 variants with improved binding to the Fc Gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of *Saccharomyces cerevisiae* for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Smit, J.J. et al. (2006) "Plasmacytoid Dendritic Cells Inhibit Pulmonary Immunopathology and Promote Clearance of Respiratory Syncytial Virus," J. Exp. Med. 203:1153-1159.
Smith and Morrison, "Recombinant polymeric IgG: an approach to engineering more potent antibodies," Bio-Technology 12:683-688, 1994.
Sondermann and Oosthuizen, "The structure of Fc receptor/Ig complexes: considerations on stoichiometry and potential inhibitors," Immunology Letters, 82:51-56, 2002.
Sondermann et al., "Crystal structure of the soluble form of the human fcgamma-receptor IIb: a new member of the immunoglobulin superfamily at 1.7 a resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2—A crystal structure of the human IgG1 Fc Fragment-Fc gammaRIII complex," Nature 406:267-273, 2000.
Song et al. (1995) "Antibody Mediated Lung Targeting of Long-Circulating Emulsions," PDA Journal of Pharmaceutical Science & Technology 50:372-397.
Staerz et al. (1985) "Hybrid Antibodies Can Target Sites for Attack by T Cells," Nature 314:628-631.
Steinkruger, J.D. et al. (2012) "The d'—d—d' Vertical Triad is Less Discriminating Than the a'—a—a' Vertical Triad in the Antiparallel Coiled-coil Dimer Motif," J. Amer. Chem. Soc. 134(5):2626-2633.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Stomski, F.C. et al. (1996) "Human Interleukin-3 (IL-3) Induces Disulfide-Linked IL-3 Receptor Alpha- and Beta-Chain Heterodimerization, Which Is Required for Receptor Activation but Not High-Affinity Binding," Mol. Cell Biol. 16(6):3035-3046.
Stork, R. et al. (2007) "A Novel Tri-Functional Antibody Fusion Protein with Improved Pharmacokinetic Properties Generated by Fusing a Bispecific Single-Chain Diabody with an Albumin-Binding Domain from Streptococcal Protein G," Protein Engineering, Design & Selection 20(11):569-576.
Straussman, R. et al. (2007) "Kinking the Coiled Coil—Negatively Charged Residues at the Coiled-coil Interface," J. Molec. Biol. 366:1232-1242.

Strohmeier et al., "Role of the Fc Gamma R Subclasses Fc gamma RII and Fc gamma RIII in the activation of human neutrophils by low and high valency immune complexes," J Leukocyte Biol 58:415-422, 1995.
Sun, Q. et al. (1996) "Monoclonal Antibody 7G3 Recognizes the N-Terminal Domain of the Human Interleukin-3 (IL-3) Receptor Alpha Chain and Funcitons as a Specific IL-3 Receptor Antagonist," Blood 87:83-92.
Sun, Z. J. et al. (2001) "Mechanisms Contributing to T Cell Receptor Signaling and Assembly Revealed by the Solution Structure of an Ectodomain Fragment of the CD3ε: γ Heterodumer," Cell 105(7):913-923.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "Augmented humoral and anaphylactic responses in Fc gamma RII-deficient mice," Nature 379:346-349, 1996.
Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Takemura, S. et al. (2000) "Construction of a Diabody (Small Recombinant Bispecific Antibody) Using a Refolding System," Protein Eng. 13(8):583-588.
Tamm et al., "The IgG binding site of human FcγRIIIB receptor involves CC' and FG loops of the membrane-proximal domain," J Biol Chem 271:3659-3666, 1996.
Tao et al., "Structural features of human immunoglobulin G that determine isotype-specific differences in complement activation," J Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Taussig, D.C. et al. (2005) "Hematopoietic Stem Cells Express Multiple Myeloid Markers: Implications for the Origin and Targeted Therapy of Acute Myeloid Leukemia," Blood 106:4086-4092.
Testa, U. et al. (2014) "CD123 is a Membrane Biomarker and a Therapeutic Target in Hematologic Malignancies," Biomark. Res. 2:4.
Tettamanti, M.S. et al. (2013) "Targeting of Acute Myeloid Leukemia by Cytokine-Induced Killer Cells Redirected with a Novel CD123-Specific Chimeric Antigen Receptor," Br. J. Haematol. 161:389-401.
Thomas, S. et al. (2010) "Molecular Immunology Lessons from Therapeutic T-Cell Receptor Gene Transfer," Immunology 129(2):170-177.
Todorovska, A. et al. (2001) "Design and Application of Diabodies, Triabodies and Tetrabodies for Cancer Targeting," J. Immunol. Methods 248(1-2):47-66.
Topp, M.S. et al. (2011) "Targeted Therapy with the T-Cell Engaging Antibody Blinatumomab Chemotherapy-Refractory Minimal Residual Disease in B-Lineage Acute Lymphoblastic Leukemia Patients Results in High Response Rate and Prolonged Leukemia-Free Survival," J. Clin. Oncol. 29:2493-2498.
Trindandapani et al. (2002) "Regulated Expression and Inhibitory Function of FcgammaRIIB in Human Monocytic Cells," J. Biol. Chem. 277(7):5082-5089.
Tripet, B. et al. (2002) "Kinetic Analysis of the Interactions between Troponin C and the C-terminal Troponin I Regulatory Region and Validation of a New Peptide Delivery-Capture System used for Surface Plasmon Resonance," J. Molec. Biol. 323:345-362.
Unkeless, J.C. et al. (1995) "Function of Human Fc Gamma RIIA and Fc Gamma RIIIB," Semin. Immunol. 7(1):37-44.
Van Sorge et al., "FcgammaR polymorphisms: Implications for function, disease susceptibility and immunotherapy," Tissue Antigens 61:189-202, 2003.
VanAntwerp and Wittrup, "Fine affinity discrimination by yeast surface display and flow cytometry," Biotechnol Prog 16:31-37, 2000.
Vergez, F. et al. (2011) "High Levels of CD34+CD38low/-CD123+ Blasts Are Predictive of an Adverse Outcome in Acute Myeloid

(56) References Cited

OTHER PUBLICATIONS

Leukemia: A Groupe Ouest-Est Des Leucemies Aigues Et Maladies Du Sang (GOELAMS) Study," Haematologica 96:1792-1798.
Veri et al. (Epub Mar. 26, 2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.
Veri, et al. (Jul. 2010) "Therapeutic Control of B Cell Activation via Recruitment of Fcγ Receptor IIb (CD32B) Inhibitory Function with a Novel Bispecific Antibody Scaffold," Arthritis & Rheumatism, vol. 62(7): 1933-1943.
Vidarte, "Serine 132 is the C3 covalent attachment point on the CH1 domain of human IgG1," J Biol Chem 276:38217-38233, 2001.
Ward and Ghetie, "The effector functions of immunoglobulins: implications for therapy," Therapeutic Immunology 2:77-94, 1995.
Wei, F. et al. (2013) "Strength of PD-1 Signaling Differentially Affects T-Cell Effector Functions," Proc. Natl. Acad. Sci. (U.S.A.) 110: E2480-E2489.
Weidle, U. et al. (2013) "The Intriguing Options of Multispecific Antibody Formats for Treatment of Cancer," Cancer Genomics Proteomics 10:1-18.
Weng and Levy, "Two immunoglobulin G Fragment C receptor polymorphisms independently predict response to rituximab in patients with follicular lymphoma," J Clin Oncol 21:3940-3947, 2003.
Wherry, E.J. (2011) "T Cell Exhaustion," Nat. Immunol. 12:492-499.
Wiener, E. et al. "Differences between the activities antibodies of human monoclonal IgG1 and IgG3 anti-D antibodies of the Rh blood group system in their abilities to mediate effector functions of monocytes," Immunol. 65:159-163 (1988).
Wilkinson, I. et al. (2009) "High Resolution NMR-Based Model for the Structure of a scFv-IL-1-Beta Complex: Potential for NMR as a Key Tool in Therapeutic Antibody Design and Development," J. Biol. Chem. 284(46):31928-31935.
Wing et al., "Mechanism of first-dose cytokine-release syndrome by CAMPATH 1-H: Involvement of CD16 (FcγRIII) and CD11a-CD18 (LFA-1) on NK cells," J Clin Invest 98 :2819-2826, 1996.
Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Wittrup, "Protein engineering by cell-surface display," Curr, Opin. Biotechnol. 12:395-399, 2001.
Woof et al., "Localisation of the monocyte-binding region on human immunoglobulin G," Mol Immunol 23 :319-330, 1986.
Woolfson, D.N. (2005) "The Design of Coiled-Coil Structures and Assemblies," Adv. Prot. Chem. 70:79-112.
Wu et al. (1987) "Receptor-Mediated in Vitro Gene Transformation by a Soluble DNA Carrier System," J. Biol. Chem. 262:4429-4432.
Wu et al., "A novel polymorphism of FcγRIIIa (CD16) alters receptor function and predisposes to autoimmune disease," J Clin Invst 100 :1059-1070, 1997.
Wu et al., "Multimerization of a chimeric anti-CD20 single-chain Fv-Fc fusion protein is mediated through variable domain exchange," Protein Engineering 14(2): 1025-1033 (2001).
Wu, A.M et al. (1999) "Designer Genes: Recombinant Antibody Fragments for Biological Imaging," Q. J. Nucl. Med. 44(3):268-283.
Wucherpfennig, K.W. et al. (2010) "Structural Biology of the T-Cell Receptor: Insights into Receptor Assembly, Ligand Recognition, and Initiation of Signaling," Cold Spring Harb. Perspect. Biol. 2(4): a005140; pp. 1-14.
Xie et al. (2005) "A New Format of Bispecific Antibody: Highly Efficient Heterodimerization, Expression and Tumor Cell Lysis," J. Immunol. Methods 296:95-101.
Xiong, D. et al. (2002) "Efficient Inhibition of Human B-Cell Lymphoma Xenografts with an Anti-CD20 x Anti-CD3 Bispecific Diabody," Cancer Lett. (2002) 177(1):29-39.
Xu et al., "Residue at position 331 in the IgG1 and IgG4 CH2 domains contributes to their differential ability to bind and activate complement," J Biol Chem 269 :3469-3474, 1994.
Yeung and Wittrup, "Quantitative screening of yeast surface-displayed polypeptide libraries by magnetic bead capture," Biotechnol Prog 18:212-220, 2002.
Zeidler et al., "The Fc-region of a new class of intact bispecific antibody mediates activation of accessory cells and NK cells and induces direct phagocytosis of tumour cells," British J Cancer 83:261-266, 2000.
Zeng, Y. et al. (2008) "A Ligand-Pseudoreceptor System Based on de novo Designed Peptides for the Generation of Adenoviral Vectors with Altered Tropism," J. Gene Med. 10:355-367.
Zhu, Z. et al. (1997) "Remodeling Domain Interfaces to Enhance Heterodimer Formation," Protein Sci. 6:781-788.
Zuckier et al., "Chimeric human-mouse IgG antibodies with shuffled constant region exons demonstrate that multiple domains contribute to in vivo half-life," Cancer Res 58 :3905-3908, 1998.
Zuo et al. (2000) (*An efficient route to the production of an IgG-like bispecific antibody*, PE 13(5):361-367).
Anonymous, "MacroGenics—Dual affinity retargeting (DART™) Platform," Press Release of MacroGenics, Inc.; 2011, 2 pages.
Anonymous, "MacroGenics, Inc. Product Pipeline Review 2013," JBS Market Research publication, 2013, 3 pages.
Supplementary European Search Report (EP 14 837858) dated Jan. 17, 2017 (10 pages).
Burton et al. (1992) "*Human Antibody Effector Function*," Advances in Immunology 51:1-64.
Johnson et al. (2010) "*Effector Cell Recruitment with Novel Fv-based Dual-affinity Re-targeting Protein Leads to Potent Tumor Cytolysis and in Vivo B-cell Depletion*," J. Mol. Biol (399):436-449.
Ko et al. (2011) "*Hypertrophic lupus erythematosus: the diagnostic utility of CD123 staining*," J. Cutan Pathol. 38(11):889-892.
Maazi et al. (2013) "*Role of plasmactyoid dendritic cell subsets in allergic asthma*," 68(6):695-701.
Cavanagh et al. (2005) "*Rheumatoid arthritis synovium contains plasmacytoid dendritic cells*," Arthritis Res. Ther. 7(2):R230-R240.

\* cited by examiner

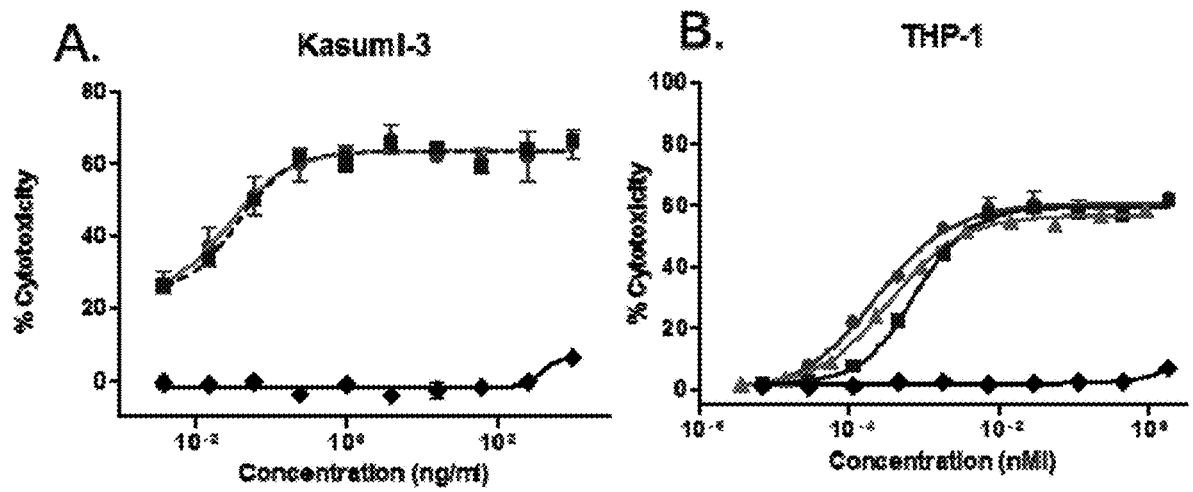
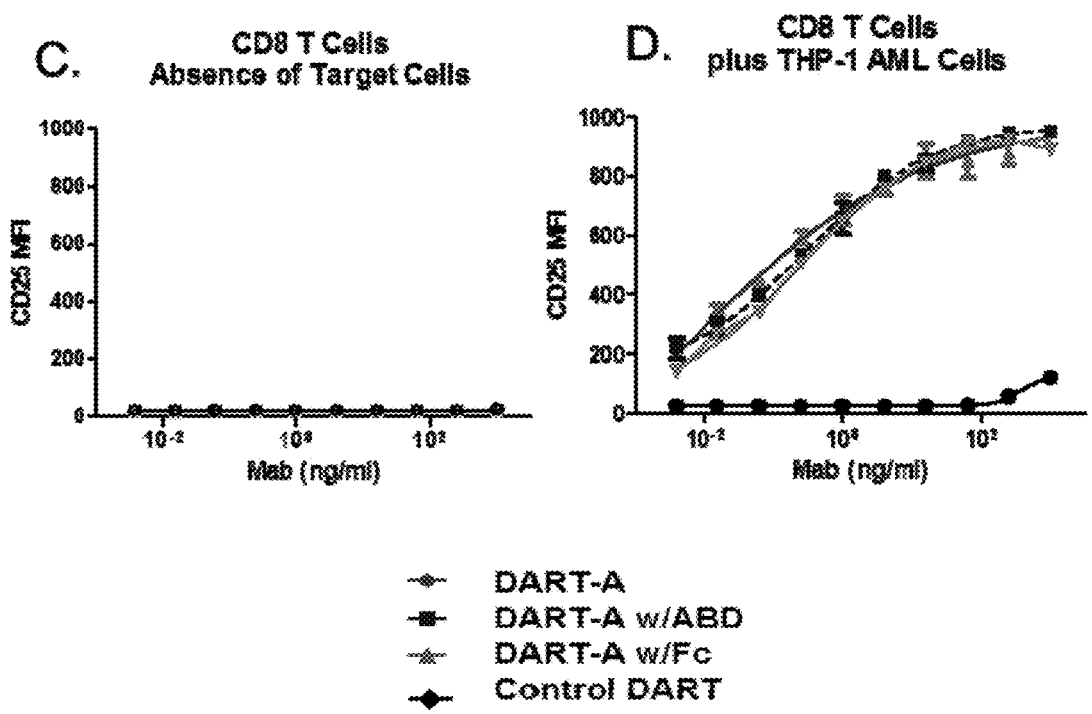
Figure 5

A.
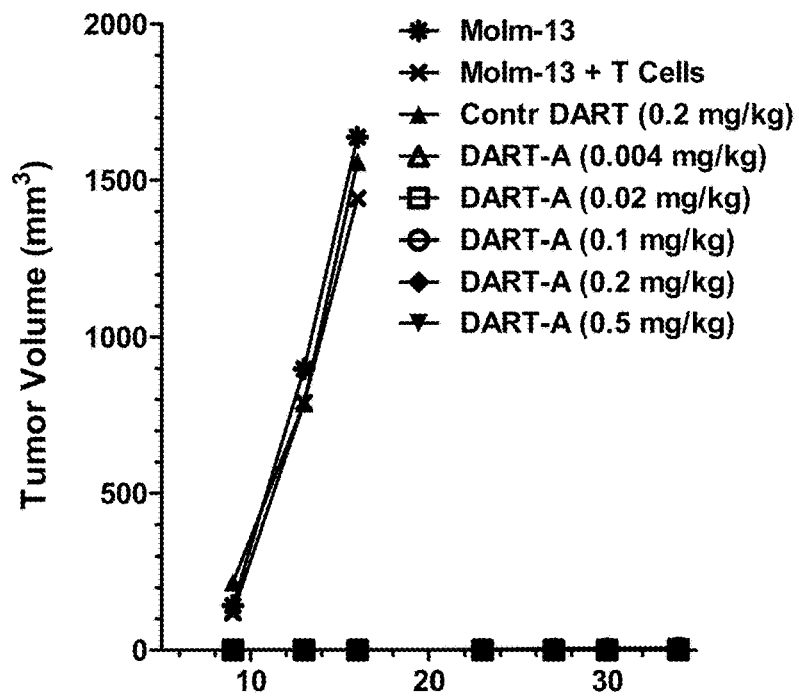
B.
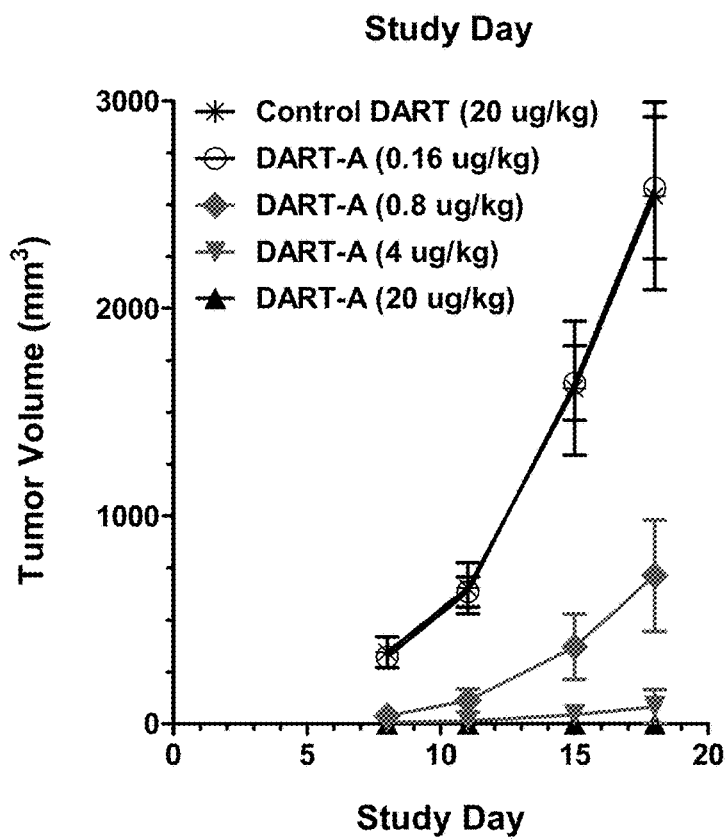
Figure 7

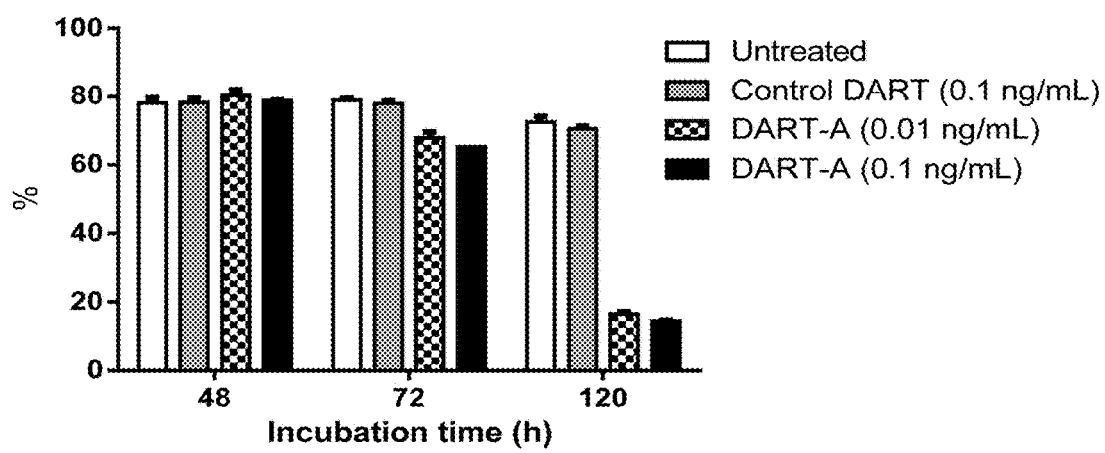
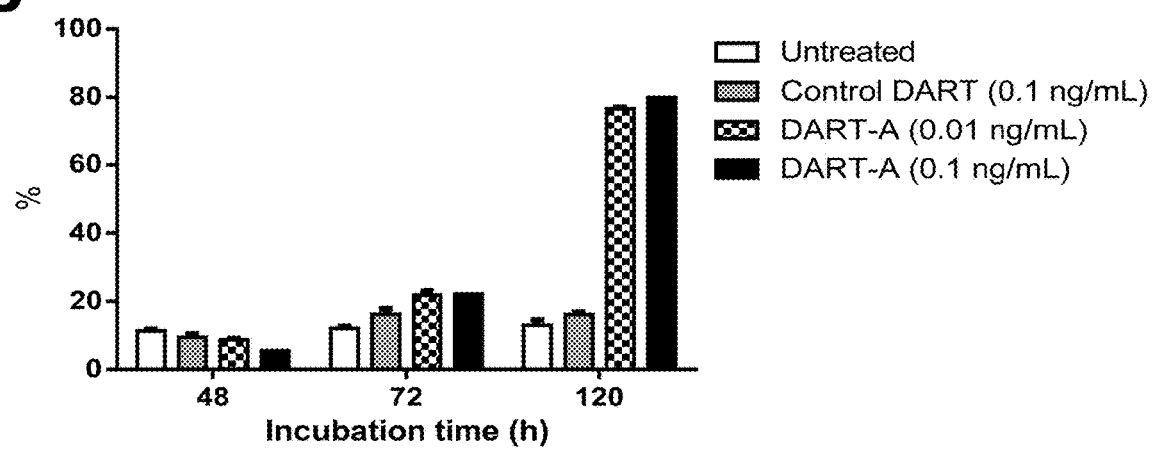
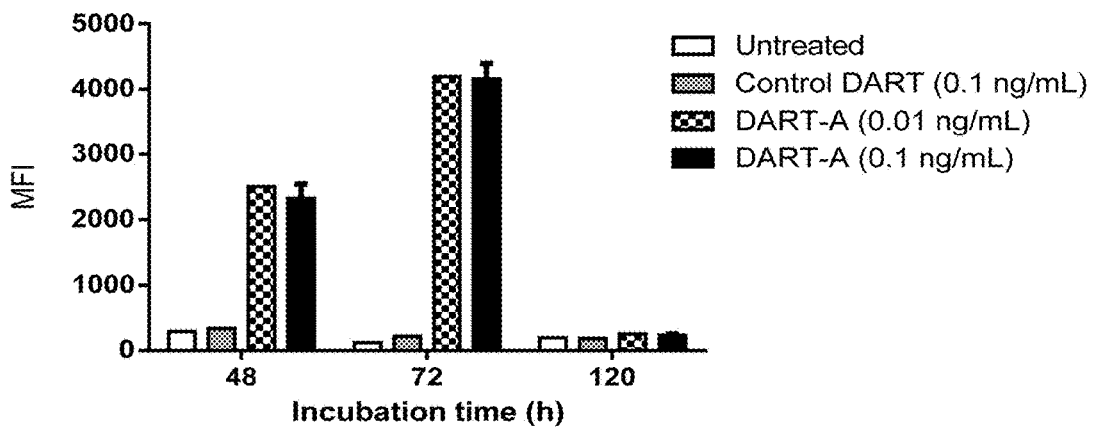
Figure 10

Figure 13

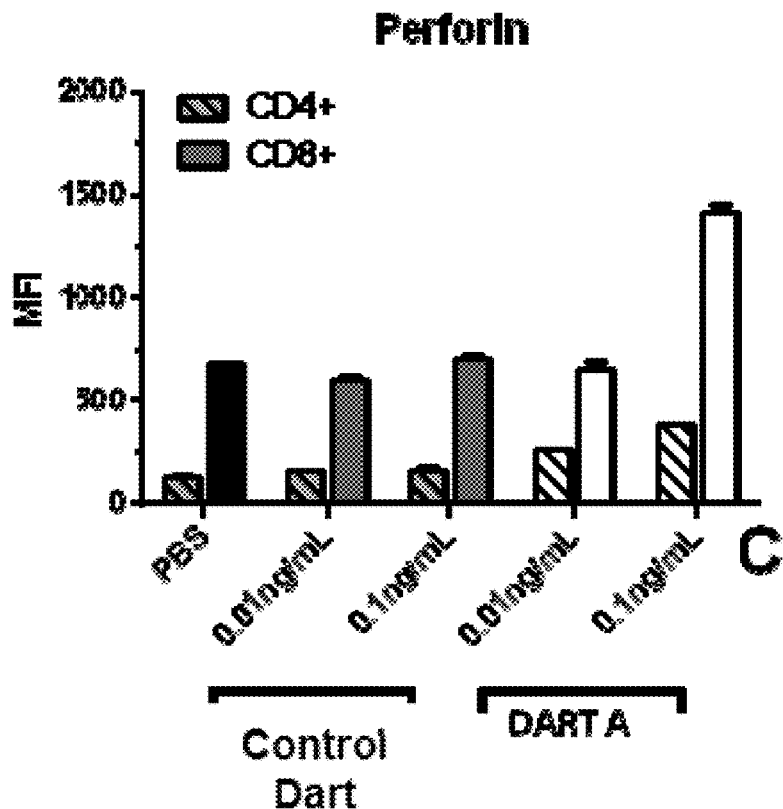
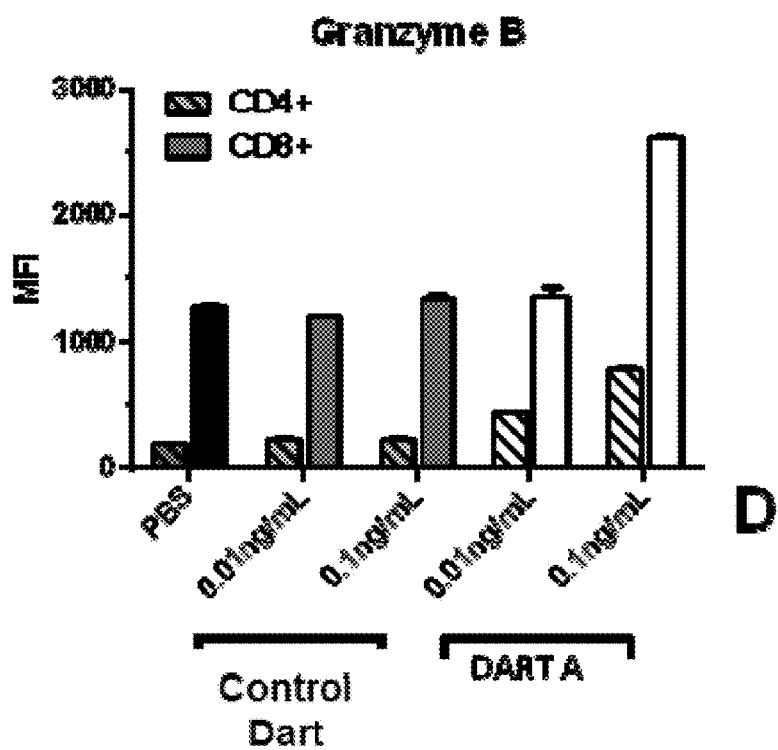
Figure 17 (Continued)

A. Autologous Monocyte Depletion of Human PBMC
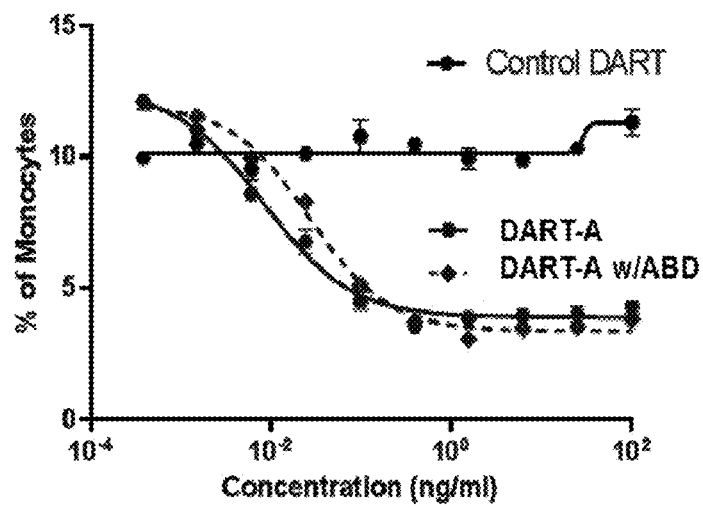
B. Autologous Monocyte Depletion of Cynomolgus Monkey PBMC
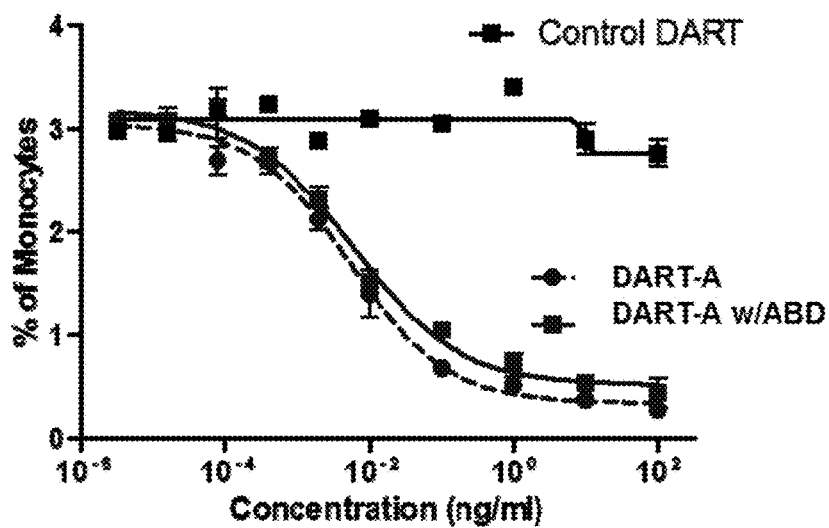
Figure 19

Control DART
100µg/kg/d
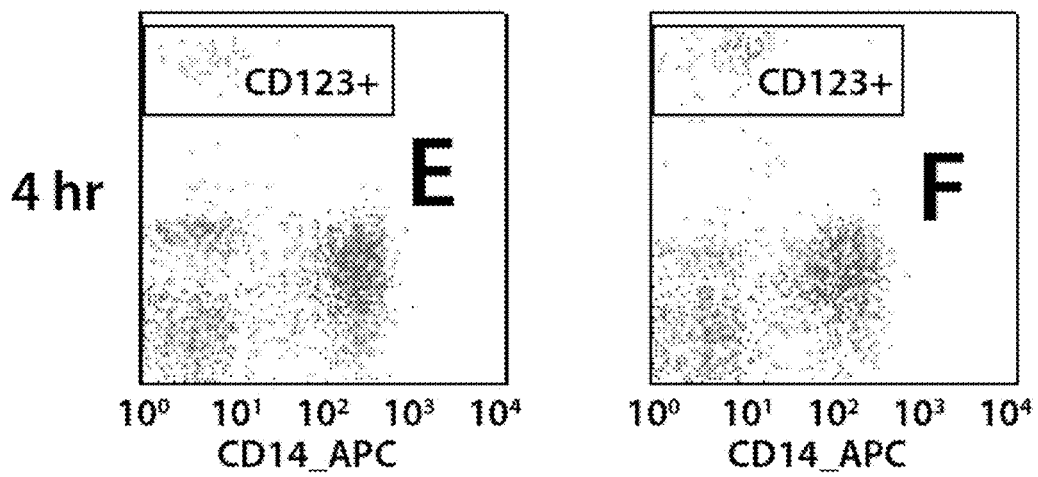
4 hr
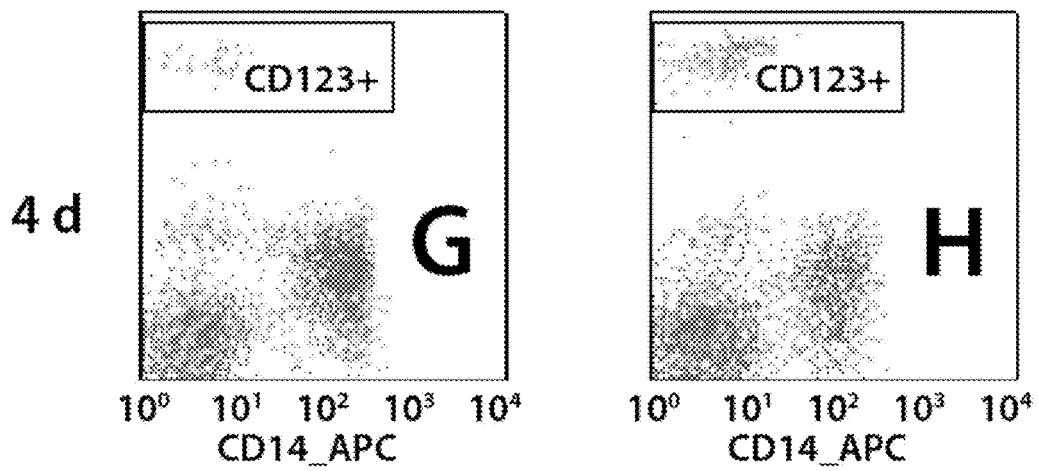
4 d
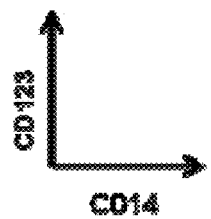
Figure 20 (Continued)

DART-A
10ng/kg/d
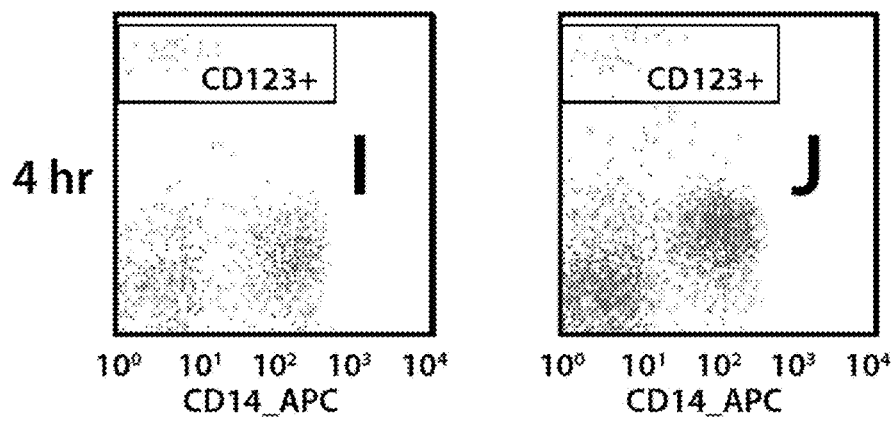
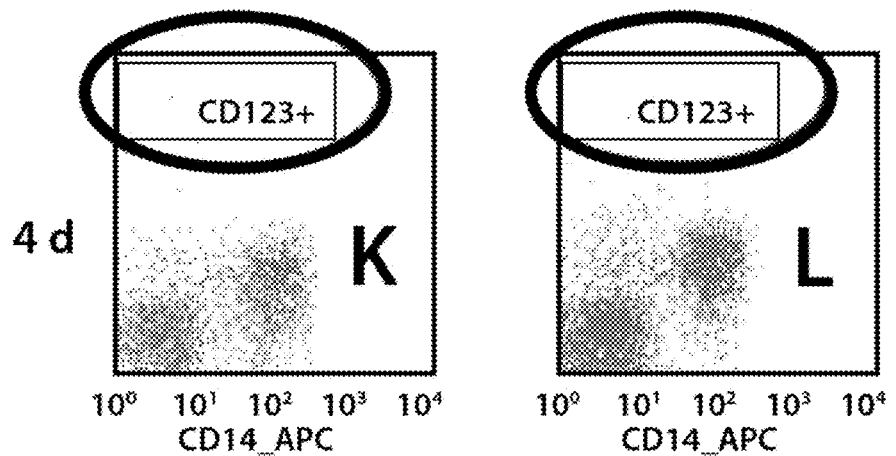
30ng/kg/d
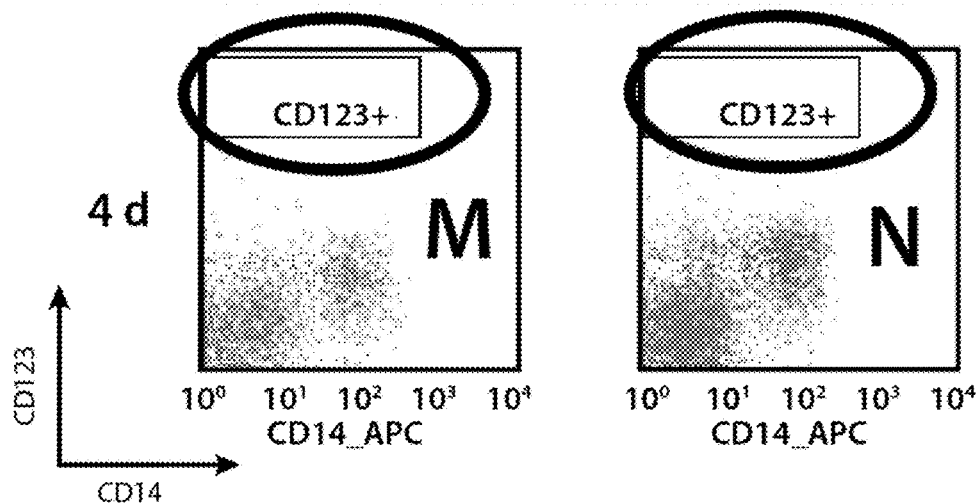
Figure 20 (Continued)

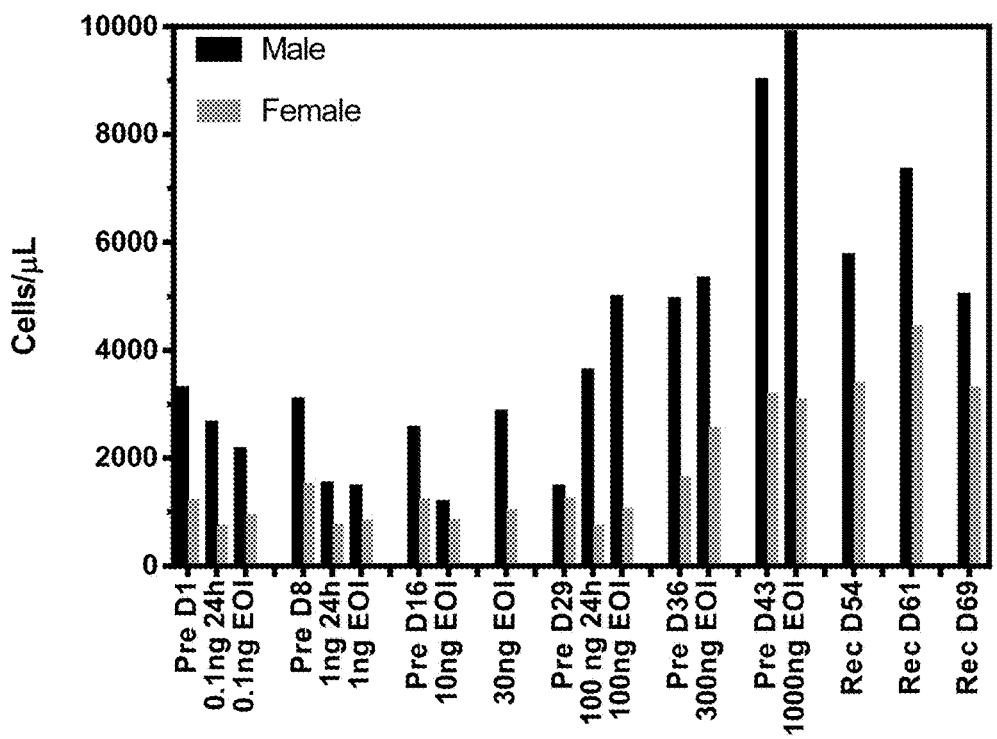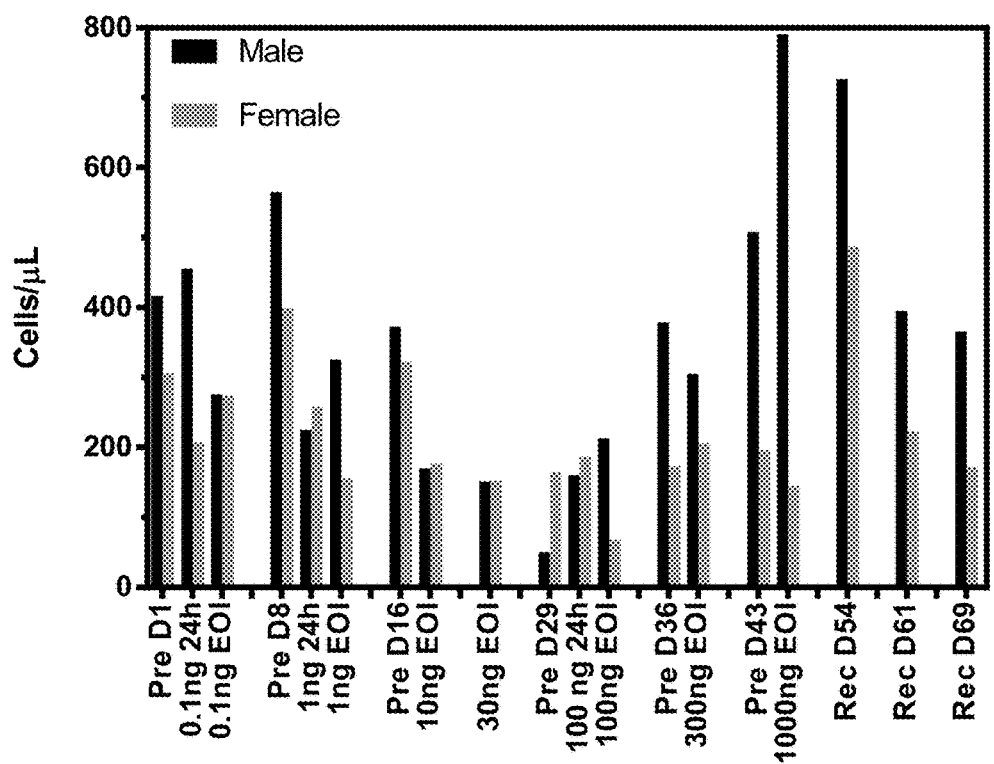
Figure 21 (Panels A-B)

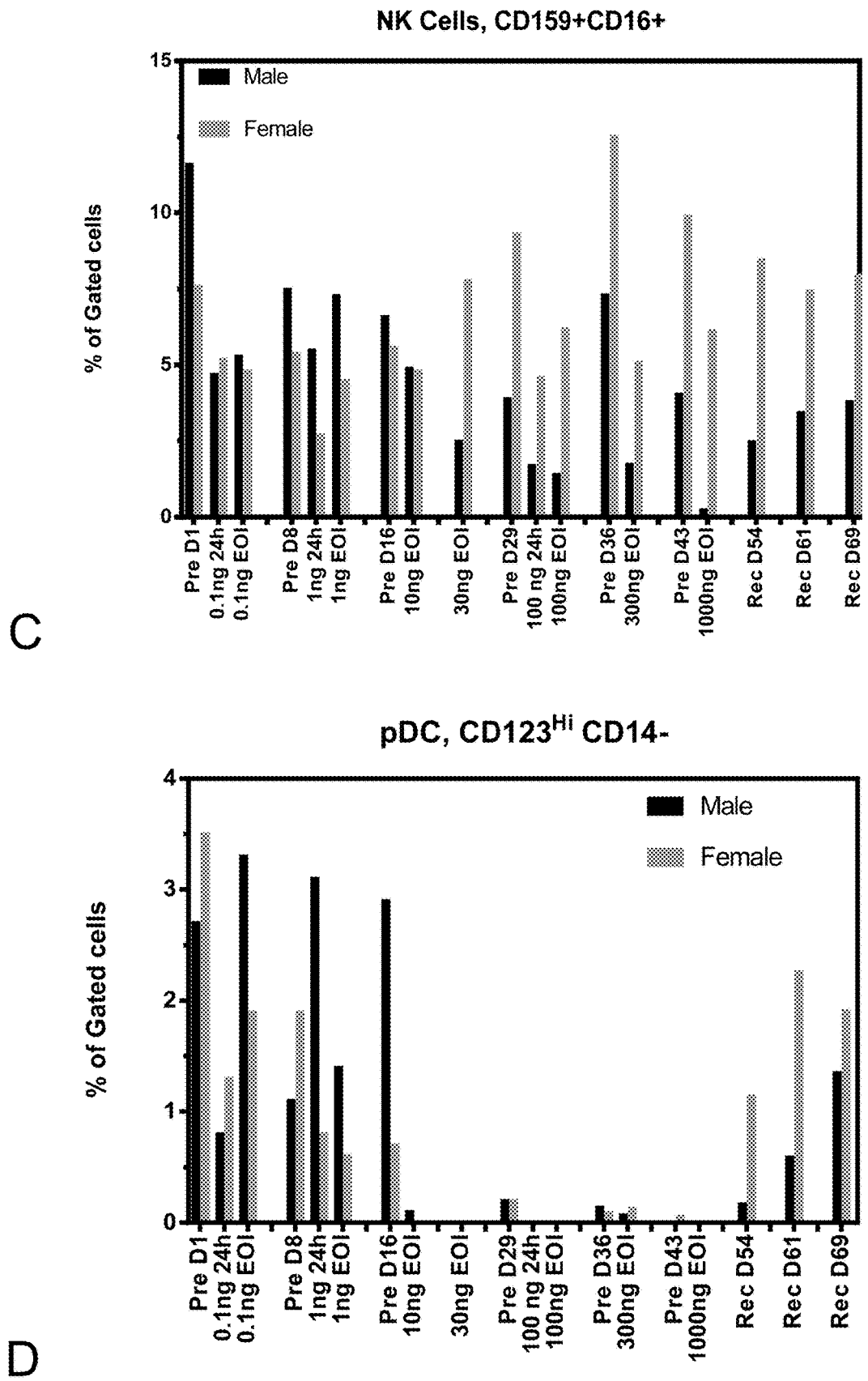
Figure 21 (Panels C-D)

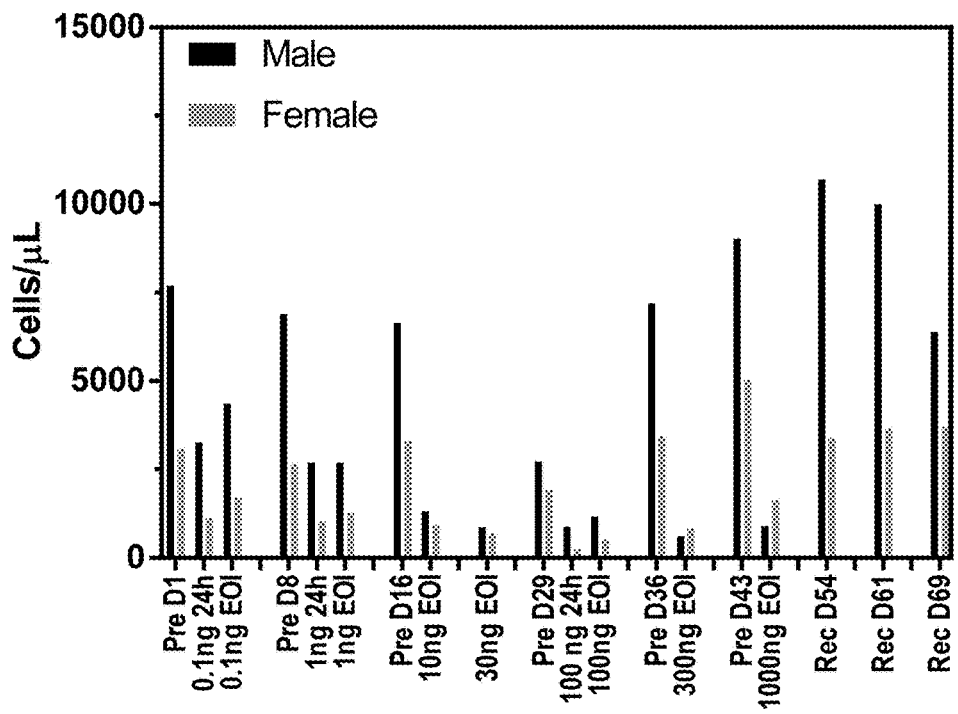
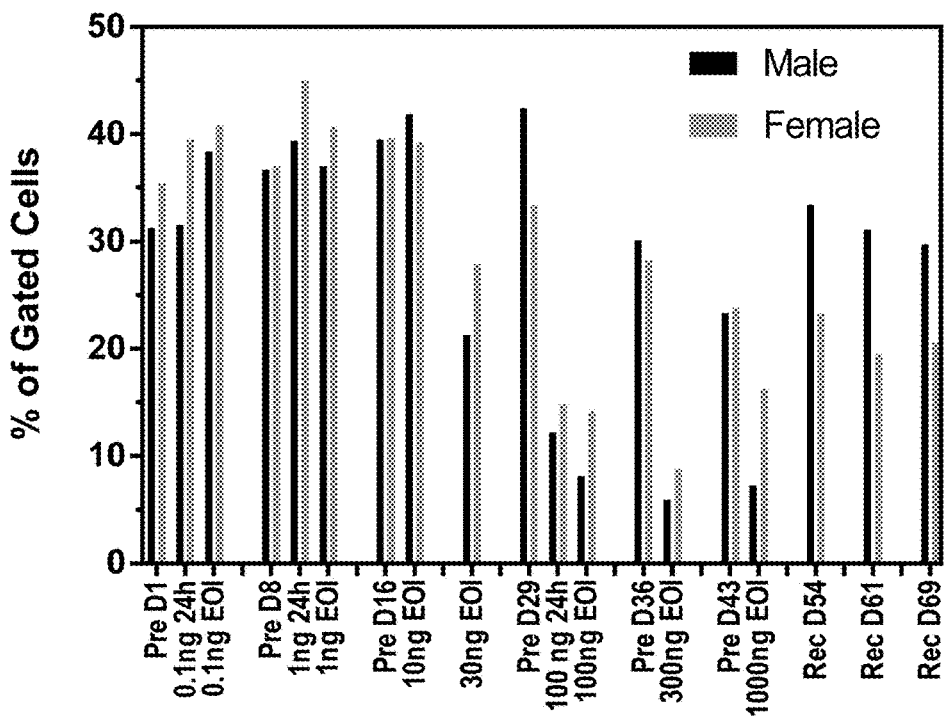
Figure 22 (Panels A-B)

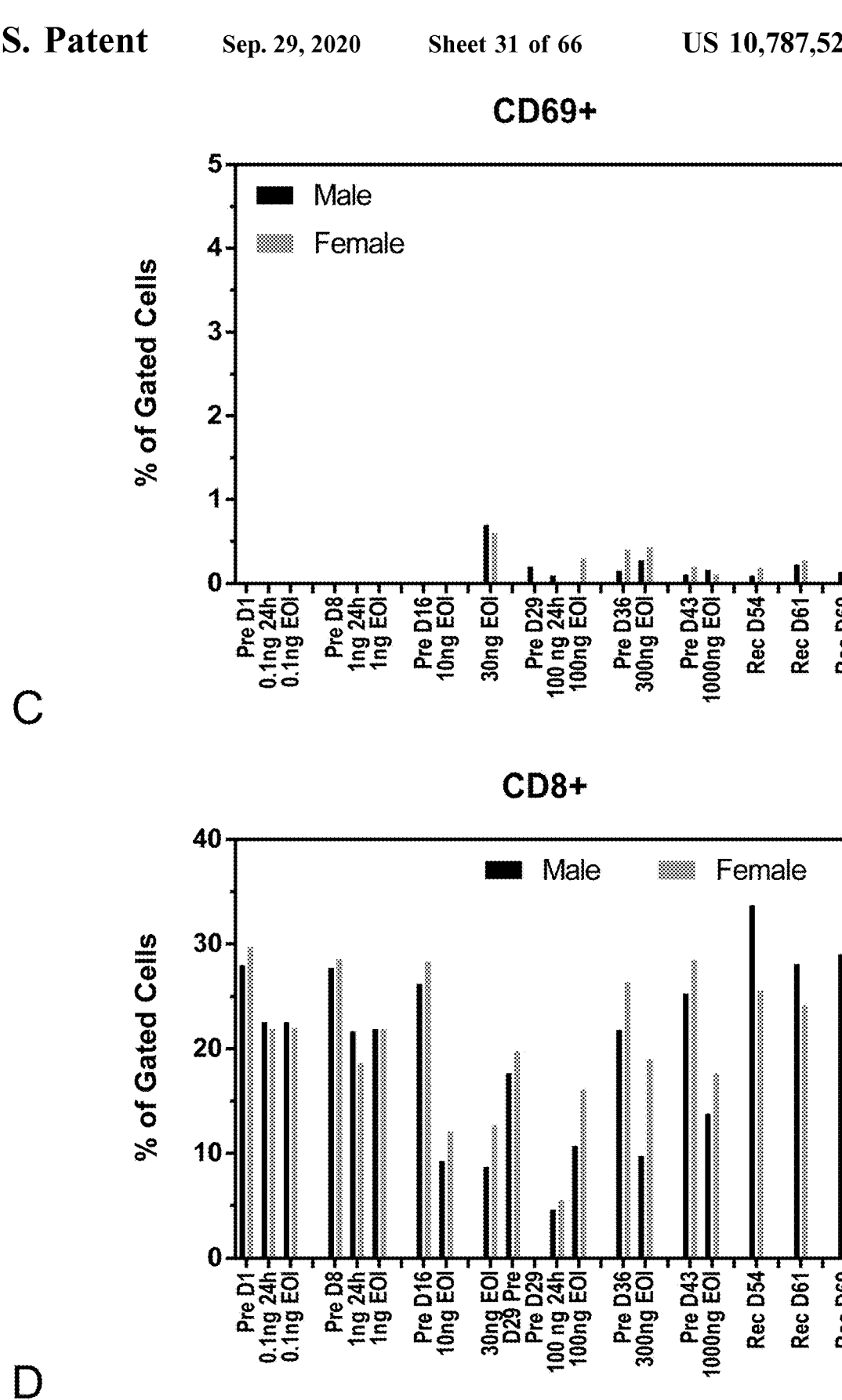
Figure 22 (Panels C-D)

Molm-13

Human T Cells

Cynomolgus Monkey T Cells

A

BI-SPECIFIC MONOVALENT DIABODIES THAT ARE CAPABLE OF BINDING CD123 AND CD3, AND USES THEREOF

CROSS-REFERENCE TO RELATED APPLICATIONS

This Application is a continuation of U.S. patent application Ser. No. 14/913,632 (filed Feb. 22, 2016), which is a § 371 National Stage Application of PCT/US2014/051790 (filed Aug. 20, 2014), which application claims priority to U.S. Patent Applications No. 61/869,510 (filed Aug. 23, 2013), 61/907,749 (filed Nov. 22, 2013), and 61/990,475 (filed May 8, 2014), and to European Patent Application No. 13198784 (filed Dec. 20, 2013), each of which applications is herein incorporated by reference in its entirety and to which priority is claimed.

REFERENCE TO SEQUENCE LISTING

This application includes one or more Sequence Listings pursuant to 37 C.F.R. 1.821 et seq., submitted herewith as an ASCII text file Sequence Listing (file name: 1301-0109 PCT_SequenceListing.txt; created Oct. 9, 2017; size 71,592 bytes) and incorporated herein by reference its entirety.

BACKGROUND OF THE INVENTION

Field of the Invention

The present invention is directed to CD123×CD3 bi-specific monovalent diabodies that are capable of simultaneous binding to CD123 and CD3, and to the uses of such molecules in the treatment of hematologic malignancies.

Description of Related Art

I. CD123

CD123 (interleukin 3 receptor alpha, IL-3Ra) is a 40 kDa molecule and is part of the interleukin 3 receptor complex (Stomski, F. C. et al. (1996) "*Human Interleukin-3 (IL-3) Induces Disulfide-Linked IL-3 Receptor Alpha-And Beta-Chain Heterodimerization, Which Is Required For Receptor Activation But Not High Affinity Binding*," Mol. Cell. Biol. 16(6):3035-3046). Interleukin 3 (IL-3) drives early differentiation of multipotent stem cells into cells of the erythroid, myeloid and lymphoid progenitors. CD123 is expressed on CD34+ committed progenitors (Taussig, D. C. et al. (2005) "*Hematopoietic Stem Cells Express Multiple Myeloid Markers: Implications For The Origin And Targeted Therapy Of Acute Myeloid Leukemia*," Blood 106:4086-4092), but not by CD34+/CD38− normal hematopoietic stem cells. CD123 is expressed by basophils, mast cells, plasmacytoid dendritic cells, some expression by monocytes, macrophages and eosinophils, and low or no expression by neutrophils and megakaryocytes. Some non-hematopoietic tissues (placenta, Leydig cells of the testis, certain brain cell elements and some endothelial cells) express CD123; however expression is mostly cytoplasmic.

CD123 is reported to be expressed by leukemic blasts and leukemia stem cells (LSC) (Jordan, C. T. et al. (2000) "*The Interleukin-3 Receptor Alpha Chain Is A Unique Marker For Human Acute Myelogenous Leukemia Stem Cells*," Leukemia 14:1777-1784; Jin, W. et al. (2009) "*Regulation Of Th17 Cell Differentiation And EAE Induction By MAP3K NIK*," Blood 113:6603-6610) (FIG. 1). In human normal precursor populations, CD123 is expressed by a subset of hematopoietic progenitor cells (HPC) but not by normal hematopoietic stem cells (HSC). CD123 is also expressed by plasmacytoid dendritic cells (pDC) and basophils, and, to a lesser extent, monocytes and eosinophils (Lopez, A. F. et al. (1989) "*Reciprocal Inhibition Of Binding Between Interleukin 3 And Granulocyte Macrophage Colony-Stimulating Factor To Human Eosinophils*," Proc. Natl. Acad. Sci. (U.S.A.) 86:7022-7026; Sun, Q. et al. (1996) "*Monoclonal Antibody 7G3 Recognizes The N-Terminal Domain Of The Human Interleukin-3 (IL-3) Receptor Alpha Chain And Functions As A Specific IL-3 Receptor Antagonist*," Blood 87:83-92; Muñoz, L. et al. (2001) "*Interleukin-3 Receptor Alpha Chain (CD123) Is Widely Expressed In Hematologic Malignancies*," Haematologica 86(12):1261-1269; Masten, B. J. et al. (2006) "*Characterization Of Myeloid And Plasmacytoid Dendritic Cells In Human Lung*," J. Immunol. 177:7784-7793; Korpelainen, E. I. et al. (1995) "*Interferon-Gamma Upregulates Interleukin-3 (IL-3) Receptor Expression In Human Endothelial Cells And Synergizes With IL-3 In Stimulating Major Histocompatibility Complex Class II Expression And Cytokine Production*," Blood 86:176-182).

CD123 has been reported to be overexpressed on malignant cells in a wide range of hematologic malignancies including acute myeloid leukemia (AML) and myelodysplastic syndrome (MDS) (Muñoz, L. et al. (2001) "*Interleukin-3 Receptor Alpha Chain (CD123) Is Widely Expressed In Hematologic Malignancies*," Haematologica 86(12):1261-1269). Overexpression of CD123 is associated with poorer prognosis in AML (Tettamanti, M. S. et al. (2013) "*Targeting Of Acute Myeloid Leukaemia By Cytokine Induced Killer Cells Redirected With A Novel CD123-Specific Chimeric Antigen Receptor*," Br. J. Haematol. 161: 389-401).

AML and MDS are thought to arise in and be perpetuated by a small population of leukemic stem cells (LSCs), which are generally dormant (i.e., not rapidly dividing cells) and therefore resist cell death (apoptosis) and conventional chemotherapeutic agents. LSCs are characterized by high levels of CD123 expression, which is not present in the corresponding normal hematopoietic stem cell population in normal human bone marrow (Jin, W. et al. (2009) "*Regulation Of Th17 Cell Differentiation And EAE Induction By MAP3K NIK*," Blood 113:6603-6610; Jordan, C. T. et al. (2000) "*The Interleukin-3 Receptor Alpha Chain Is A Unique Marker For Human Acute Myelogenous Leukemia Stem Cells*," Leukemia 14:1777-1784). CD123 is expressed in 45%-95% of AML, 85% of Hairy cell leukemia (HCL), and 40% of acute B lymphoblastic leukemia (B-ALL). CD123 expression is also associated with multiple other malignancies/pre-malignancies: chronic myeloid leukemia (CML) progenitor cells (including blast crisis CML); Hodgkin's Reed Sternberg (RS) cells; transformed non-Hodgkin's lymphoma (NHL); some chronic lymphocytic leukemia (CLL) (CD11c+); a subset of acute T lymphoblastic leukemia (T-ALL) (16%, most immature, mostly adult), plasmacytoid dendritic cell (pDC) (DC2) malignancies and CD34+/CD38− myelodysplastic syndrome (MDS) marrow cell malignancies.

AML is a clonal disease characterized by the proliferation and accumulation of transformed myeloid progenitor cells in the bone marrow, which ultimately leads to hematopoietic failure. The incidence of AML increases with age, and older patients typically have worse treatment outcomes than do younger patients (Robak, T. et al. (2009) "*Current And Emerging Therapies For Acute Myeloid Leukemia*," Clin. Ther. 2:2349-2370). Unfortunately, at present, most adults with AML die from their disease.

Treatment for AML initially focuses in the induction of remission (induction therapy). Once remission is achieved, treatment shifts to focus on securing such remission (post-remission or consolidation therapy) and, in some instances, maintenance therapy. The standard remission induction paradigm for AML is chemotherapy with an anthracycline/cytarabine combination, followed by either consolidation chemotherapy (usually with higher doses of the same drugs as were used during the induction period) or human stem cell transplantation, depending on the patient's ability to tolerate intensive treatment and the likelihood of cure with chemotherapy alone (see, e.g., Roboz, G. J. (2012) "*Current Treatment Of Acute Myeloid Leukemia*," Curr. Opin. Oncol. 24:711-719).

Agents frequently used in induction therapy include cytarabine and the anthracyclines. Cytarabine, also known as AraC, kills cancer cells (and other rapidly dividing normal cells) by interfering with DNA synthesis. Side effects associated with AraC treatment include decreased resistance to infection, a result of decreased white blood cell production; bleeding, as a result of decreased platelet production; and anemia, due to a potential reduction in red blood cells. Other side effects include nausea and vomiting. Anthracyclines (e.g., daunorubicin, doxorubicin, and idarubicin) have several modes of action including inhibition of DNA and RNA synthesis, disruption of higher order structures of DNA, and production of cell damaging free oxygen radicals. The most consequential adverse effect of anthracyclines is cardiotoxicity, which considerably limits administered life-time dose and to some extent their usefulness.

Thus, unfortunately, despite substantial progress in the treatment of newly diagnosed AML, 20% to 40% of patients do not achieve remission with the standard induction chemotherapy, and 50% to 70% of patients entering a first complete remission are expected to relapse within 3 years. The optimum strategy at the time of relapse, or for patients with the resistant disease, remains uncertain. Stem cell transplantation has been established as the most effective form of anti-leukemic therapy in patients with AML in first or subsequent remission (Roboz, G. J. (2012) "*Current Treatment Of Acute Myeloid Leukemia*," Curr. Opin. Oncol. 24:711-719).

II. CD3

CD3 is a T cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling*," Cold Spring Harb. Perspect. Biol. 2(4):a005140; pages 1-14). In mammals, the complex contains a CD3γ chain, a CD3δ chain, and two CD3ε chains. These chains associate with a molecule known as the T cell receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer*," Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105 (7): 913-923; Kuhns, M. S. et al. (2006) "*Deconstructing The Form And Function Of The TCR/CD3 Complex*," Immunity. 2006 February; 24(2):133-139).

III. Bi-Specific Diabodies

The ability of an intact, unmodified antibody (e.g., an IgG) to bind an epitope of an antigen depends upon the presence of variable domains on the immunoglobulin light and heavy chains (i.e., the VL and VH domains, respectively). The design of a diabody is based on the single chain Fv construct (scFv) (see, e.g., Holliger et al. (1993) "*'Diabodies': Small Bivalent And Bispecific Antibody Fragments*," Proc. Natl. Acad. Sci. (U.S.A.) 90:6444-6448; US 2004/0058400 (Holliger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20): 19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng. Des. Sel. 17(1):21-27; Wu, A. et al. (2001) "*Multimerization Of A Chimeric Anti-CD20 Single Chain Fv-Fc Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8): 583-588; Baeuerle, P. A. et al. (2009) "*Bispecific T-Cell Engaging Antibodies For Cancer Therapy*," Cancer Res. 69(12):4941-4944).

Interaction of an antibody light chain and an antibody heavy chain and, in particular, interaction of its VL and VH domains forms one of the epitope binding sites of the antibody. In contrast, the scFv construct comprises a VL and VH domain of an antibody contained in a single polypeptide chain wherein the domains are separated by a flexible linker of sufficient length to allow self-assembly of the two domains into a functional epitope binding site. Where self-assembly of the VL and VH domains is rendered impossible due to a linker of insufficient length (less than about 12 amino acid residues), two of the scFv constructs interact with one another other to form a bivalent molecule in which the VL of one chain associates with the VH of the other (reviewed in Marvin et al. (2005) "*Recombinant Approaches To IgG-Like Bispecific Antibodies*," Acta Pharmacol. Sin. 26:649-658).

Natural antibodies are capable of binding to only one epitope species (i.e., mono-specific), although they can bind multiple copies of that species (i.e., exhibiting bi-valency or multi-valency). The art has noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "*'Diabodies': Small Bivalent And Bispecific Antibody Fragments*," Proc. Natl. Acad. Sci. (U.S.A.) 90:6444-6448; US 2004/0058400 (Holliger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20): 19665-19672; WO 02/02781 (Mertens et al.); Mertens, N. et al., "*New Recombinant Bi-and Trispecific Antibody Derivatives*," In: NOVEL FRONTIERS IN THE PRODUCTION OF COMPOUNDS FOR BIOMEDICAL USE, A. VanBroekhoven et al. (Eds.), Kluwer Academic Publishers, Dordrecht, The Netherlands (2001), pages 195-208; Wu, A. et al. (2001) "*Multimerization Of A Chimeric Anti-CD20 Single Chain Fv-Fc Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8): 583-588; Baeuerle, P. A. et al. (2009) "*Bispecific T-Cell Engaging Antibodies For Cancer Therapy*," Cancer Res. 69(12):4941-4944).

The provision of non-monospecific diabodies provides a significant advantage: the capacity to co-ligate and co-localize cells that express different epitopes. Bi-specific diabodies thus have wide-ranging applications including therapy and immunodiagnosis. Bi-specificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305).

Diabody epitope binding domains may also be directed to a surface determinant of any immune effector cell such as CD3, CD16, CD32, or CD64, which are expressed on T lymphocytes, natural killer (NK) cells or other mononuclear cells. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197).

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bi-specific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies (see, e.g., WO 2006/113665; WO/2008/157379; WO 2010/080538; WO 2012/018687; WO/2012/162068; Johnson, S. et al. (2010) "*Effector Cell Recruitment With Novel Fv-Based Dual-Affinity Re-Targeting Protein Leads To Potent Tumor Cytolysis And In Vivo B-Cell Depletion*," J. Molec. Biol. 399(3):436-449; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Moore, P. A. et al. (2011) "*Application Of Dual Affinity Retargeting Molecules To Achieve Optimal Redirected T-Cell Killing Of B-Cell Lymphoma*," Blood 117(17):4542-4551). Such approaches involve engineering one or more cysteine residues into each of the employed polypeptide species. For example, the addition of a cysteine residue to the C-terminus of such constructs has been shown to allow disulfide bonding between the polypeptide chains, stabilizing the resulting heterodimer without interfering with the binding characteristics of the bivalent molecule.

Notwithstanding such success, the production of stable, functional heterodimeric, non-monospecific diabodies can be further optimized by the careful consideration and placement of cysteine residues in one or more of the employed polypeptide chains. Such optimized diabodies can be produced in higher yield and with greater activity than non-optimized diabodies. The present invention is thus directed to the problem of providing polypeptides that are particularly designed and optimized to form heterodimeric diabodies. The invention solves this problem through the provision of exemplary, optimized CD123×CD3 diabodies.

SUMMARY OF THE INVENTION

The present invention is directed to CD123×CD3 bi-specific diabodies that are capable of simultaneous binding to CD123 and CD3, and to the uses of such molecules in the treatment of disease, in particular hematologic malignancies.

The CD123×CD3 bi-specific diabodies of the invention comprise at least two different polypeptide chains that associate with one another in a heterodimeric manner to form one binding site specific for an epitope of CD123 and one binding site specific for an epitope of CD3. A CD123×CD3 diabody of the invention is thus monovalent in that it is capable of binding to only one copy of an epitope of CD123 and to only one copy of an epitope of CD3, but bi-specific in that a single diabody is able to bind simultaneously to the epitope of CD123 and to the epitope of CD3. The individual polypeptide chains of the diabodies are covalently bonded to one another, for example by disulfide bonding of cysteine residues located within each polypeptide chain. In particular embodiments, the diabodies of the present invention further have an immunoglobulin Fc Domain or an Albumin-Binding Domain to extend half-life in vivo.

In detail, the invention also provides a sequence-optimized CD123×CD3 bi-specific monovalent diabody capable of specific binding to an epitope of CD123 and to an epitope of CD3, wherein the diabody comprises a first polypeptide chain and a second polypeptide chain, covalently bonded to one another, wherein:

A. the first polypeptide chain comprises, in the N-terminal to C-terminal direction:
  i. a Domain 1, comprising:
    (1) a sub-Domain (1A), which comprises a VL Domain of a monoclonal antibody capable of binding to CD3 ($VL_{CD3}$) (SEQ ID NO:21); and
    (2) a sub-Domain (1B), which comprises a VH Domain of a monoclonal antibody capable of binding to CD123 ($VH_{CD123}$) (SEQ ID NO:26);
    wherein the sub-Domains 1A and 1B are separated from one another by a peptide linker (SEQ ID NO:29);
  ii. a Domain 2, wherein the Domain 2 is an E-coil Domain (SEQ ID NO:34) or a K-coil Domain (SEQ ID NO:35), wherein the Domain 2 is separated from the Domain 1 by a peptide linker (SEQ ID NO:30); and
B. the second polypeptide chain comprises, in the N-terminal to C-terminal direction:
  i. a Domain 1, comprising:
    (1) a sub-Domain (1A), which comprises a VL Domain of a monoclonal antibody capable of binding to CD123 ($VL_{CD123}$) (SEQ ID NO:25); and
    (2) a sub-Domain (1B), which comprises a VH Domain of a monoclonal antibody capable of binding to CD3 ($VH_{CD3}$) (SEQ ID NO:22);
    wherein the sub-Domains 1A and 1B are separated from one another by a peptide linker (SEQ ID NO:29);
  ii. a Domain 2, wherein the Domain 2 is a K-coil Domain (SEQ ID NO:35) or an E-coil Domain (SEQ ID NO:34), wherein the Domain 2 is separated from the Domain 1 by a peptide linker (SEQ ID NO:30); and wherein the Domain 2 of the first and the second polypeptide chains are not both E-coil Domains or both K-coil Domains;
and wherein:
(a) said VL Domain of said first polypeptide chain and said VH Domain of said second polypeptide chain form an Antigen Binding Domain capable of specifically binding to an epitope of CD3; and
(b) said VL Domain of said second polypeptide chain and said VH Domain of said first polypeptide chain form an Antigen Binding Domain capable of specifically binding to an epitope of CD123.

The invention also provides a non-sequence-optimized CD123×CD3 bi-specific monovalent diabody capable of specific binding to an epitope of CD123 and to an epitope of CD3, wherein the diabody comprises a first polypeptide chain and a second polypeptide chain, covalently bonded to one another, wherein:

A. the first polypeptide chain comprises, in the N-terminal to C-terminal direction:
  i. a Domain 1, comprising:
    (1) a sub-Domain (1A), which comprises a VL Domain of a monoclonal antibody capable of binding to CD3 ($VL_{CD3}$) (SEQ ID NO:23); and
    (2) a sub-Domain (1B), which comprises a VH Domain of a monoclonal antibody capable of binding to CD123 ($VH_{CD123}$) (SEQ ID NO:28);
    wherein the sub-Domains 1A and 1B are separated from one another by a peptide linker (SEQ ID NO:29);
  ii. a Domain 2, wherein the Domain 2 is an E-coil Domain (SEQ ID NO:34) or a K-coil Domain (SEQ ID NO:35), wherein the Domain 2 is separated from the Domain 1 by a peptide linker (SEQ ID NO:30); and
B. the second polypeptide chain comprises, in the N-terminal to C-terminal direction:
  i. a Domain 1, comprising:
    (1) a sub-Domain (1A), which comprises a VL Domain of a monoclonal antibody capable of binding to CD123 ($VL_{CD123}$) (SEQ ID NO:27); and
    (2) a sub-Domain (1B), which comprises a VH Domain of a monoclonal antibody capable of binding to CD3 ($VH_{CD3}$) (SEQ ID NO:24);
    wherein the sub-Domains 1A and 1B are separated from one another by a peptide linker (SEQ ID NO:29);
  ii. a Domain 2, wherein the Domain 2 is a K-coil Domain (SEQ ID NO:35) or an E-coil Domain (SEQ ID NO:34), wherein the Domain 2 is separated from the Domain 1 by a peptide linker (SEQ ID NO:30); and
  wherein the Domain 2 of the first and the second polypeptide chains are not both E-coil Domains or both K-coil Domains
and wherein:
(a) said VL Domain of said first polypeptide chain and said VH Domain of said second polypeptide chain form an Antigen Binding Domain capable of specifically binding to an epitope of CD3; and
(b) said VL Domain of said second polypeptide chain and said VH Domain of said first polypeptide chain form an Antigen Binding Domain capable of specifically binding to an epitope of CD123.

The invention additionally provides the embodiment of the above-described bi-specific monovalent diabodies, wherein the first or second polypeptide chain additionally comprises an Albumin-Binding Domain (SEQ ID NO:36)

linked, C-terminally to Domain 2 or N-terminally to Domain 1, via a peptide linker (SEQ ID NO:31).

The invention additionally provides the embodiment of the above-described bi-specific monovalent diabodies wherein the first or second polypeptide chain additionally comprises a Domain 3 comprising a CH2 and CH3 Domain of an immunoglobulin IgG Fc Domain (SEQ ID NO:37), wherein the Domain 3 is linked, N-terminally, to the Domain 1A via a peptide linker (SEQ ID NO:33).

The invention additionally provides the embodiment of the above-described bi-specific monovalent diabodies wherein the first or second polypeptide chain additionally comprises a Domain 3 comprising a CH2 and CH3 Domain of an immunoglobulin IgG Fc Domain (SEQ ID NO:37), wherein the Domain 3 is linked, C-terminally, to the Domain 2 via a peptide linker (SEQ ID NO:32).

The invention additionally provides the embodiment of any of the above-described bi-specific monovalent diabodies wherein the Domain 2 of the first polypeptide chain is a K-coil Domain (SEQ ID NO:35) and the Domain 2 of the second polypeptide chain is an E-coil Domain (SEQ ID NO:34).

The invention additionally provides the embodiment of any of the above-described bi-specific monovalent diabodies wherein the Domain 2 of the first polypeptide chain is an E-coil Domain (SEQ ID NO:34) and the Domain 2 of the second polypeptide chain is a K-coil Domain (SEQ ID NO:35).

The invention additionally provides the embodiment of a bi-specific monovalent diabody capable of specific binding to an epitope of CD123 and to an epitope of CD3, wherein the diabody comprises a first polypeptide chain and a second polypeptide chain, covalently bonded to one another, wherein: said bi-specific diabody comprises:
  A. a first polypeptide chain having the amino acid sequence of SEQ ID NO:1; and
  B. a second polypeptide chain having the amino acid sequence of SEQ ID NO:3;
wherein said first and said second polypeptide chains are covalently bonded to one another by a disulfide bond.

The diabodies of the invention exhibit unexpectedly enhanced functional activities as further described below.

The diabodies of the invention are preferably capable of cross-reacting with both human and primate CD123 and CD3 proteins, preferably cynomolgus monkey CD123 and CD3 proteins.

The diabodies of the invention are preferably capable of depleting, in an in vitro cell-based assay, plasmacytoid dendritic cells (pDC) from a culture of primary PBMCs with an IC50 of about 1 ng/ml or less, about 0.8 ng/ml or less, about 0.6 ng/ml or less, about 0.4 ng/ml or less, about 0.2 ng/ml or less, about 0.1 ng/ml or less, about 0.05 ng/ml or less, about 0.04 ng/ml or less, about 0.03 ng/ml or less, about 0.02 ng/ml or less or about 0.01 ng/ml or less. Preferably, the IC50 is about 0.01 ng/ml or less. In the above-described assay, the culture of primary PBMCs may be from cynomolgus monkey in which case said depletion is of cynomolgus monkey plasmacytoid dendritic cells (pDC). Optionally the diabodies of the invention may be capable of depleting plasmacytoid dendritic cells (pDC) from a primary culture of PBMCs as described above wherein the assay is conducted by or in accordance with the protocol of Example 14, as herein described, or by modification of such assay as would be understood by those of ordinary skill, or by other means known to those of ordinary skill.

The diabodies of the invention preferably exhibit cytotoxicity in an in vitro Kasumi-3 assay with an EC50 of about 0.05 ng/mL or less. Preferably, the EC50 is about 0.04 ng/mL or less, about 0.03 ng/mL or less, about 0.02 ng/mL or less, or about 0.01 ng/mL or less. Optionally the diabodies of the invention may exhibit cytotoxicity as described above wherein the assay is conducted by or in accordance with the protocol of Example 3 as herein described, or by modification of such assay as would be understood by those of ordinary skill, or by other means known to those of ordinary skill.

The diabodies of the invention preferably exhibit cytotoxicity in an in vitro Molm-13 assay with an EC50 of about 5 ng/mL or less. Preferably, the EC50 is about 3 ng/mL or less, about 2 ng/mL or less, about 1 ng/mL or less, about 0.75 ng/mL or less, or about 0.2 ng/mL or less. Optionally the diabodies of the invention may exhibit cytotoxicity as described above wherein the assay is conducted by or in accordance with the protocol of Example 3 as herein described, or by modification of such assay as would be understood by those of ordinary skill, or by other means known to those of ordinary skill.

The diabodies of the invention are preferably capable of inhibiting the growth of a MOLM-13 tumor xenograft in a mouse. Preferably the diabodies of the invention may be capable of inhibiting the growth of a MOLM-13 tumor xenograft in a mouse at a concentration of at least about 20 µg/kg, at least about 4 µg/kg, at least about 0.8 µg/kg, at least about 0.6 µg/kg or at least about 0.4 µg/kg. Preferred antibodies of the invention will inhibit growth of a MOLM-13 tumor xenograft in a mouse by at least 25%, but possibly by at least about 40% or more, by at least about 50% or more, by at least about 60% or more, by at least about 70% or more, by at least about 80% or more, by at least about 90% or more, or even by completely inhibiting MOLM-13 tumor growth after some period of time or by causing tumor regression or disappearance. This inhibition will take place for at least an NSG mouse strain. Optionally, the diabodies of the invention may be capable of inhibiting the growth of a MOLM-13 tumor xenograft in a mouse in the above-described manner by or in accordance with the protocol of Example 6 as herein described, or by modification of such assay as would be understood by those of ordinary skill, or by other means known to those of ordinary skill.

The diabodies of the invention are preferably capable of inhibiting the growth of an RS4-11 tumor xenograft in a mouse. Preferably the diabodies of the invention may be capable of inhibiting the growth of a RS4-11 tumor xenograft in a mouse at a concentration of at least about 0.5 mg/kg, at least about 0.2 mg/kg, at least about 0.1 mg/kg, at least about 0.02 mg/kg or at least about 0.004 mg/kg. Preferred antibodies of the invention will inhibit growth of a RS4-11 tumor xenograft in a mouse by at least about 25%, but possibly at least about 40%, at least about 50%, at least about 60%, at least about 70%, at least about 80%, at least about 90%, or even by completely inhibiting RS4-11 tumor growth after some period of time or by causing tumor regression or disappearance. This inhibition will take place for at least an NSG mouse strain. Optionally, the diabodies of the invention may be capable of inhibiting the growth of a RS4-11 tumor xenograft in a mouse in the above-described manner by or in accordance with the protocol of Example 6 as herein described, or by modification of such assay as would be understood by those of ordinary skill, or by other means known to those of ordinary skill.

The diabodies of the invention are preferably capable of depleting leukemic blast cells in vitro in a primary culture of AML bone marrow cells. Preferably the diabodies of the invention may be capable of depleting leukemic blast cells in vitro in a primary culture of AML bone marrow cells at concentrations of at least about 0.01 ng/ml, at least about 0.02 ng/ml, at least about 0.04 ng/ml, at least about 0.06 ng/ml, at least about 0.08 ng/ml or at least about 0.1 ng/ml. Preferably, the diabodies of the invention may be capable of depleting leukemic blast cells in vitro in a primary culture of AML bone marrow cells to less than 20% of the total population of primary leukemic blast cells at diabody concentrations of at least about 0.01 ng/ml, at least about 0.02 ng/ml, at least about 0.04 ng/ml, at least about 0.06 ng/ml, at least about 0.08 ng/ml or at least about 0.1 ng/ml, optionally following incubation of the primary culture with diabody for about 120 hours. Preferably leukemic blast cells are depleted in vitro in a primary culture of AML bone marrow cells to less than 20% of the total population of primary leukemic blast cells at diabody concentrations of about 0.01 ng/ml or 0.1 ng/ml following incubation of the primary culture with diabody for about 120 hours.

The diabodies of the invention are preferably capable of inducing an expansion of a T cell population in vitro in a primary culture of AML bone marrow cells. Preferably, such expansion may be to about 70% or more of the maximum T cell population which can be expanded in the assay. Preferably the diabodies of the invention may be capable of inducing an expansion of a T cell population in vitro in a primary culture of AML bone marrow cells to about 70% or more of the maximum T cell population which can be expanded in the assay at diabody concentrations of at least about 0.01 ng/ml, at least about 0.02 ng/ml, at least about 0.04 ng/ml, at least about 0.06 ng/ml, at least about 0.08 ng/ml or at least about 0.1 ng/ml, optionally following incubation of the primary culture with diabody for about 120 hours. Preferably, a T cell population is expanded in vitro in a primary culture of AML bone marrow cells to about 70% or more of the maximum T cell population which can be expanded in the assay at diabody concentrations of about 0.01 ng/ml or about 0.1 ng/ml following incubation of the primary culture with diabody for about 120 hours.

The diabodies of the invention are preferably capable of inducing an activation of a T cell population in vitro in a primary culture of AML bone marrow cells. Such activation may occur at diabody concentrations of at least about 0.01 ng/ml, at least about 0.02 ng/ml, at least about 0.04 ng/ml, at least about 0.06 ng/ml, at least about 0.08 ng/ml or at least about 0.1 ng/ml, optionally following incubation of the primary culture with diabody for about 72 hours. Such activation may be measured by the expression of a T cell activation marker such as CD25. Preferably, activation of a T cell population in vitro in a primary culture of AML bone marrow cells as measured by expression of CD25 may occur at diabody concentrations of about 0.01 ng/ml or about 0.1 ng/ml following incubation of the primary culture with diabody for about 72 hours.

The diabodies of the invention are preferably capable of depleting leukemic blast cells in vitro in a primary culture of AML bone marrow cells to less than 20% of the total population of primary leukemic blast cells and at the same time inducing an expansion of the T cell population in vitro in the primary culture of AML bone marrow cells to about 70% or more of the maximum T cell population which can be expanded in the assay at diabody concentrations of at least about 0.01 ng/ml, at least about 0.02 ng/ml, at least about 0.04 ng/ml, at least about 0.06 ng/ml, at least about 0.08 ng/ml or at least about 0.1 ng/ml, optionally following incubation of the primary culture with diabody for about 120 hours. Preferably, the diabody concentrations are about 0.01 ng/ml or about 0.1 ng/ml and the primary culture is incubated with diabody for about 120 hours.

The diabodies of the invention may be capable of depleting leukemic blast cells in vitro in a primary culture of AML bone marrow cells and/or inducing an expansion of a T cell population in vitro in a primary culture of AML bone marrow cells and/or inducing an activation of a T cell population in vitro in a primary culture of AML bone marrow cells in the above-described manner by or in accordance with the protocol of Example 8 as herein described, or by modification of such assay as would be understood by those of ordinary skill, or by other means known to those of ordinary skill.

For the avoidance of any doubt, the diabodies of the invention may exhibit one, two, three, more than three or all of the functional attributes described herein. Thus the diabodies of the invention may exhibit any combination of the functional attributes described herein.

The diabodies of the invention may be for use as a pharmaceutical. Preferably, the diabodies are for use in the treatment of a disease or condition associated with or characterized by the expression of CD123. The invention also relates to the use of diabodies of the invention in the manufacture of a pharmaceutical composition, preferably for the treatment of a disease or condition associated with or characterized by the expression of CD123 as further defined herein.

The disease or condition associated with or characterized by the expression of CD123 may be cancer. For example, the cancer may be selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

The disease or condition associated with or characterized by the expression of CD123 may be an inflammatory condition. For example, the inflammatory condition may be selected from the group consisting of: Autoimmune Lupus (SLE), allergy, asthma and rheumatoid arthritis.

The invention additionally provides a pharmaceutical composition comprising any of the above-described diabodies and a physiologically acceptable carrier.

The invention additionally provides a use of the above-described pharmaceutical composition in the treatment of a disease or condition associated with or characterized by the expression of CD123.

The invention is particularly directed to the embodiment of such use, wherein the disease or condition associated with or characterized by the expression of CD123 is cancer (especially a cancer selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma).

The invention is also particularly directed to the embodiment of such use, wherein the disease or condition associated with or characterized by the expression of CD123 is an inflammatory condition (especially an inflammatory condition selected from the group consisting of: Autoimmune Lupus (SLE), allergy, asthma, and rheumatoid arthritis).

Terms such as "about" should be taken to mean within 10%, more preferably within 5%, of the specified value, unless the context requires otherwise.

BRIEF DESCRIPTION OF THE DRAWINGS

FIG. 5 (Panels A-D) shows the ability of the sequence-optimized CD123×CD3 bi-specific diabody (DART-A), sequence-optimized CD123×CD3 bi-specific diabody having an Albumin-Binding Domain (DART-A with ABD "w/ABD") and sequence-optimized CD123×CD3 bi-specific diabody having an immunoglobulin IgG Fc Domain (DART-A with Fc "w/Fc") to mediate T cell activation during redirected killing of target cells. The Figure presents dose-response curves showing the cytotoxicity mediated by DART-A, DART-A w/ABD and DART-A w/Fc in Kasumi-3 (Panel A) and THP-1 (Panel B) cells and purified CD8 T cells at an E:T (effector cell:target cell) ratio of 10:1 (18 hour incubation). Panels C and D show dose-response curves of T cell activation using the marker CD25 on CD8 T cells in the presence (Panel D) and absence (Panel C) of target cells.

FIG. 7 (Panels A-B) shows the in vivo antitumor activity of the sequence-optimized CD123×CD3 bi-specific diabody (DART-A) at nanogram per kilogram dosing levels. MOLM-13 cells (intermediate CD123 expression) were co-mixed with T cells and implanted subcutaneously (T:E 1:1) in NSG mice. Intravenous treatment was once daily for 8 days (QD×8) starting at implantation. Various concentrations of DART-A were compared to a control bi-specific diabody (Control DART). Panel A shows the Molm-13 cells alone or with T cells, and the effect of various doses of DART-A on tumor volume even to times beyond 30 days. Panel B shows the effect of increasing doses of DART-A on tumor volume seen in NSG mice receiving MOLM-13 cells and T cells (T:E 1:1) for a time course of 0-18 days.

FIG. 10 (Panels A-C) shows the ability of the sequence-optimized CD123×CD3 bi-specific diabody (DART-A) to mediate blast reduction in primary AML at 120h (Panel A), drive T cell expansion in primary AML at 120h (Panel B) and induce T cell activation in AML at 48h and 72 h (Panel C).

FIG. 13 (Panels A-H) shows the ability of the sequence-optimized CD123×CD3 bi-specific diabody (DART-A) to mediate ALL blast depletion with autologous CTL. Panels A and E show the forward and side scatter of the input population of normal PBMC (Panel A) and ALL PBMCs (Panel E). The PBMCs were untreated (Panels B and F), treated with a control bi-specific diabody (Control DART) (Panels C and G) or treated with DART-A (Panels D and H) and incubated for 7 days followed by staining for CD34 and CD19.

FIG. 19 (Panels A-B) shows the ability of the sequence-optimized CD123×CD3 bi-specific diabody (DART-A) to mediate autologous monocyte depletion in vitro with human and cynomolgus monkey PBMCs. The Panels present the results of dose-response curves of DART-A-mediated cytotoxicity with primary human PBMCs (Panel A) or cynomolgus monkey PBMCs (Panel B).

FIG. 21 (Panels A-D) shows the ability of the sequence-optimized CD123×CD3 bi-specific diabody (DART-A) to mediate dose-dependent depletion of pDC in cynomolgus monkeys. Cynomolgus monkeys were dosed with DART-A at 0.1, 1, 10, 30 100, 300, or 1000 ng/kg. PBMCs were evaluated at the indicated time and total B cells (Panel A), monocytes (Panel B), NK cells (Panel C) and pDC (Panel D) were counted.

FIG. 22 (Panels A-D) shows the ability of the sequence-optimized CD123×CD3 bi-specific diabody (DART-A) to intermittently modulate T cells in cynomolgus monkeys. Cynomolgus monkeys were dosed with DART-A at at 0.1, 1, 10, 30 100, 300, or 1000 ng/kg. PBMCs were evaluated at the indicated time and total T cells (Panel A), CD4 T cells (Panel B), CD69 cells (Panel C) and CD8 T cells (Panel D) were counted.

FIG. 24A: SEC profile of DART-A protein on a calibrated TSK G3000SW×L column. FIG. 24B: Mass spectrum of DART-A protein.

FIG. 26A-26B provides the results of a bifunctional ELISA and demonstrates simultaneous engagement of both target antigens of DART-A. ELISA plates were coated with human CD123 (FIG. 26A) or cynomolgus monkey CD123 (FIG. 26B). Titrating DART-A and Control DART concentrations were followed by detection with human CD3-biotin. FIGS. 26C-26E demonstrate cell-surface binding of DART-A on CD123+ Molm-13 target cell (FIG. 26C), human T cells (FIG. 26D) and cynomolgus T cells (FIG. 26E). Binding was detected by FACS analysis using a monoclonal antibody specific to E-coil and K-coil region of the DART-A or Control DART molecule.

FIG. 27A shows the relative anti-CD123-PE binding sites on U937 and Kasumi-3 leukemic cell lines as determined by QFACS analysis. FIG. 27B shows the relatively low percent cytotoxicity mediated by DART-A or Control DART on an AML cell line (U937 cells) which, as shown in FIG. 27A have relatively few CD123 binding sites). FIG. 27C shows the percent cytotoxicity mediated by DART-A or Control DART in the presence of purified human T cells (as effector cells) on an AML cell line (Kasumi-3 cells) which, as shown in FIG. 27A have a substantial number of CD123 binding sites. In FIGS. 27B-27C, the E:T ratio is 10:1. FIG. 27D shows the percent cytotoxicity mediated by DART-A or Control DART in the presence of purified cynomolgus monkey PBMCs (as effector cells) on Kasumi-3 cells (the E:T ratio is 15:1), and demonstrates that DART-A can bind cynomolgus monkey T cells. FIG. 27E shows the relative anti-CD123-PE binding sites on Kasumi-3 cells, human monocytes, human plasmacytoid dendritic cells ("pDC"), cynomolgus monkey monocytes and cynomolgus monkey plasmacytoid dendritic cells as determined by QFACS analysis. FIG. 27F shows the ability of DART-A to deplete $CD14^- CD123^{lo}$ cells. FIG. 27G shows the ability of DART-A to deplete human $CD14^- CD123^{Hi}$ cells. FIG. 27H shows the ability of DART-A to deplete cynomolgus monkey $CD14^- CD123^{Hi}$ cells. Cytotoxicity was determined by LDH release, with EC50 values determined using GraphPad PRISM® software.

DETAILED DESCRIPTION OF THE INVENTION

The present invention is directed to sequence-optimized CD123×CD3 bi-specific monovalent diabodies that are capable of simultaneous binding to CD123 and CD3, and to the uses of such molecules in the treatment of hematologic malignancies. Although non-optimized CD123×CD3 bi-specific diabodies are fully functional, analogous to the improvements obtained in gene expression through codon optimization (see, e.g., Grosjean, H. et al. (1982) "*Preferential Codon Usage In Prokaryotic Genes: The Optimal Codon Anticodon Interaction Energy And The Selective Codon Usage In Efficiently Expressed Genes*" Gene 18(3): 199-209), it is possible to further enhance the stability and/or function of CD123×CD3 bi-specific diabodies by modifying or refining their sequences.

Figure 1:
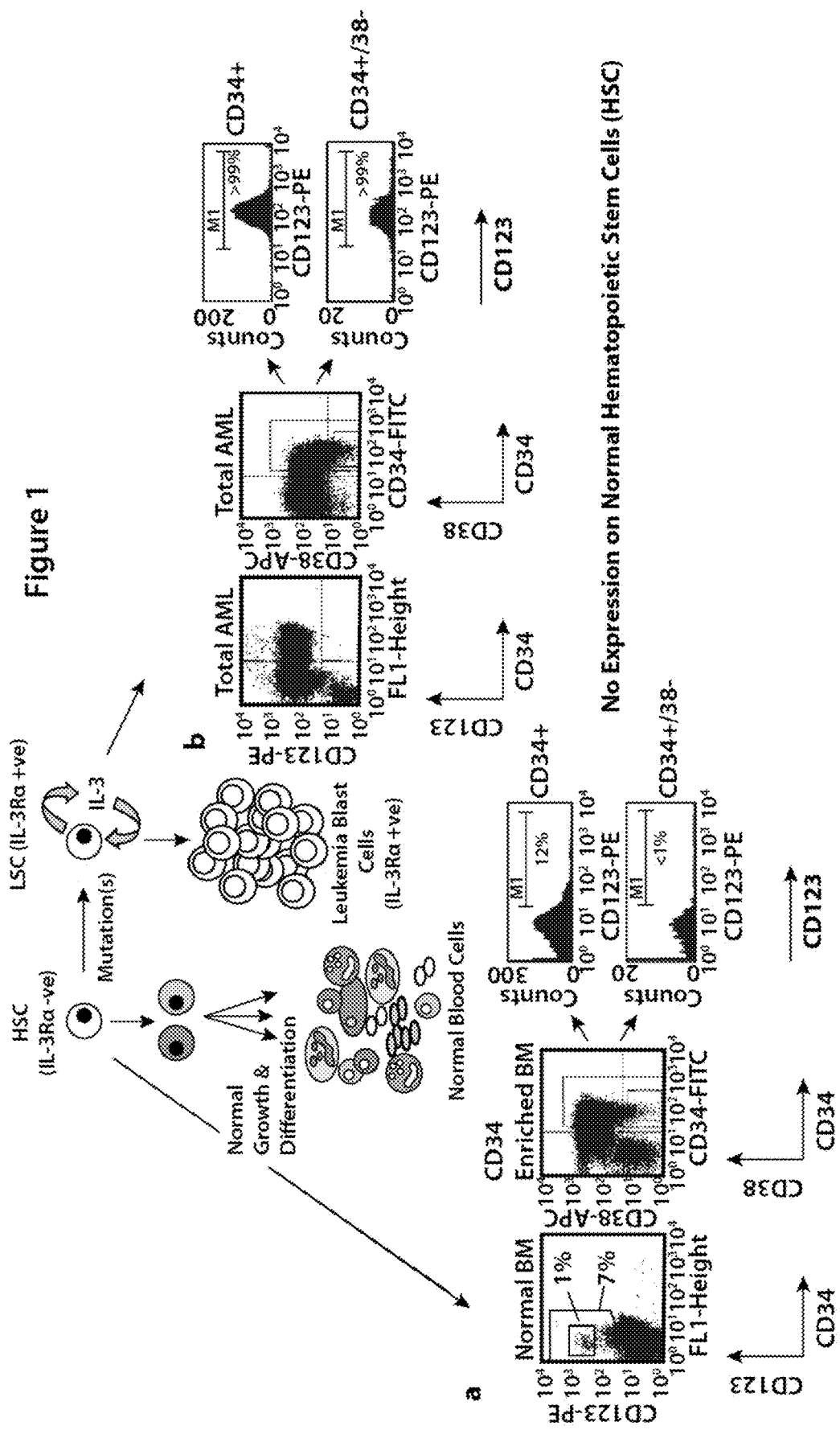
FIG. 1 shows that CD123 was known to be expressed on leukemic stem cells.
Figure 2:
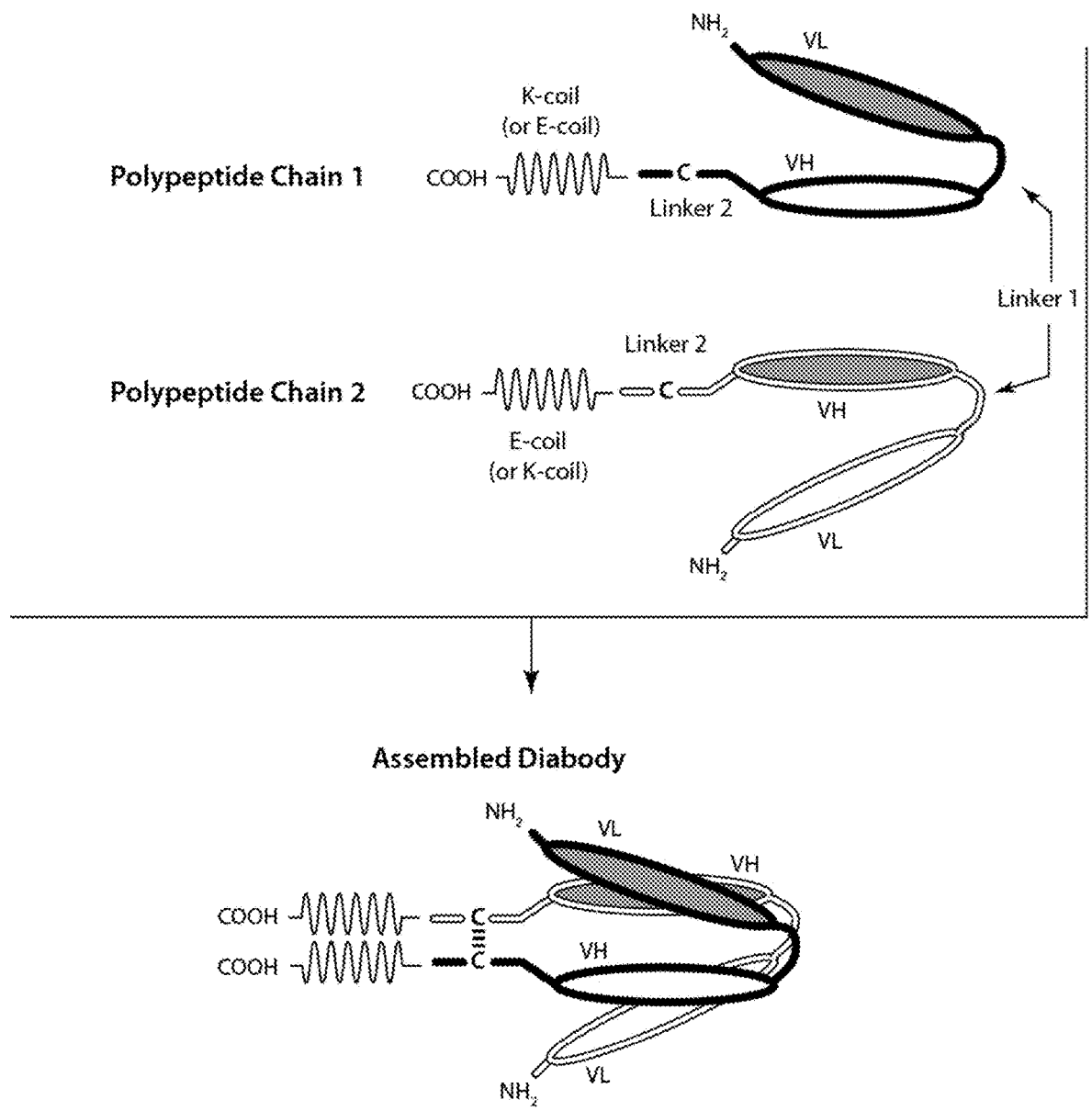
FIG. 2 illustrates the structures of the first and second polypeptide chains of a two chain CD123×CD3 bi-specific monovalent diabody of the present invention.

The preferred CD123×CD3 bi-specific diabodies of the present invention are composed of at least two polypeptide chains that associate with one another to form one binding site specific for an epitope of CD123 and one binding site specific for an epitope of CD3 (FIG. 2). The individual polypeptide chains of the diabody are covalently bonded to one another, for example by disulfide bonding of cysteine residues located within each polypeptide chain. Each polypeptide chain contains an Antigen Binding Domain of a Light Chain Variable Domain, an Antigen Binding Domain of a Heavy Chain Variable Domain and a heterodimerization domain. An intervening linker peptide (Linker 1) separates the Antigen Binding Domain of the Light Chain Variable Domain from the Antigen Binding Domain of the Heavy Chain Variable Domain. The Antigen Binding Domain of the Light Chain Variable Domain of the first polypeptide chain interacts with the Antigen Binding Domain of the Heavy Chain Variable Domain of the second polypeptide chain in order to form a first functional antigen binding site that is specific for the first antigen (i.e., either CD123 or CD3). Likewise, the Antigen Binding Domain of the Light Chain Variable Domain of the second polypeptide chain interacts with the Antigen Binding Domain of the Heavy Chain Variable Domain of the first polypeptide chain in order to form a second functional antigen binding site that is specific for the second antigen (i.e., either CD123 or CD3, depending upon the identity of the first antigen). Thus, the selection of the Antigen Binding Domain of the Light Chain Variable Domain and the Antigen Binding Domain of the Heavy Chain Variable Domain of the first and second polypeptide chains are coordinated, such that the two polypeptide chains collectively comprise Antigen Binding Domains of light and Heavy Chain Variable Domains capable of binding to CD123 and CD3.

The formation of heterodimers of the first and second polypeptide chains can be driven by the heterodimerization domains. Such domains include GVEPKSC (SEQ ID NO:50) (or VEPKSC; SEQ ID NO:51) on one polypeptide chain and GFNRGEC (SEQ ID NO:52) (or FNRGEC; SEQ ID NO:53) on the other polypeptide chain (US2007/0004909). Alternatively, such domains can be engineered to contain coils of opposing charges. The heterodimerization domain of one of the polypeptide chains comprises a sequence of at least six, at least seven or at least eight positively charged amino acids, and the heterodimerization domain of the other of the polypeptide chains comprises a sequence of at least six, at least seven or at least eight negatively charged amino acids. For example, the first or the second heterodimerization domain will preferably comprise a sequence of eight positively charged amino acids and the other of the heterodimerization domains will preferably comprise a sequence of eight negatively charged amino acids. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid.

The CD123×CD3 bi-specific diabodies of the present invention are engineered so that such first and second polypeptide chains covalently bond to one another via cysteine residues along their length. Such cysteine residues may be introduced into the intervening linker that separates the VL and VH domains of the polypeptides. Alternatively, and more preferably, a second peptide (Linker 2) is introduced into each polypeptide chain, for example, at the amino-terminus of the polypeptide chains or a position that places Linker 2 between the heterodimerization domain and the Antigen Binding Domain of the Light Chain Variable Domain or Heavy Chain Variable Domain.

In particular embodiments, the sequence-optimized CD123×CD3 bi-specific monovalent diabodies of the present invention further have an immunoglobulin Fc Domain or an Albumin-Binding Domain to extend half-life in vivo.

Figure 3A:
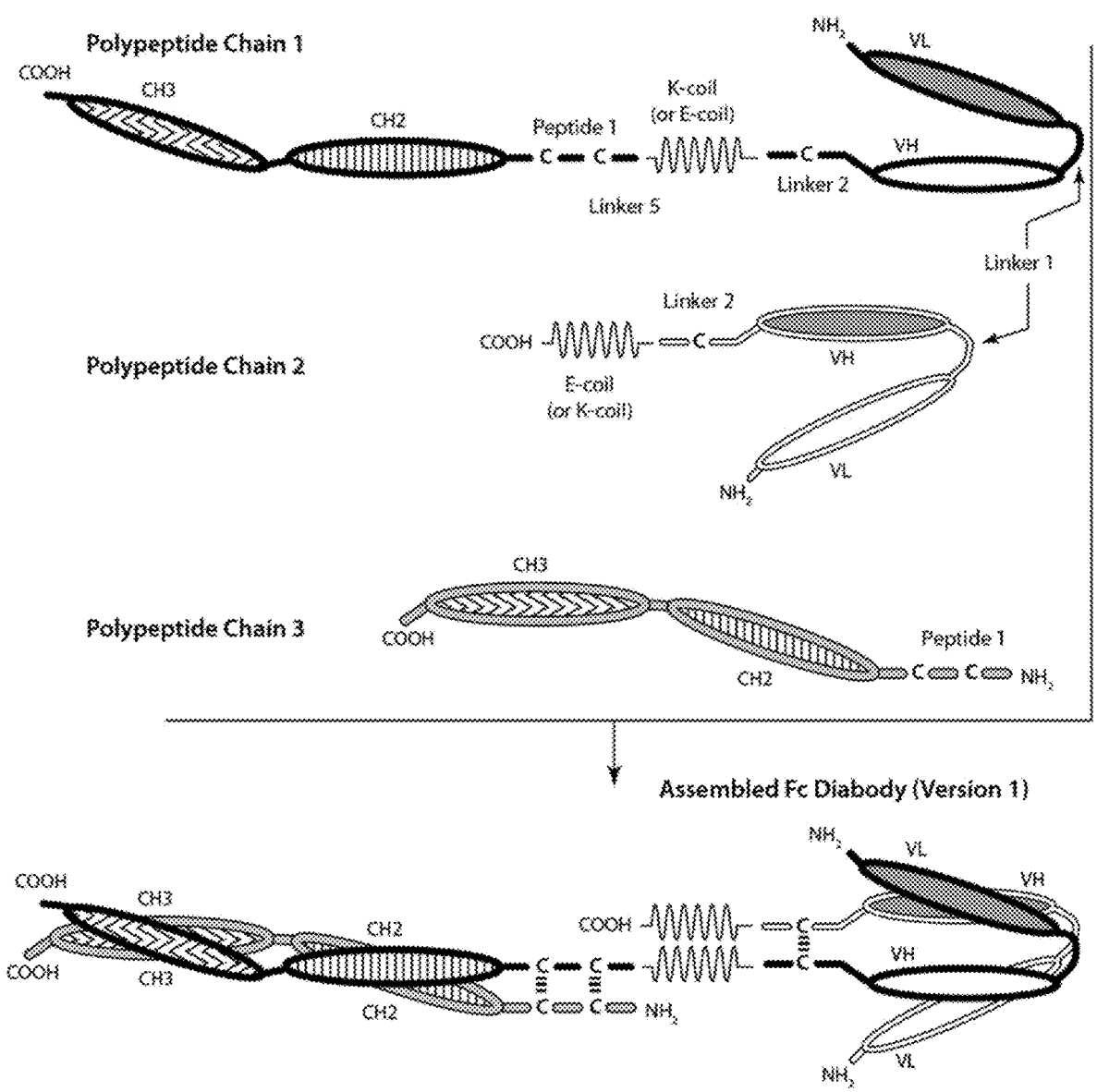
FIGS. 3A and 3B illustrate the structures of two versions of the first, second and third polypeptide chains of a three chain CD123×CD3 bi-specific monovalent Fc diabody of the present invention (Version 1, FIG. 3A; Version 2, FIG. 3B).
Figure 3B:
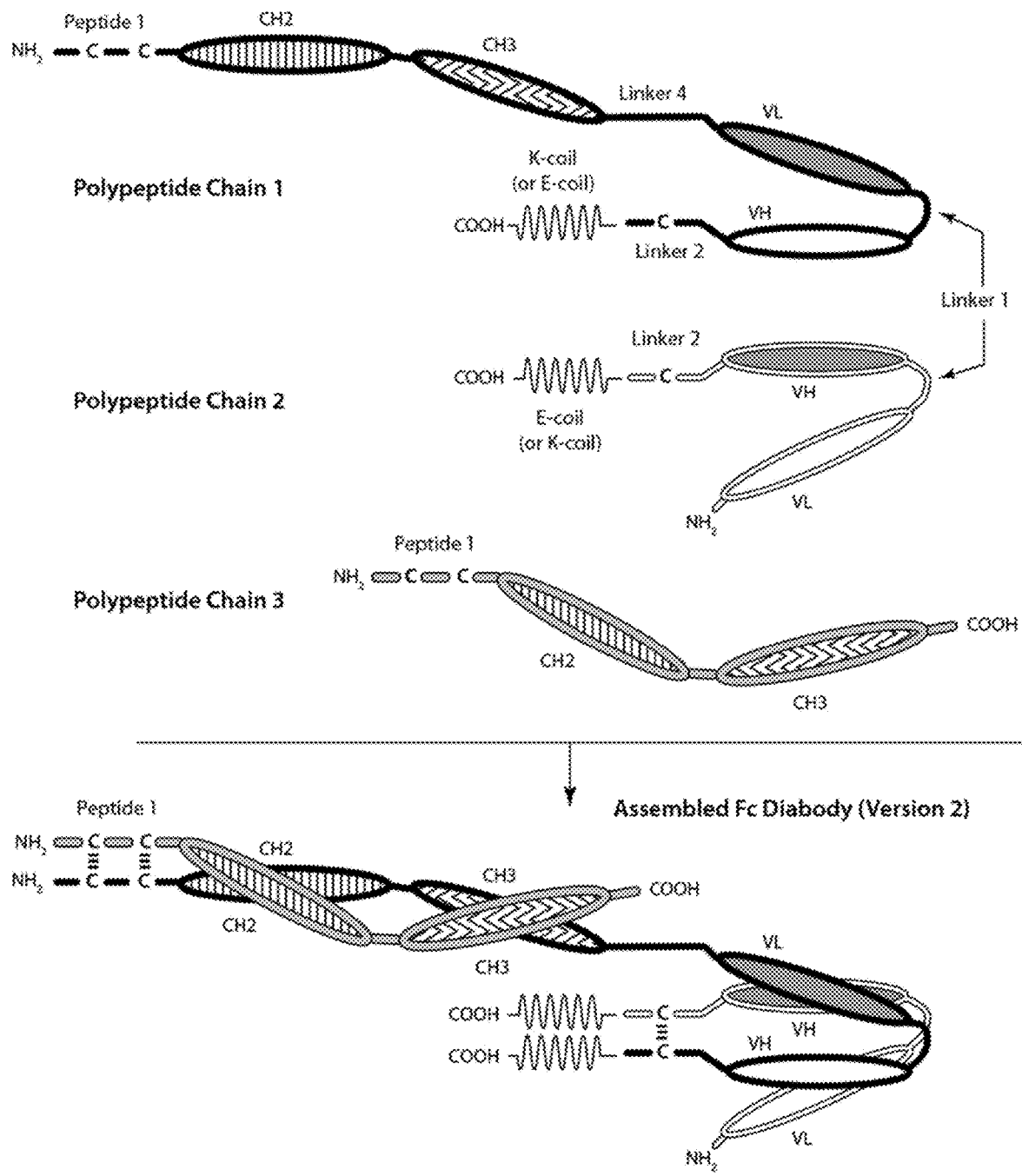

The CD123×CD3 bi-specific monovalent diabodies of the present invention that comprise an immunoglobulin Fc Domain (i.e., CD123×CD3 bi-specific monovalent Fc diabodies) are composed of a first polypeptide chain, a second polypeptide chain and a third polypeptide chain. The first and second polypeptide chains associate with one another to form one binding site specific for an epitope of CD123 and one binding site specific for an epitope of CD3. The first polypeptide chain and the third polypeptide chain associate with one another to form an immunoglobulin Fc Domain (FIG. 3A and FIG. 3B). The first and second polypeptide chains of the bi-specific monovalent Fc diabody are covalently bonded to one another, for example by disulfide bonding of cysteine residues located within each polypeptide chain.

The first and third polypeptide chains are covalently bonded to one another, for example by disulfide bonding of cysteine residues located within each polypeptide chain. The first and second polypeptide chains each contain an Antigen Binding Domain of a Light Chain Variable Domain, an Antigen Binding Domain of a Heavy Chain Variable Domain and a heterodimerization domain. An intervening linker peptide (Linker 1) separates the Antigen Binding Domain of the Light Chain Variable Domain from the Antigen Binding Domain of the Heavy Chain Variable Domain. The Antigen Binding Domain of the Light Chain Variable Domain of the first polypeptide chain interacts with the Antigen Binding Domain of the Heavy Chain Variable Domain of the second polypeptide chain in order to form a first functional antigen binding site that is specific for the first antigen (i.e., either CD123 or CD3). Likewise, the Antigen Binding Domain of the Light Chain Variable Domain of the second polypeptide chain interacts with the Antigen Binding Domain of the Heavy Chain Variable Domain of the first polypeptide chain in order to form a second functional antigen binding site that is specific for the second antigen (i.e., either CD3 or CD123, depending upon the identity of the first antigen). Thus, the selection of the Antigen Binding Domain of the Light Chain Variable Domain and the Antigen Binding Domain of the Heavy Chain Variable Domain of the first and second polypeptide chains are coordinated, such that the two polypeptide chains collectively comprise Antigen Binding Domains of light and Heavy Chain Variable Domains capable of binding to CD123 and CD3. The first and third polypeptide chains each contain some or all of the CH2 Domain and/or some or all of the CH3 Domain of a complete immunoglobulin Fc Domain and a cysteine-containing peptide. The some or all of the CH2 Domain and/or the some or all of the CH3 Domain associate to form the immunoglobulin Fc Domain of the bi-specific monovalent Fc diabodies of the present invention. The first and third polypeptide chains of the bi-specific monovalent Fc diabodies of the present invention are covalently bonded to one another, for example by disulfide bonding of cysteine residues located within the cysteine-containing peptide of the polypeptide chains.

I. The Sequence-Optimized CD123×CD3 Bi-Specific Diabody, "DART-A"

The invention provides a sequence-optimized bi-specific diabody capable of simultaneously and specifically binding to an epitope of CD123 and to an epitope of CD3 (a "CD123×CD3" bi-specific diabody or DART-A). As discussed below, DART-A was found to exhibit enhanced functional activity relative to other non-sequence-optimized CD123×CD3 bi-specific diabodies of similar composition, and is thus termed a "sequence-optimized" CD123×CD3 bi-specific diabody.

The sequence-optimized CD123×CD3 bi-specific diabody (DART-A) comprises a first polypeptide chain and a second polypeptide chain. The first polypeptide chain of the bi-specific diabody will comprise, in the N-terminal to C-terminal direction, an N-terminus, a Light Chain Variable Domain (VL Domain) of a monoclonal antibody capable of binding to CD3 ($VL_{CD3}$), an intervening linker peptide (Linker 1), a Heavy Chain Variable Domain (VH Domain) of a monoclonal antibody capable of binding to CD123 ($VH_{CD123}$), and a C-terminus. A preferred sequence for such a $VL_{CD3}$ Domain is SEQ ID NO:21:

```
QAVVTQEPSLTVSPGGIVTLICRSSTGAVITSNYANWVQQKPGQAPRGLI
GGTNKRAPWTPARFSGSLLGGKAALTITGAQAEDEADYYCALWYSNLWVF
GGGTKLTVLG
```

The Antigen Binding Domain of $VL_{CD3}$ comprises CDR1 SEQ ID NO:38: RSSTGAVTTSNYAN, CDR2 SEQ ID NO:39: GTNKRAP, and CDR3 SEQ ID NO:40: ALWYSNLWV.

A preferred sequence for such Linker 1 is SEQ ID NO:29: GGGSGGGG. A preferred sequence for such a $VH_{CD123}$ Domain is SEQ ID NO:26:

EVQLVQSGAELKKPGASVKVSCKASGYTFTDYYMKWVRQAPGQGLEWIGD
IIPSNGATFYNQKFKGRVTITVDKSTSTAYMELSSLRSEDTAVYYCARSH
LLRASWFAYWGQGTLVTVSS

The Antigen Binding Domain of $VH_{CD123}$ comprises CDR1 SEQ ID NO:47: DYYMK, CDR2 SEQ ID NO:48: DIIPSNGATFYNQKFKG, and CDR3 SEQ ID NO:49: SHLLRAS.

The second polypeptide chain will comprise, in the N-terminal to C-terminal direction, an N-terminus, a VL domain of a monoclonal antibody capable of binding to CD123 ($VL_{CD123}$), an intervening linker peptide (e.g., Linker 1), a VH domain of a monoclonal antibody capable of binding to CD3 ($VH_{CD3}$), and a C-terminus. A preferred sequence for such a $VL_{CD123}$ Domain is SEQ ID NO:25:

DFVMTQSPDSLAVSLGERVIMSCKSSQSLLNSGNQKNYLTWYQQKPGQPP

KLLIYWASTRESGVPDRFSGSGSGTDFILTISSLQAEDVAVYYCQNDYSY

PYTFGQGTKLEIK

The Antigen Binding Domain of $VL_{CD123}$ comprises CDR1 SEQ ID NO:44: KSSQSLLNSGNQKNYLT, CDR2 SEQ ID NO:45: WASTRES, and CDR3 SEQ ID NO:46: QNDYSYPYT.

A preferred sequence for such a $VH_{CD3}$ Domain is SEQ ID NO:22:

EVQLVESGGGLVQPGGSLRLSCAASGFTFSTYAMNWVRQAPGKGLEWVGR

IRSKYNNYATYYADSVKDRFTISRDDSKNSLYLQMNSLKTEDTAVYYCVR

HGNFGNSYVSWFAYWGQGTLVTVSS

The Antigen Binding Domain of $VH_{CD3}$ comprises CDR1 SEQ ID NO:41: TYAMN, CDR2 SEQ ID NO:42: RIRSKYNNYATYYADSVKD, and CDR3 SEQ ID NO:43: HGNFGNSYVSWFAY.

The sequence-optimized CD123×CD3 bi-specific diabodies of the present invention are engineered so that such first and second polypeptides covalently bond to one another via cysteine residues along their length. Such cysteine residues may be introduced into the intervening linker (e.g., Linker 1) that separates the VL and VH domains of the polypeptides. Alternatively, and more preferably, a second peptide (Linker 2) is introduced into each polypeptide chain, for example, at a position N-terminal to the VL domain or C-terminal to the VH domain of such polypeptide chain. A preferred sequence for such Linker 2 is SEQ ID NO:30: GGCGGG.

The formation of heterodimers can be driven by further engineering such polypeptide chains to contain polypeptide coils of opposing charge. Thus, in a preferred embodiment, one of the polypeptide chains will be engineered to contain an "E-coil" domain (SEQ ID NO:34: EVAAL<u>E</u>K<u>E</u>VAAL<u>E</u>K<u>E</u>VAAL<u>E</u>K<u>E</u>VAAL<u>E</u>K) whose residues will form a negative charge at pH 7, while the other of the two polypeptide chains will be engineered to contain an "K-coil" domain (SEQ ID NO:35: <u>K</u>VAAL<u>K</u>E<u>K</u>VAAL<u>K</u>E<u>K</u>VAAL<u>K</u>E<u>K</u>VAAL<u>K</u>E) whose residues will form a positive charge at pH 7. The presence of such charged domains promotes association between the first and second polypeptides, and thus fosters heterodimerization.

It is immaterial which coil is provided to the first or second polypeptide chains. However, a preferred sequence-optimized CD123×CD3 bi-specific diabody of the present invention ("DART-A") has a first polypeptide chain having the sequence (SEQ ID NO:1):

QAVVTQEPSLTVSPGGIVTLICRSSTGAVITSNYANWVQQKPGQAPRGLI

GGTNKRAPWTPARFSGSLLGGKAALTITGAQAEDEADYYCALWYSNLWVF

GGGTKLTVLGGGGSGGGGEVQLVQSGAELKKPGASVKVSCKASGYTFTDY

YMKWVRQAPGQGLEWIGDIIPSNGATFYNQKFKGRVTITVDKSTSTAYME

LSSLRSEDTAVYYCARSHLLRASWFAYWGQGTLVTVSSGGCGGGEVAALE

KEVAALEKEVAALEKEVAALEK

DART-A Chain 1 is composed of: SEQ ID NO:21-SEQ ID NO:29-SEQ ID NO:26-SEQ ID NO:30-SEQ ID NO:34. A DART-A Chain 1 encoding polynucleotide is SEQ ID NO:2:

caggctgtggtgactcaggagccttcactgaccgtgtccccaggcggaac tgtgaccctgacatgcagatccagcacaggcgcagtgaccacatctaact acgccaattgggtgcagcagaagccaggacaggcaccaaggggcctgatc gggggtacaaacaaaagggctccctggacccctgcacggttttctggaag tctgctgggcggaaaggccgctctgactattaccggggcacaggccgagg acgaagccgattactattgtgctctgtggtatagcaatctgtgggtgttc gggggtggcacaaaactgactgtgctgggaggggtggatccggcggcgg aggcgaggtgcagctggtgcagtccggggctgagctgaagaaacccggag cttccgtgaaggtgtcttgcaaagccagtggctacaccttcacagactac tatatgaagtgggtcaggcaggctccaggacagggactggaatggatcgg cgatatcattccttccaacggggccactttctacaatcagaagtttaaag gcagggtgactattaccgtggacaaatcaacaagcactgcttatatggag ctgagctccctgcgctctgaagatacagccgtgtactattgtgctcggtc acacctgctgagagccagctggtttgcttattggggacagggcaccctgg tgacagtgtcttccggaggatgtggcggtggagaagtggccgcactggag aaagaggttgctgctttggagaaggaggtcgctgcacttgaaaaggaggt cgcagccctggagaaa The second polypeptide chain of DART-A has the sequence (SEQ ID NO:3):

DFVMTQSPDSLAVSLGERVTMSCKSSQSLLNSGNQKNYLTWYQQKPGQPP

KLLIYWASTRESGVPDRFSGSGSGTDFTLTISSLQAEDVAVYYCQNDYSY

PYTFGQGTKLEIKGGGSGGGGEVQLVESGGGLVQPGGSLRLSCAASGFTF

STYAMNWVRQAPGKGLEWVGRIRSKYNNYATYYADSVKDRFTISRDDSKN

SLYLQMNSLKTEDTAVYYCVRHGNFGNSYVSWFAYWGQGTLVTVSSGGCG

GGKVAALKEKVAALKEKVAALKEKVAALKE

DART-A Chain 2 is composed of: SEQ ID NO:25-SEQ ID NO:29-SEQ ID NO:22-SEQ ID NO:30-SEQ ID NO:35. A DART-A Chain 2 encoding polynucleotide is SEQ ID NO:4:

gacttcgtgatgacacagtctcctgatagtctggccgtgagtctggggga gcgggtgactatgtcttgcaagagctcccagtcactgctgaacagcggaa atcagaaaaactatctgacctggtaccagcagaagccaggccagcccct aaactgctgatctattgggcttccaccagggaatctggcgtgcccgacag attcagcggcagcggcagcggcacagattttaccctgacaatttctagtc tgcaggccgaggacgtggctgtgtactattgtcagaatgattacagctat ccctacactttcggccaggggaccaagctggaaattaaaggaggcggatc cggcggcggaggcgaggtgcagctggtggagtctgggggaggcttggtcc agcctggagggtccctgagactctcctgtgcagcctctggattcaccttc agcacatacgctatgaatgggtccgccaggctccagggaaggggctgga gtgggttggaaggatcaggtccaagtacaacaattatgcaacctactatg ccgactctgtgaaggatagattcaccatctcaagagatgattcaaagaac tcactgtatctgcaaatgaacagcctgaaaaccgaggacacggccgtgta ttactgtgtgagacacggtaacttcggcaattcttacgtgtcttggtttg cttattggggacaggggacactggtgactgtgtcttccggaggatgtggc ggtggaaaagtggccgcactgaaggagaaagttgctgctttgaaagagaa ggtcgccgcacttaaggaaaaggtcgcagccctgaaagag As discussed below, the sequence-optimized CD123×CD3 bi-specific diabody (DART-A) was found to have the ability to simultaneously bind CD123 and CD3 as arrayed by human and monkey cells. Provision of DART-A was found to cause T cell activation, to mediate blast reduction, to drive T cell expansion, to induce T cell activation and to cause the redirected killing of target cancer cells.

II. Comparative Non-Sequence-Optimized CD123×CD3 Bi-Specific Diabody, "DART-B"

DART-B is a non-sequence-optimized CD123×CD3 bi-specific diabody having a gross structure that is similar to that of DART-A. The first polypeptide chain of DART-B will comprise, in the N-terminal to C-terminal direction, an N-terminus, a VL domain of a monoclonal antibody capable of binding to CD3 ($VL_{CD3}$), an intervening linker peptide (Linker 1), a VH domain of a monoclonal antibody capable of binding to CD123 ($VH_{CD123}$), an intervening Linker 2, an E-coil Domain, and a C-terminus. The $VL_{CD3}$ Domain of the first polypeptide chain of DART-B has the sequence (SEQ ID NO:23):

DIQLTQSPAIMSASPGEKVTMTCRASSSVSYMNWYQQKSGTSPKRWIYDT

SKVASGVPYRFSGSGSGTSYSLTISSMEAEDAATYYCQQWSSNPLTFGAG

TKLELK

The $VH_{CD123}$ Domain of the first polypeptide chain of DART-B has the sequence (SEQ ID NO:28):

QVQLVQSGAELKKPGASVKVSCKASGYTFTDYYMKWVRQAPGQGLEWIGD

IIPSNGATFYNQKFKGRVTITVDKSTSTAYMELSSLRSEDTAVYYCARSH

LLRASWFAYWGQGTLVTVSS

Thus, DART-B Chain 1 is composed of: SEQ ID NO:23-SEQ ID NO:29-SEQ ID NO:28-SEQ ID NO:30-SEQ ID NO:34. The sequence of the first polypeptide chain of DART-B is (SEQ ID NO:5):

DIQLTQSPAIMSASPGEKVTMTCRASSSVSYMNWYQQKSGTSPKRWIYDT

SKVASGVPYRFSGSGSGTSYSLTISSMEAEDAATYYCQQWSSNPLTFGAG

TKLELKGGGSGGGGQVQLVQSGAELKKPGASVKVSCKASGYTFTDYYMKW

VRQAPGQGLEWIGDIIPSNGATFYNQKFKGRVTITVDKSTSTAYMELSSL

RSEDTAVYYCARSHLLRASWFAYWGQGTLVTVSSGGCGGGEVAALEKEVA

ALEKEVAALEKEVAALEK

A DART-B Chain 1 encoding polynucleotide is SEQ ID NO:6:

gacattcagctgacccagtctccagcaatcatgtctgcatctccagggga gaaggtcaccatgacctgcagagccagttcaagtgtaagttacatgaact ggtaccagcagaagtcaggcacctcccccaaaagatggatttatgacaca tccaaagtggcttctggagtcccttatcgcttcagtggcagtgggtctgg gacctcatactctctcacaatcagcagcatggaggctgaagatgctgcca cttattactgccaacagtggagtagtaacccgctcacgttcggtgctggg accaagctggagctgaaaggaggcggatccggcggcggaggccaggtgca gctggtgcagtccggggctgagctgaagaaacccggagcttccgtgaagg tgtcttgcaaagccagtggctacaccttcacagactactatatgaagtgg gtcaggcaggctccaggacagggactggaatggatcggcgatatcattcc ttccaacggggccactttctacaatcagaagtttaaaggcagggtgacta ttaccgtggacaaatcaacaagcactgcttatatggagctgagctccctg cgctctgaagatacagccgtgtactattgtgctcggtcacacctgctgag agccagctggtttgcttattggggacagggcaccctggtgacagtgtctt ccggaggatgtggcggtggagaagtggccgcactggagaaagaggttgct gctttggagaaggaggtcgctgcacttgaaaaggaggtcgcagccctgga gaaa The second polypeptide chain of DART-B will comprise, in the N-terminal to C-terminal direction, an N-terminus, a VL domain of a monoclonal antibody capable of binding to CD123 ($VL_{CD123}$), an intervening linker peptide (Linker 1) and a VH domain of a monoclonal antibody capable of binding to CD3 ($VH_{CD3}$), an intervening Linker 2, a K-coil Domain, and a C-terminus.

The $VL_{CD123}$ Domain of the second polypeptide chain of DART-B has the sequence (SEQ ID NO:27):

DFVMTQSPDSLAVSLGERVIMSCKSSQSLLNSGNQKNYLTWYQQKPGQPP

KLLIYWASTRESGVPDRFSGSGSGTDFILTISSLQAEDVAVYYCQNDYSY

PYTFGQGTKLEIK

The VH$_{CD3}$ Domain of the second polypeptide chain of DART-B has the sequence (SEQ ID NO:24):

DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSS

Thus, DART-B Chain 2 is composed of: SEQ ID NO:27-SEQ ID NO:29-SEQ ID NO:24-SEQ ID NO:30-SEQ ID NO:35. The sequence of the second polypeptide chain of DART-B is (SEQ ID NO:7):

DFVMTQSPDSLAVSLGERVIMSCKSSQSLLNSGNQKNYLTWYQQKPGQPP

KLLIYWASTRESGVPDRFSGSGSGTDFILTISSLQAEDVAVYYCQNDYSY

PYTFGQGTKLEIKGGGSGGGGDIKLQQSGAELARPGASVKMSCKTSGYTF

TRYTMHWVKQRPGQGLEWIGYINPSRGYTNYNQKFKDKATLTTDKSSSTA

YMQLSSLTSEDSAVYYCARYYDDHYCLDYWGQGTTLIVSSGGCGGGKVAA

LKEKVAALKEKVAALKEKVAALKE

A DART-B Chain 2 encoding polynucleotide is SEQ ID NO:8:

gacttcgtgatgacacagtctcctgatagtctggccgtgagtctggggga gcgggtgactatgtcttgcaagagctcccagtcactgctgaacagcggaa atcagaaaactatctgacctggtaccagcagaagccaggccagcccct aaactgctgatctattgggcttccaccaggaatctggcgtgccgacag attcagcggcagcggcagcggcacagattttaccctgacaatttctagtc tgcaggccgaggacgtggctgtgtactattgtcagaatgattacagctat ccctacactttcggccaggggaccaagctggaaattaaaggaggcggatc cggcggcggaggcgatatcaaactgcagcagtcaggggctgaactggcaa gacctgggcctcagtgaagatgtcctgcaagacttctggctacacctt actaggtacacgatgcactgggtaaaacagaggcctggacagggtctgga atggattggatacattaatcctagccgtggttatactaattacaatcaga agttcaaggacaaggccacattgactacagacaaatcctccagcacagcc tacatgcaactgagcagcctgacatctgaggactctgcagtctattactg tgcaagatattatgatgatcattactgccttgactactgggccaaggca ccactctcacagtctcctccggaggatgtggcggtggaaaagtggccgca ctgaaggagaaagttgctgctttgaaagagaaggtcgccgcacttaagga aaaggtcgcagccctgaaagag III. Modified Variants of Sequence-Optimized CD123×CD3 Bi-Specific Diabody (DART-A)

A. Sequence-Optimized CD123×CD3 Bi-Specific Diabody Having an Albumin-Binding Domain (DART-A with ABD "w/ABD")

In a second embodiment of the invention, the sequence-optimized CD123×CD3 bi-specific diabody (DART-A) will comprise one or more Albumin-Binding Domain ("ABD") (DART-A with ABD "w/ABD") on one or both of the polypeptide chains of the diabody.

As disclosed in WO 2012/018687, in order to improve the in vivo pharmacokinetic properties of diabodies, the diabodies may be modified to contain a polypeptide portion of a serum-binding protein at one or more of the termini of the diabody. Most preferably, such polypeptide portion of a serum-binding protein will be installed at the C-terminus of the diabody. A particularly preferred polypeptide portion of a serum-binding protein for this purpose is the Albumin-Binding Domain (ABD) from streptococcal protein G. The Albumin-Binding Domain 3 (ABD3) of protein G of Streptococcus strain G148 is particularly preferred.

The Albumin-Binding Domain 3 (ABD3) of protein G of Streptococcus strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules,*" J. Biol. Chem. 277(10): 8114-8120). Albumin is the most abundant protein in plasma and has a half-life of 19 days in humans. Albumin possesses several small molecule binding sites that permit it to non-covalently bind to other proteins and thereby extend their serum half-lives.

Thus, the first polypeptide chain of such a sequence-optimized CD123×CD3 bi-specific diabody having an Albumin-Binding Domain contains a third linker (Linker 3), which separates the E-coil (or K-coil) of such polypeptide chain from the Albumin-Binding Domain. A preferred sequence for such Linker 3 is SEQ ID NO:31: GGGS. A preferred Albumin-Binding Domain (ABD) has the sequence (SEQ ID NO:36): LAEAKVLANRELDKYGVS-DYYKNLIDNAKSAEGVKALIDEILAALP.

Thus, a preferred first chain of a sequence-optimized CD123×CD3 bi-specific diabody having an Albumin-Binding Domain has the sequence (SEQ ID NO:9):

QAVVTQEPSLTVSPGGIVTLICRSSTGAVITSNYANWVQQKPGQAPRGLI

GGTNKRAPWTPARFSGSLLGGKAALTITGAQAEDEADYYCALWYSNLWVF

GGGTKLTVLGGGGSGGGGEVQLVQSGAELKKPGASVKVSCKASGYTFTDY

YMKWVRQAPGQGLEWIGDIIPSNGATFYNQKFKGRVTITVDKSTSTAYME

LSSLRSEDTAVYYCARSHLLRASWFAYWGQGTLVTVSSGGCGGGEVAALE

KEVAALEKEVAALEKEVAALEKGGGSLAEAKVLANRELDKYGVSDYYKNL

IDNAKSAEGVKALIDEILAALP

A sequence-optimized CD123×CD3 diabody having an Albumin-Binding Domain is composed of: SEQ ID NO:21-SEQ ID NO:29-SEQ ID NO:26-SEQ ID NO:30-SEQ ID NO:34-SEQ ID NO:31-SEQ ID NO:36. A polynucleotide encoding such a sequence-optimized CD123×CD3 diabody having an Albumin-Binding Domain derivative is SEQ ID NO:10:

caggctgtggtgactcaggagccttcactgaccgtgtcccaggcggaa ctgtgaccctgacatgcagatccagcacaggcgcagtgaccacatctaa ctacgccaattgggtgcagcagaagccaggacaggcaccaaggggcctg atcggggtacaaacaaaagggctccctggaccctgcacggttttctg gaagtctgctgggcggaaaggccgctctgactattaccggggcacaggc cgaggacgaagccgattactattgtgctctgtggtatagcaatctgtgg gtgttcggggggtggcacaaaactgactgtgctgggaggggggtggatccg gcggcggaggcgaggtgcagctggtgcagtccggggctgagctgaagaa -continued

```
acccggagcttccgtgaaggtgtcttgcaaagccagtggctacaccttc acagactactatatgaagtgggtcaggcaggctccaggacagggactgg aatggatcggcgatatcattccttccaacggggccactttctacaatca gaagtttaaaggcagggtgactattaccgtggacaaatcaacaagcact gcttatatggagctgagctccctgcgctctgaagatacagccgtgtact attgtgctcggtcacacctgctgagagccagctggtttgcttattgggg acagggcaccctggtgacagtgtcttccggaggatgtggcggtggagaa gtggccgcactggagaaagaggttgctgctttggagaaggaggtcgctg cacttgaaaaggaggtcgcagccctggagaaaggcggcgggtctctggc cgaagcaaaagtgctggccaaccgcgaactggataaatatggcgtgagc gattattataagaacctgattgacaacgcaaaatccgcggaaggcgtga aagcactgattgatgaaattctggccgccctgcct
```

The second polypeptide chain of such a sequence-optimized CD123×CD3 diabody having an Albumin-Binding Domain has the sequence described above (SEQ ID NO:3) and is encoded by a polynucleotide having the sequence of SEQ ID NO:4.

B. Sequence-Optimized CD123×CD3 Bi-Specific Diabodies Having an IgG Fc Domain (DART-A with Fc "w/Fc")

In a third embodiment, the invention provides a sequence-optimized CD123×CD3 bi-specific diabody composed of three polypeptide chains and possessing an IgG Fc Domain (DART-A with Fc "w/Fc" Version 1 and Version 2) (FIG. 3A-3B).

In order to form such IgG Fc Domain, the first and third polypeptide chain of the diabodies contain, in the N-terminal to C-terminal direction, a cysteine-containing peptide, (most preferably, Peptide 1 having the amino acid sequence (SEQ ID NO:55): DKTHTCPPCP), some or all of the CH2 Domain and/or some or all of the CH3 Domain of a complete immunoglobulin Fc Domain, and a C-terminus. The some or all of the CH2 Domain and/or the some or all of the CH3 Domain associate to form the immunoglobulin Fc Domain of the bi-specific monovalent Fc Domain-containing diabodies of the present invention. The first and second polypeptide chains of the bi-specific monovalent Fc diabodies of the present invention are covalently bonded to one another, for example by disulfide bonding of cysteine residues located within the cysteine-containing peptide of the polypeptide chains.

The CH2 and/or CH3 Domains of the first and third polypeptides need not be identical, and advantageously are modified to foster complexing between the two polypeptides. For example, an amino acid substitution (preferably a substitution with an amino acid comprising a bulky side group forming a 'knob', e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the bi-specific monovalent Fc diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety). Preferably the 'knob' is engineered into the CH2-CH3 Domains of the first polypeptide chain and the 'hole' is engineered into the CH2-CH3 Domains of the third polypeptide chain. Thus, the 'knob' will help in preventing the first polypeptide chain from homodimerizing via its CH2 and/or CH3 Domains. As the third polypeptide chain preferably contains the 'hole' substitution it will heterodimerize with the first polypeptide chain as well as homodimerize with itself. A preferred knob is created by modifying a native IgG Fc Domain to contain the modification T366W. A preferred hole is created by modifying a native IgG Fc Domain to contain the modification T366S, L368A and Y407V. To aid in purifying the third polypeptide chain homodimer from the final bi-specific monovalent Fc diabody comprising the first, second and third polypeptide chains, the protein A binding site of the CH2 and CH3 Domains of the third polypeptide chain is preferably mutated by amino acid substitution at position 435 (H435R). Thus, the third polypeptide chain homodimer will not bind to protein A, whereas the bi-specific monovalent Fc diabody will retain its ability to bind protein A via the protein A binding site on the first polypeptide chain.

A preferred sequence for the CH2 and CH3 Domains of an antibody Fc Domain present in the first polypeptide chain is (SEQ ID NO:56):

APEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSREEMTKNQVSLWCLVKGFYPSDI

AVEWESNGQPENNYKTTPPVLDSDGSFFLYSKLTVDKSRWQQGNVFSCS

VMHEALHNHYTQKSLSLSPGK

A preferred sequence for the CH2 and CH3 Domains of an antibody Fc Domain present in the third polypeptide chain is (SEQ ID NO:11):

APEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSREEMTKNQVSLSCAVKGFYPSDI

AVEWESNGQPENNYKTTPPVLDSDGSFFLVSKLTVDKSRWQQGNVFSCS

VMHEALHNRYTQKSLSLSPGK

C. DART-A w/Fc Version 1 Construct

In order to illustrate such Fc diabodies, the invention provides a DART-A w/Fc version 1 construct. The first polypeptide of the DART-A w/Fc version 1 construct comprises, in the N-terminal to C-terminal direction, an N-terminus, a VL domain of a monoclonal antibody capable of binding to CD123 ($VL_{CD123}$), an intervening linker peptide (Linker 1), a VH domain of a monoclonal antibody capable of binding to CD3 ($VH_{CD3}$), a Linker 2, an E-coil Domain, a Linker 5, Peptide 1, a polypeptide that contains the CH2 and CH3 Domains of an Fc Domain and a C-terminus. A preferred Linker 5 has the sequence (SEQ ID NO:32): GGG. A preferred polypeptide that contains the CH2 and CH3 Domains of an Fc Domain has the sequence (SEQ ID NO:37):

APEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSREEMTKNQVSLWCLVKGFYPSDI

AVEWESNGQPENNYKTTPPVLDSDGSFFLYSKLTVDKSRWQQGNVFSCS

VMHEALHNHYTQKSLSLSPGK

Thus, the first polypeptide of such a DART-A w/Fc version 1 construct is composed of: SEQ ID NO:25-SEQ ID NO:29-SEQ ID NO:22-SEQ ID NO:30-SEQ ID NO:34-SEQ ID NO:32-SEQ ID NO:55-SEQ ID NO:37.

A preferred sequence of the first polypeptide of such a DART-A w/Fc version 1 construct has the sequence (SEQ ID NO:13):

DFVMTQSPDSLAVSLGERVTMSCKSSQSLLNSGNQKNYLTWYQQKPGQP

PKLLIYWASTRESGVPDRFSGSGSGTDFTLTISSLQAEDVAVYYCQNDY

SYPYTFGQGTKLEIKGGGSGGGGEVQLVESGGGLVQPGGSLRLSCAASG

FTFSTYAMNWVRQAPGKGLEWVGRIRSKYNNYATYYADSVKDRFTISRD

DSKNSLYLQMNSLKTEDTAVYYCVRHGNFGNSYVSWFAYWGQGTLVTVS

SGGCGGGEVAALEKEVAALEKEVAALEKEVAALEKGGGDKTHTCPPCPA

PEAAGGPSVFLFPPKPKDTLMISRIPEVTCVVVDVSHEDPEVKFNWYVD

GVEVHNAKTKPREEQYNSTYRVVSVLTVLHQDWLNGKEYKCKVSNKALP

APIEKTISKAKGQPREPQVYTLPPSREEMTKNQVSLWCLVKGFYPSDIA

VEWESNGQPENNYKTTPPVLDSDGSFFLYSKLTVDKSRWQQGNVFSCSV

MHEALHNHYTQKSLSLSPGK

A preferred polynucleotide encoding such a polypeptide is (SEQ ID NO:14):

gacttcgtgatgacacagtctcctgatagtctggccgtgagtctggggga gcgggtgactatgtcttgcaagagctcccagtcactgctgaacagcggaa atcagaaaaactatctgacctggtaccagcagaagccaggccagccccct aaactgctgatctattgggcttccaccagggaatctggcgtgcccgacag attcagcggcagcggcagcggcacagattttaccctgacaatttctagtc tgcaggccgaggacgtggctgtgtactattgtcagaatgattacagctat ccctacactttcggccaggggaccaagctggaaattaaaggaggcggatc cggcggcggaggcgaggtgcagctggtggagtctgggggaggcttggtcc agcctggagggtccctgagactctcctgtgcagcctctggattccacttc agcacatacgctatgaattgggtccgccaggctccagggaaggggctgga gtgggttggaaggatcaggtccaagtacaacaattatgcaacctactatg ccgactctgtgaaggatagattcaccatctcaagagatgattcaaagaac tcactgtatctgcaaatgaacagcctgaaaaccgaggacacggccgtgta ttactgtgtgagacacggtaacttgcaattcttacgtgtcttggtttgct tattggggacaggggacactggtgactgtgtcttccggaggatgtggcgg tggagaagtggccgcactggagaaagaggttgctgctttggagaaggagg tcgctgcacttgaaaaggaggtcgcagctggagaaaggcggcggggacaa aactcacacatgcccaccgtgcccagcacctgaagccgcgggggaccgt cagtcttcctcttccccccaaaacccaaggacaccctcatgatctcccgg acccctgaggtcacatgcgtggtggtggacgtgagccacgaagaccctga ggtcaagttcaactggtacgtggacggcgtggaggtgcataatgccaaga caaagccgcgggaggagcagtacaacagcacgtaccgtgtggtcagcgtc ctcaccgtcctgcaccaggactggctgaatggcaaggagtacaagtgcaa ggtctccaacaaagccctcccagcccccatcgagaaaaccatctccaaag ccaaagggcagccccgagaaccacaggtgtacaccctgcccccatcccgg gaggagatgaccaagaaccaggtcagcctgtggtgcctggtcaaaggctt ctatcccagcgacatcgccgtggagtgggagagcaatgggcagccggaga acaactacaagaccacgcctcccgtgctggactccgacggctccttcttc ctctacagcaagctcaccgtggacaagagcaggtggcagcagggaacgt cttctcatgctccgtgatgcatgaggctctgcacaaccactacacgcaga agagcctctccctgtctccgggtaaa The second chain of such a DART-A w/Fc version 1 construct will comprise, in the N-terminal to C-terminal direction, an N-terminus, a VL domain of a monoclonal antibody capable of binding to CD3 (VL$_{CD3}$), an intervening linker peptide (Linker 1), a VH domain of a monoclonal antibody capable of binding to CD123 (VH$_{CD123}$), a Linker 2, a K-coil Domain, and a C-terminus. Thus, the second polypeptide of such a DART-A w/Fc version 1 construct is composed of: SEQ ID NO:21-SEQ ID NO:29-SEQ ID NO:26-SEQ ID NO:30-SEQ ID NO:35. Such a polypeptide has the sequence (SEQ ID NO:15):

QAVVTQEPSLTVSPGGIVTLICRSSTGAVITSNYANWVQQKPGQAPRGLI

GGTNKRAPWTPARFSGSLLGGKAALTITGAQAEDEADYYCALWYSNLWVF

GGGTKLTVLGGGGSGGGGEVQLVQSGAELKKPGASVKVSCKASGYTFTDY

YMKWVRQAPGQGLEWIGDIIPSNGATFYNQKFKGRVTITVDKSTSTAYME

LSSLRSEDTAVYYCARSHLLRASWFAYWGQGTLVTVSSGGCGGGKVAALK

EKVAALKEKVAALKEKVAALKE

A preferred polynucleotide encoding such a polypeptide has the sequence (SEQ ID NO:16):

caggctgtggtgactcaggagccttcactgaccgtgtcccaggcggaac tgtgaccctgacatgcagatccagcacaggcgcagtgaccacatctaact acgccaattgggtgcagcagaagccaggacaggcaccaagggggcctgatc ggggtacaaacaaaagggctccctggacccctgcacggttttctggaag tctgctgggcggaaaggccgctctgactattaccggggcacaggccgagg -continued
```
acgaagccgattactattgtgctctgtggtatagcaatctgtgggtgttc gggggtggcacaaaactgactgtgctgggagggggtggatccggcggcgg aggcgaggtgcagctggtgcagtccggggctgagctgaagaaacccggag cttccgtgaaggtgtcttgcaaagccagtggctacaccttcacagactac tatatgaagtgggtcaggcaggctccaggacagggactggaatggatcgg cgatatcattccttccaacggggccactttctacaatcagaagtttaaag gcagggtgactattaccgtggacaaatcaacaagcactgcttatatggag ctgagctccctgcgctctgaagatacagccgtgtactattgtgctcggtc acacctgctgagagccagctggtttgcttattggggacagggcaccctgg tgacagtgtcttccggaggatgtggcggtggaaaagtggccgcactgaag gagaaagttgctgctttgaaagagaaggtcgccgcacttaaggaaaaggt cgcagccctgaaagag
```

The third polypeptide chain of such a DART-A w/Fc version 1 will comprise the CH2 and CH3 Domains of an IgG Fc Domain. A preferred polypeptide that is composed of Peptide 1 (SEQ ID NO:55) and the CH2 and CH3 Domains of an Fc Domain (SEQ ID NO:11) and has the sequence of SEQ ID NO:54:

DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLSCAVK

GFYPSDIAVEWESNGQPENNYKTTPPVLDSDGSFFLVSKLTVDKSRWQQG

NVFSCSVMHEALHNRYTQKSLSLSPGK

A preferred polynucleotide that encodes such a polypeptide has the sequence (SEQ ID NO:12):

```
gacaaaactcacacatgcccaccgtgcccagcacctgaagccgcggggg gaccgtcagtcttcctcttccccccaaaacccaaggacaccctcatgat ctcccggacccctgaggtcacatgcgtggtggtggacgtgagccacgaa gaccctgaggtcaagttcaactggtacgtggacggcgtggaggtgcata atgccaagacaaagccgcgggaggagcagtacaacagcacgtaccgtgt ggtcagcgtcctcaccgtcctgcaccaggactggctgaatggcaaggag tacaagtgcaaggtctccaacaaagccctcccagcccccatcgagaaaa ccatctccaaagccaaagggcagccccgagaaccacaggtgtaccct gcccccatcccgggaggagatgaccaagaaccaggtcagcctgagttgc gcagtcaaaggcttctatcccagcgacatcgccgtggagtgggagagca atgggcagccggagaacaactacaagaccacgcctcccgtgctggactc cgacggctccttcttcctcgtcagcaagctcaccgtggacaagagcagg tggcagcaggggaacgtcttctcatgctccgtgatgcatgaggctctgc acaaccgctacacgcagaagagcctctccctgtctccgggtaaa
```

D. DART-A w/Fc Version 2 Construct

As a second example of such a DART-A w/Fc diabody, the invention provides a three chain diabody, "DART-A w/Fc Diabody Version 2" (FIG. 3B).

The first polypeptide of such a DART-A w/Fc version 2 construct comprises, in the N-terminal to C-terminal direction, an N-terminus, a peptide linker (Peptide 1), a polypeptide that contains the CH2 and CH3 Domains of an Fc Domain linked (via a Linker 4) to the VL domain of a monoclonal antibody capable of binding to CD123 ($VL_{CD23}$), an intervening linker peptide (Linker 1), a VH domain of a monoclonal antibody capable of binding to CD3 ($VH_{CD3}$), a Linker 2, a K-coil Domain, and a C-terminus.

A preferred polypeptide that contains the CH2 and CH3 Domains of an Fc Domain has the sequence (SEQ ID NO:37):

APEAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLWCLVKGFYPSDIAVE

WESNGQPENNYKTTPPVLDSDGSFFLYSKLTVDKSRWQQGNVFSCSVMHE

ALHNHYTQKSLSLSPGK

"Linker 4" will preferably comprise the amino acid sequence (SEQ ID NO:57): APSSS. A preferred "Linker 4" has the sequence (SEQ ID NO:33): APSSSPME. Thus, the first polypeptide of such a DART-A w/Fc version 2 construct is composed of: SEQ ID NO:55-SEQ ID NO:37-SEQ ID NO:33-SEQ ID NO:25-SEQ ID NO:29-SEQ ID NO:22-SEQ ID NO:30-SEQ ID NO:35. A polypeptide having such a sequence is (SEQ ID NO:17):

DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLWC

LVKGFYPSDIAVEWESNGQPENNYKTTPPVLDSDGSFFLYSKLTVDKSR

WQQGNVFSCSVMHEALHNHYTQKSLSLSPGKAPSSSPMEDFVMTQSPDS

LAVSLGERVTMSCKSSQSLLNSGNQKNYLTWYQQKPGQPPKLLIYWAST

RESGVPDRFSGSGSGTDFTLTISSLQAEDVAVYYCQNDYSYPYTFGQGT

KLEIKGGGSGGGGEVQLVESGGGLVQPGGSLRLSCAASGFTFSTYAMNW

VRQAPGKGLEWVGRIRSKYNNYATYYADSVKDRFTISRDDSKNSLYLQM

NSLKTEDTAVYYCVRHGNFGNSYVSWFAYWGQGTLVTVSSGGCGGGKVA

ALKEKVAALKEKVAALKEKVAALKE

A preferred polynucleotide encoding such a polypeptide has the sequence (SEQ ID NO:18):

```
gacaaaactcacacatgcccaccgtgcccagcacctgaagccgcggggg accgtcagtcttcctcttccccccaaaacccaaggacaccctcatgatct cccggacccctgaggtcacatgcgtggtggtggacgtgagccacgaagac cctgaggtcaagttcaactggtacgtggacggcgtggaggtgcataatgc caagacaaagccgcgggaggagcagtacaacagcacgtaccgtgtggtca gcgtcctcaccgtcctgcaccaggactggctgaatggcaaggagtacaag tgcaaggtctccaacaaagccctcccagcccccatcgagaaaaccatctc caaagccaaagggcagccccgagaaccacaggtgtaccctgccccat
```

```
cccgggaggagatgaccaagaaccaggtcagcctgtggtgcctggtcaaa ggcttctatcccagcgacatcgccgtggagtgggagagcaatgggcagcc ggagaacaactacaagaccacgcctcccgtgctggactccgacggctcct tcttcctctacagcaagctcaccgtggacaagagcaggtggcagcagggg aacgtcttctcatgctccgtgatgcatgaggctctgcacaaccactacac gcagaagagcctctccctgtctccgggtaaagcccttccagctcccta tggaagacttcgtgatgacacagtctcctgatagtctggccgtgagtctg ggggagcgggtgactatgtcttgcaagagctcccagtcactgctgaacag cggaaatcagaaaaactatctgacctggtaccagcagaagccaggccagc cccctaaactgctgatctattgggcttccaccagggaatctggcgtgccc gacagattcagcggcagcggcagcggcacagattttaccctgacaattc tagtctgcaggccgaggacgtggctgtgtactattgtcagaatgattaca gctatcctacactttcggccaggggaccaagctggaaattaaaggaggc ggatccggcggcggaggcgaggtgcagctggtggagtctggggaggctt ggtccagcctggagggtccctgagactctcctgtgcagcctctggattca ccttcagcacatacgctatgaattgggtccgccaggctccagggaagggg ctggagtgggttggaaggatcaggtccaagtacaacaattatgcaaccta ctatgccgactctgtgaaggatagattcaccatctcaagagatgattcaa agaactcactgtatctgcaaatgaacagcctgaaaaccgaggacacggcc gtgtattactgtgtgagacacggtaacttcggcaattcttacgtgtcttg gtttgcttattgggacaggggacactggtgactgtgtcttccggaggat gtggcggtggaaaagtggccgcactgaaggagaaagttgctgctttgaaa gagaaggtcgccgcacttaaggaaaaggtcgcagccctgaaagag
```

The second polypeptide chain of such a DART-A w/Fc version 2 construct comprises, in the N-terminal to C-terminal direction, the VL domain of a monoclonal antibody capable of binding to CD3 (VL$_{CD3}$), an intervening linker peptide (Linker 1) and a VH domain of a monoclonal antibody capable of binding to CD123 (VH$_{CD123}$). This portion of the molecule is linked (via Linker 2) to an E-coil Domain. Thus, the third polypeptide of such a DART-A w/Fc version 2 construct is composed of: SEQ ID NO:21-SEQ ID NO:29-SEQ ID NO:26-SEQ ID NO:30-SEQ ID NO:34. A polypeptide having such a sequence is (SEQ ID NO:1), and is preferably encoded by a polynucleotide having the sequence of SEQ ID NO:2.

The third polypeptide chain will comprise the CH2 and CH3 Domains of an IgG Fc Domain. A preferred polypeptide is composed of Peptide 1 (SEQ ID NO:55) and the CH2 and CH3 Domains of an Fc Domain (SEQ ID NO:11) and has the sequence of SEQ ID NO:54.

In order to assess the activity of the above-mentioned CD123×CD3 bi-specific diabodies (DART-A, DART-A w/ABD, DART-A w/Fc, DART-B), a control bi-specific diabody (Control DART) was produced. The Control DART is capable of simultaneously binding to FITC and CD3. Its two polypeptide chains have the following respective sequences:

Control DART Chain 1 (SEQ ID NO: 19):
DVVMTQTPFSLPVSLGDQASISCRSSQSLVHSNGNTYLRWYLQKPGQSPK

VLTYKVSNRFSGVPDRFSGSGSGTDFTLKISRVEAEDLGVYFCSQSTHVP

WTFGGGTKLEIKGGGSGGGGEVQLVESGGGLVQPGGSLRLSCAASGFTFN

TYAMNWVRQAPGKGLEWVARIRSKYNNYATYYADSVKDRFTISRDDSKNS

LYLQMNSLKTEDTAVYYCVRHGNFGNSYVSWFAYWGQGTLVTVSSGGCGG

GEVAALEKEVAALEKEVAALEKEVAALEK

Control DART Chain 2 (SEQ ID NO: 20):
QAVVTQEPSLTVSPGGIVTLICRSSTGAVITSNYANWVQQKPGQAPRGLI

GGTNKRAPWTPARFSGSLLGGKAALTITGAQAEDEADYYCALWYSNLWVF

GGGTKLTVLGGGGSGGGGEVKLDETGGGLVQPGRPMKLSCVASGFTFSDY

WMNWVRQSPEKGLEWVAQIRNKPYNYETYYSDSVKGRFTISRDDSKSSVY

LQMNNLRVEDMGIYYCTGSYYGMDYWGQGTSVTVSSGGCGGGKVAALKEK

VAALKEKVAALKEKVAALKE

IV. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the sequence-optimized CD123×CD3 bi-specific diabodies of the present invention, or a combination of such agents and a pharmaceutically acceptable carrier. Preferably, compositions of the invention comprise a prophylactically or therapeutically effective amount of the sequence-optimized CD123×CD3 bi-specific diabody of the invention and a pharmaceutically acceptable carrier.

The invention also encompasses pharmaceutical compositions comprising sequence-optimized CD123×CD3 bi-specific diabodies of the invention, and a second therapeutic antibody (e.g., tumor specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with sequence-optimized CD123×CD3 bi-specific diabodies of the invention alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise sequence-optimized CD123×CD3 bi-specific diabodies of the invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

V. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the sequence-optimized CD123×CD3 bi-specific diabodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,800,078; and PCT Publication Nos. WO 92/19244; WO 97/32572; WO 97/44013; WO 98/31346; and WO 99/66903, each of which is incorporated herein by reference in its entirety.

The invention also provides that the sequence-optimized CD123×CD3 bi-specific diabodies of the invention are packaged in a hermetically sealed container such as an ampoule or sachette indicating the quantity of the molecule. In one embodiment, the sequence-optimized CD123×CD3 bi-specific diabodies of the invention are supplied as a dry sterilized lyophilized powder or water free concentrate in a hermetically sealed container and can be reconstituted, e.g., with water or saline to the appropriate concentration for administration to a subject. Preferably, the sequence-optimized CD123×CD3 bi-specific diabodies of the invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized sequence-optimized CD123×CD3 bi-specific diabodies of the invention should be stored at between 2 and 8° C. in their original container and the molecules should be administered within 12 hours, preferably within 6 hours, within 5 hours, within 3 hours, or within 1 hour after being reconstituted. In an alternative embodiment, sequence-optimized CD123×CD3 bi-specific diabodies of the invention are supplied in liquid form in a hermetically sealed container indicating the quantity and concentration of the molecule, fusion protein, or conjugated molecule. Preferably, the liquid form of the sequence-optimized CD123×CD3 bi-specific diabodies of the invention are supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For sequence-optimized CD123×CD3 bi-specific diabodies encompassed by the invention, the dosage administered to a patient is preferably determined based upon the body weight (kg) of the recipient subject. The dosage administered is typically from at least about 0.3 ng/kg per day to about 0.9 ng/kg per day, from at least about 1 ng/kg per day to about 3 ng/kg per day, from at least about 3 ng/kg per day to about 9 ng/kg per day, from at least about 10 ng/kg per day to about 30 ng/kg per day, from at least about 30 ng/kg per day to about 90 ng/kg per day, from at least about 100 ng/kg per day to about 300 ng/kg per day, from at least about 200 ng/kg per day to about 600 ng/kg per day, from at least about 300 ng/kg per day to about 900 ng/kg per day, from at least about 400 ng/kg per day to about 800 ng/kg per day, from at least about 500 ng/kg per day to about 1000 ng/kg per day, from at least about 600 ng/kg per day to about 1000 ng/kg per day, from at least about 700 ng/kg per day to about 1000 ng/kg per day, from at least about 800 ng/kg per day to about 1000 ng/kg per day, from at least about 900 ng/kg per day to about 1000 ng/kg per day, or at least about 1,000 ng/kg per day.

In another embodiment, the patient is administered a treatment regimen comprising one or more doses of such prophylactically or therapeutically effective amount of the sequence-optimized CD123×CD3 bi-specific diabodies encompassed by the invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the sequence-optimized CD123×CD3 bi-specific diabodies encompassed by the invention (for example, administering a dose on day 1, day 2, day 3 and day 4 of a given week and not administering doses of the prophylactically or therapeutically effective amount of the sequence-optimized CD123×CD3 bi-specific diabodies encompassed by the invention on day 5, day 6 and day 7 of the same week). Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the sequence-optimized CD123×CD3 bi-specific diabodies encompassed by the invention is achieved.

TABLE 1

| Regimen | Day | Diabody Dosage (ng diabody per kg subject weight per day) | | | | |
|---|---|---|---|---|---|---|
| 1 | 1, 2, 3, 4 | 100 | 100 | 100 | 100 | 100 |
|   | 5, 6, 7 | none | none | none | none | none |
| 2 | 1, 2, 3, 4 | 300 | 500 | 700 | 900 | 1,000 |
|   | 5, 6, 7 | none | none | none | none | none |
| 3 | 1, 2, 3, 4 | 300 | 500 | 700 | 900 | 1,000 |
|   | 5, 6, 7 | none | none | none | none | none |
| 4 | 1, 2, 3, 4 | 300 | 500 | 700 | 900 | 1,000 |
|   | 5, 6, 7 | none | none | none | none | none |

The dosage and frequency of administration of sequence-optimized CD123×CD3 bi-specific diabodies of the invention may be reduced or altered by enhancing uptake and tissue penetration of the sequence-optimized CD123×CD3 bi-specific diabodies by modifications such as, for example, lipidation.

The dosage of the sequence-optimized CD123×CD3 bi-specific diabodies of the invention administered to a patient may be calculated for use as a single agent therapy. Alternatively, the sequence-optimized CD123×CD3 bi-specific diabodies of the invention are used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 3 17-327; see generally ibid.).

The compositions of the invention can be delivered in a controlled-release or sustained-release system. Any technique known to one of skill in the art can be used to produce sustained-release formulations comprising one or more sequence-optimized CD123×CD3 bi-specific diabodies of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained-release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,115). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled-release systems are discussed in the review by Langer (1990, *"New Methods Of Drug Delivery,"* Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) *"Intratumoral Radioimmunotheraphy Of A Human Colon Cancer Xenograft Using A Sustained-Release Gel,"* Radiotherapy & Oncology 39:179-189, Song et al. (1995) *"Antibody Mediated Lung Targeting Of Long-Circulating Emulsions,"* PDA Journal of Pharmaceutical Science & Technology 50:372-397; Cleek et al. (1997) *"Biodegradable Polymeric Carriers For A bFGF Antibody For Cardiovascular Application,"* Pro. Int'l. Symp. Control. Rel. Bioact. Mater. 24:853-854; and Lam et al. (1997) *"Microencapsulation Of Recombinant Humanized Monoclonal Antibody For Local Delivery,"* Proc. Int'l. Symp. Control Rel. Bioact. Mater. 24:759-760, each of which is incorporated herein by reference in its entirety.

Where the composition of the invention is a nucleic acid encoding a sequence-optimized CD123×CD3 bi-specific diabody of the invention, the nucleic acid can be administered in vivo to promote expression of its encoded sequence-optimized CD123×CD3 bi-specific diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) *"Antennapedia Homeobox Peptide Regulates Neural Morphogenesis,"* Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of sequence-optimized CD123× CD3 bi-specific diabodies of the invention can include a single treatment or, preferably, can include a series of treatments. In a preferred example, a subject is treated with sequence-optimized CD123×CD3 bi-specific diabodies of the invention one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

VI. Uses of the Compositions of the Invention

The sequence-optimized CD123×CD3 bi-specific diabodies of the present invention have the ability to treat any disease or condition associated with or characterized by the expression of CD123. Thus, without limitation, such molecules may be employed in the diagnosis or treatment of acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma (see Example 2); Autoimmune Lupus (SLE), allergy, asthma and rheumatoid arthritis. The bi-specific diabodies of the present invention may additionally be used in the manufacture of medicaments for the treatment of the above-described conditions.

Having now generally described the invention, the same will be more readily understood through reference to the following examples, which are provided by way of illustration and are not intended to be limiting of the present invention unless specified.

Example 1

Construction of CD123×CD3 Bi-Specific Diabodies and Control Protein

Table 2 contains a list of bi-specific diabodies that were expressed and purified. Sequence-optimized CD123×CD3 bi-specific diabody (DART-A) and non-sequence-optimized CD123×CD3 bi-specific diabody (DART-B) are capable of simultaneously binding to CD123 and CD3. The control bi-specific diabody (Control DART) is capable of simultaneously binding to FITC and CD3. The bi-specific diabodies are heterodimers or heterotrimers of the recited amino acid sequences. Methods for forming bi-specific diabodies are provided in WO 2006/113665, WO 2008/157379, WO 2010/080538, WO 2012/018687, WO 2012/162068 and WO 2012/162067.

TABLE 2

| Bi-Specific Diabodies | Polypeptide Chain Amino Acid Sequences | Nucleic Acid Encoding Sequences |
|---|---|---|
| Sequence-Optimized CD123 × CD3 Bi-Specific Diabody (DART-A) (Binds to CD3 at epitope 1) | SEQ ID NO: 1 SEQ ID NO: 3 | SEQ ID NO: 2 SEQ ID NO: 4 |

TABLE 2-continued

| Bi-Specific Diabodies | Polypeptide Chain Amino Acid Sequences | Nucleic Acid Encoding Sequences |
|---|---|---|
| Non-Sequence-Optimized CD123 × CD3 Bi-Specific Diabody (DART-B) (Binds to CD3 at epitope 2) | SEQ ID NO: 5 SEQ ID NO: 7 | SEQ ID NO: 6 SEQ ID NO: 8 |
| Sequence-Optimized CD123 × CD3 Bi-Specific Diabody Having an Albumin-Binding Domain (DART-A w/ABD) (Binds to CD3 at epitope 1) Comprises an Albumin-Binding Domain (ABD) for extension of half-life in vivo | SEQ ID NO: 9 SEQ ID NO: 3 | SEQ ID NO: 10 SEQ ID NO: 4 |
| Sequence-Optimized CD123 × CD3 Bi-Specific Diabody Having an IgG Fc Domain Version 1 (DART-A w/Fc version 1) (Binds to CD3 at epitope 1) Comprises an Fc Domain for extension of half-life in vivo | SEQ ID NO: 54 SEQ ID NO: 13 SEQ ID NO: 15 | SEQ ID NO: 12 SEQ ID NO: 14 SEQ ID NO: 16 |
| Sequence-Optimized CD123 × CD3 Bi-Specific Diabody Having an IgG Fc Domain Version 2 (DART-A w/Fc version 2) (Binds to CD3 at epitope 1) Comprises an Fc Domain for extension of half-life in vivo | SEQ ID NO: 54 SEQ ID NO: 17 SEQ ID NO: 1 | SEQ ID NO: 12 SEQ ID NO: 18 SEQ ID NO: 2 |
| Control Bi-Specific Diabody (Control DART (or Control DART) (Binds to CD3 at epitope 1) (Binds to an irrelevant target - FITC) | SEQ ID NO: 19 SEQ ID NO: 20 | |

Example 2

Antibody Labeling of Target Cells for Quantitative FACS (QFACS)

A total of $10^6$ target cells were harvested from the culture, resuspended in 10% human AB serum in FACS buffer (PBS+1% BSA+0.1% NaAzide) and incubated for 5 min for blocking Fc receptors. Antibody labeling of microspheres with different antibody binding capacities (Quantum™ Simply Cellular® (QSC), Bangs Laboratories, Inc., Fishers, Ind.) and target cells were labeled with anti-CD123 PE antibody (BD Biosciences) according to the manufacturer's instructions. Briefly, one drop of each QSC microsphere was added to a 5 mL polypropylene tube and PE labeled-anti-CD123 antibody was added at 1 µg/mL concentration to both target cells and microspheres. Tubes were incubated in the dark for 30 minutes at 4° C. Cells and microspheres were washed by adding 2 mL FACS buffer and centrifuging at 2500×G for 5 minutes. One drop of the blank microsphere population was added after washing. Microspheres were analyzed first on the flow cytometer to set the test-specific instrument settings (PMT voltages and compensation). Using the same instrument settings, geometric mean fluorescence values of microspheres and target cells were recorded. A standard curve of antibody binding sites on microsphere populations was generated from geometric mean fluorescence of microsphere populations. Antibody binding sites on target cells were calculated based on geometric mean fluorescence of target cells using the standard curve generated for microspheres in QuickCal spreadsheet (Bangs Laboratories).

To determine suitable target cell lines for evaluating CD123×CD3 bi-specific diabodies, CD123 surface expression levels on target lines Kasumi-3 (AML), Molm13 (AML), THP-1 (AML), TF-1 (Erythroleukemia), and RS4-11 (ALL) were evaluated by quantitative FACS (QFACS). Absolute numbers of CD123 antibody binding sites on the cell surface were calculated using a QFACS kit. As shown in Table 3, the absolute number of CD123 antibody binding sites on cell lines were in the order of Kasumi-3 (high)>Molm13 (medium)>THP-1(medium)>TF-1 (medium low)>RS4-11 (low). The three highest expressing cell lines were the AML cell lines: Kasumi-3, MOLM13, and THP-1. The non-AML cell lines: TF-1 and RS4-11 had medium-low/low expression of CD123, respectively.

TABLE 3

| Target Cell Line | CD123 Surface Expression (Antibody Binding Sites) |
|---|---|
| Kasumi-3 | 118620 |
| Molm13 | 27311 |
| THP-1 | 58316 |
| TF-1 | 14163 |
| RS4-11 | 957 |
| A498 | Negative |
| HT29 | Negative |

Example 3

CTL Cytotoxicity Assay (LDH Release Assay)

Adherent target tumor cells were detached with 0.25% Trypsin-EDTA solution and collected by centrifugation at 1000 rpm for 5 min. Suspension target cell lines were harvested from the culture, washed with assay medium. The cell concentration and viability were measured by Trypan Blue exclusion using a Beckman Coulter Vi-Cell counter. The target cells were diluted to $4\times10^5$ cells/mL in the assay medium. 50 µL of the diluted cell suspension was added to a 96-well U-bottom cell culture treated plate (BD Falcon Cat #353077).

Three sets of controls to measure target maximal release (MR), antibody independent cellular cytotoxicity (AICC) and target cell spontaneous release (SR) were set up as follows:

1) MR: 200 µL assay medium without CD123×CD3 bi-specific diabodies and 50 µL target cells; detergent added at the end of the experiment to determine the maximal LDH release.
2) AICC: 50 µL assay medium without CD123×CD3 bi-specific diabodies, 50 µL target cells and 100 µL T cells.
3) SR: 150 µL medium without CD123×CD3 bi-specific diabodies and 50 µL target cells.

CD123×CD3 bi-specific diabodies (DART-A, DART-A w/ABD and DART-B) and controls were initially diluted to a concentration of 4 µg/mL, and serial dilutions were then prepared down to a final concentration of 0.00004 ng/mL (i.e., 40 fg/mL). 50 µL of dilutions were added to the plate containing 50 µL target cells/well.

Purified T cells were washed once with assay medium and resuspended in assay medium at cell density of $2\times10^6$ cells/mL. $2\times10^5$ T cells in 100 µL were added to each well, for a final effector-to-target cell (E:T) ratio of 10:1. Plates were incubated for approximately 18 hr at 37° C. in 5% $CO_2$.

Following incubation, 25 µL of 10× lysis solution (Promega # G182A) or 1 mg/mL digitonin was added to the maximum release control wells, mixed by pipetting 3 times and plates were incubated for 10 min to completely lyse the target cells. The plates were centrifuged at 1200 rpm for 5 minutes and 50 μL of supernatant were transferred from each assay plate well to a flat bottom ELISA plate and 50 μl of LDH substrate solution (Promega # G1780) was added to each well. Plates were incubated for 10-20 min at room temperature (RT) in the dark, then 50 μl of Stop solution was added. The optical density (O.D.) was measured at 490 nm within 1 hour on a Victor2 Multilabel plate reader (Perkin Elmer #1420-014). The percent cytotoxicity was calculated as described below and dose-response curves were generated using GraphPad PRISM5® software.

Specific cell lysis was calculated from O.D. data using the following formula:

Cytotoxicity (%)=100×(*OD* of Sample−*OD* of AICC)/(*OD* of MR−*OD* of SR)

Figure 4:
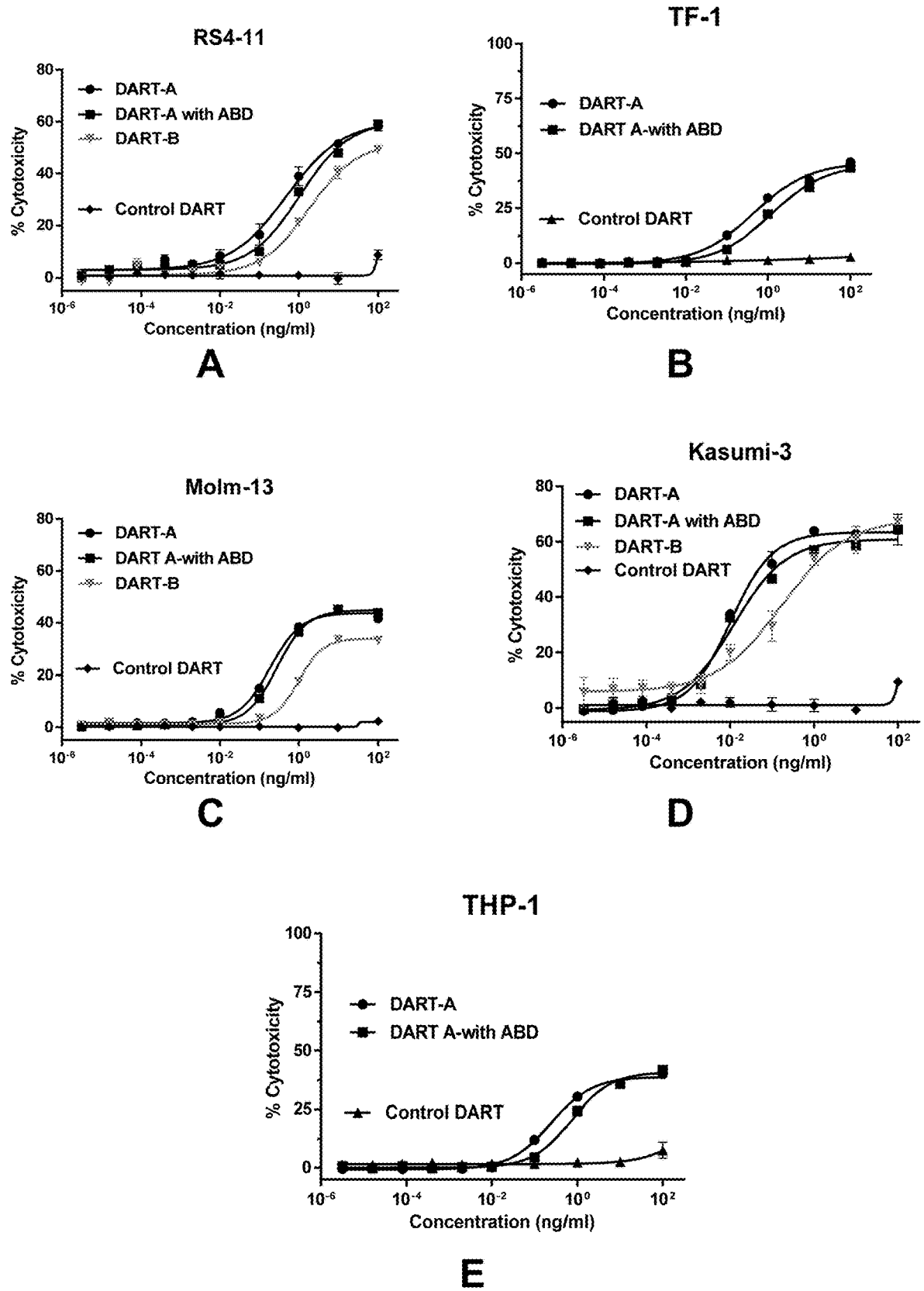
FIG. 4 (Panels A-E) shows the ability of different CD123× CD3 bi-specific diabodies to mediate T cell redirected killing of target cells displaying varying amount of CD123. The Figure provides dose-response curves indicating that the sequence-optimized CD123×CD3 bi-specific diabody ("DART-A") having an Albumin-Binding Domain (DART-A with ABD "w/ABD") exhibited greater cytotoxicity than a control bi-specific diabody (Control DART) or a non-sequence-optimized CD123×CD3 bi-specific diabody ("DART-B") in multiple target cell types: RS4-11 (Panel A); TF-1 (Panel B); Molm-13 (Panel C); Kasumi-3 (Panel D); and THP-1 (Panel E) at an E:T (effector:target) ratio of 10:1.

Redirected Killing of Target Cell Lines with Different Levels of CD123 Surface Levels:

The CD123×CD3 bi-specific diabodies exhibited a potent redirected killing ability with concentrations required to achieve 50% of maximal activity (EC50s) in sub-ng/mL range, regardless of CD3 epitope binding specificity (DART-A versus DART-B) in target cell lines with high CD123 expression, Kasumi-3 (EC50=0.01 ng/mL) (FIG. 4 Panel D), medium CD123-expression, Molm13 (EC50=0.18 ng/mL) and THP-1 (EC50=0.24 ng/mL) (FIG. 4, Panel C and E, respectively) and medium low or low CD123 expression, TF-1 (EC50=0.46 ng/mL) and RS4-11 (EC50=0.5 ng/mL) (FIG. 4, Panel B and A, respectively). Similarly, CD123×CD3 bi-specific molecules mediated redirected killing was also observed with multiple target cell lines with T cells from different donors and no redirected killing activity was observed in cell lines that do not express CD123. Results are summarized in Table 4.

TABLE 4

| Target cell line | CD123 surface expression (antibody binding sites) | EC50 of Sequence-optimized CD123 × CD3 bi-specific diabodies (ng/mL) E:T = 10:1 | Max % killing |
|---|---|---|---|
| Kasumi-3 | 118620 | 0.01 | 94 |
| Molm13 | 27311 | 0.18 | 43 |
| THP-1 | 58316 | 0.24 | 40 |
| TF-1 | 14163 | 0.46 | 46 |
| RS4-11 | 957 | 0.5 | 60 |
| A498 | Negative | No activity | No activity |
| HT29 | Negative | No activity | No activity |

Should it be necessary to replicate this example it will be appreciated that one of skill in the art may, within reasonable and acceptable limits, vary the above-described protocol in a manner appropriate for replicating the described results. Thus, the exemplified protocol is not intended to be adhered to in a precisely rigid manner.

Example 4

T Cell Activation During Redirected Killing by Sequence-Optimized CD123×CD3 Bi-Specific Diabodies (DART-A, DART-A w/ABD and DART-A w/Fc)

The sequence-optimized CD123×CD3 bi-specific diabodies exhibited a potent redirected killing ability regardless of the presence or absence of half-life extension technology (DART-A versus DART-A w/ABD versus DART-A w/Fc) in target cell lines with high CD123 expression, Kasumi-3, and medium, THP-1, CD123-expression, (FIG. 5, Panels A and B, respectively) To characterize T cell activation during sequence-optimized CD123×CD3 bi-specific diabody mediated redirected killing process, T cells from redirected killing assays were stained for T cell activation marker CD25 and analyzed by FACS. As shown in FIG. 5, Panel D, CD25 was up-regulated in CD8 T cells in a dose-dependent manner indicating that sequence-optimized CD123×CD3 bi-specific diabodies induce T cell activation in the process of redirected killing. Conversely, in the absence of target cells there is no activation of CD8 T cells (FIG. 5, Panel C) indicating the sequence-optimized CD123×CD3 bi-specific diabodies do not activate T cells in the absence of target cells. Likewise, CD8 T cells are not activated when incubated with target cells and a control bi-specific diabody (Control DART) (FIG. 5, Panel D) indicating the requirement of cross-linking the T cell and target cell with the sequence-optimized CD123×CD3 bi-specific diabodies.

Example 5

Intracellular Staining for Granzyme B and Perforin

To determine the intracellular levels of granzyme B and perforin in T cells, a CTL assay was setup as described above. After approximately 18 h, cells from the assay plate were stained with anti-CD4 and anti-CD8 antibodies by incubating for 30 minutes at 4° C. Following surface staining, cells were incubated in 100 μL fixation and permeabilization buffer (BD BioSciences) for 20 min at 4° C. Cells were washed with permeabilization/wash buffer (BD BioSciences) and incubated in 50 μL of granzyme B and a perforin antibody mixture (prepared in 1× permeabilization/wash buffer) at 4° C. for 30 minutes. Then cells were washed with 250 μL permeabilization/wash buffer and resuspended in permeabilization/wash buffer for FACS acquisition.

Figure 6:
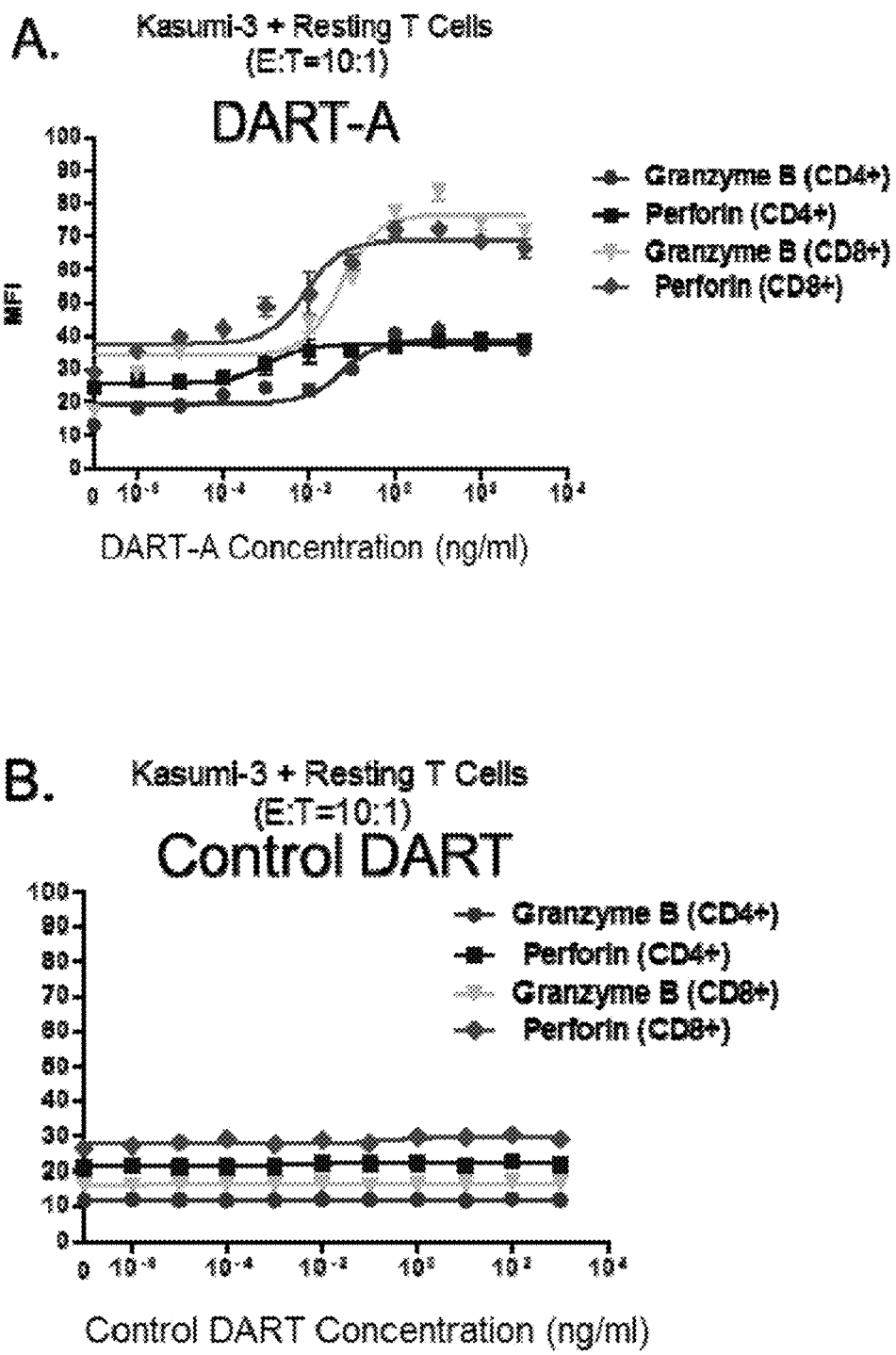
FIG. 6 (Panels A-B) shows Granzyme B and Perforin levels in CD4 and CD8 T cells after treatment with the sequence-optimized CD123×CD3 bi-specific diabody (DART-A) (Panel A) or a control bi-specific diabody (Control DART) (Panel B) in the presence of Kasumi-3 target cells and resting T cells at an E:T ratio of 10:1.

Upregulation of Granzyme B and Perforin by Sequence-Optimized CD123×CD3 Bi-Specific Diabody (DART-A) in T Cells During Redirected Killing To investigate the possible mechanism for sequence-optimized CD123×CD3 bi-specific diabody (DART-A) mediated cytotoxicity by T cells, intracellular granzyme B and perforin levels were measured in T cells after the redirected killing. Dose-dependent upregulation of granzyme B and perforin levels in both CD8 and CD4 T cells was observed following incubation of T cells and Kasumi-3 cells with DART-A (FIG. 6, Panel A). Interestingly, the upregulation was almost two-fold higher in CD8 T cells compared to CD4 T cells (FIG. 6, Panel A). When the assay was performed in the presence of granzyme B and perforin inhibitors no cell killing was observed. There was no upregulation of granzyme B or perforin in CD8 or CD4 T cells when T cells were incubated with Kasumi-3 target cells and a control bi-specific diabody (Control DART) (FIG. 5, Panel B). These data indicate that DART-A mediated target cell killing may be mediated through granzyme B and perforin mechanisms.

Example 6

In Vivo Antitumor Activity of Sequence-Optimized CD123×CD3 Bi-Specific Diabody (DART-A)

Isolation of PBMCs and T Cells from Human Whole Blood
PBMCs from healthy human donors were isolated from whole blood by using Ficoll gradient centrifugation. In brief, whole blood was diluted 1:1 with sterile PBS. Thirty-five mL of the diluted blood was layered onto 15 mL Ficoll- Paque™ Plus in 50-mL tubes and the tubes were centrifuged at 1400 rpm for 20 min with the brake off The buffy coat layer between the two phases was collected into a 50 mL tube and washed with 45 mL PBS by centrifuging the tubes at 600×g (1620 rpm) for 5 min. The supernatant was discarded and the cell pellet was washed once with PBS and viable cell count was determined by Trypan Blue dye exclusion. The PBMCs were resuspended to a final concentration of $2.5 \times 10^6$ cells/mL in complete medium (RPMI 1640, 10% FBS, 2 mM Glutamine, 10 mM HEPES, 100μ/100μ/mL penicillin/Streptomycin (P/S).

T Cell Isolation:

Untouched T cells were isolated by negative selection from PBMCs from human whole blood using Dynabeads Untouched Human T Cell isolation kit (Life Technologies) according to manufacturer's instructions. After the isolation, T cells were cultured overnight in RPMI medium with 10% FBS, 1% penicillin/Streptomycin.

Tumor Model

Human T cells and tumor cells (Molm13 or RS4-11) were combined at a ratio of 1:5 ($1 \times 10^6$ and $5 \times 10^6$, respectively) and suspended in 200 μL of sterile saline and injected subcutaneously (SC) on Study Day 0 (SD0). Sequence-optimized CD123×CD3 bi-specific diabody (DART-A) or a control bi-specific diabody (Control DART) were administered intravenously (IV) via tail vein injections in 100 μL as outlined in Table 5 (MOLM13) and Table 6 (RS4-11).

TABLE 5

Study Design for MOLM13 Model

| Treatment Group | Dose (mg/kg) | Schedule | Number of Animals |
|---|---|---|---|
| Vehicle Control (MOLM-13 cells alone implanted or + T cells) | — | SD0, 1, 2, 3 | 8 |
| DART-A | 0.5 | SD0, 1, 2, 3 | 8 |
| DART-A | 0.2 | SD0, 1, 2, 3 | 8 |
| DART-A | 0.1 | SD0, 1, 2, 3 | 8 |
| DART-A | 0.02 | SD0, 1, 2, 3 | 8 |
| DART-A | 0.004 | SD0, 1, 2, 3 | 8 |
| DART-A | 0.0008 | SD0, 1, 2, 3 | 8 |
| DART-A | 0.00016 | SD0, 1, 2, 3 | 8 |

TABLE 6

Study Design for RS4-11 Model

| Treatment Group | Dose (mg/kg) | Schedule | Number of Animals |
|---|---|---|---|
| Vehicle Control (RS4-11 cells alone implanted) | — | SD0, 1, 2, 3 | 8 |
| Vehicle Control (RS4-11 + T cells implanted) | — | SD0, 1, 2, 3 | 8 |
| Control DART | 0.2 | SD0, 1, 2, 3 | 8 |
| DART-A | 0.5 | SD0, 1, 2, 3 | 8 |
| DART-A | 0.2 | SD0, 1, 2, 3 | 8 |
| DART-A | 0.1 | SD0, 1, 2, 3 | 8 |
| DART-A | 0.02 | SD0, 1, 2, 3 | 8 |
| DART-A | 0.004 | SD0, 1, 2, 3 | 8 |

Data Collection and Statistical Analysis:

Animal Weights—

Individual animal weights were recorded twice weekly until study completion beginning at the time of tumor cell injection.

Moribundity/Mortality—

Animals were observed twice weekly for general moribundity and daily for mortality. Animal deaths were assessed as drug-related or technical based on factors including gross observation and weight loss; animal deaths were recorded daily.

Tumor Volume—

Individual tumor volumes were recorded twice weekly beginning within one week of tumor implantation and continuing until study completion.

$$\text{Tumor Volume}(\text{mm}^3) = \frac{\text{Length}(\text{mm}) \times \text{width}^2}{2}$$

Animals experiencing technical or drug-related deaths were censored from the data calculations.

Tumor Growth Inhibition—

Tumor growth inhibition (TGI) values were calculated for each group containing treated animals using the formula:

$$1 - \frac{\text{Mean Final Tumor Volume (Treated)} - \text{Mean Initial Tumor Volume (Treated)}}{\text{Mean Final Tumor Volume (Control)} - \text{Mean Initial Tumor Volume (Control)}} \times 100$$

Animals experiencing a partial or complete response, or animals experiencing technical or drug-related deaths were censored from the TGI calculations. The National Cancer Institute criteria for compound activity is TGI>58% (Corbett et al. (2004) Anticancer Drug Development Guide; Totowa, N.J.: Humana 99-123).

Partial/Complete Tumor Response—

Individual mice possessing tumors measuring less than 1 mm$^3$ on Day 1 were classified as having partial response (PR) and a percent tumor regression (% TR) value was determined using the formula:

$$1 - \frac{\text{Final Tumor Volume}(\text{mm}^3)}{\text{Initial Tumor Volume}(\text{mm}^3)} \times 100\%$$

Individual mice lacking palpable tumors were classified as undergoing a complete response (CR).

Tumor Volume Statistics—

Statistical analyses were carried out between treated and control groups comparing tumor volumes. For these analyses, a two-way analyses of variance followed by a Bonferroni post-test were employed. All analyses were performed using GraphPad PRISM® software (version 5.02). Weight and tumor data from individual animals experiencing technical or drug-related deaths were censored from analysis. However, tumor data from animals reporting partial or complete responses were included in these calculations.

MOLM13 Results

The AML cell line MOLM13 was pre-mixed with activated T cells and implanted SC in NOD/SCID gamma (NSG) knockout mice (N=8/group) on SD0 as detailed above. The MOLM13 tumors in the vehicle-treated group (MOLM13 cells alone or plus T cells) demonstrated a relatively aggressive growth profile in vivo (FIG. 7, Panels A and B). At SD8, the average volume of the tumors in the vehicle-treated group was 129.8±29.5 mm$^3$ and by SD15 the tumors had reached an average volume of 786.4±156.7 mm³. By the end of the experiment on SD18, the tumors had reached an average volume of 1398.8±236.9 mm³.

Treatment with DART-A was initiated on the same day the tumor cell/T cell mixture was implanted [(SD0)] and proceeded subsequently with daily injections for an additional 7 days for a total of 8 daily injections. The animals were treated with DART-A at 9 dose levels (0.5, 0.2, 0.1, 0.02, and 0.004 mg/kg and 20, 4, 0.8 and 0.16 µg/kg). Results are shown in FIG. 7, Panel A (0.5, 0.2, 0.1, 0.02, and 0.004 mg/kg) and FIG. 7, Panel B (20, 4, 0.8 and 0.16 µg/kg). By Study Day 11, the growth of the MOLM13 tumors was significantly inhibited at the 0.16, 0.5, 0.2, 0.1, 0.02, and 0.004 mg/kg dose levels ($p<0.001$). Moreover, the treatment of the MOLM13 tumor-bearing mice at the 20 and 4 µg/kg dose levels resulted in 8/8 and 7/8 CRs, respectively. By the end of the experiment on SD18, the average volume of the tumors treated with DART-A at the 0.8-20 µg/kg) ranged from 713.6.0±267.4 to 0 mm³, all of which were significantly smaller than the tumors in the vehicle-treated control group. The TGI values were 100, 94, and 49% for the 20, 4, and 0.8 µg/kg dose groups, respectively. In comparison to the vehicle-treated MOLM13 tumor cell group, the groups that received DART-A at the 20 and 4 µg/kg dose level reached statistical significance by SD15 while the group treated with 0.8 µg/kg reached significance on SD18.

RS4-11 Results

Figure 8:
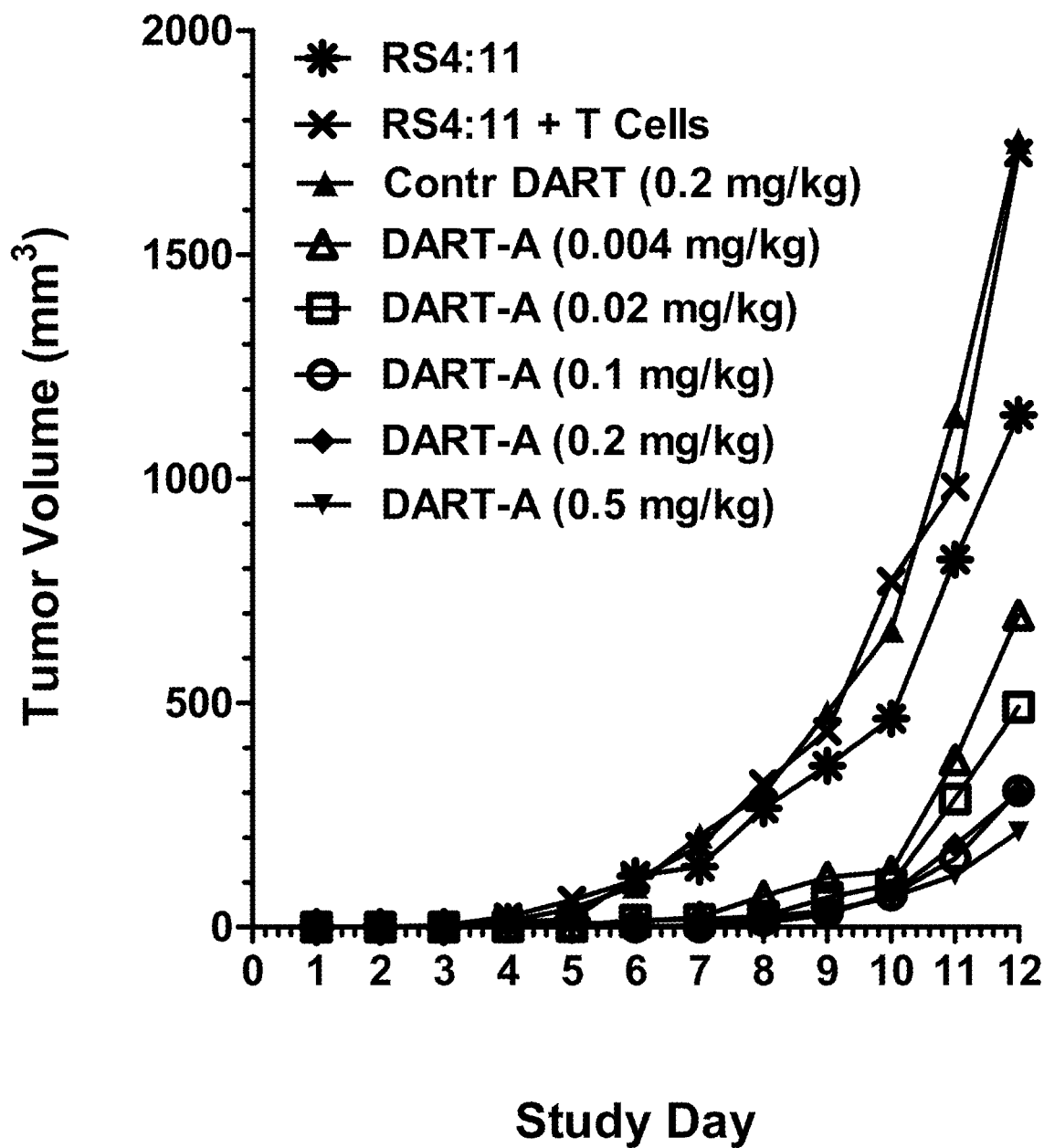
FIG. 8 shows the in vivo antitumor activity of the sequence-optimized CD123×CD3 bi-specific diabody (DART-A) on RS4-11 cells (ALL with monocytic features). Cells were co-mixed with T cells and implanted subcutaneously (T:E 1:1) in NSG mice. Intravenous treatment was once daily for 4 days (QD×4) starting at implantation. Various concentrations of DART-A were compared to a control bi-specific diabody (Control DART).

The ALL cell line RS4-11 was pre-mixed with activated T cells and implanted SC in NOD/SCID gamma knockout mice (N=8/group) on SD0 as detailed above. The RS4-11 tumors in the vehicle-treated group (RS4-11 cells alone or plus T cells) demonstrated a relatively aggressive growth profile in vivo (FIG. 8).

Treatment with DART-A was initiated on the same day the tumor cell/T cell mixture was implanted [(SD0)] and proceeded subsequently with daily injections for an additional 3 days for a total of 4 daily injections. The animals were treated with DART-A at 5 dose levels (0.5, 0.2, 0.1, 0.02, and 0.004 mg/kg). Results are shown in FIG. 8.

Sequence-optimized CD123×CD3 bi-specific diabody (DART-A) effectively inhibited the growth of both MOLM13 AML and RS4-11ALL tumors implanted SC in NOD/SCID mice in the context of the Winn model when dosing was initiated on the day of implantation and continued for 3 or more consecutive days. Based on the criteria established by the National Cancer Institute, DART-A at the 0.1 mg/kg dose level and higher (TGI>58) is considered active in the RS4-11 model and an DART-A dose of 0.004 mg/kg and higher was active in the MOLM13 model. The lower DART-A doses associated with the inhibition of tumor growth in the MOLM13 model compared with the RS4-11 model are consistent with the in vitro data demonstrating that MOLM13 cells have a higher level of CD123 expression than RS4-11 cells, which correlated with increased sensitivity to DART-A mediated cytotoxicity in vitro in MOLM13 cells.

Should it be necessary to replicate this example it will be appreciated that one of skill in the art may, within reasonable and acceptable limits, vary the above-described protocol in a manner appropriate for replicating the described results. Thus, the exemplified protocol is not intended to be adhered to in a precisely rigid manner.

Example 7

CD123 Surface Expression on Leukemic Blast Cells and Stem Cells in Primary Tissue Sample from AML Patient 1

To define the CD123 expression pattern in AML patient 1 primary samples, cryopreserved primary AML patient bone marrow and PBMC samples were evaluated for CD123 surface expression on leukemic blast cells.

AML Bone Marrow Sample—Clinical Report
Age: 42
Gender: Female
AML Subtype: M2
Cancer cell percentage based on morphology: 67.5%
Bone marrow immunophenotyping:
CD15=19%, CD33=98.5%, CD38=28.8%, CD45=81.8%, CD64=39.7%,
CD117=42.9%, HLA-DR=17%, CD2=1.8%, CD5=0.53%, CD7=0.2%,
CD10=0.41%, CD19=1.1%, CD20=1.4%, CD22=0.71% CD34=0.82%

CD123 Expression in Leukemic Blast Cells in Bone Marrow Mononucleocytes (BM MNC)

Figure 9:
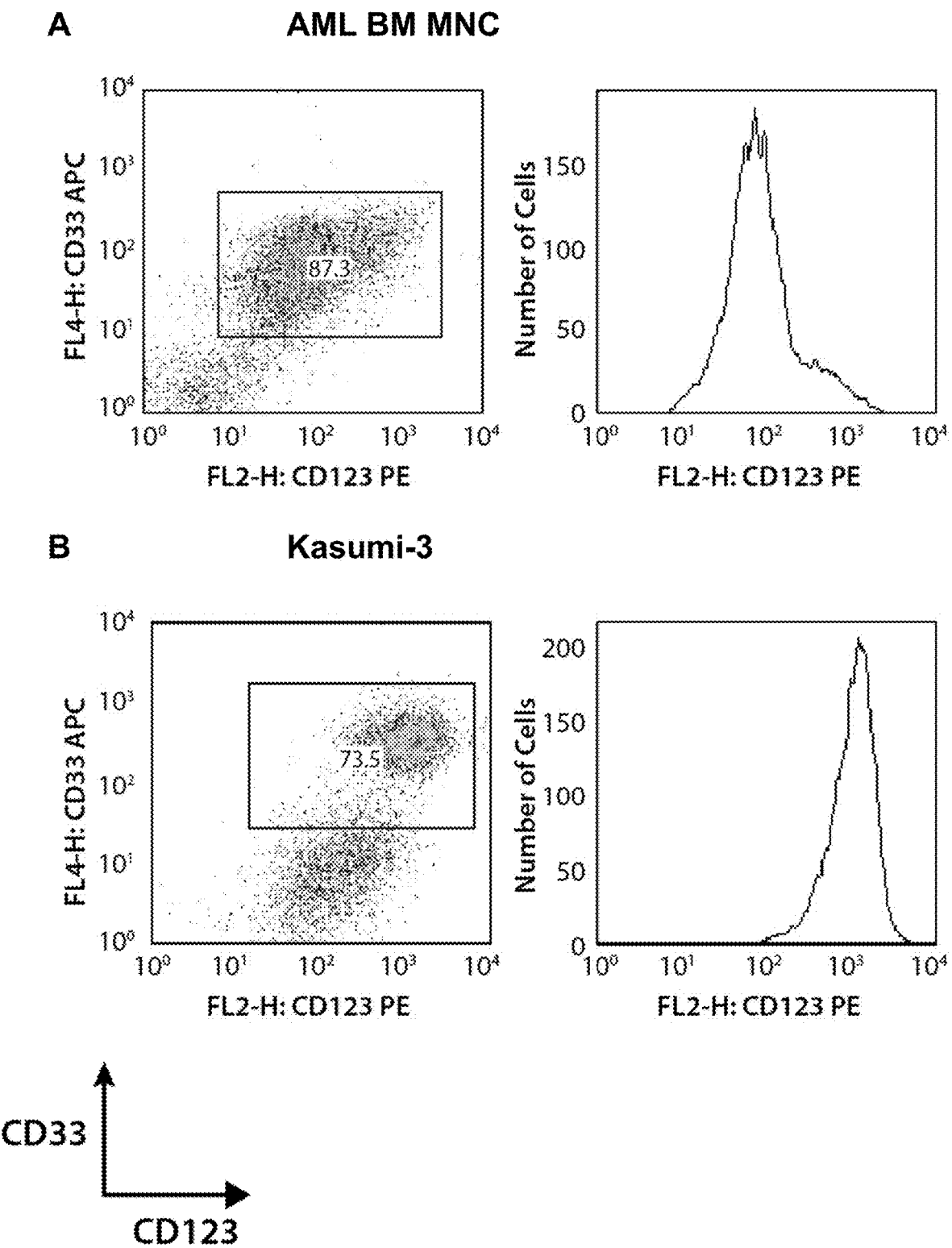
FIG. 9 (Panels A-B) shows CD123+ blasts in bone marrow mononucleocytes (BM MNC) and peripheral blood mononucleocytes (PBMCs) from AML patient 1 (Panel A) compared to Kasumi-3 AML cell line (Panel B).

A total of $0.5 \times 10^6$ bone marrow mononucleocytes (BM MNC) and peripheral blood mononucleocytes (PBMC)) from AML patient 1 were evaluated for CD123 expression. The Kasumi-3 cell line was included as a control. Leukemic blast cells were identified using the myeloid marker CD33. As shown in FIG. 9, Panel A, 87% of the cells from AML bone marrow from patient 1 expressed CD123 and CD33. CD123 expression levels were slightly lower than the CD123 high-expressing Kasumi-3 AML cell line (FIG. 9, Panel B).

Example 8

Autologous CTL Killing Assay Using AML Patient Primary Specimens

Cryopreserved primary AML specimen (bone marrow mononucleocytes (BMNC) and peripheral blood mononucleocytes (PBMC)) from AML patient 1 were thawed in RPMI 1640 with 10% FBS and allowed to recover overnight at 37° C. in 5% $CO_2$. Cells were washed with assay medium (RPMI 1640+10% FBS) and viable cell count was determined by Trypan Blue exclusion. 150,000 cells/well in 150 µL assay medium were added to 96-well U-bottom plate (BD Biosciences). Sequence-optimized CD123×CD3 bi-specific diabody (DART-A) was diluted to 0.1, and 0.01 ng/mL and 50 µL of each dilution was added to each well (final volume=200 µL). Control bi-specific diabody (Control DART) was diluted to 0.1 ng/mL and 50 µL of each dilution was added to each well (final volume=200 µL). A separate assay plate was set up for each time point (48, 72, 120 and 144 hours) and plates were incubated at 37° C. in a 5% CO2 incubator. At each time point, cells were stained with CD4, CD8, CD25, CD45, CD33, and CD123 antibodies. Labeled cells were analyzed in FACS Calibur flow cytometer equipped with CellQuest Pro acquisition software, Version 5.2.1 (BD Biosciences). Data analysis was performed using Flowjo v9.3.3 software (Treestar, Inc).T cell expansion was measured by gating on CD4+ and CD8+ populations and activation was determined by measuring CD25 mean fluorescent intensity (MFI) on the CD4+ and CD8+-gated populations. Leukemic blast cell population was identified by CD45+CD33+ gating.

Autologous Tumor Cell Depletion, T Cell Expansion and Activation by Sequence-Optimized CD123×CD3 Bi-Specific Diabody (DART-A) in Primary Specimens from AML Patient 1

To determine the sequence-optimized CD123×CD3 bi-specific diabody (DART-A) mediated activity in AML patient 1, patient samples were incubated with 0.1 ng/mL or 0.01 ng/mL of DART-A and percentages of leukemic blast cells and T cells were measured at different time points following the treatment. Leukemic blast cells were identified by CD45+/CD33+ gating. Incubation of primary AML bone marrow samples with DART-A resulted in depletion of the leukemic cell population over time (FIG. 10, Panel A), accompanied by a concomitant expansion of the residual T cells (FIG. 10, Panel B) and the induction of T cell activation markers (FIG. 10, Panel C). In DART-A treated samples, T cells were expanded from around 7% to around 80% by 120 hours. T cell activation measured by CD25 expression on CD4 and CD8 cells peaked at 72 h and decreased by the 120 h timepoint.

Should it be necessary to replicate this example it will be appreciated that one of skill in the art may, within reasonable and acceptable limits, vary the above-described protocol in a manner appropriate for replicating the described results. Thus, the exemplified protocol is not intended to be adhered to in a precisely rigid manner.

Example 9

CD123 Surface Expression on Leukemic Blast Cells and Stem Cells in Primary Tissue Sample from ALL Patient To define the CD123 expression pattern in ALL patient primary samples, cryopreserved primary ALL patient PBMC sample was evaluated for CD123 surface expression on leukemic blast cells.
CD123 Expression in Leukemic Blast Cells in Peripheral Blood Mononucleocytes (PBMC)

Figure 11:
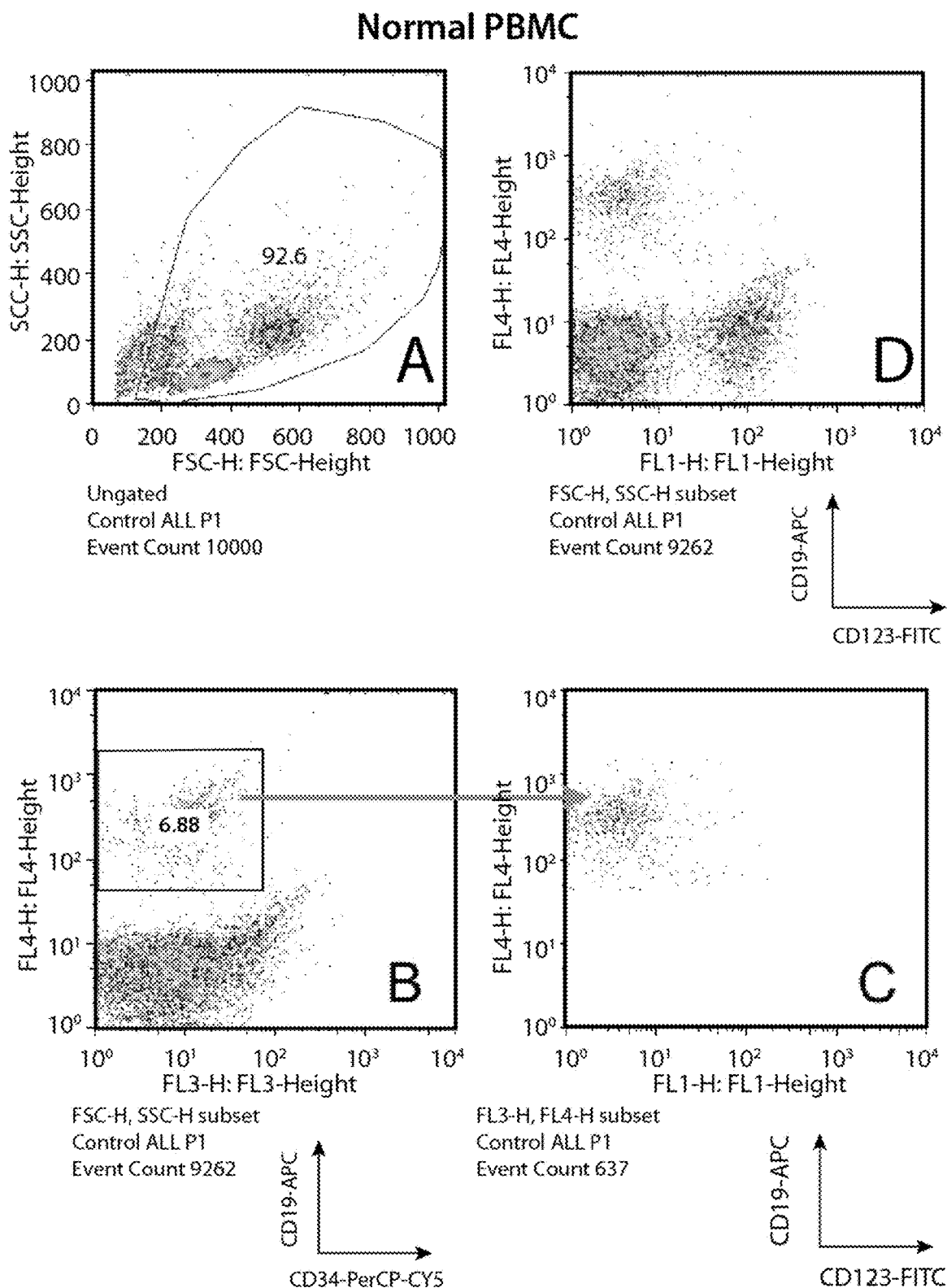
FIG. 11 (Panels A-H) shows the identification of the CD123+ blast population in a primary sample of ALL PBMCs. Panels A and E show the forward and side scatter of the input population of normal PBMC (Panel A) and ALL PBMCs (Panel E). Panels B and F show the identification of the lymphocyte population as primarily B cells (Panel B) and leukemic blast cells (Panel F). Panels C and G show identification of the population of lymphocytes that are CD123+. Panels D and H show the identification of CD19+ cells and CD123+ cells.
Figure 11:
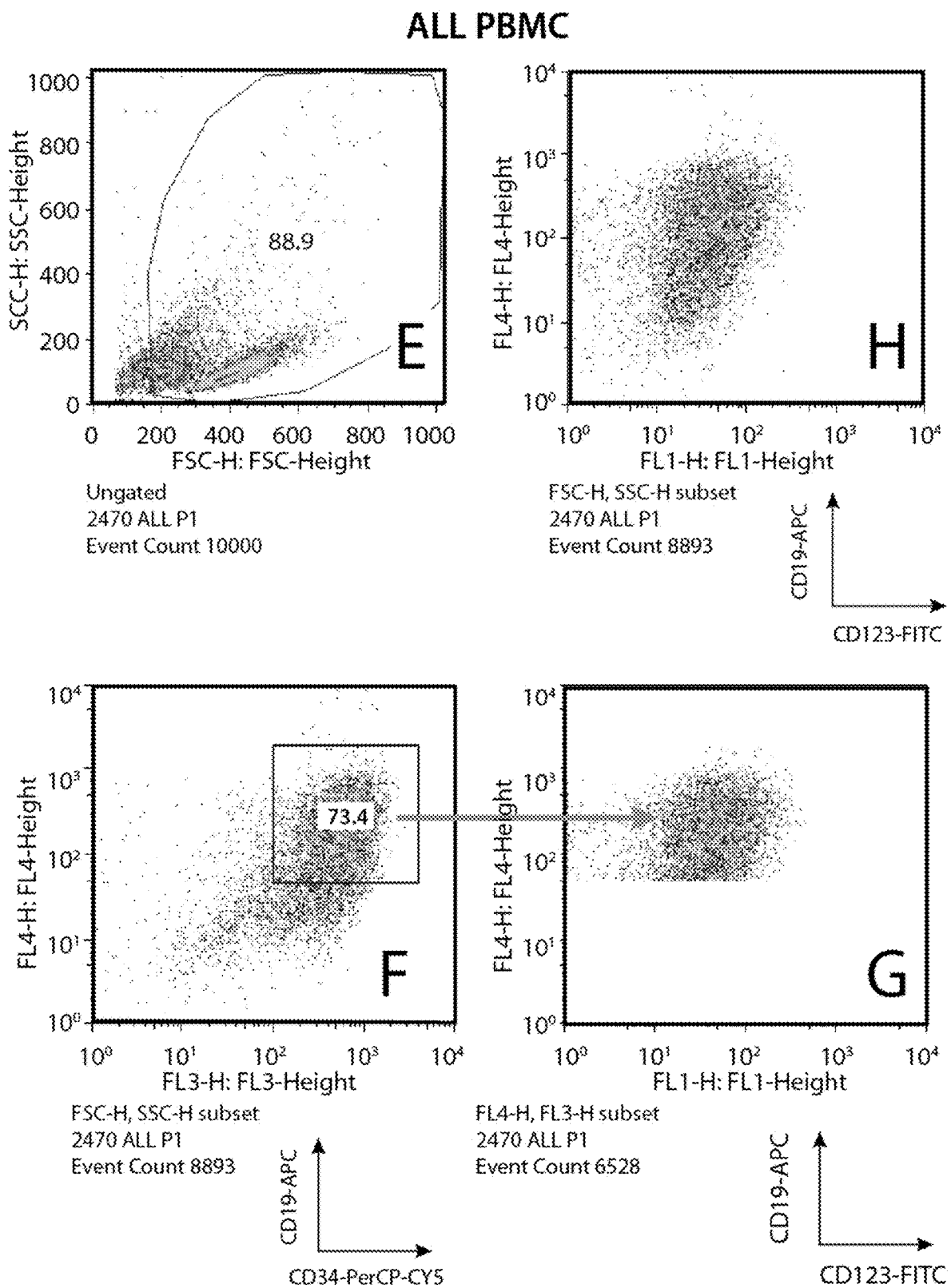

A total of $0.5 \times 10^6$ peripheral blood mononucleocytes (PBMC)) from a healthy donor and an ALL patient were evaluated for CD123 expression. As shown in FIG. 11, Panels E-H, the vast majority of the cells from ALL bone marrow expressed CD123. Conversely, as expected in the normal donor B cells are CD123 negative and pDCs and monocytes are CD123 positive (FIG. 11, Panel D).

Figure 12:
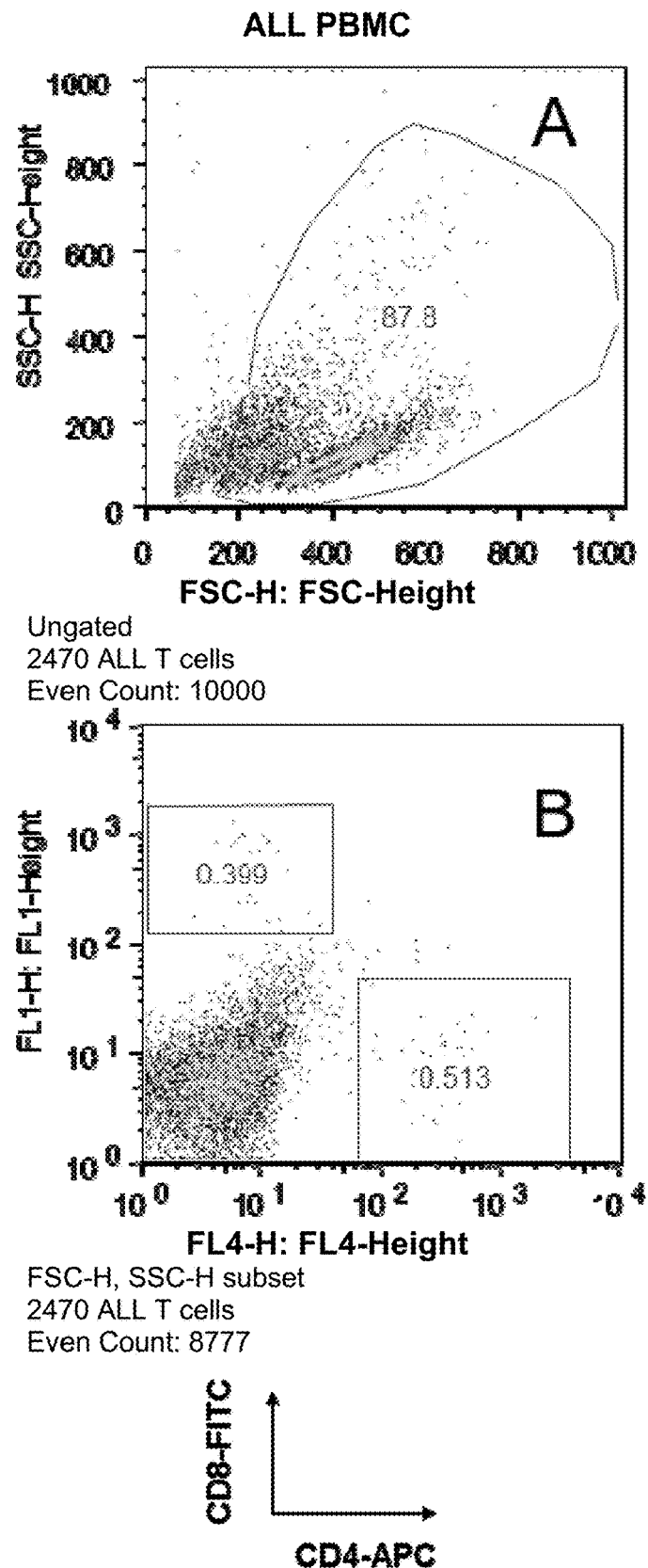
FIG. 12 (Panels A-B) shows the identification of the CD4 and CD8 populations of T cells in a primary sample of ALL PBMCs. Panel A shows the forward and side scatter of the input ALL PBMCs. Panel B shows the CD4 or CD8 populations of T cells present in the samples. The numbers indicate that CD4 T cells represent approximately 0.5% of the total cells and CD8 T cells represent approximately 0.4% of the total cells present in the ALL PBMC sample.

The T cell population was identified in the ALL patent sample by staining the cells for CD4 and CD8. As shown in FIG. 12, Panel B, only a small fraction of the total PBMCs in the ALL patient sample are T cells (approximately 0.5% are CD4 T cells and approximately 0.4% are CD8 T cells.

Example 10

Autologous CTL Killing Assay Using ALL Patient Primary Specimens

Figure 13:
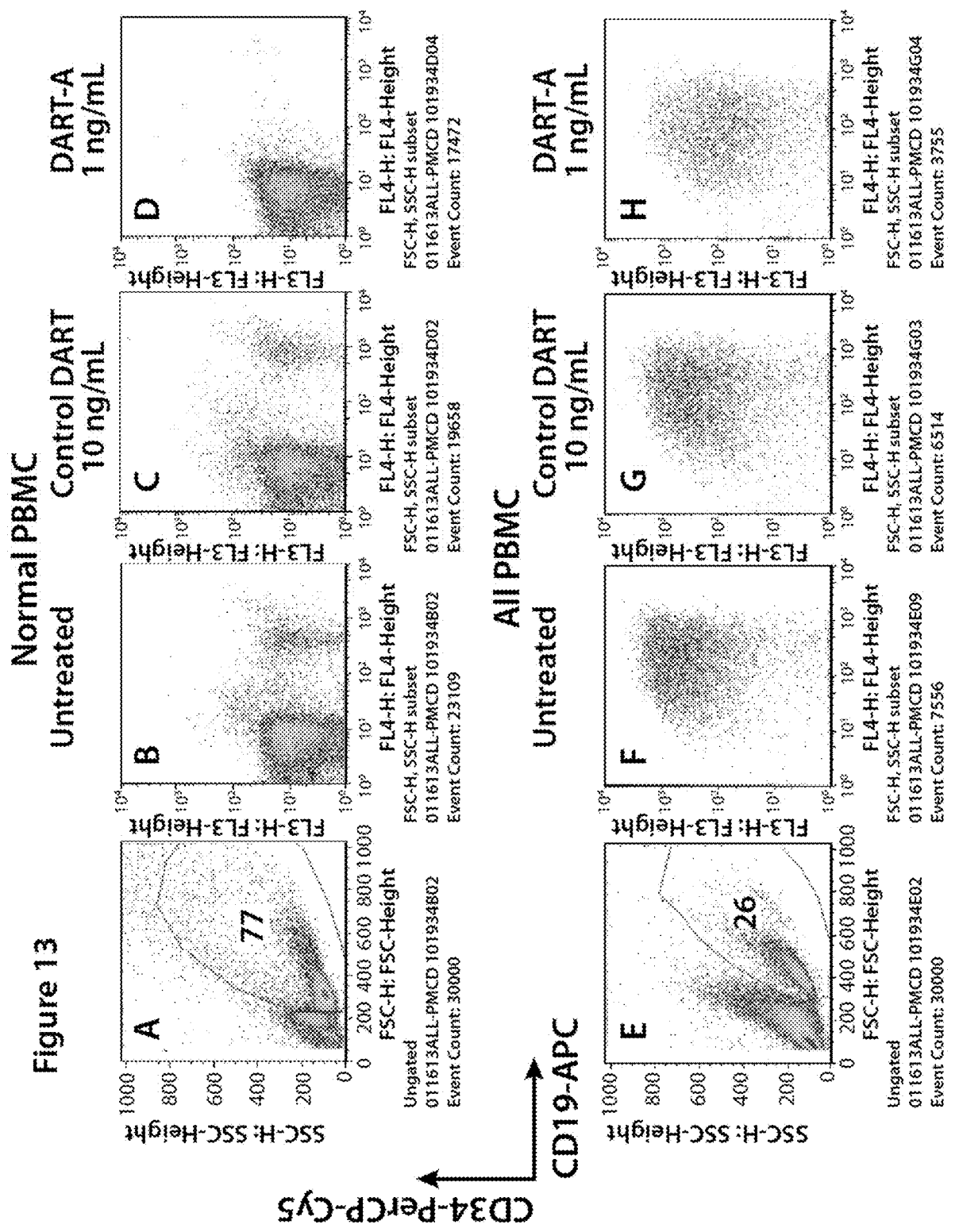
Figure 14:
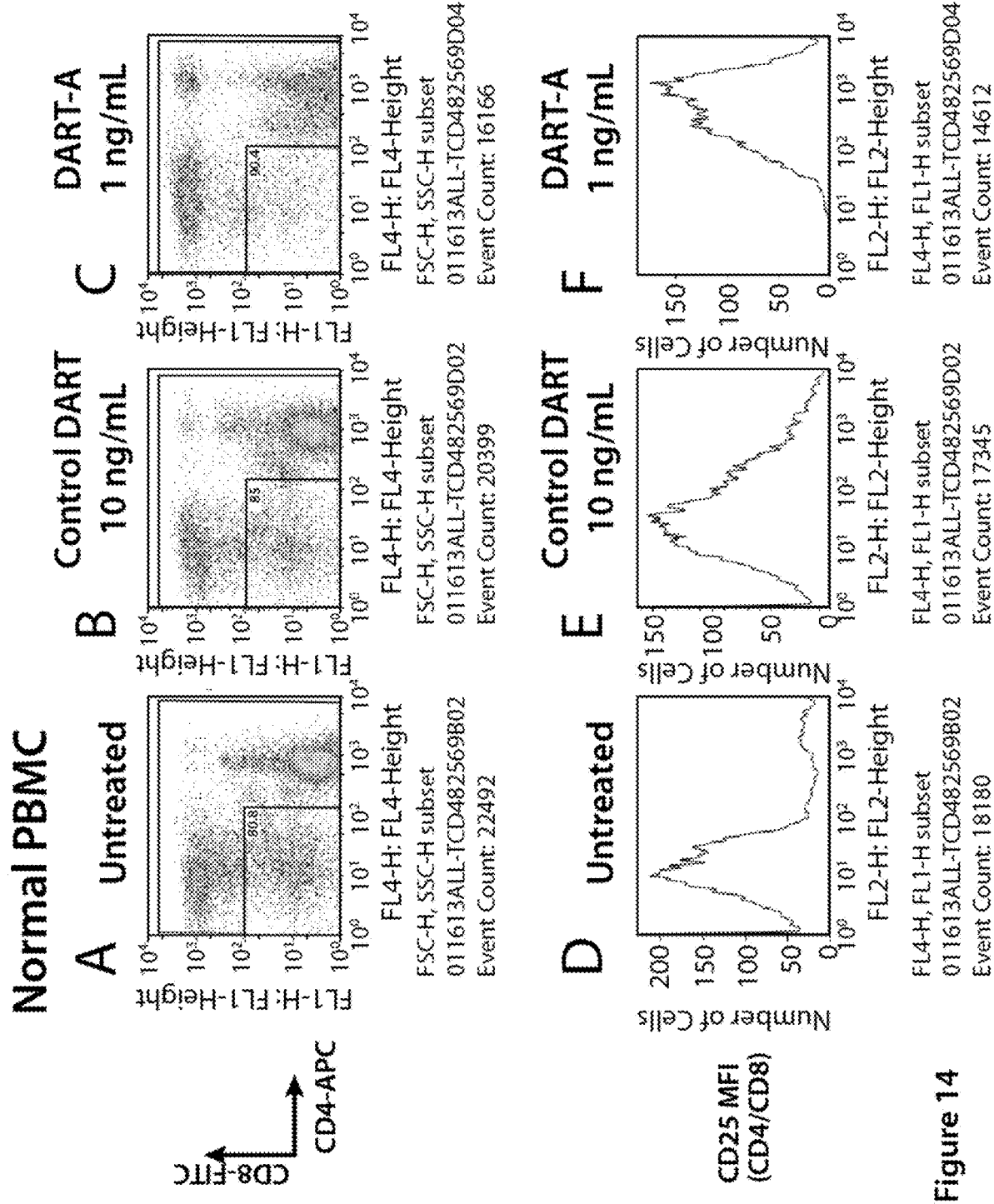
FIG. 14 (Panels A-L) shows the ability of the sequence-optimized CD123×CD3 bi-specific diabody (DART-A) to mediate T cell expansion (Panels A, B, C, G, H and I) and activation (Panels D, E, F, J, K and L) in normal PBMC (Panels A-F) and ALL PBMC (Panels G-L). The cells were untreated (Panels A, D, G and J), or treated with a control bi-specific diabody (Control DART) (Panels B, E, H and K) or DART-A (Panels C, F, I and L) for 7 days.
Figure 14:
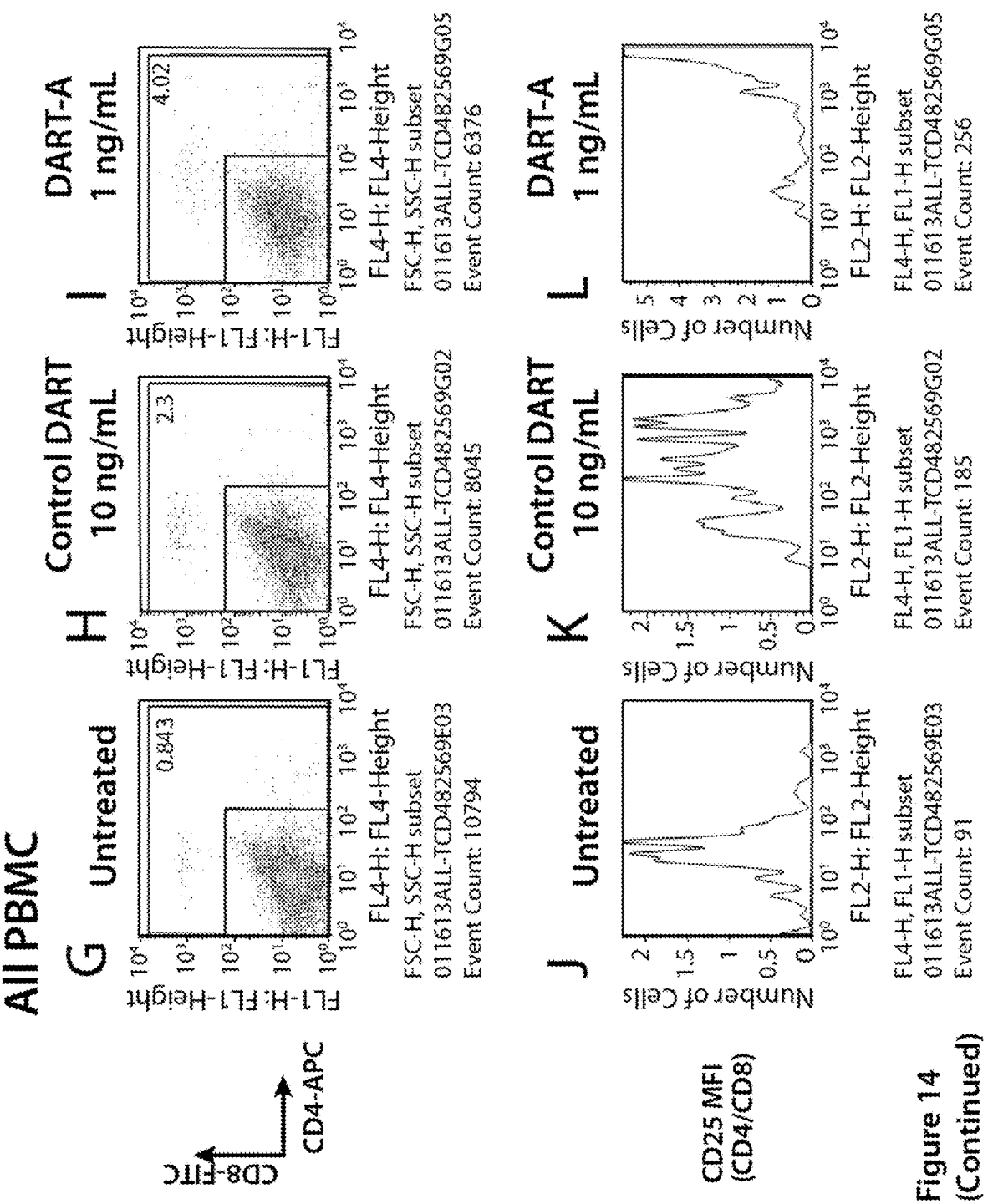

Cryopreserved primary ALL specimen (peripheral blood mononucleocytes (PBMC)) were thawed in RPM 11640 with 10% FBS and allowed to recover overnight at 37° C. in 5% CO2. Cells were washed with assay medium (RPMI 1640+10% FBS) and viable cell count was determined by Trypan Blue exclusion. 150,000 cells/well in 150 μL assay medium were added to 96-well U-bottom plate (BD Biosciences). Sequence-optimized CD123×CD3 bi-specific diabody (DART-A) was diluted to 10, 1 ng/mL and 50 μL of each dilution was added to each well (final volume=200 μL). A separate assay plate was set up for each time point (48, 72, 120 and 144 hours) and plates were incubated at 37° C. in a 5% CO2 incubator. At each time point, cells were stained with CD4, CD8, CD25, CD45, CD33, and CD123 antibodies. Labeled cells were analyzed in FACS Calibur flow cytometer equipped with CellQuest Pro acquisition software, Version 5.2.1 (BD Biosciences). Data analysis was performed using Flowjo v9.3.3 software (Treestar, Inc).T cell expansion was measured by gating on CD4+ and CD8+ populations and activation was determined by measuring CD25 MFI on the CD4$^+$ and CD8$^+$-gated populations. Leukemic blast cell population was identified by CD45$^+$ CD33$^+$ gating.
Autologous Tumor Cell Depletion, T Cell Expansion and Activation by Sequence-Optimized CD123×CD3 Bi-Specific Diabody (DART-A) in Primary Specimens from ALL Patients To determine the sequence-optimized CD123×CD3 bi-specific diabody (DART-A) mediated activity in ALL patient primary patient samples, patient samples were incubated with 1 ng/mL of DART-A and percentages of leukemic blast cells and T cells were measured at different time points following the treatment. Leukemic blast cells were identified by CD45$^+$/CD33$^+$ gating. Incubation of primary ALL bone marrow samples with DART-A resulted in depletion of the leukemic cell population over time compared to untreated control or Control DART (FIG. 13, Panel H versus Panels F and G). When the T cells were counted (CD8 and CD4 staining) and activation (CD25 staining) were assayed, the T cells expanded and were activated in the DART-A sample (FIG. 14, Panels I and L, respectively) compared to untreated or Control DART samples (FIG. 14, Panels H, G, K and J, respectively).

Example 11

CD123 Surface Expression on Leukemic Blast Cells and Stem Cells in Primary Tissue Sample from AML Patient 2

To define the CD123 expression pattern in AML patient 2 primary samples, cryopreserved primary AML patient bone marrow and PBMC samples were evaluated for CD123 surface expression on leukemic blast cells.
CD123 Expression in Leukemic Blast Cells in Bone Marrow Mononucleocytes (BMNC)

Figure 15:
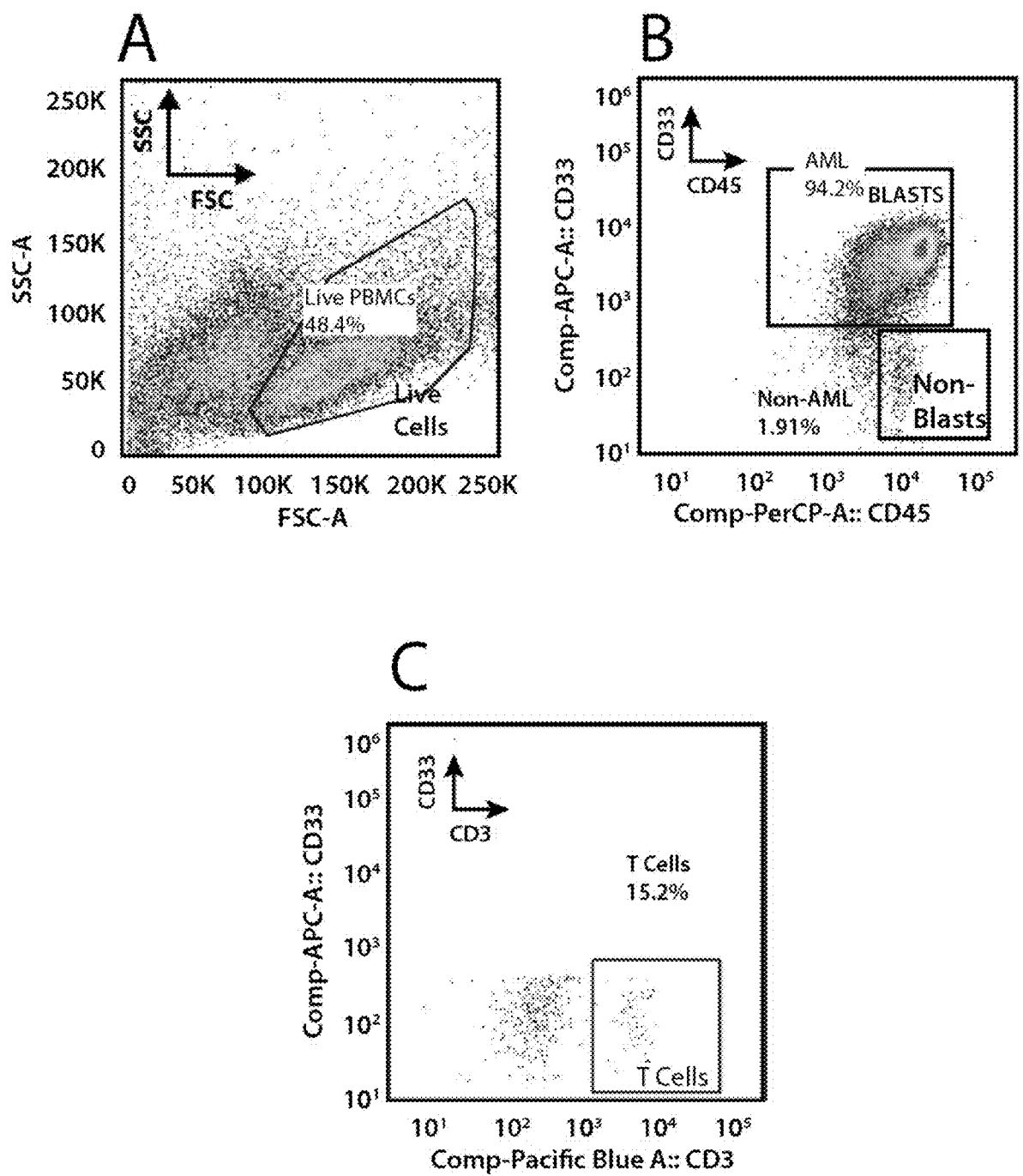
FIG. 15 (Panels A-C) shows the identification of the AML blast population and T cells in a primary AML sample. Panel A shows the forward and side scatter of the input AML PBMCs. Panel B shows the identification of the AML blast population in the AML sample. Panel C shows the identification of the T cell population in the AML sample.

A total of $0.5 \times 10^6$ bone marrow mononucleocytes (BM MNC) and peripheral blood mononucleocytes (PBMC)) from an AML patient 2 were evaluated for leukemic blast cell identification. Leukemic blast cells were identified using the myeloid markers CD33 and CD45. As shown in FIG. 15, Panel B, 94% of the cells from AML bone marrow are leukemic blast cells. The T cell population was identified by CD3 expression. As shown in FIG. 15, Panel C, approximately 15% of the cell from the AML bone marrow and PBMC sample are T cells.

Example 12

Autologous CTL Killing Assay Using AML Patient 2 Primary Specimens

Cryopreserved primary AML specimen (bone marrow mononucleocytes (BM MNC) and peripheral blood mononucleocytes (PBMC)) from AML patient 2 were thawed in RPMI 1640 with 10% FBS and allowed to recover overnight at 37° C. in 5% CO2. Cells were washed with assay medium (RPMI 1640+10% FBS) and viable cell count was determined by Trypan Blue exclusion. 150,000 cells/well in 150 μL assay medium were added to 96-well U-bottom plate (BD Biosciences). Sequence-optimized CD123×CD3 bi-specific diabody (DART-A) and control bi-specific diabody (Control DART) were diluted to 0.1, and 0.01 ng/mL and 50 μL of each dilution was added to each well (final volume=200 μL). A separate assay plate was set up for each time point (48, 72, 120 and 144 hours) and plates were incubated at 37° C. in a 5% CO2 incubator. At each time point, cells were stained with CD4, CD8, CD25, CD45, CD33, and CD123 antibodies. Labeled cells were analyzed in FACS Calibur flow cytometer equipped with CellQuest Pro acquisition software, Version 5.2.1 (BD Biosciences). Data analysis was performed using Flowjo v9.3.3 software (Treestar, Inc). T cell expansion was measured by gating on CD4+ and CD8+ populations and activation was determined by measuring CD25 MFI on the CD4+ and CD8+-gated populations. Leukemic blast cell population was identified by CD45+CD33+ gating.

Autologous Tumor Cell Depletion, T Cell Expansion and Activation in Primary Specimens from AML Patient 2

Figure 16:
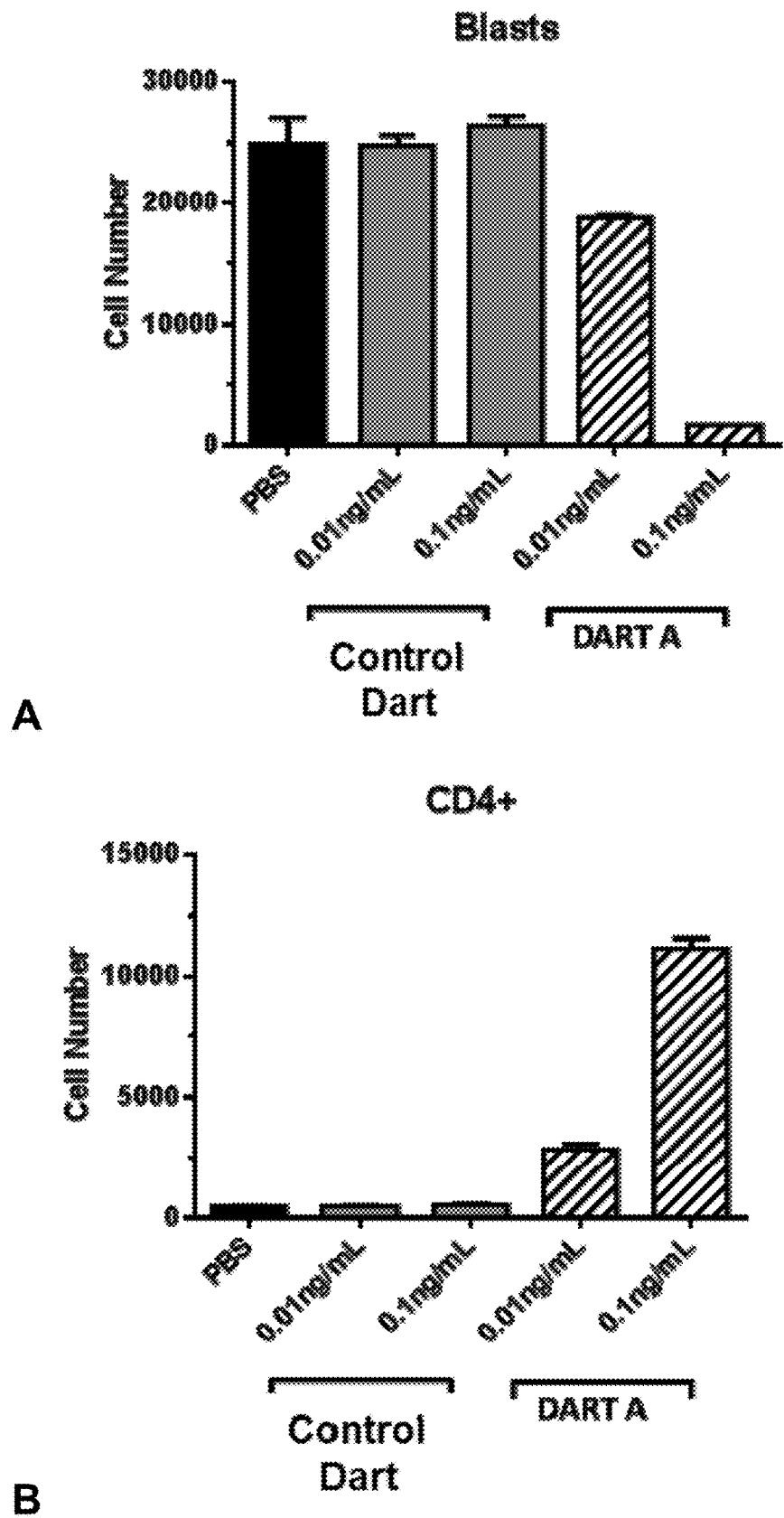
FIG. 16 (Panels A-C) shows the ability of the sequence-optimized CD123×CD3 bi-specific diabody (DART-A) to mediate AML blast depletion with autologous CTL and T cell expansion. Primary AML PBMCs from patient 2 were incubated with PBS, a control bi-specific diabody (Control DART) or DART-A for 144h. Blast cells (Panel A), CD4 T cells (Panel B) and CD8 T cells (Panel C) were counted.
Figure 16:
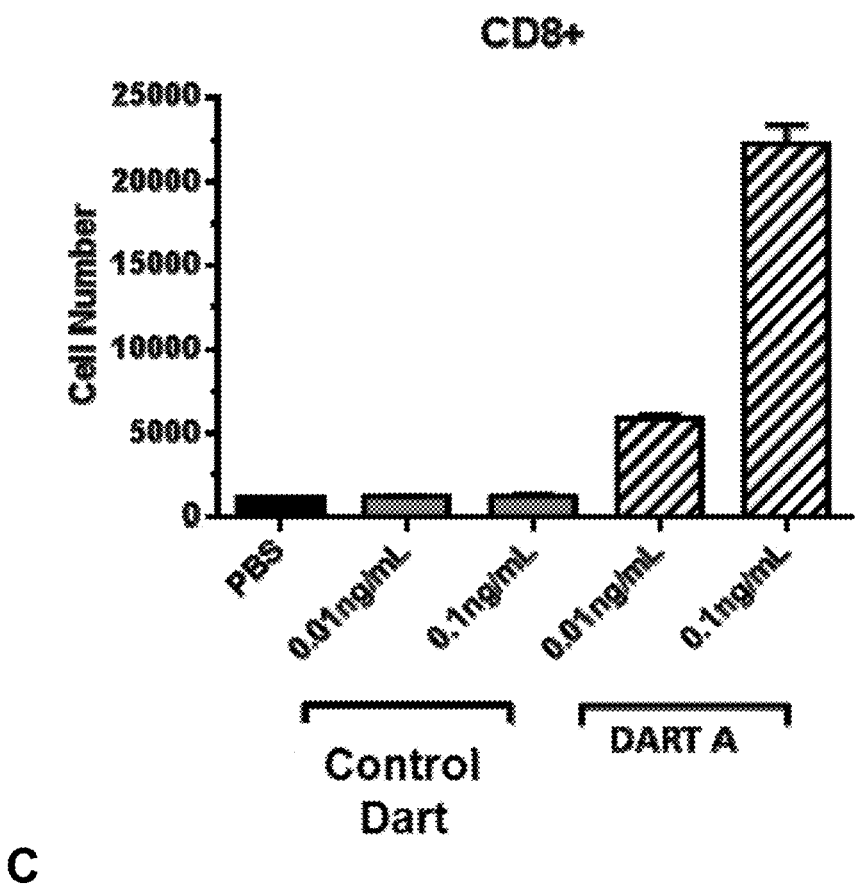
Figure 17:
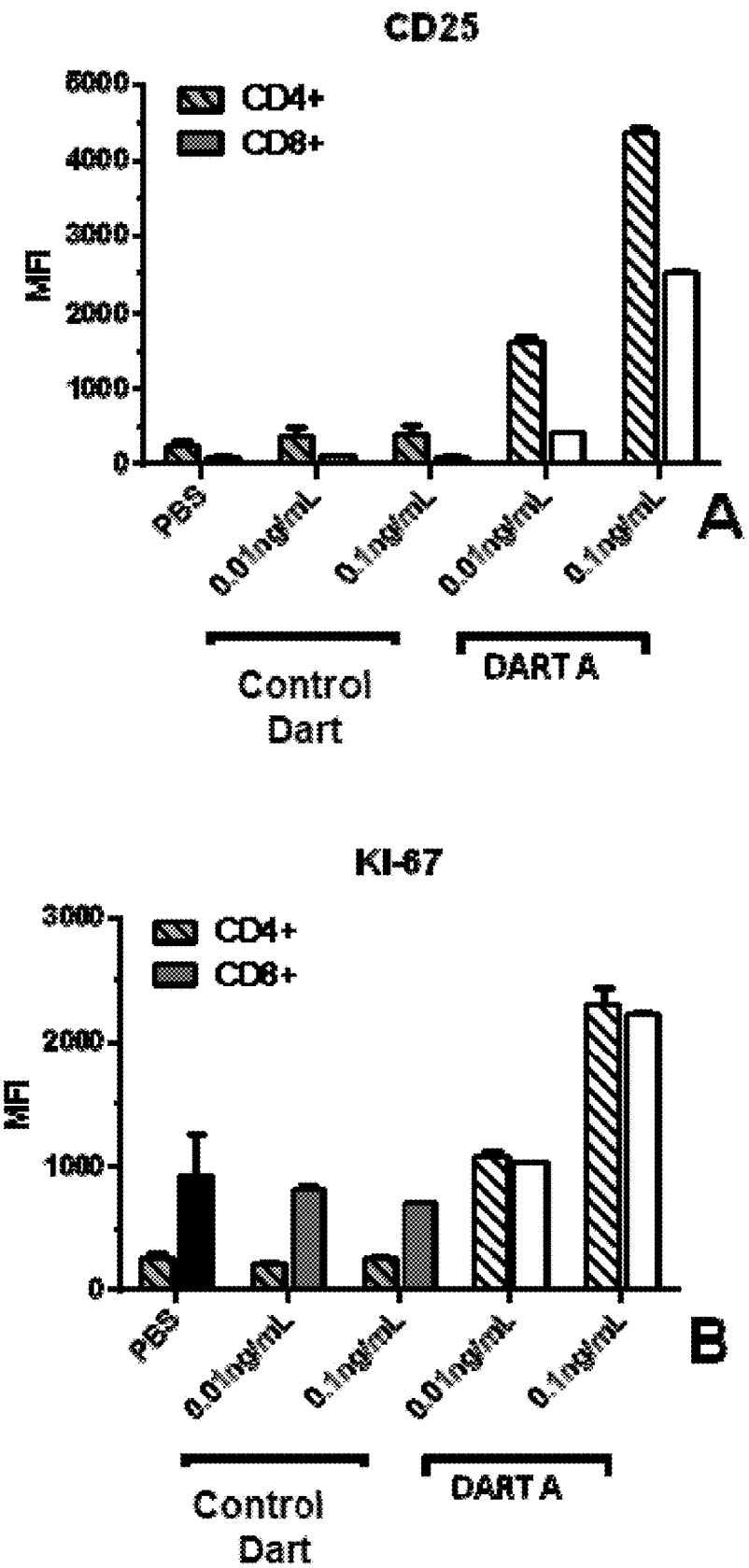
FIG. 17 (Panels A-D) shows the ability of the sequence-optimized CD123×CD3 bi-specific diabody (DART-A) to mediate T cell activation in AML. CD25 (Panel A) and Ki-67 (Panel B) expression was determined for the CD4 and CD8 T cells from AML patient 2 following incubation with a control bi-specific diabody (Control DART) or DART-A with autologous PBMCs. The level of perforin (Panel C) and granzyme B (Panel D) was determined for the CD4 and CD8 T cells from AML patient 2 following incubation with Control DART or DART-A with autologous PBMCs.

To determine the sequence-optimized CD123×CD3 bi-specific diabody (DART-A) mediated activity in AML patient primary patient 2 samples, patient samples were incubated with 0.1 or 0.01 ng/mL of DART-A and percentages of leukemic blast cells and T cells were measured at different time points following the treatment. Incubation of primary AML bone marrow samples with DART-A resulted in depletion of the leukemic cell population over time (FIG. 16, Panel A), accompanied by a concomitant expansion of the residual T cells (both CD4 and CD8) (FIG. 16, Panel B and FIG. 16, Panel C, respectively). To determine if the T cells were activated, cells were stained for CD25 or Ki-67, both markers of T cell activation. As shown in FIG. 17, Panels A and B, incubation of primary AML bone marrow samples with DART-A resulted in T cell activation. These data represent the 144h time point.

Intracellular Staining for Granzyme B and Perforin

To determine the intracellular levels of granzyme B and Perforin in T cells, CTL assay was setup. After approximately 18 h, cells from the assay plate were stained with anti-CD4 and anti-CD8 antibodies by incubating for 30 minutes at 4° C. Following surface staining, cells were incubated in 100 μl Fixation and Permeabilization buffer for 20 min at 4° C. Cells were washed with permeabilization/wash buffer and incubated in 50 μl of granzyme B and perforin antibody mixture prepared in 1× Perm/Wash buffer at 4 C for 30 minutes. Then cells were washed with 250 μl Perm/Wash buffer and resuspended in Perm/Wash buffer for FACS acquisition.

Upregulation of Granzyme B and Perforin by Sequence-Optimized CD123×CD3 Bi-Specific Diabody (DART-A) in T Cells During Redirected Killing.

To investigate the possible mechanism for sequence-optimized CD123×CD3 bi-specific diabody (DART-A) mediated cytotoxicity by T cells, intracellular granzyme B and perforin levels were measured in T cells after the redirected killing. There was no upregulation of granzyme B and perforin when T cells were incubated with control bi-specific diabody (Control DART). Upregulation of granzyme B and perforin levels in both CD8 and CD4 T cells was observed with sequence-optimized CD123×CD3 bi-specific diabody (DART-A) (FIG. 17, Panels C and D). Interestingly, the upregulation was almost two-fold higher in CD8 T cells compared to CD4 T cells (FIG. 17, Panel C and FIG. 17, Panel D). These data indicate that DART-A-mediated target cell killing was mediated through granzyme B and perforin pathway.

Example 13

Figure 18:
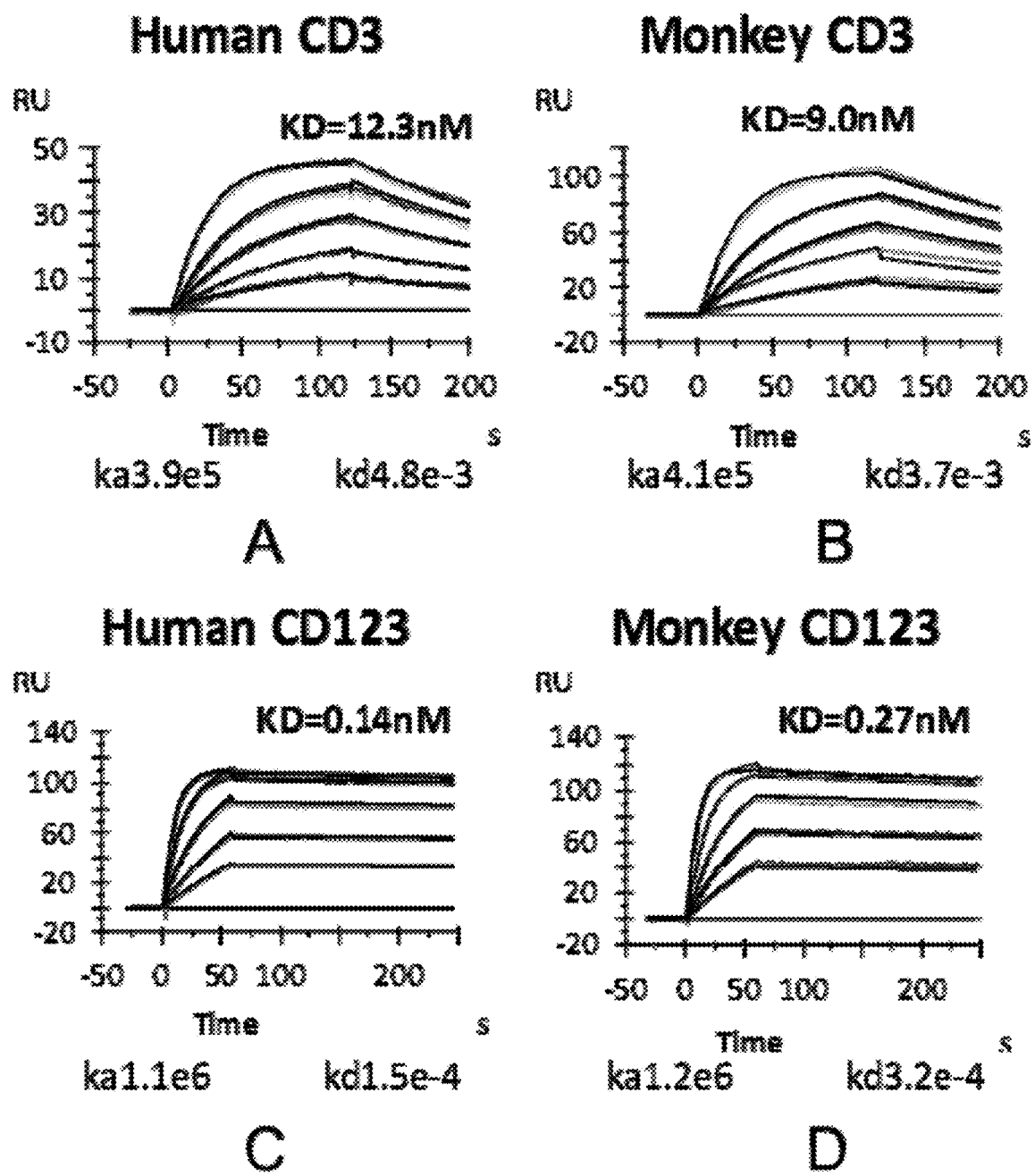
FIG. 18 (Panels A-D) shows that the sequence-optimized CD123×CD3 bi-specific diabody (DART-A) is capable of cross-reacting with both human and primate CD123 and CD3 proteins. The panels show BIACORE™ sensogram traces of the results of analyses conducted to assess the ability of DART-A to bind to human (Panels A and C) and non-human primate (Panels B and D) CD3 (Panels A and B) and CD123 (Panels C and D) proteins. The KD values are provided.

Sequence-Optimized CD123×CD3 Bi-Specific Diabody Cross-Reacts with Non-Human Primate CD123 and CD3 Proteins In order to quantitate the extent of binding between sequence-optimized CD123×CD3 bi-specific diabody (DART-A) and human or cynomolgus monkey CD3, BIACORE™ analyses were conducted. BIACORE™ analyses measure the dissociation off-rate, kd. The binding affinity (KD) between an antibody and its target is a function of the kinetic constants for association (on rate, ka) and dissociation (off-rate, kd) according to the formula: KD=[kd]/[ka]. The BIACORE™ analysis uses surface plasmon resonance to directly measure these kinetic parameters. Recombinant human or cynomolgus monkey CD3 was directly immobilized to a support. Purified human or cynomolgus monkey CD123 was captured and immobilized to a support. The time course of dissociation was measured and a bivalent fit of the data conducted. Binding constants and affinity were obtained using a 1:1 binding fit. The results of the BIACORE™ analyses comparing binding to human versus cynomologus monkey CD123 and CD3 proteins are shown in FIG. 18. Binding affinities to the cynomolgus monkey CD123 (FIG. 18D) and CD3 (FIG. 18B) proteins is comparable to binding affinities for human CD123 (FIG. 18C) and CD3 (FIG. 18A) proteins.

Example 14

Autologus Monocyte Depletion In Vitro with Human and Cynomolgus Monkey PBMCs

PBMCs from human or cynomolgus monkey whole blood samples were added to U-bottom plates at cell density of 200,000 cells/well in 150 μl of assay medium. Dilutions of sequence-optimized CD123×CD3 bi-specific diabodies (DART-A or DART-A w/ABD) were prepared in assay medium. 50 μL of each DART-A or DART-A w/ABD dilution was added to the plate containing PBMCs in duplicate wells. The plates were incubated for ~18-24 h at 37° C. Supernatants were used to determine the cytotoxicity as described above. As shown in FIG. 19 (Panels A and B), depletion of pDCs cells was observed in both human (FIG. 19, Panel A) and cynomolgus monkey PBMCs (FIG. 19, Panel B). These results indicate that circulating pDC can be used as a pharmacodynamic marker for preclinical toxicology studies in cynomolgus monkeys.

Should it be necessary to replicate this example it will be appreciated that one of skill in the art may, within reasonable and acceptable limits, vary the above-described protocol in a manner appropriate for replicating the described results. Thus, the exemplified protocol is not intended to be adhered to in a precisely rigid manner.

Example 15

Plasmacytoid Dendritic Cell Depletion in Cynomolgus Monkeys Treated with Sequence-Optimized CD123×CD3 Bi-Specific Diabody (DART-A)

Figure 20:
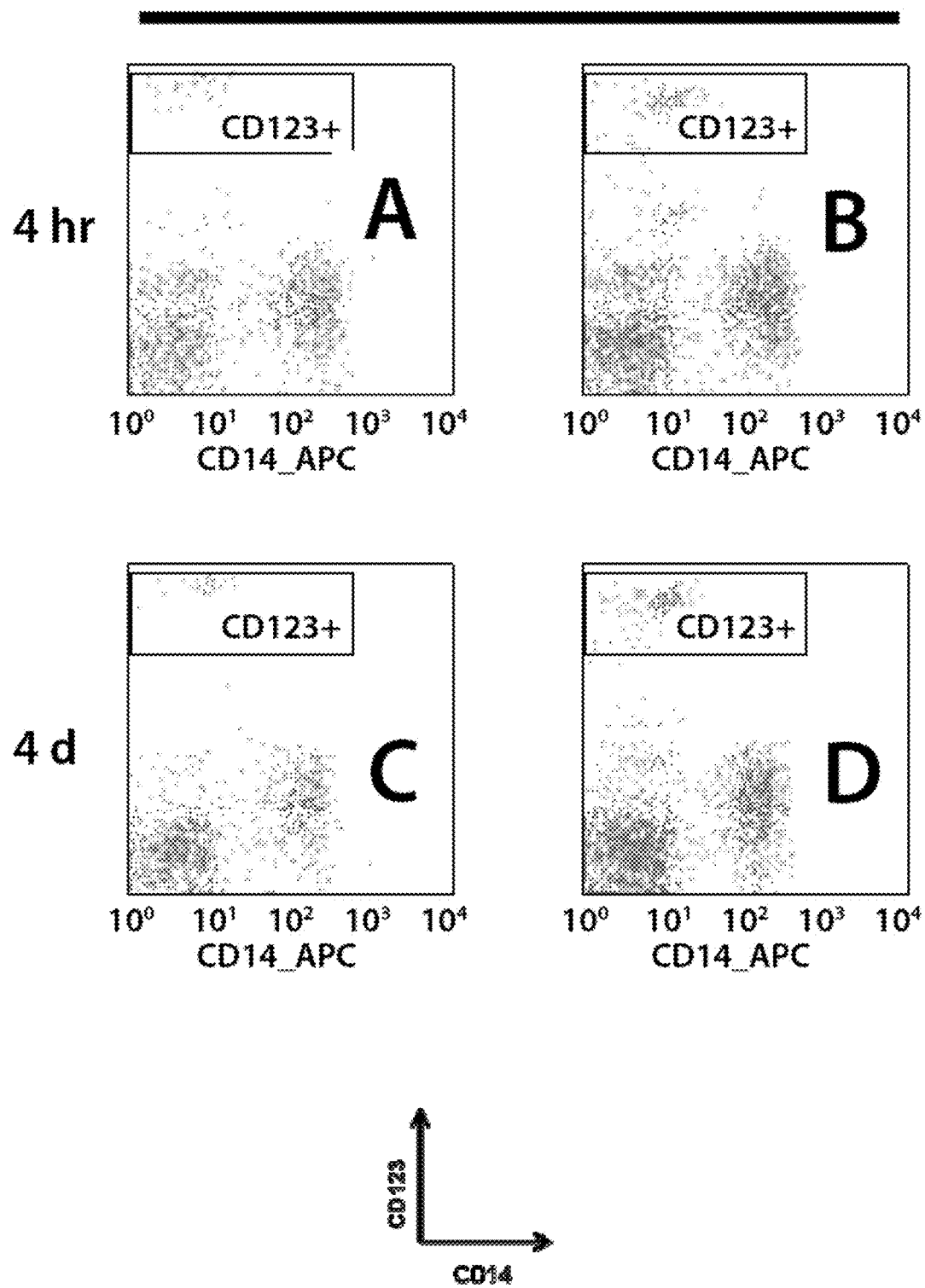
FIG. 20 (Panels A-N) shows the ability of the sequence-optimized CD123×CD3 bi-specific diabody (DART-A) to mediate the depletion of pDC in cynomolgus monkeys without systemic cytokine induction. Panels A-D show control results obtained at 4h and 4d with vehicle and carrier. Panels E-H show control results obtained at 4h and 4d with a control bi-specific diabody (Control DART). Panels I-N show results obtained at 4h and 4d at 10 ng/kg/d and at 4d with 30 ng/kg/d of DART-A.

As part of a dose-range finding toxicology study, cynomolgus monkeys were administered sequence-optimized CD123×CD3 bi-specific diabody (DART-A) as 4-day infusions at doses of 0.1, 1, 10, 30 100, 300, or 1000 ng/kg. The Control DART was administered at 100 ng/kg. To identify pDCs and monocyte populations in cynomolgus monkey PBMCs, cells were labeled with CD14-FITC antibody. Monocytes were identified as the CD14$^+$ population and pDCs were identified as the CD14$^-$CD123$^+$ population. As shown in FIG. 20 Panels K and L, the pDCs were depleted as early as 4 days post infusion with as little as 10 ng/kg DART-A. No pDC depletion was seen in the control bispecific diabody-(Control DART) treated monkeys or the vehicle+ carrier-treated monkeys at the 4d time point (FIG. 20, Panels G, H, C and D, respectively). Cytokine levels of interferon-gamma, TNF-alpha, IL6, IL5, IL4 and IL2 were determined at 4 hours after infusion. There was little to no elevation in cytokine levels at the DART-A treated animals compared to Control DART or vehicle-treated animals.

FIG. 21 and FIG. 22 provide the results of the FACS analysis for B cells (CD20$^+$) (FIG. 21, Panel A), monocytes (CD14$^+$) (FIG. 21, Panel B), NK cells (CD159$^+$CD16$^+$) (FIG. 21, Panel C), pDC (CD123$^{HI}$, CD14$^-$) (FIG. 21, Panel D), and T cells (total, CD4$^+$, and CD8$^+$) (FIG. 22, Panel A, FIG. 22, Panel B, and FIG. 22, Panel D, respectively).

Treatment of monkeys with Control DART had no noticeable effects on T or B lymphocytes, NK cells, monocytes and pDCs. Treatment of monkeys with DART-A at doses of 10 ng/kg/d or higher resulted in the abrogation of pDCs (FIG. 21, Panel D). The depletion of pDC was complete and durable, returning to pre-dose levels several weeks after completion of dosing. Circulating levels of T lymphocytes decreased upon DART-A administration, but returned to pre-dose level by the end of each weekly cycle, suggesting changes in trafficking rather than true depletion. Both CD4 and CD8 T lymphocytes followed the same pattern. The T-lymphocyte activation marker, CD69 (FIG. 22, Panel C), was only marginally positive among circulating cells and did not track with DART-A dosing. B lymphocytes, monocytes and NK cells fluctuated over the course of DART-A dosing with substantial variability observed among monkeys. A trend toward increased circulating levels of B lymphocytes and monocytes was observed in both monkeys at the highest doses.

In summary, the above results demonstrate the therapeutic efficacy of the sequence-optimized CD123×CD3 bi-specific diabody (DART-A). The sequence-optimized CD123×CD3 bi-specific diabody (DART-A) may be employed as a therapeutic agent for the treatment of multiple diseases and conditions, including: AML, ABL (ALL), CLL, MDS, pDCL, mantel cell leukemia, hairy cell leukemia, Ricter transformation of CLL, Blastic crisis of CML, BLL (subset are CD123+) (see Example 2); Autoimmune Lupus (SLE), allergy (basophils are CD123+), asthma, etc.

Example 16

Comparative Properties of Sequence-Optimized CD123×CD3 Bi-Specific Diabody (DART-A) and Non-Sequence-Optimized CD123×CD3 Bi-Specific Diabody (DART-B)

Unexpected Advantage and Attributes of the Sequence-Optimized CD123×CD3 Bi-Specific Diabodies As discussed above, DART-A and DART-B are similarly designed and the first polypeptide of both constructs comprise, in the N-terminal to C-terminal direction, an N-terminus, a VL domain of a monoclonal antibody capable of binding to CD3 (VL$_{CD3}$), an intervening linker peptide (Linker 1), a VH domain of a monoclonal antibody capable of binding to CD123 (VH$_{CD123}$), a Linker 2, an E-coil Domain, and a C-terminus. Likewise, the second polypeptide of both constructs comprise, in the N-terminal to C-terminal direction, an N-terminus, a VL domain of a monoclonal antibody capable of binding to CD123 (VL$_{CD123}$), an intervening linker peptide (Linker 1), a VH domain of a monoclonal antibody capable of binding to CD3 (VH$_{CD3}$), a Linker 2, a K-coil Domain and a C-terminus.

As indicated in Example 1, both CD123×CD3 bi-specific diabodies were found to be capable of simultaneously binding to CD3 and CD123. Additionally, as disclosed in Example 3 and in FIG. 4, Panels C and D, the two CD123×CD3 bi-specific diabodies exhibited a potent redirected killing ability with concentrations required to achieve 50% of maximal activity (EC50s) in sub-ng/mL range, regardless of CD3 epitope binding specificity (DART-A versus DART-B) in target cell lines with high CD123 expression. Thus, slight variations in the specific sequences of the CD123× CD3 bi-specific diabodies do not completely abrogate biological activity.

However, in all cell lines tested, DART-A was found to be more active and more potent at redirected killing than DART-B (see, e.g., FIG. 4, Panels A, C, and D). Thus DART-A exhibited an unexpected advantage over similar DART-B.

Example 17

Non-Human Primate Pharmacology of DART-A for the Treatment of Hematological Malignancies The interleukin 3 (IL-3) receptor alpha chain, CD123, is overexpressed on malignant cells in a wide range of hematological malignancies (Muñoz, L. et al. (2001) "*Interleukin-3 Receptor Alpha Chain (CD123) Is Widely Expressed In Hematologic Malignancies*," Haematologica 86:1261-1269; Testa, U. et al. (2014) "CD123 Is A Membrane Biomarker And A Therapeutic Target In Hematologic Malignancies," Biomark. Res. 2:4) and is associated with poor prognosis (Vergez, F. et al. (2011) "*High Levels Of CD34+CD38low/− CD123+ Blasts Are Predictive Of An Adverse Outcome In Acute Myeloid Leukemia: A Groupe Ouest-Est Des Leucemies Aigues Et Maladies Du Sang (GOELAMS) Study*," Haematologica 96:1792-1798). Moreover, CD123 has been reported to be expressed by leukemia stem cells (LSC) (Jordan, C. T. et al. (2000) "*The Interleukin-3 Receptor Alpha Chain Is A Unique Marker For Human Acute Myelogenous Leukemia Stem Cells*," Leukemia 14:1777-1784; Jin, L. et al. (2009) "*Monoclonal Antibody Mediated Targeting Of CD123, IL-3 Receptor Alpha Chain, Eliminates Human Acute Myeloid Leukemic Stem Cells*," Cell Stem Cell 5:31-42), which is an attractive feature that enables targeting the root cause of such diseases. Consistent with this conclusion, CD123 also takes part in an IL-3 autocrine loop that sustains leukemogenesis, as shown by the ability of a CD123-blocking monoclonal antibody to reduce leukemic stem cell engraftment and improve survival in a mouse model of acute myelogenous leukemia (AML) (Jin, L. et al. (2009) "*Monoclonal Antibody-Mediated Targeting Of CD123, IL-3 Receptor Alpha Chain, Eliminates Human Acute Myeloid Leukemic Stem Cells*," Cell Stem Cell 5:31-42). In a phase 1 study in high-risk AML patients, however, the monoclonal antibody exhibited no anti-leukemic activity (Roberts, A. W. et al. (2010) "*A Phase I Study Of Anti-CD123 Monoclonal Antibody (mAb) CSL360 Targeting Leukemia Stem Cells (LSC) In AML*," J. Clin. Oncol. 28(Suppl): e13012). Thus, alternate CD123-targeting approaches, including depleting strategies are desired. Although CD123 is expressed by a subset of normal hematopoietic progenitor cells (HPC), hematopoietic stem cells (HSC) express little to no CD123 (Jordan, C. T. et al. (2000) "*The Interleukin-3 Receptor Alpha Chain Is A Unique Marker For Human Acute Myelogenous Leukemia Stem Cells*," Leukemia 14:1777-1784; Jin, W. et al. (2009) "*Regulation Of Th17 Cell Differentiation And EAE Induction By MAP3K NIK*," Blood 113:6603-6610), indicating that CD123 cell-depleting strategies allow reconstitution via normal hematopoiesis.

Enabling a patient's own T lymphocytes to target leukemic cells represents a promising immunotherapeutic strategy for the treatment of hematological malignancies. The therapeutic potential of this approach has been attempted using blinatumomab (a bi-specific antibody-based BiTE having the ability to bond CD3 and the B cell CD19 antigen) in patients with B cell lymphomas and B-precursor acute lymphoblastic leukemia (Klinger, M. et al. (2012) "*Immunopharmacologic Response Of Patients With B-Lineage Acute Lymphoblastic Leukemia To Continuous Infusion Of T Cell-Engaging CD19/CD3-Bispecific BiTE Antibody Blinatumomab*," Blood 119:6226-6233; Topp, M. S. et al. (2012) "*Long-Term Follow-Up Of Hematologic Relapse-Free Survival In A Phase 2 Study Of Blinatumomab In Patients With MRD In B-Lineage ALL*," Blood 120:5185-5187; Topp, M. S. et al. (2011) "*Targeted Therapy With The T-Cell-Engaging Antibody Blinatumomab Of Chemotherapy-Refractory Minimal Residual Disease In B-Lineage Acute Lymphoblastic Leukemia Patients Results In High Response Rate And Prolonged Leukemia-Free Survival*," J. Clin. Oncol. 29:2493-2498).

The CD123×CD3 bi-specific diabody molecules of the present invention, such as DART-A, comprise an alternate bi-specific, antibody-based modality that offers improved stability and more robust manufacturability properties (Johnson, S. et al. (2010) "*Effector Cell Recruitment With Novel Fv-Based Dual-Affinity Re-Targeting Protein Leads To Potent Tumor Cytolysis And In Vivo B-Cell Depletion*," J. Mol. Biol. 399:436-449; Moore, P. A. et al. (2011) "*Application Of Dual Affinity Retargeting Molecules To Achieve Optimal Redirected T-Cell Killing Of B-Cell Lymphoma*," Blood 117:4542-4551).

In order to demonstrate the superiority and effectiveness of the CD123×CD3 bi-specific diabody molecules of the present invention, the biological activity of the above-described DART-A in in vitro and preclinical models of leukemia was confirmed, and its pharmacokinetics, pharmacodynamics and safety pharmacology in cynomolgus macaques (*Macaca fascicularis*) was assessed relative to either the above-described Control DART (bi-specific for CD3 and fluorescein) or a "Control DART-2" that was bi-specific for CD123 and fluorescein).

```
Amino Acid Sequence of First Polypeptide Chain of
"Control DART-2" (CD123VL-Linker-4-4420VH-Linker-
E-coil; linkers are underlined)
(SEQ ID NO: 58):
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIKGGGSGGG

GEVKLDETGG GLVQPGRPMK LSCVASGFTF SDYWMNWVRQ

SPEKGLEWVA QIRNKPYNYE TYYSDSVKGR FTISRDDSKS

SVYLQMNNLR VEDMGIYYCT GSYYGMDYWG QGTSVTVSSG

GCGGGEVAAL EKEVAALEKE VAALEKEVAA LEK

Amino Acid Sequence of Second Polypeptide Chain
of "Control DART-2" (4420VL-Linker-CD123VH-Linker-
K-coil) (SEQ ID NO: 59):
DVVMTQTPFS LPVSLGDQAS ISCRSSQSLV HSNGNTYLRW

YLQKPGQSPK VLIYKVSNRF SGVPDRFSGS GSGTDFTLKI
```

-continued
```
SRVEAEDLGV YFCSQSTHVP WTFGGGTKLE IKGGGSGGGG

EVQLVQSGAE LKKPGASVKV SCKASGYTFT DYYMKWVRQA

PGQGLEWIGD IIPSNGATFY NQKFKGRVTI TVDKSTSTAY

MELSSLRSED TAVYYCARSH LLRASWFAYW GQGTLVTVSS

GGCGGGKVAA LKEKVAALKE KVAALKEKVA ALKE
```

Bifunctional ELISA

A MaxiSorp ELISA plate (Nunc) coated overnight with the soluble human or cynomolgus IL3R-alpha (0.5 µg/mL) in bicarbonate buffer was blocked with 0.5% BSA; 0.1% Tween-20 in PBS (PBST/BSA) for 30 minutes at room temperature. DART-A molecules were applied, followed by the sequential addition of human CD3εδ-biotin and Streptavidin HRP (Jackson ImmunoResearch). HRP activity was detected by conversion of tetramethylbenzidine (BioFX) as substrate for 5 min; the reaction was terminated with 40 µL/well of 1% H2SO4 and the absorbance read at 450 nm.

Surface Plasmon Resonance Analysis

The ability of DART-A to bind to human and cynomolgus monkey CD3 or CD123 proteins was analyzed using a BIAcore 3000 biosensor (GE, Healthcare) as described by Johnson, S. et al. (2010) ("*Effector Cell Recruitment With Novel Fv-Based Dual Affinity Re-Targeting Protein Leads To Potent Tumor Cytolysis And In Vivo B-Cell Depletion*," J. Mol. Biol. 399:436-449) and Moore, P. A. et al. (2011) ("*Application Of Dual Affinity Retargeting Molecules To Achieve Optimal Redirected T-Cell Killing Of B-Cell Lymphoma*," Blood 117:4542-4551). Briefly, the carboxyl groups on the CMS sensor chip were activated with an injection of 0.2M N-ethyl-N-(3dietylamino-propyl) carbodiimide and 0.05M N-hydroxy-succinimide. Soluble CD3 or CD123 (1 µg/ml) was injected over the activated CMS surface in 10 mM sodium-acetate, pH 5.0, at flow rate 5 µL/min, followed by 1 M ethanolamine for deactivation. Binding experiments were performed in 10 mM HEPES, pH 7.4, 150 mM NaCl, 3 mM EDTA and 0.005% P20 surfactant. Regeneration of the immobilized receptor surfaces was performed by pulse injection of 10 mM glycine, pH 1.5. KD values were determined by a global fit of binding curves to the Langmuir 1:1 binding model (BIAevaluation software v4.1).

Cell Killing Assay

Cell lines used for cell killing assays were obtained from the American Type Culture Collection (ATCC) (Manassas, Va.). PBMCs were isolated from healthy donor blood using the Ficoll-Paque Plus kit (GE Healthcare); T cells were purified with a negative selection kit (Life Technologies). CD123 cell-surface density was determined using Quantum Simply Cellular beads (Bangs Laboratories, Inc., Fishers, Ind.). Cytotoxicity assays were performed as described by Moore, P. A. et al. (2011) ("*Application Of Dual Affinity Retargeting Molecules To Achieve Optimal Redirected T-Cell Killing Of B-Cell Lymphoma*," Blood 117:4542-4551). Briefly, target cell lines ($10^5$ cells/mL) were treated with serial dilutions of DART-A or Control DART proteins in the presence of T cells at the indicated effector cells:target cells ratios and incubated at 37° C. overnight. Cell killing was determined as the release of lactate dehydrogenase (LDH, Promega) in culture supernatant. For flow-based killing, target cells were labeled with CMTMR (Life Technologies) and cell killing was monitored using a FACSCalibur flow cytometer. Data were analyzed by using PRISM® 5 software (GraphPad) and presented as percent cytotoxicity.

Cynomolgus Monkey Pharmacology

Non-human primate experiments were performed at Charles River Laboratories (Reno, Nev.), according to the guidelines of the local Institutional Animal Care and Use Committee (IACUC). Purpose-bred, naïve cynomolgus monkeys (Macaca fascicularis) of Chinese origin (age range 2.5-9 years, weight range of 2.7-5 kg) were provided with vehicle or DART-A via intravenous infusion through femoral and jugular ports using battery-powered programmable infusion pumps (CADD-Legacy®, SIMS Deltec, Inc., St. Paul, Minn.). Peripheral blood or bone marrow samples were collected in anticoagulant containing tubes at the indicated time points. Cell-surface phenotype analyses were performed with an LSR Fortessa analyzer (BD Biosciences) equipped with 488 nm, 640 nm and 405 nm lasers and the following antibodies: CD4-V450, CD8-V450, CD123-PE-Cy7, CD45-PerCP, CD4-APC-H7, CD8-FITC, CD25-PE-Cy7, CD69-PerCP, PD-1-PE, TIM3-APC, CD3-Pacific Blue, CD95-APC, CD28-BV421, CD16-FITC, CD3-Alexa488, CD38-PE, CD123-PE-Cy7, CD117-PerCP-Cy5.5, CD34-APC, CD90-BV421, CD45RA-APC-H7 and CD33-APC (BD Biosciences). The absolute number of cells was determined using TruCOUNT (BD Biosciences). Serum levels of IL-2, IL-4, IL-5, IL-6, TNF-$\alpha$, and IFN-$\gamma$ cytokines were measured with the Non-Human Primate Th1/Th2 Cytokine Cytometric Bead Array Kit (BD Bioscience). The concentration of DART-A in monkey serum samples was measured using a sandwich immunoassay with electrochemiluminescence detection (MesoScale Diagnostics, MSD, Rockville, Md.). Briefly, the assay plate (MSD) was coated with recombinant human IL-3 Ra (R&D System) and blocked with 5% BSA. Calibration standards or diluted test samples were applied, followed by the addition of a biotinylated monoclonal antibody exhibiting specific binding for the above-described E-coil (SEQ ID NO:34) and K-coil (SEQ ID NO:35) domains of the molecule A SULFO-TAG™ labeled streptavidin conjugate (MSD) was added and the formation of complexes was analyzed in an MSD SECTOR® imager. DART-A concentrations were determined from standard curves generated by fitting light intensity data in a five-parameter logistic model.

Figure 23:
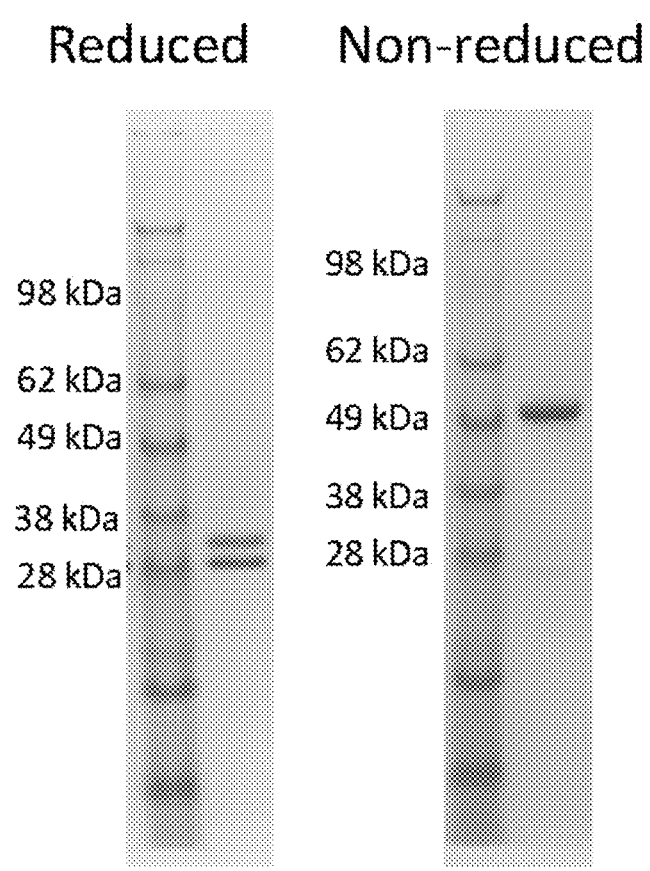
FIG. 23 shows the SDS-PAGE analysis of purified DART-A protein under reducing (left) and non-reducing (right) conditions.
Figure 24A:
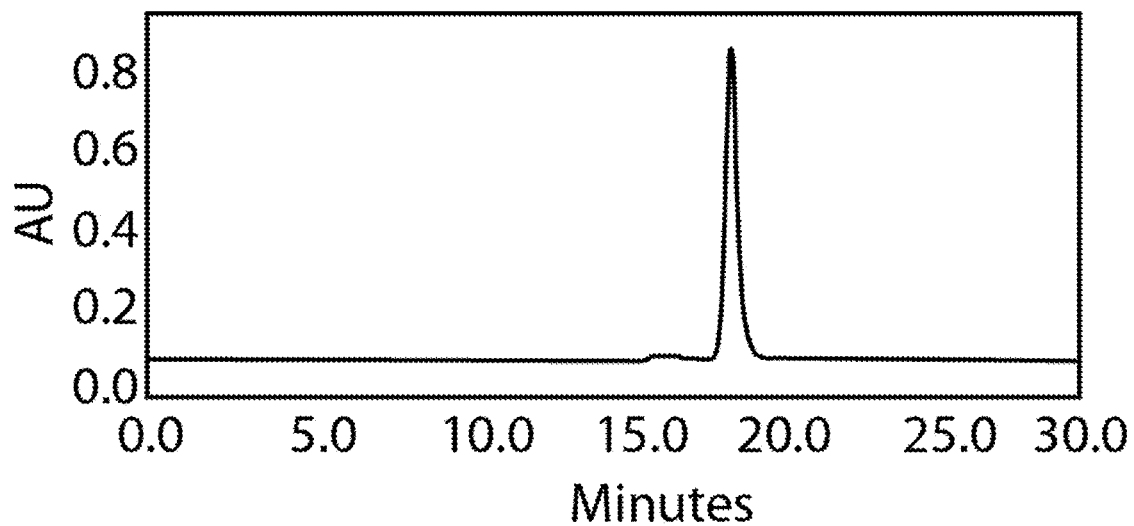
FIGS. 24A-24B show the physicochemical characterization of purified DART-A.
Figure 24B:
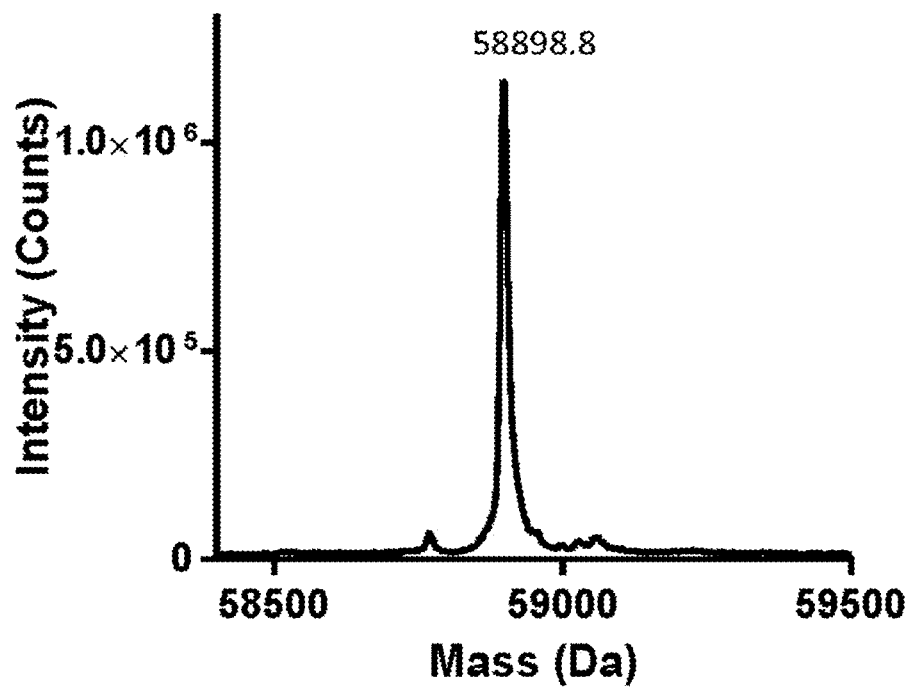
Figure 25A:
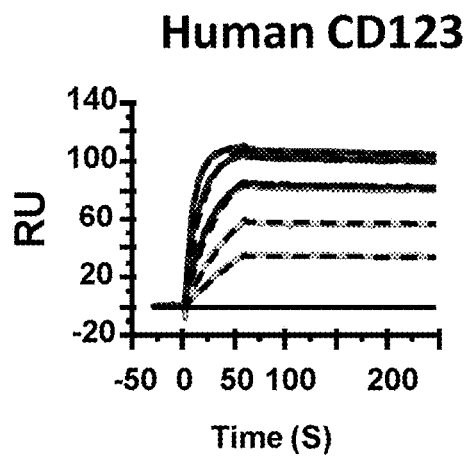
FIGS. 25A-25D show SPR analysis of DART-A binding to immobilized human or cynomolgus monkey CD123 and CD3. Dashed lines represent the global fit to a 1:1 Langmuir model of the experimental binding curves obtained at DART-A concentrations of 0, 6.25, 12.5, 25, 50 or 100 nM (continuous lines). The data are representative of three independent experiments.
Figure 25B:
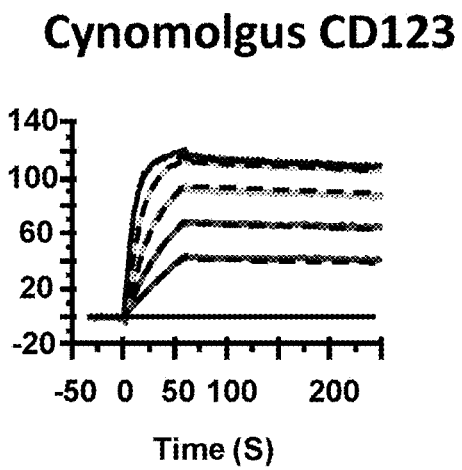
Figure 25C:
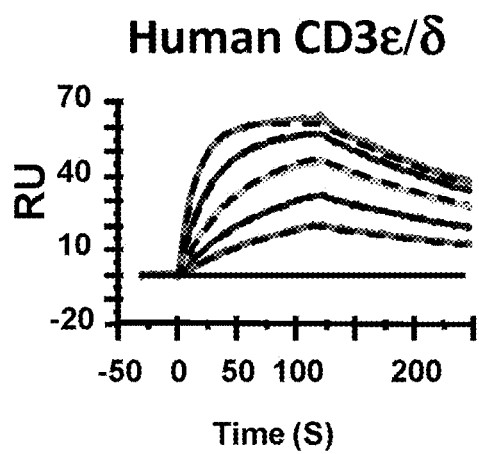
Figure 25D:
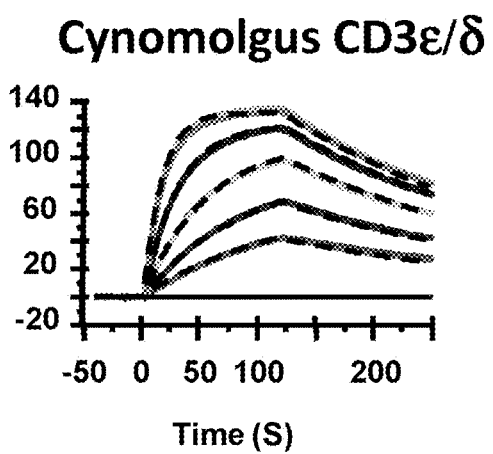
Figure 26A:
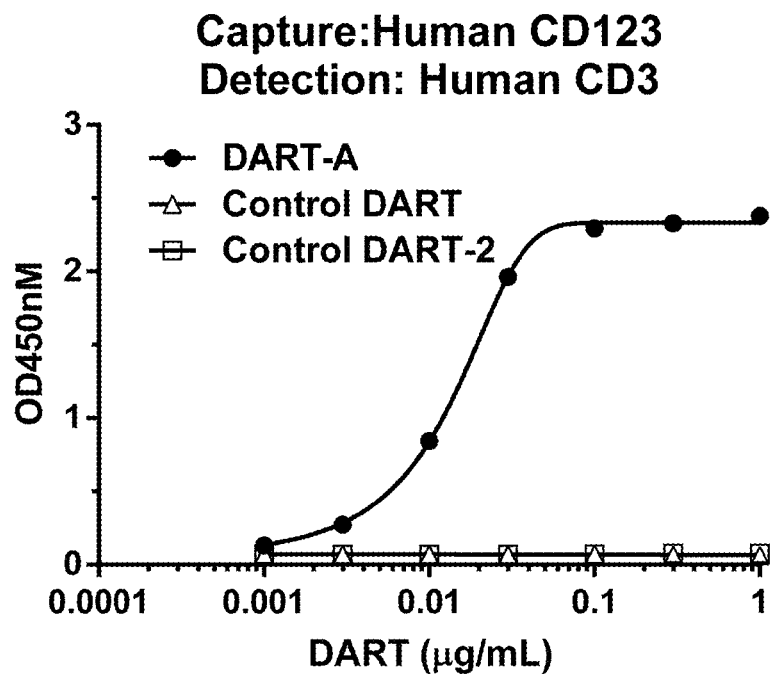
FIGS. 26A-26E show that DART-A was capable of simultaneously binding both CD3 and CD123.
Figure 26B:
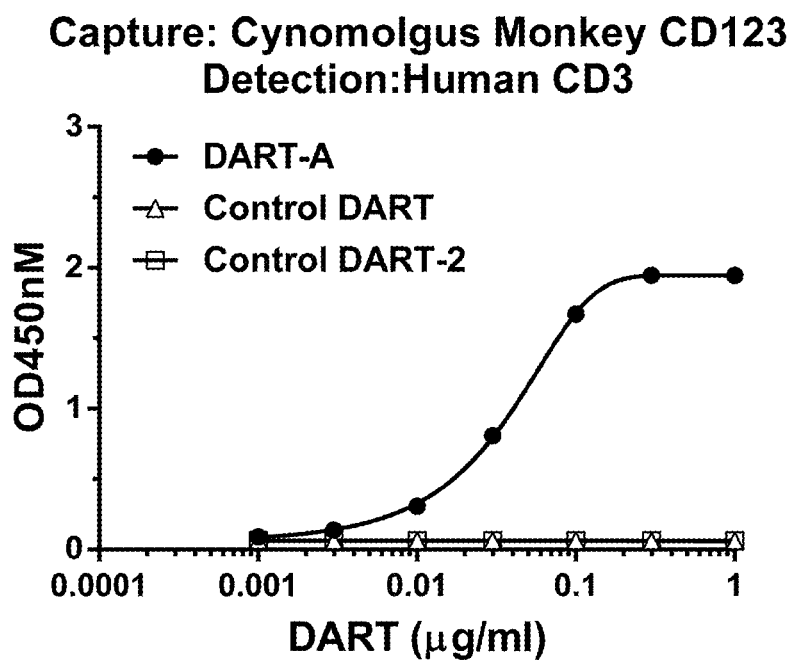
Figure 26C:
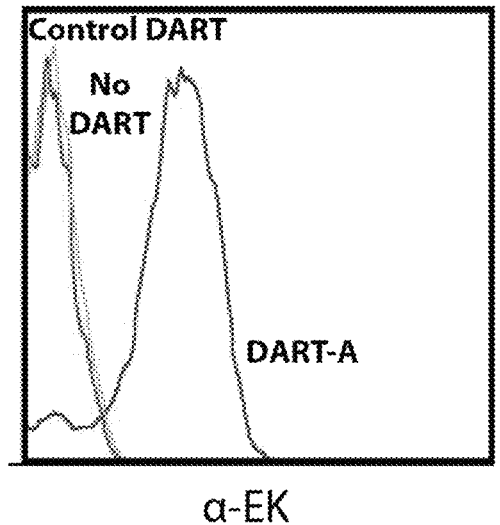
Figure 26D:
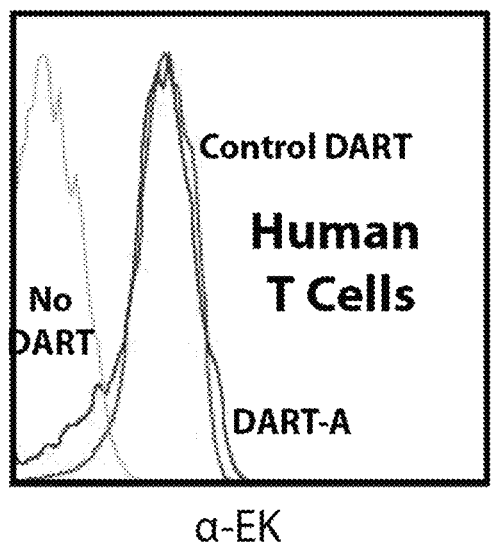
Figure 26E:
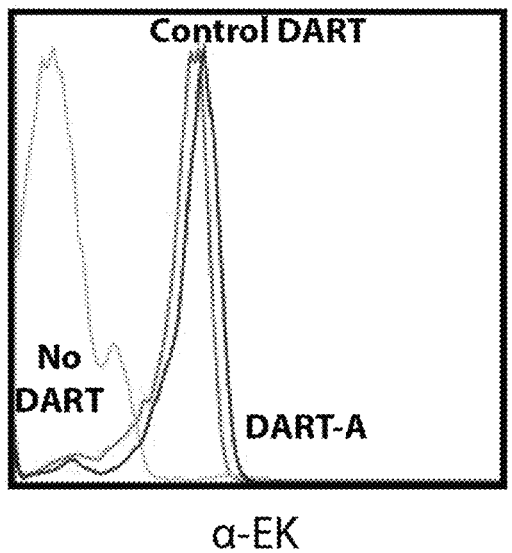

Physicochemical characterization of the purified DART-A demonstrated a homogeneous heterodimer with a molecular mass of 58.9 kDa (FIG. 23; FIGS. 24A-24B), which was stable at 2-8° C. for up to 12 months in PBS. SPR analysis demonstrated nearly identical binding affinities of DART-A to the corresponding soluble human and cynomolgus monkey CD3 and CD123 antigens (FIGS. 25A-25D and Table 7). Furthermore, DART-A simultaneously bound both antigens in an ELISA format that employed human or monkey CD123 for capture and human CD3 for detection (FIGS. 26A-26B), and demonstrated similar binding to human and monkey T lymphocytes (FIGS. 26C-26E). The data in Table 7 are averages of 3 independent experiments each performed in duplicates.

TABLE 7

Equilibrium Dissociation Constants ($K_D$) for the Binding of DART-A to Human and Cynomolgus Monkey CD3 and CD123

| Antigens | $k_a$ ($\pm$SD) ($M^{-1}s^{-1}$) | $k_d$ ($\pm$SD) ($s^{-1}$) | $K_D$ ($\pm$SD) (nM) |
|---|---|---|---|
| Human CD3$\epsilon$/$\delta$ | 5.7 ($\pm$0.6) × 10$^5$ | 5.0 ($\pm$0.9) × 10$^{-3}$ | 9.0 $\pm$ 2.3 |
| Cynomolgus CD3$\epsilon$/$\delta$ | 5.5 ($\pm$0.5) × 10$^5$ | 5.0 ($\pm$0.9) × 10$^{-3}$ | 9.2 $\pm$ 2.3 |

TABLE 7-continued

Equilibrium Dissociation Constants ($K_D$) for the Binding of DART-A to Human and Cynomolgus Monkey CD3 and CD123

| Antigens | $k_a$ ($\pm$SD) ($M^{-1}s^{-1}$) | $k_d$ ($\pm$SD) ($s^{-1}$) | $K_D$ ($\pm$SD) (nM) |
|---|---|---|---|
| Human CD123-His | 1.6 ($\pm$0.4) × 10$^6$ | 1.9 ($\pm$0.4) × 10$^{-4}$ | 0.13 $\pm$ 0.01 |
| Cynomolgus CD123-His | 1.5 ($\pm$0.3) × 10$^6$ | 4.0 ($\pm$0.7) × 10$^{-4}$ | 0.27 $\pm$ 0.02 |

DART-A Mediates Redirected Killing by Human or Cynomolgus Monkey T Lymphocytes

Figure 27A:
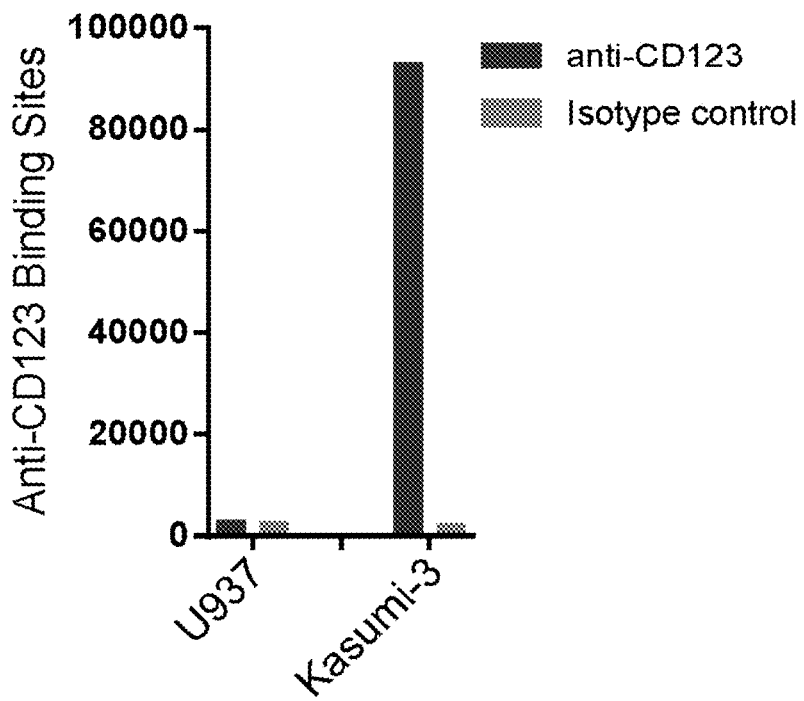
FIGS. 27A-27H show the ability of DART-A to mediate redirected target cell killing by human or monkey effector cells against CD123+ Kasumi-3 leukemic cell lines, demonstrate the ability of the molecules to bind to subsets of normal circulating leukocytes, including pDCs and monocytes and demonstrate the ability of the molecules to deplete $CD14^-CD123^{high}$ cells (pDC and basophils) without affecting monocytes (CD14+ cells).
Figure 27B:
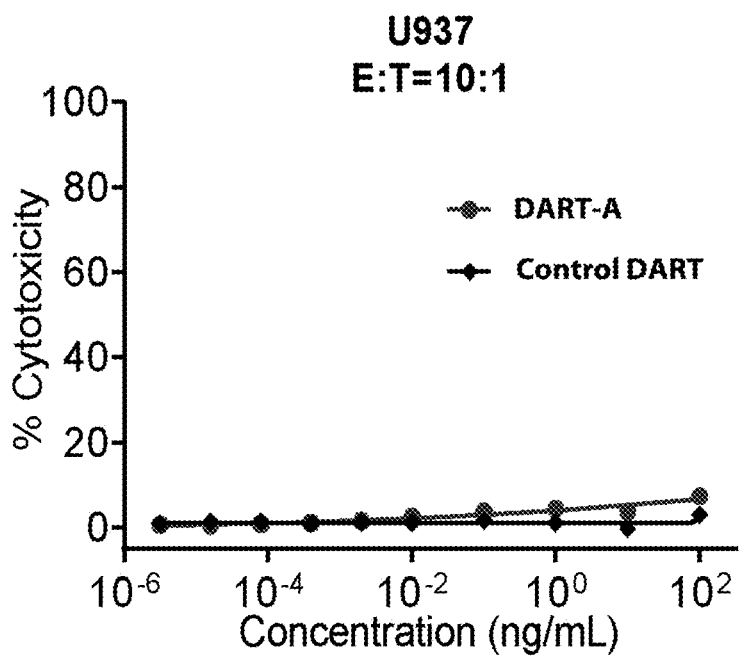
Figure 27C:
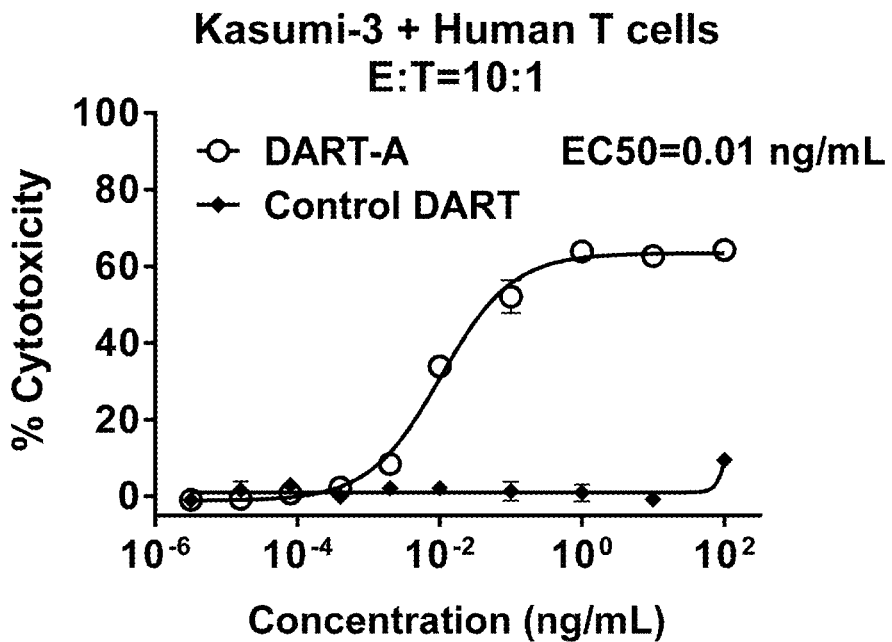
Figure 27D:
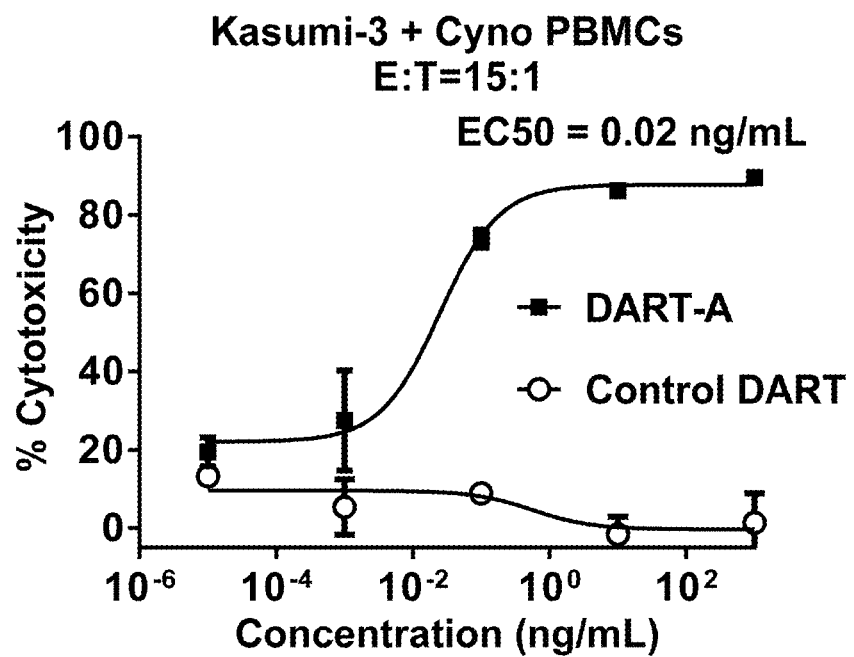
Figure 27E:
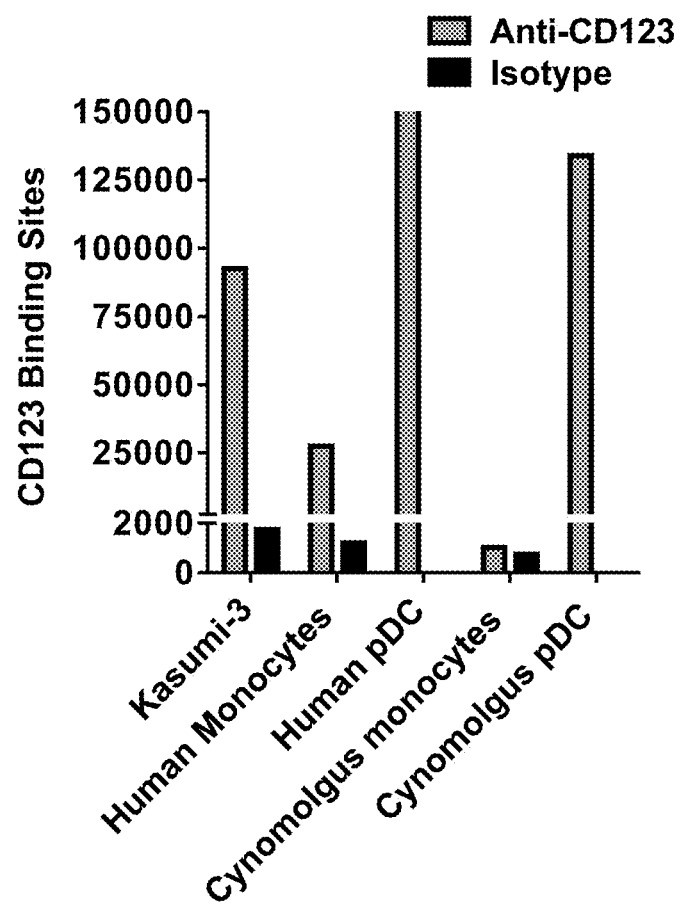

DART-A mediated redirected target cell killing by human or monkey effector cells against CD123+ Kasumi-3 leukemic cell lines (FIG. 27A-27D), which was accompanied by induction of activation markers. No activity was observed against CD123-negative targets (U937 cells) or with Control DART, indicating that T cell activation is strictly dependent upon target cell engagement and that monovalent engagement of CD3 by DART-A was insufficient to trigger T cell activation. Since CD123 is expressed by subsets of normal circulating leukocytes, including pDCs and monocytes (FIG. 27E), the effect of DART-A were further investigated in normal human and monkey's PBMCs.

Figure 27F:
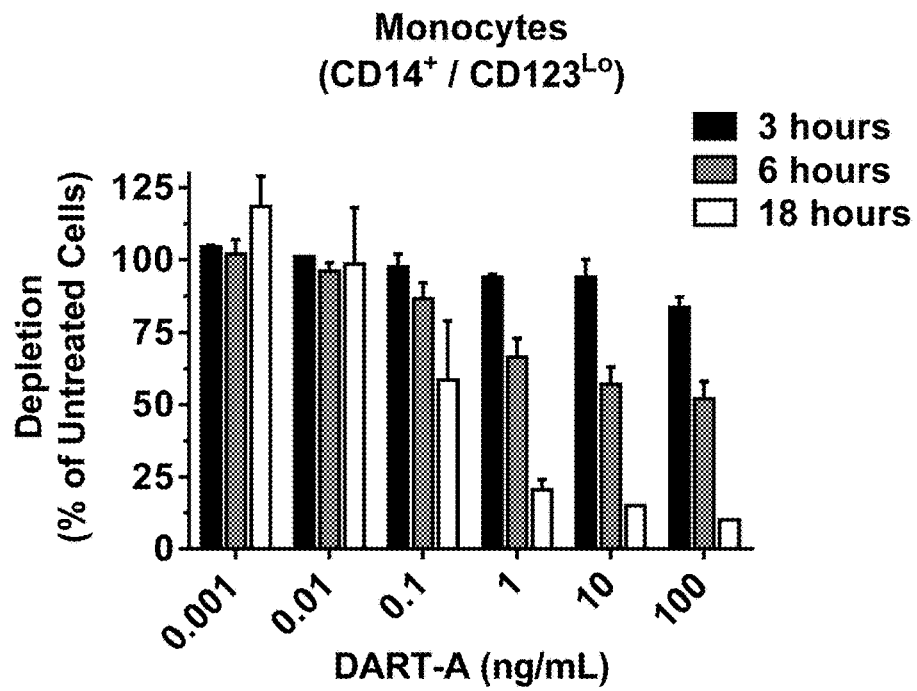
Figure 27G:
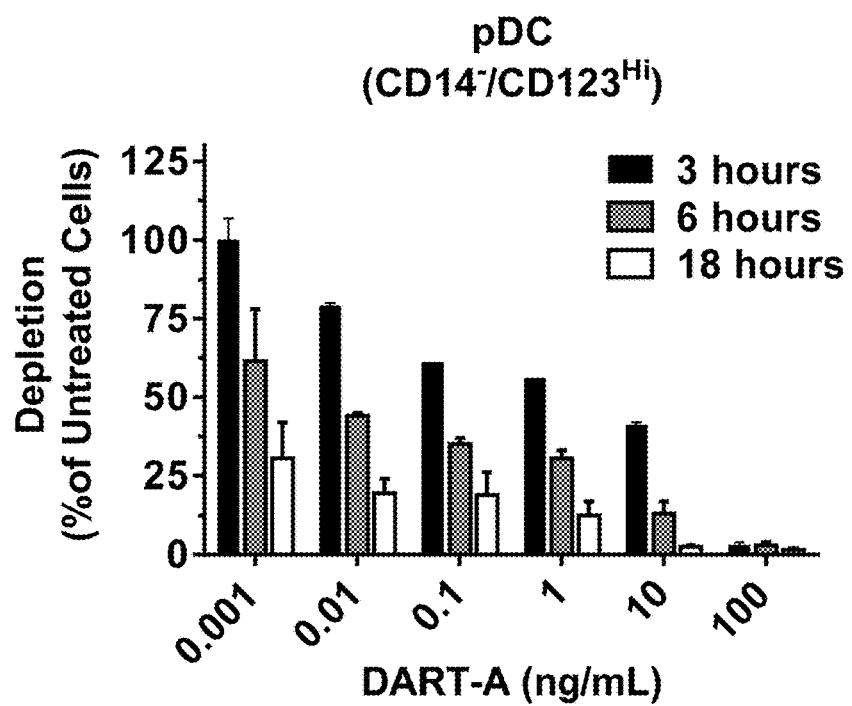
Figure 27H:
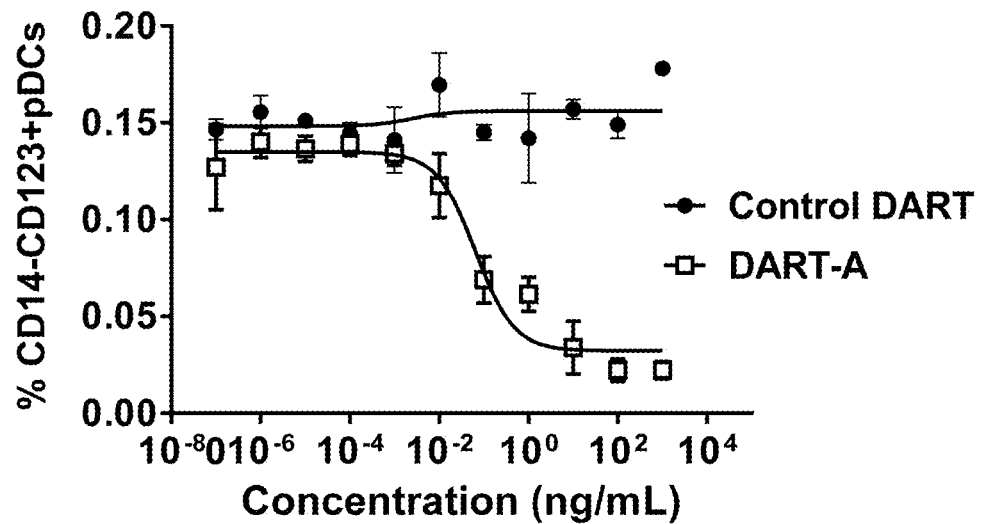

A graded effect was observed among human PBMC, with a dose-dependent rapid depletion of CD14$^-$CD123$^{high}$ cells (pDC and basophils) observed as early as 3 hours following initiation of treatment, while monocytes (CD14+ cells) remained unaffected at this time point (FIGS. 27F-27G). CD14$^-$CD123$^{high}$ cells depletion increased over time across all DART-A molecule concentrations, while monocytes were slightly decreased by 6 hours and depleted only after 18 hours and at the concentrations higher than 1 ng/mL. Incubation of monkey PBMCs with DART-A resulted in a comparable dose-dependent depletion of CD14$^-$CD123$^{high}$ cells (FIG. 27H), further supporting the relevance of this species for DART-A pharmacology (CD14+ monkey cells express little to no CD123 and were not depleted).

Pharmacokinetics of DART-A in Cynomolgus Monkeys

The cynomolgus monkey was selected as an appropriate pharmacological model for DART-A analysis based on the equivalent distribution of both target antigens in this species compared to humans based on immunohistochemistry with the precursor mAbs, consistent with published information (Muñoz, L. et al. (2001) "Interleukin-3 Receptor Alpha Chain (CD123) Is Widely Expressed In Hematologic Malignancies," Haematologica 86:1261-1269; Korpelainen, E. I. et al. (1996) "IL-3 Receptor Expression, Regulation And Function In Cells Of The Vasculature," Immunol. Cell Biol. 74:1-7).

The study conducted in accordance with the present invention included 6 treatment groups consisting of 8 cynomolgus monkeys per group (4 males, 4 females) (Table 8). All groups received vehicle control for the first infusion; then vehicle or DART-A were administered intravenously for 4 weekly cycles. Group 1 animals received vehicle control for all 4 subsequent infusions, whereas Groups 2-5 received weekly escalating doses of DART-A for 4 days a week for all subsequent infusions. Group 6 animals were treated with 7-day uninterrupted weekly escalating doses of DART-A for all infusions. The 4-day-on/3-day-off and 7-day-on schedules were designed to distinguish between durable from transient effects associated with DART-A administration. Two males and 2 females per group were sacrificed at the end of the treatment phase (Day 36), while the remaining monkeys were necropsied after a 4-week recovery (Day 65). A subset of monkeys developed anti-drug antibodies (ADA) directed against the humanized Fv of both CD3 and CD123 and the data points following the appearance of ADA were excluded from the PK analysis. All monkeys were exposed to DART-A during the study period.

TABLE 8

| | | | DART-A Infusion | | | | |
|---|---|---|---|---|---|---|---|
| | | | (4-day-on/3-day-off) ng/kg/day [ng/kg/4 days] | | | | (7-day-on) ng/kg/day [ng/kg/7 days] |
| Infusion No. | Study Days | Vehicle Group 1 | Group 2 | Group 3 | Group 4 | Group 5 | Group 6 |
| 1 | 1 | Vehicle | Vehicle | Vehicle | Vehicle | Vehicle | Vehicle |
| 2 | 8 | Vehicle | 100 [400] | 100 [400] | 100 [400] | 100 [400] | 100 [700] |
| 3 | 15 | Vehicle | 100 [400] | 300 [1200] | 300 [1200] | 300 [1200] | 300 [2100] |
| 4 | 22 | Vehicle | 100 [400] | 300 [1200] | 600 [2400] | 600 [2400] | 600 [4200] |
| 5 | 29 | Vehicle | 100 [400] | 300 [1200] | 600 [2400] | 1000 [4000] | 1000 [7000] |
| Recovery | 36-65 | | | | | | |

Figure 28:
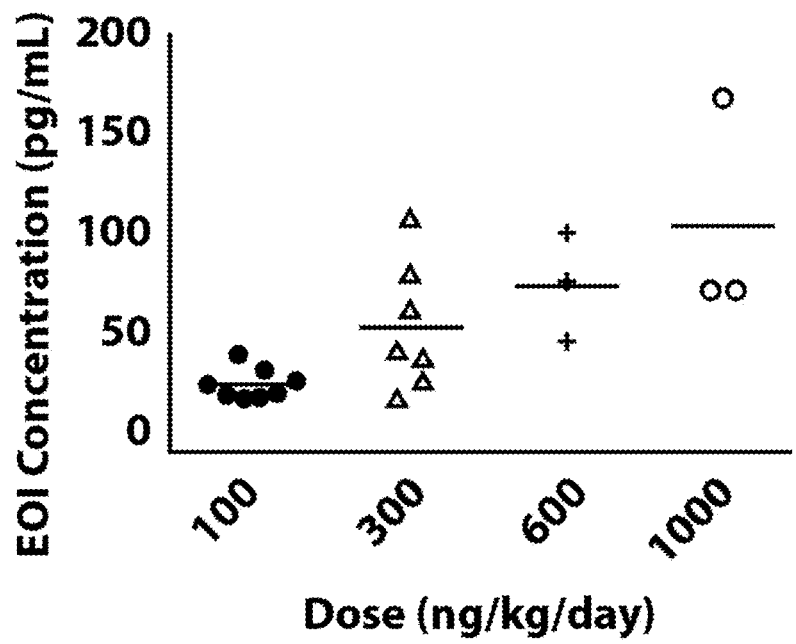
FIG. 28 shows the use of a two-compartment model to estimate pharmacokinetic parameters of DART-A. The data show the end of infusion (EOI) serum concentrations of DART-A in cynomolgus monkeys after receiving a 96-hour infusion at 100 ng/kg/day 300 ng/kg/day, 600 ng/kg/day, and 1000 ng/kg/day Dose. Each point represents an individual animal; horizontal lines represent the mean value for the dose group.

A two-compartment model was used to estimate PK parameters (Table 9 and FIG. 28). $T_{1/2}\alpha$ was short (4-5 min), reflecting rapid binding to circulating targets; $T_{1/2}\beta$ was also rapid, as expected for a molecule of this size, which is subject to renal clearance. Analysis of serum samples collected at the end of each infusion from group 6 monkeys showed a dose-dependent increase in DART-A $C_{max}$. In Table 9, Vehicle was PBS, pH 6.0, containing 0.1 mg/mL recombinant human albumin, 0.1 mg/mL PS-80, and 0.24% benzyl alcohol was used for all vehicle infusions during the first 4 days of each infusion week followed the same formulation without benzyl alcohol for the remaining 3 days of each weekly infusion. DART-A was administered for the indicated times as a continuous IV infusion of a solution of PBS, pH 6.0, containing 0.1 mg/mL recombinant human albumin, 0.1 mg/mL PS-80, and 0.24% benzyl alcohol at the required concentration.

TABLE 9

Two-Compartment Analysis of PK Parameters of DART-A in Cynomolgus Monkeys

| Attribute | 300 ng/kg/d (mean ± SD) | 600 ng/kg/d (mean ± SD) |
|---|---|---|
| $C_{max}$ (pg/mL) | 77.4 ± 9.4 | 113.8 ± 33.5 |
| AUC (h * pg/mL) | 7465 ± 913 | 11188 ± 3282 |
| $V_{ss}$ (L/kg) | 1.078 ± 0.511 | 2.098 ± 1.846 |
| $t_{1/2}$, alpha (h) | 0.07 ± 0.018 | 0.067 ± 0.023 |
| $t_{1/2}$, beta (h) | 13.79 ± 4.928 | 21.828 ± 18.779 |
| MRT (h) | 6.73 ± 3.327 | 9.604 ± 8.891 |

Cytokine Release in DART-A-Treated Cynomolgus Monkeys

Figure 29A:
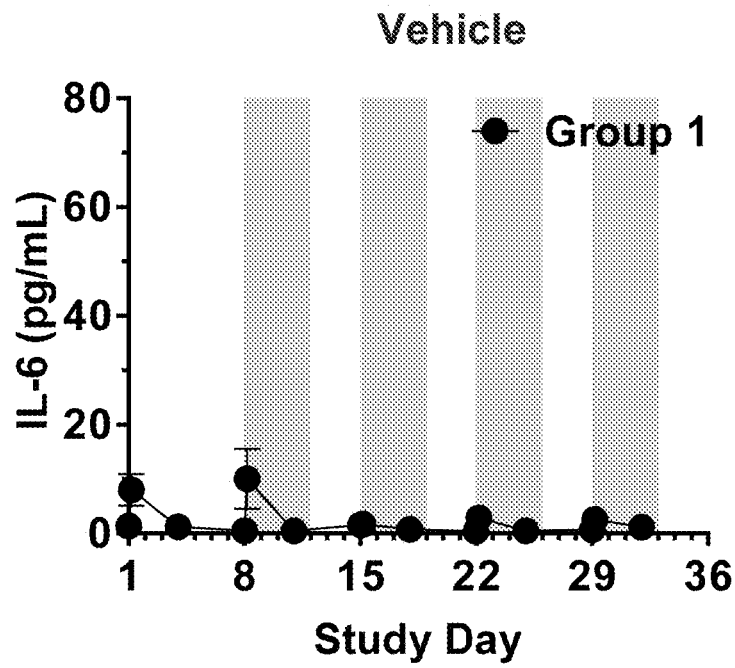
FIGS. 29A-29C show the effect of DART-A infusions on the production of the cytokine, IL-6. Serum IL-6 levels (mean±SEM) in monkeys infused with DART-A are shown by treatment group. Cynomolgus monkeys were treated with vehicle control on Day 1, followed by 4 weekly infusions of either vehicle (Group 1) (FIG. 29A) or DART-A administered as 4-day weekly infusions starting on Days 8, 15, 22, and 29 (Groups 2-5) (FIG. 29B) or as a 7-day/week infusion for 4 weeks starting on Days 8 (Group 6) (FIG. 29C). Treatment intervals are indicated by the filled gray bars.
Figure 29B:
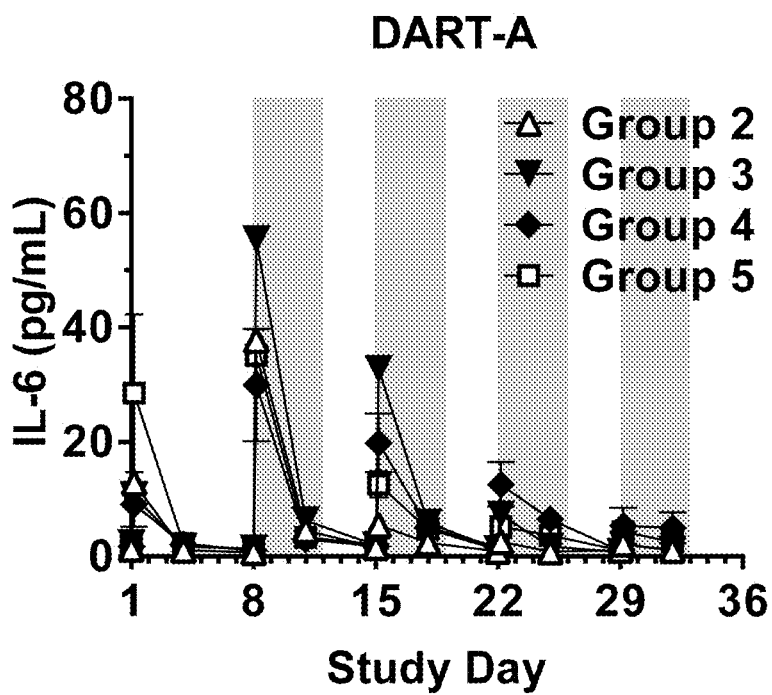
Figure 29C:
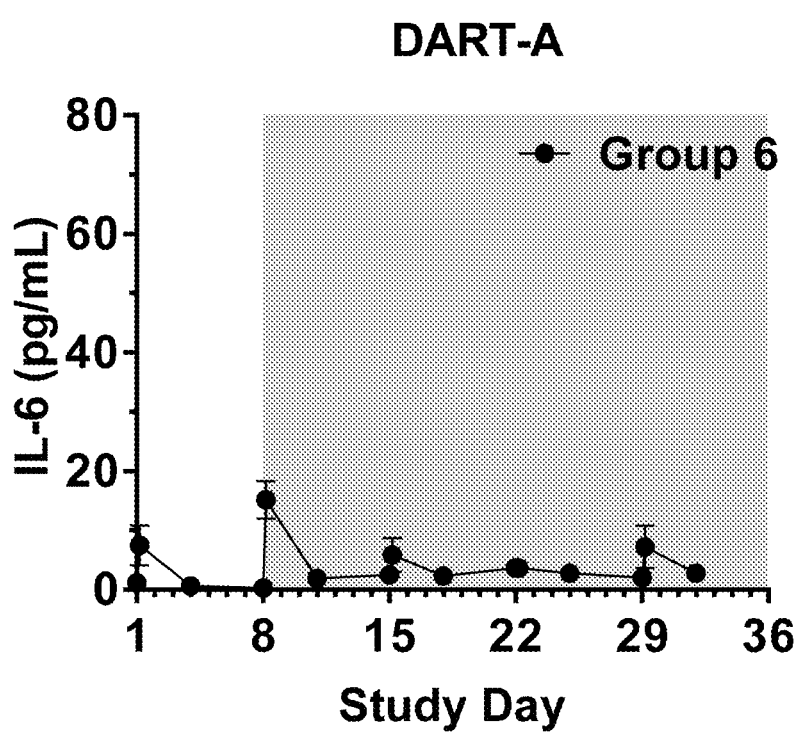

Given the T cell activation properties of DART-A, an increase in circulating cytokines accompanying the infusion was anticipated and a low starting dose was therefore used as a "desensitization" strategy, based on previous experience with similar compounds (see, e.g., Topp, M. S. et al. (2011) "*Targeted Therapy With The T-Cell-Engaging Antibody Blinatumomab Of Chemotherapy-Refractory Minimal Residual Disease In B-Lineage Acute Lymphoblastic Leukemia Patients Results In High Response Rate And Prolonged Leukemia-Free Survival*," J. Clin. Oncol. 29:2493-2498; Bargou, R. et al. (2008) "*Tumor Regression In Cancer Patients By Very Low Doses Of A T Cell-Engaging Antibody*," Science 321:974-977). Of the cytokine tested, IL-6 demonstrated the largest changes upon infusion, albeit transient in nature, of minimal magnitude and with large inter-animal and inter-group variations (FIGS. 29A-29C). Small, transient increases in IL-6 were also observed after vehicle infusions (all Group 1 and all Day 1 infusions), indicating a sensitivity of this cytokine to manipulative stress. Nonetheless, DART-A-dependent increases (<80 pg/mL) in serum IL-6 were seen in some monkeys following the first DART-A infusion (100/kg/day), which returned to baseline by 72 hours. Interestingly, the magnitude of IL-6 release decreased with each successive DART-A infusion, even when the dose level was increased to up to 1000 ng/kg/day. Minimal and transient DART-A-related increases in serum TNF-α (<10 pg/mL) were also observed; as with IL-6, the largest magnitude in TNF-α release was observed following the first infusion. There were no DART-A-related changes in the levels of IL-5, IL-4, IL-2, or IFN-γ throughout the study when compared with controls. In conclusion, cytokine release in response to treatment of monkeys with DART-A was minimal, transient and represented a first-dose effect manageable via intra-subject dose escalation.

DART-A-Mediated Depletion of Circulating CD14−/CD123+ Leukocytes In Vivo

Figure 30A:
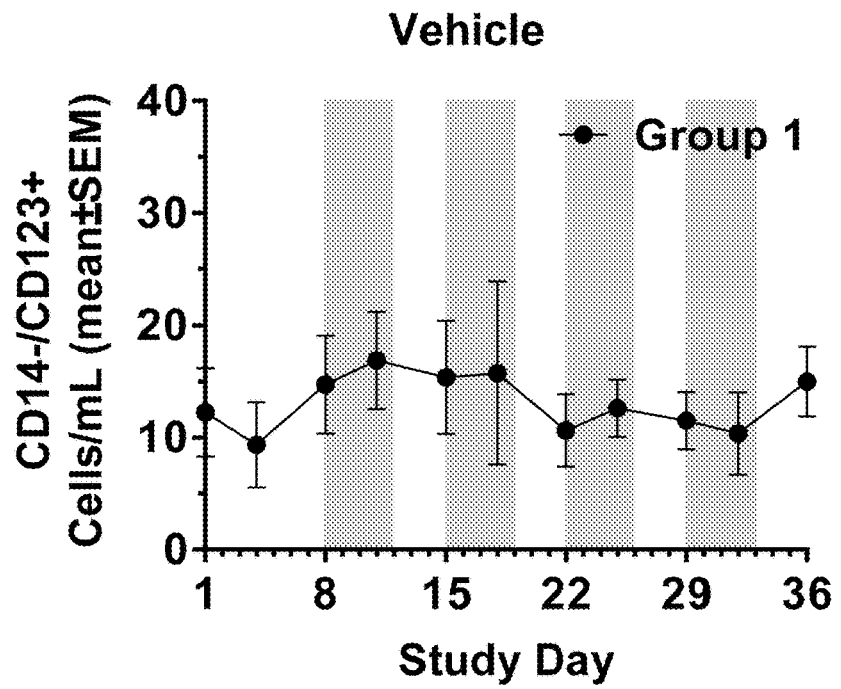
FIGS. 30A-30F show the effect of DART-A infusions on the depletion of CD14−/CD123+ cells (FIGS. 30A-30C) and CD303+ cells (FIGS. 30D-30F). The mean±SEM of the circulating levels of CD14−/CD123+(FIGS. 30A-30C) or CD303+(FIGS. 30D-30F) by Study Day and by group is shown. Cynomolgus monkeys were treated with vehicle control on Day 1, followed by 4 weekly infusions of either vehicle (Group 1) (FIGS. 30A and 30D) or DART-A administered as 4-day weekly infusions starting on Days 8, 15, 22, and 29 (Groups 2-5) (FIGS. 30A and 30E) or as a 7-day/week infusion for 4 weeks starting on Days 8 (Group 6) (FIGS. 30C and 30F). Treatment intervals are indicated by the filled gray bars.
Figure 30B:
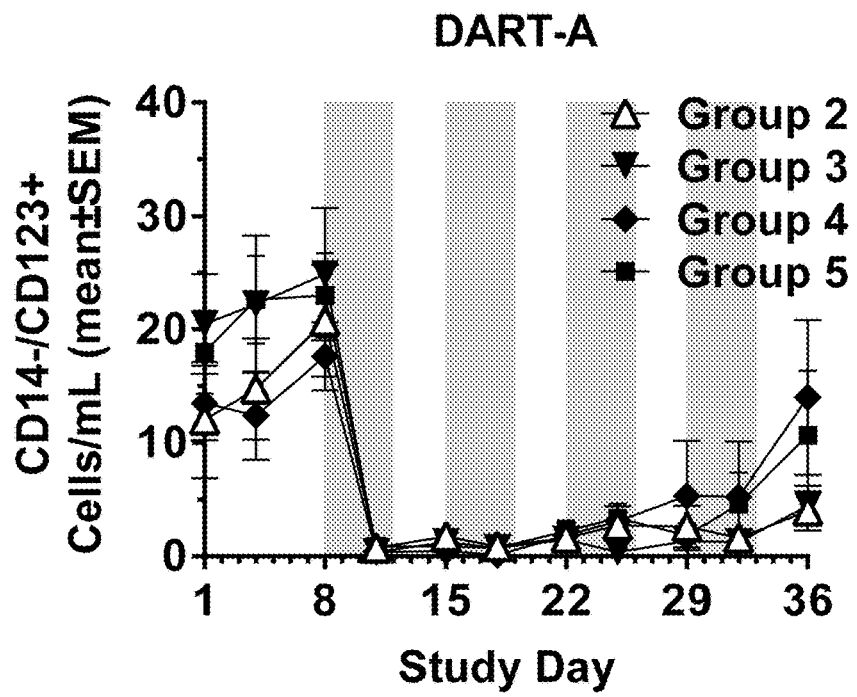
Figure 30C:
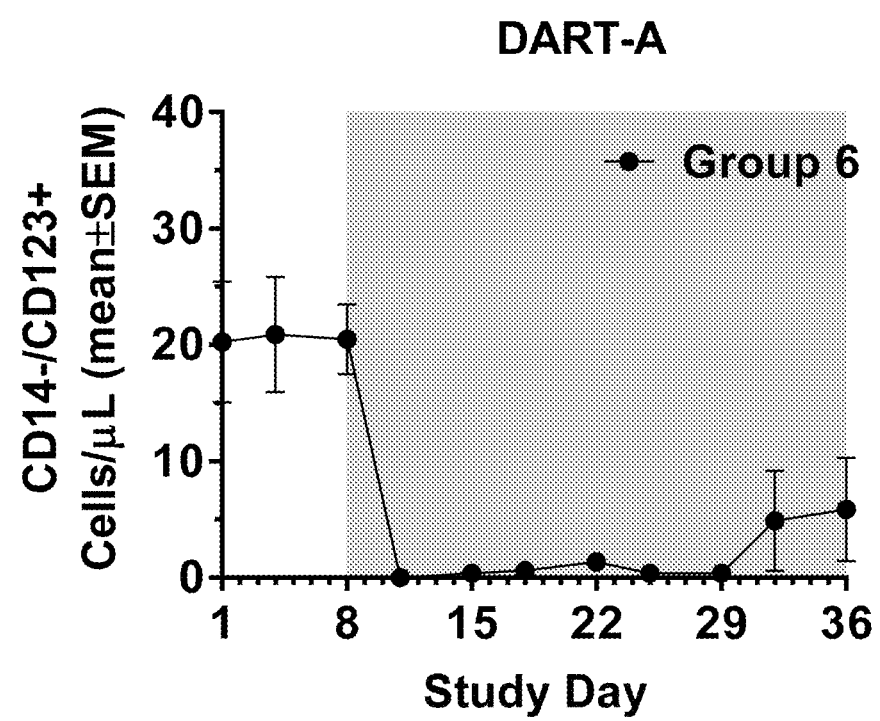
Figure 30D:
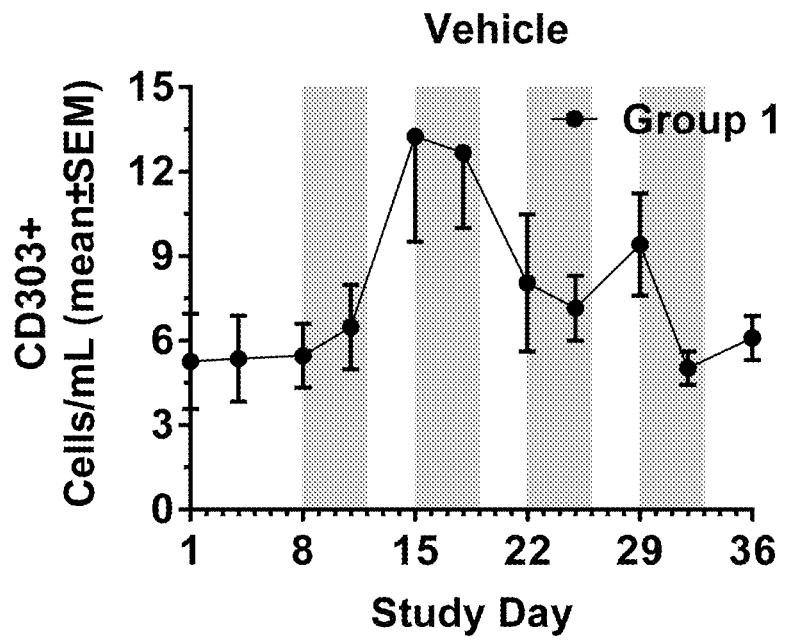
Figure 30E:
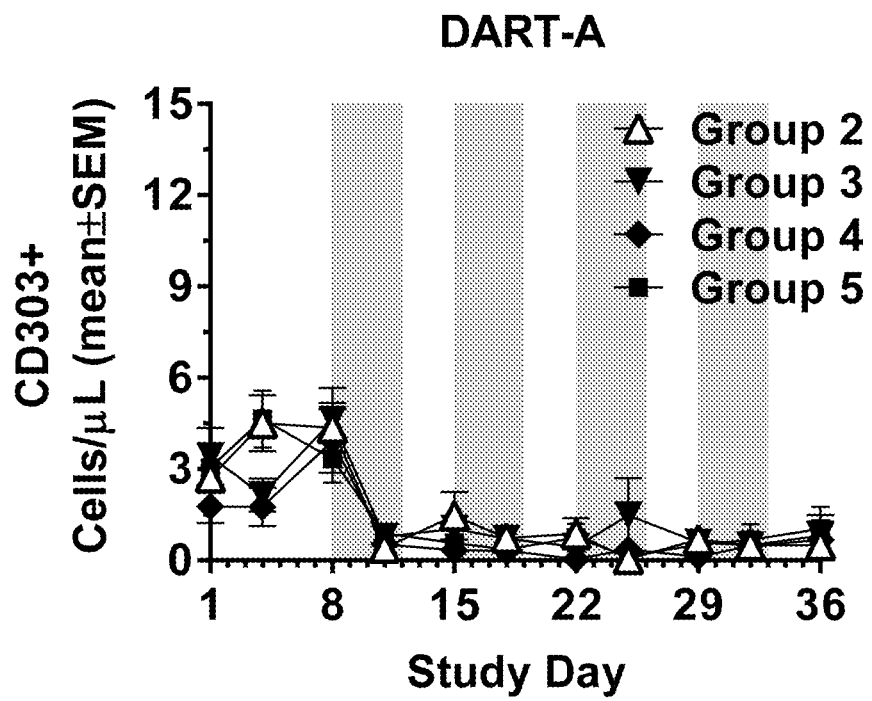
Figure 30F:
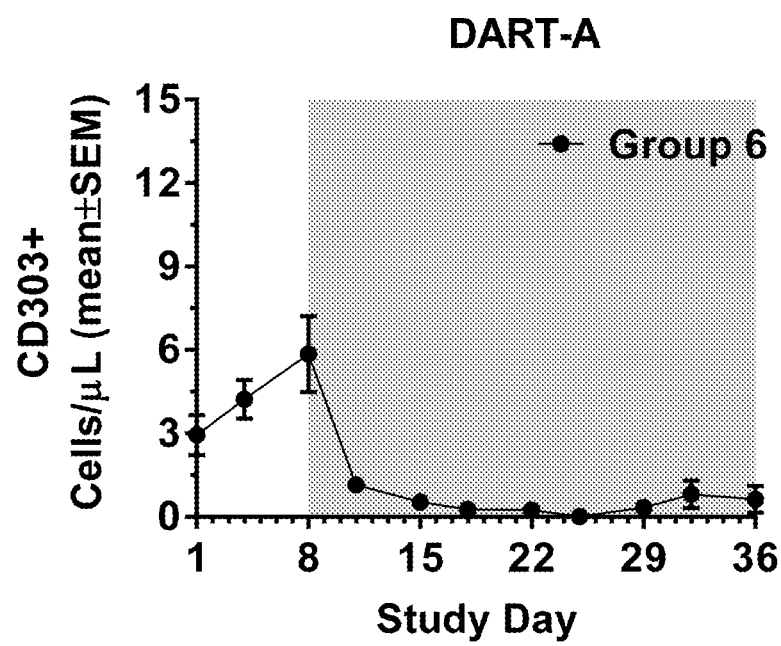

The circulating absolute levels of CD14−/CD123+ cells were measured throughout the study as a pharmacodynamic endpoint. While the number of CD123+ cells in control Group 1 remained stable over time, DART-A treatment was associated with extensive depletion of circulating CD14−/CD123+ cells (94-100% from prestudy baseline) observable from the first time point measured (72 hours) following the start of the first DART-A infusion (100 ng/kg/day) in all animals across all active treatment groups (FIGS. 30A-30C). The depletion was durable, as it persisted during the 3-day weekly dosing holiday in Group 2-5, returning to baseline levels only during the prolonged recovery period. To eliminate the possibility of DART-A masking or modulating CD123 (an unlikely scenario, given the low circulating DART-A levels), pDCs were enumerated by the orthogonal marker, CD303. Consistent with the CD123 data, CD303+ pDC were similarly depleted in monkeys treated with DART-A (FIGS. 30D-30F).

Circulating T-Lymphocyte Levels, Activation and Subset Analysis

Figure 31A:
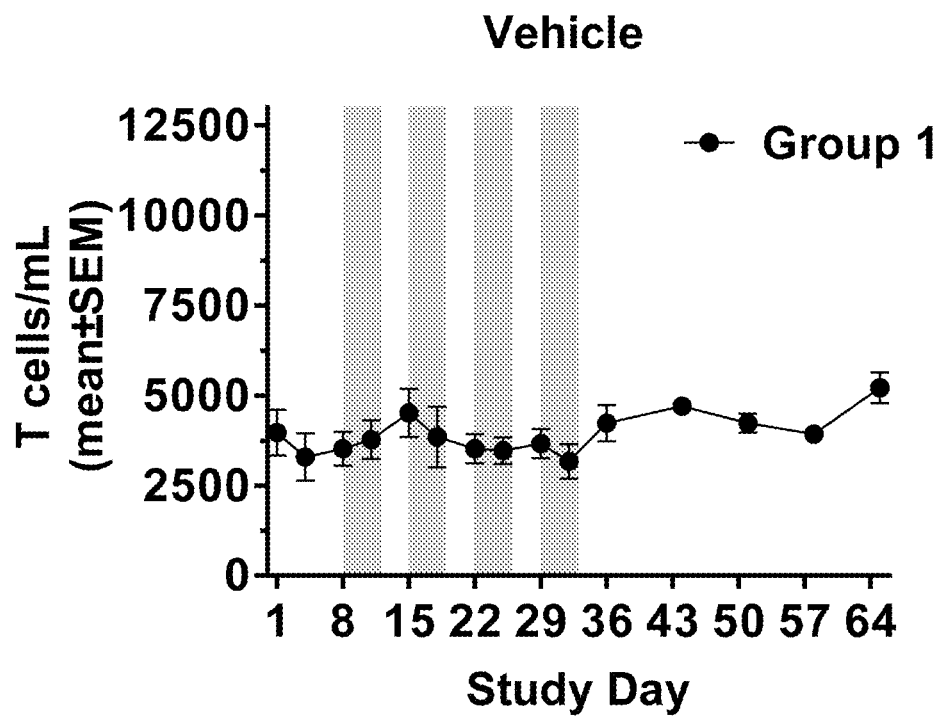
FIGS. 31A-31I show the observed changes in T cell populations (FIGS. 31A-31C), CD4+ cell populations (FIGS. 31D-31F) and CD8+ cell populations (FIGS. 31G-31I) receiving DART-A administered as 4-day infusions starting on Days 8, 15, 22, and 29. Legend: CD25+(gray squares); CD69+(gray triangles), PD-1+(white triangles); Tim-3+(white squares). T cells were enumerated via the CD4 and CD8 markers, rather than the canonical CD3, to eliminate possible interference the DART-A. Cynomolgus monkeys were treated with vehicle control on Day 1, followed by 4 weekly infusions of either vehicle (Group 1) or DART-A administered as 4-day weekly infusions starting on Days 8, 15, 22, and 29 (Group 5) or as a 7-day/week infusion for 4 weeks starting on Days 8 (Group 6). Treatment intervals are indicated by the filled gray bars. The mean±SEM of the absolute number of total circulating T cells by Study Day and group is shown (FIGS. 31A-31C). Relative values (mean percent±SEM) of CD25+, CD69+, PD-1+ and Tim-3+ of CD4 (FIGS. 31D-31E) or CD8 T cells (FIGS. 31F-31H) by Study Day and by group is shown.
Figure 31B:
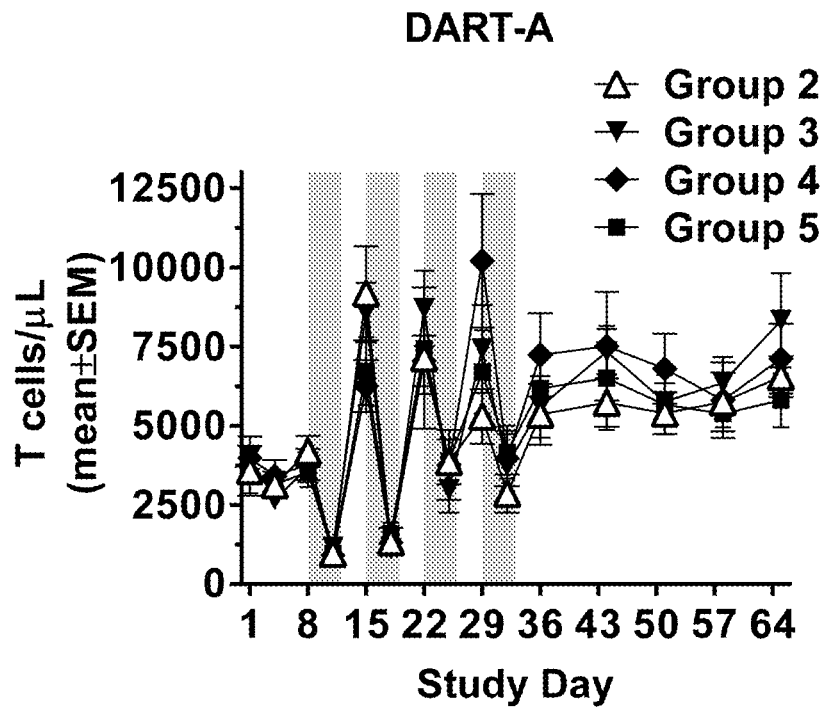
Figure 31C:
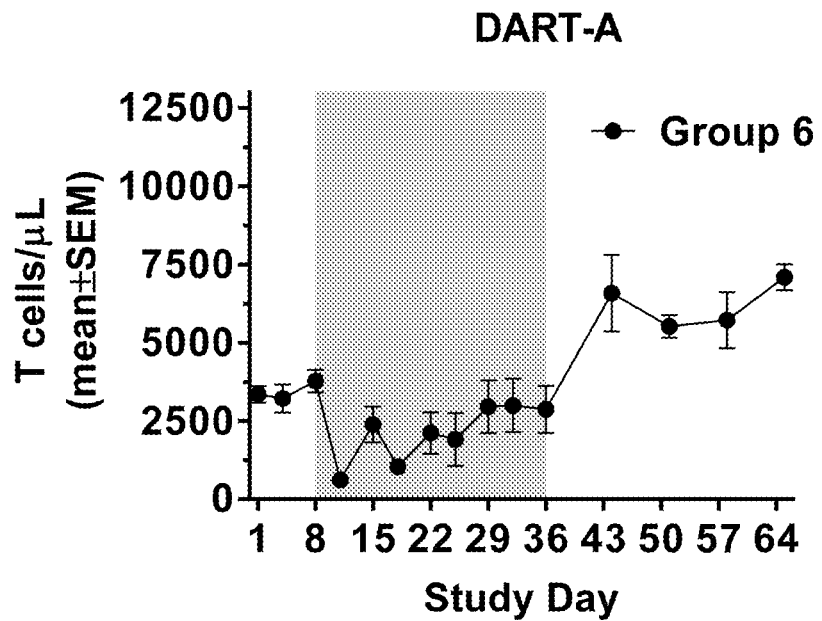
Figure 31D:
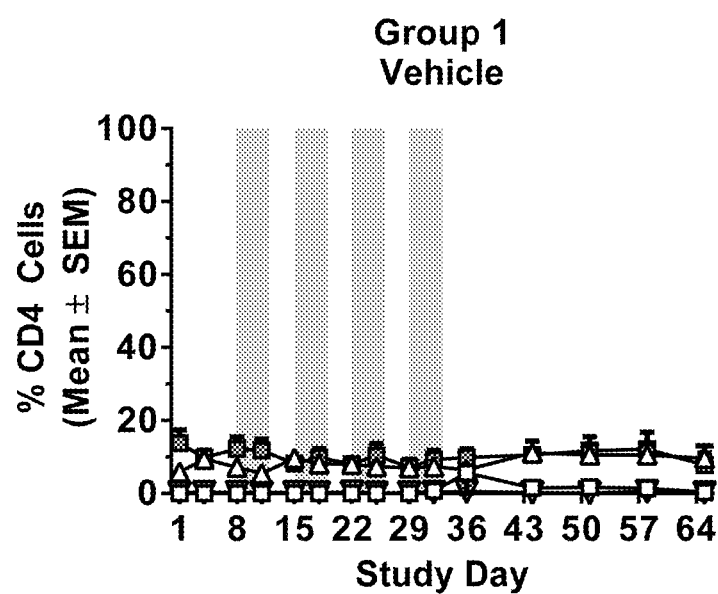
Figure 31E:
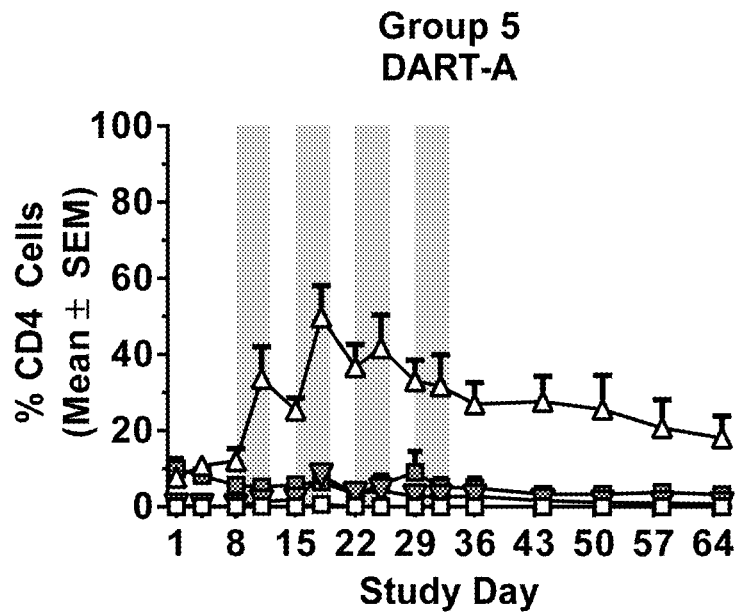
Figure 31F:
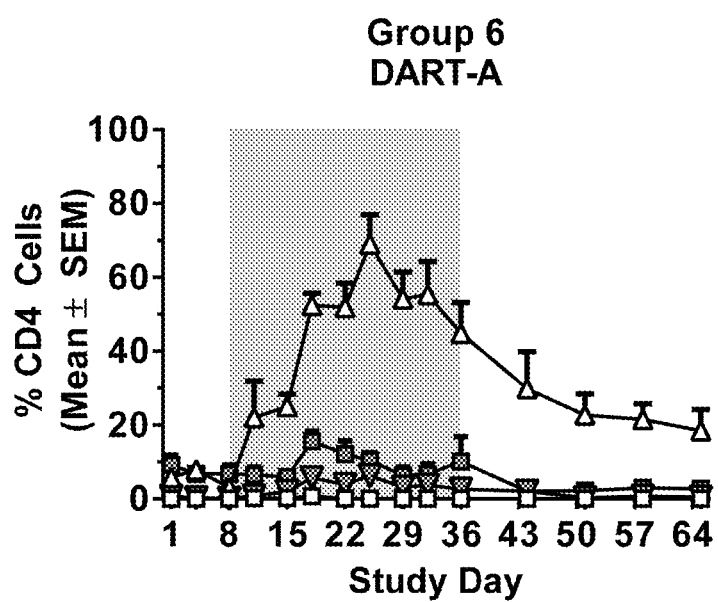
Figure 31G:
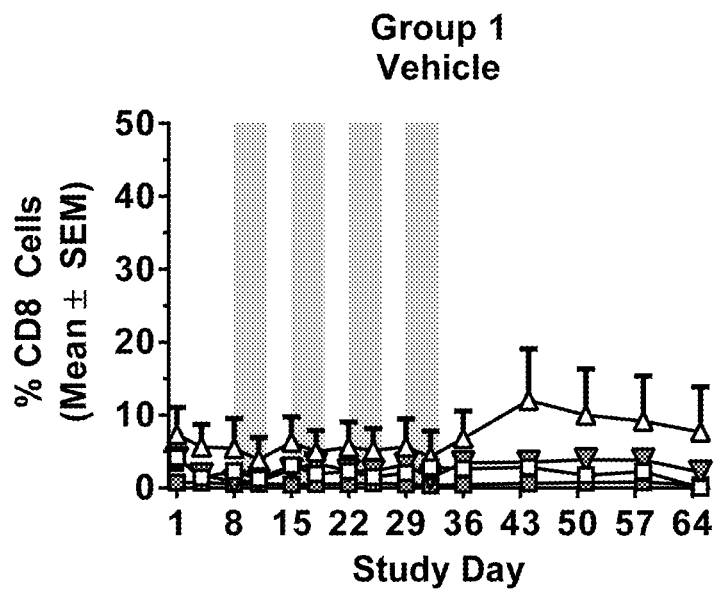
Figure 31H:
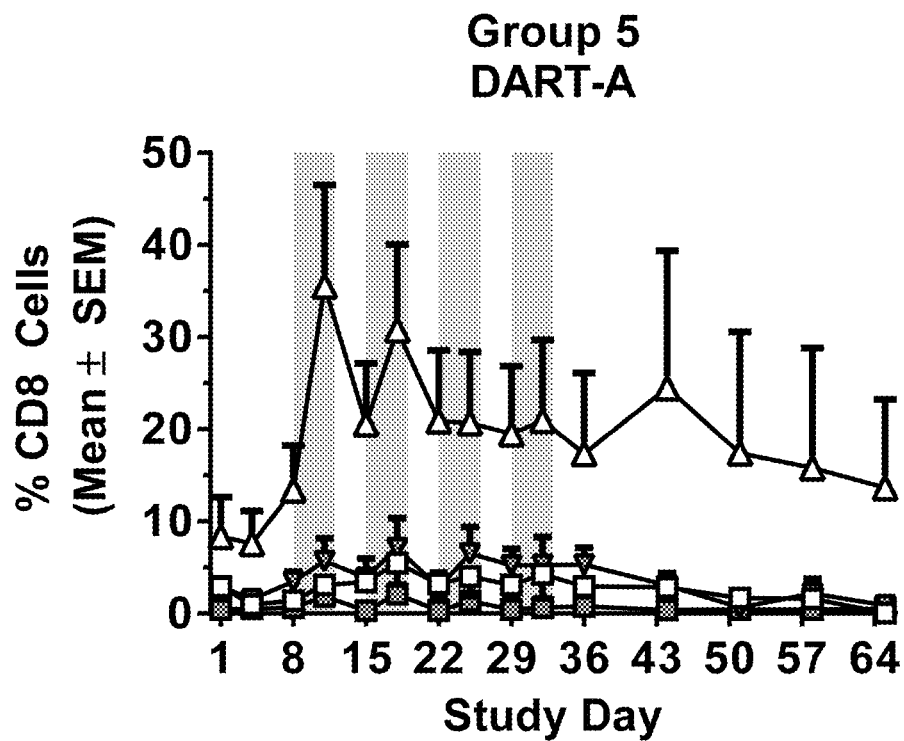
Figure 31I:
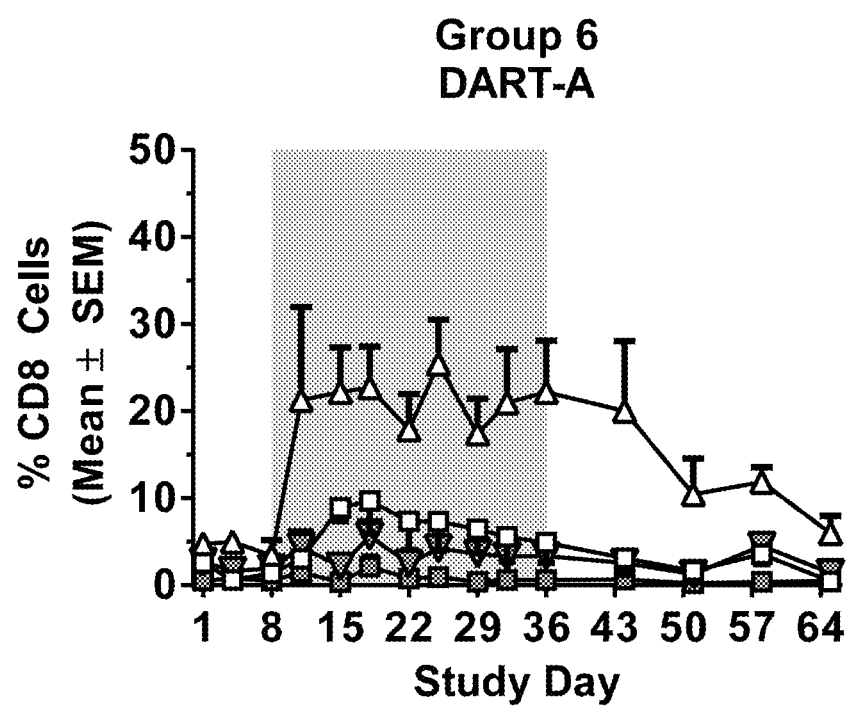
Figure 32A:
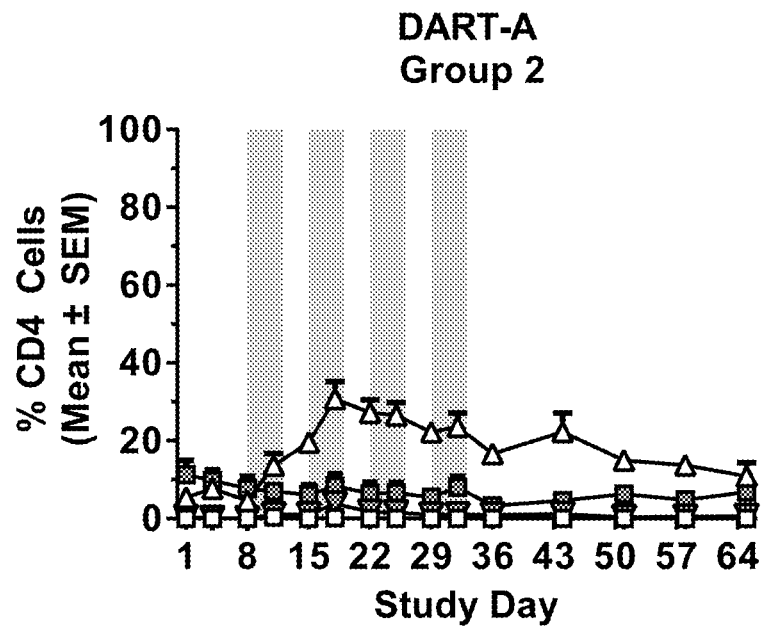
FIGS. 32A-32F show the observed changes in T CD4+ cell populations (FIGS. 32A-32C) and CD8+ cell populations (FIGS. 32D-32F) during and after a continuous 7-day infusion of DART-A. The mean±SEM percent of CD25+, CD69+, PD-1+ and Tim-3+ on CD4 (FIGS. 32A-32C) or CD8 (FIGS. 32D-32F) T cells by Study Day for Groups 2, 3 and 4 are shown. Treatment intervals are indicated by the filled gray bars. Legend: CD25+(gray squares); CD69+(gray triangles), PD-1+(white triangles); Tim-3+(white squares).
Figure 32B:
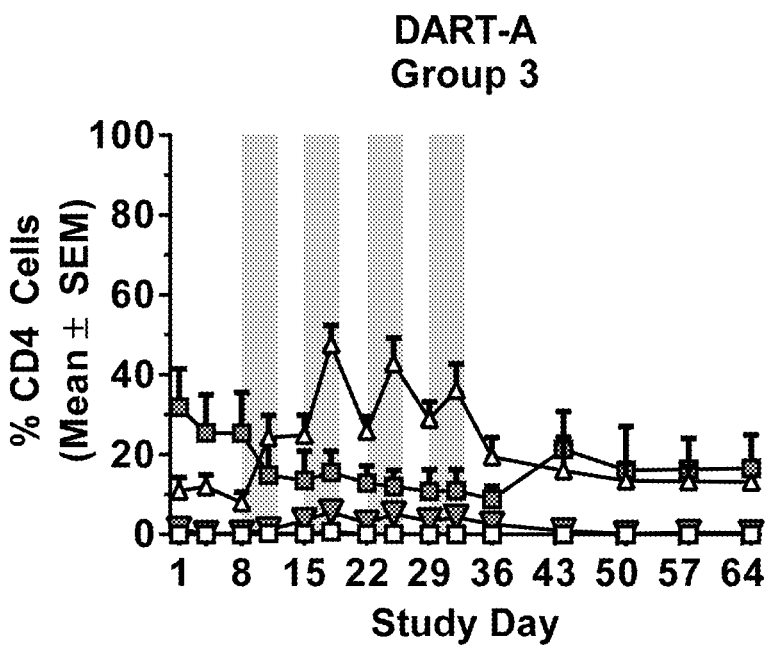
Figure 32C:
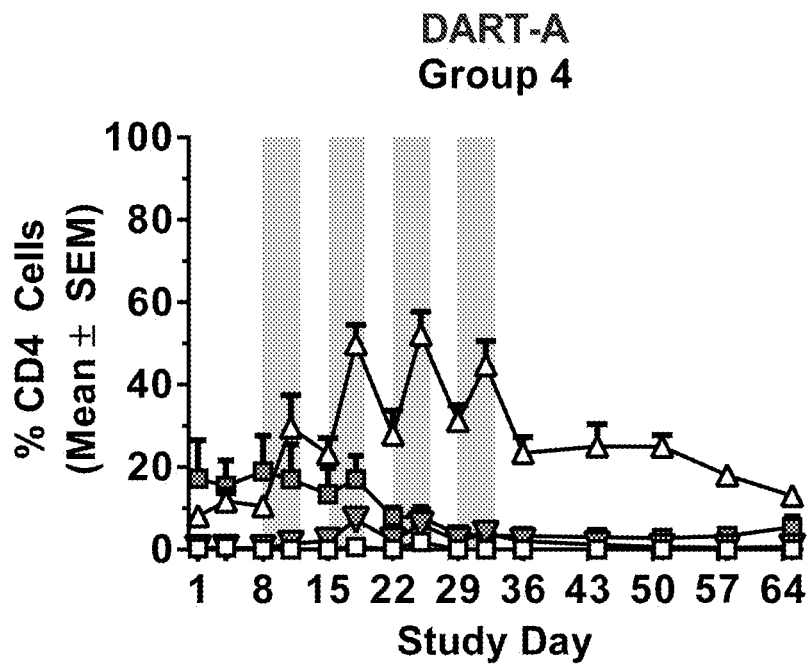
Figure 32D:
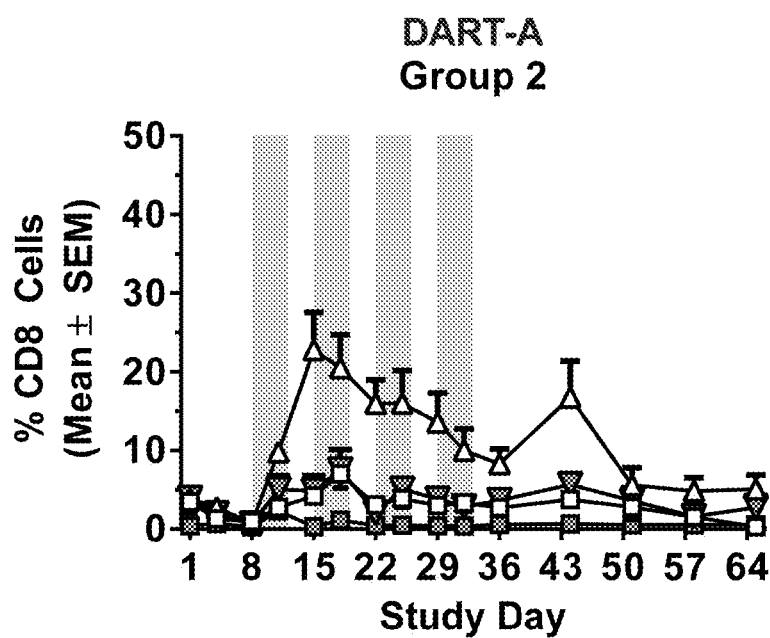
Figure 32E:
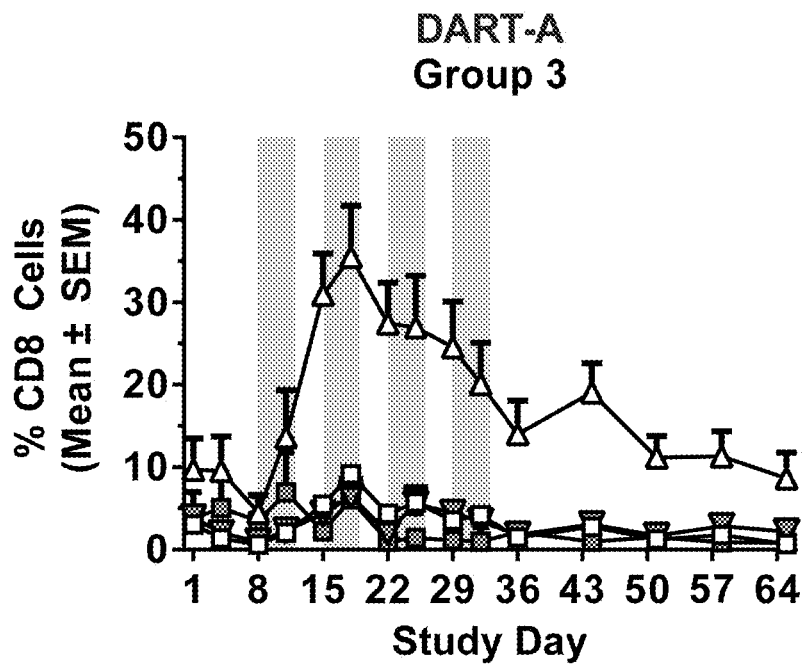
Figure 32F:
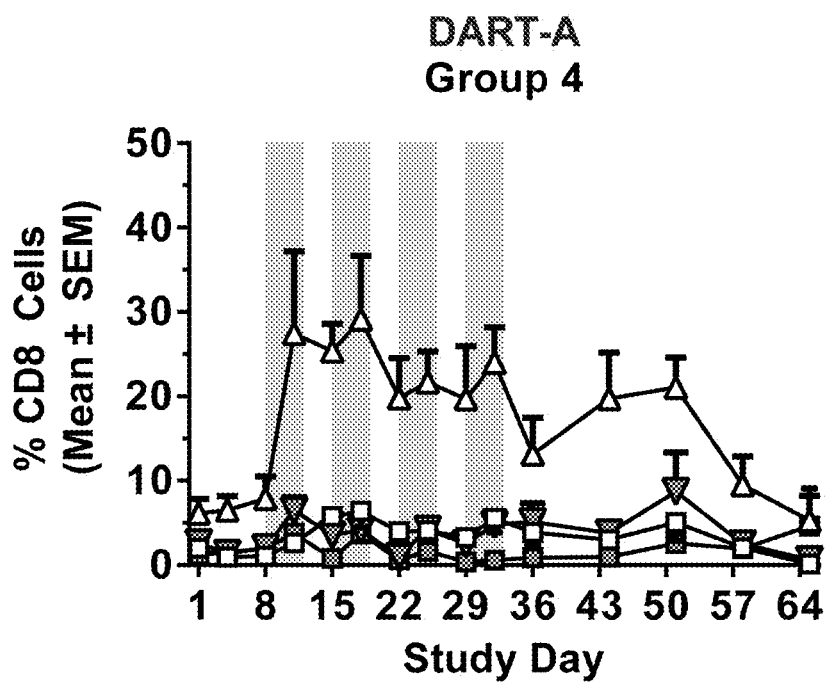
Figure 33A:
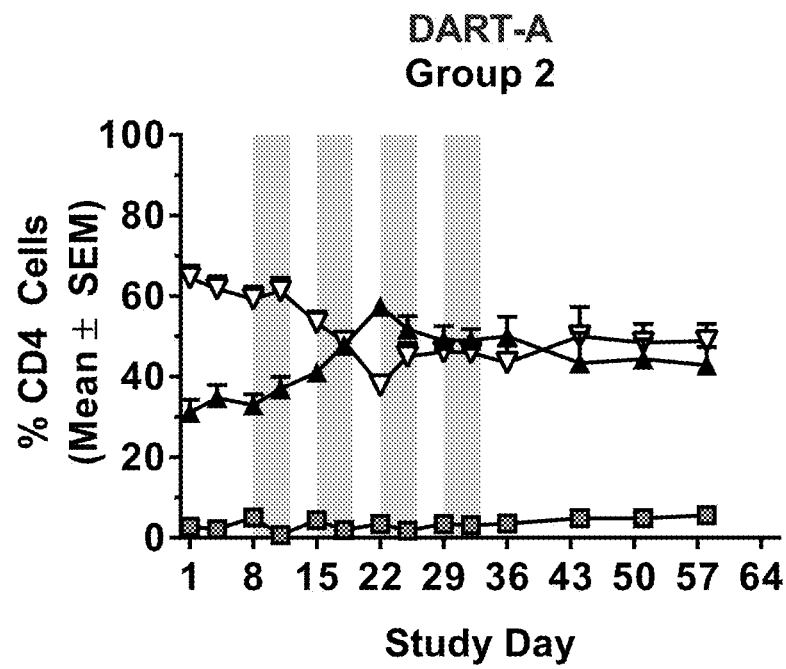
FIGS. 33A-33F show the observed changes in T CD4+ cell populations (FIGS. 33A-33C) and CD8+ cell populations (FIGS. 33D-33F) during and after a continuous 7-day infusion of DART-A. The mean±SEM percent of CD4+ Naïve (CD95−/CD28+), CMT (CD95+/CD28+), and EMT (CD95+/CD28−) T cells in CD4+ population (FIGS. 33A-33C) or CD8 population (FIGS. 33D-33F) by Study Day for Groups 2, 3 and 4 are shown. Cynomolgus monkeys were treated with vehicle control on Day 1, followed by 4 weekly infusions of or DART-A administered as 4-day weekly infusions starting on Days 8, 15, 22, and 29 (Groups 2-4). Treatment intervals are indicated by the filled gray bars. Legend: Naïve (white triangles); CMT (black triangles), EMT (gray squares).
Figure 33B:
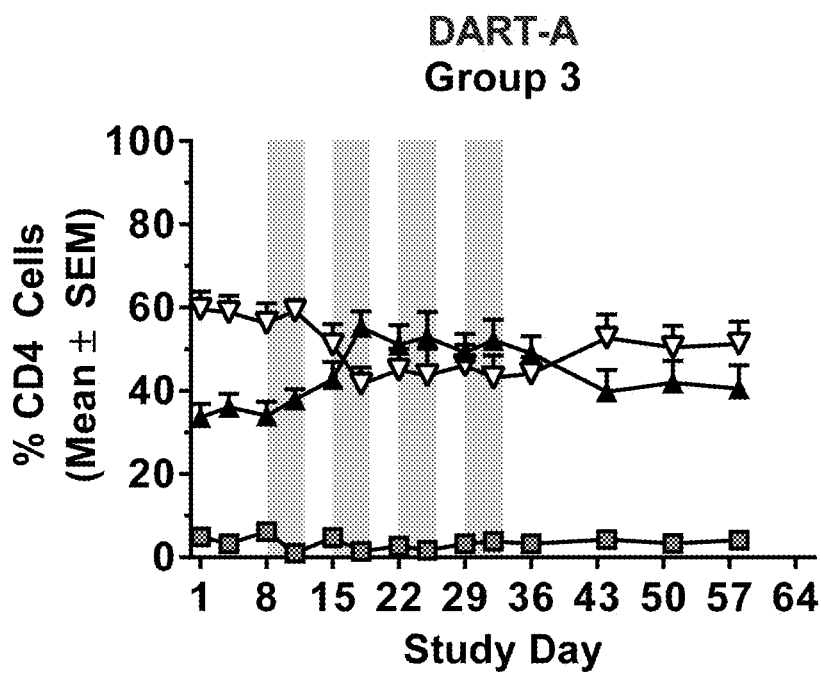
Figure 33C:
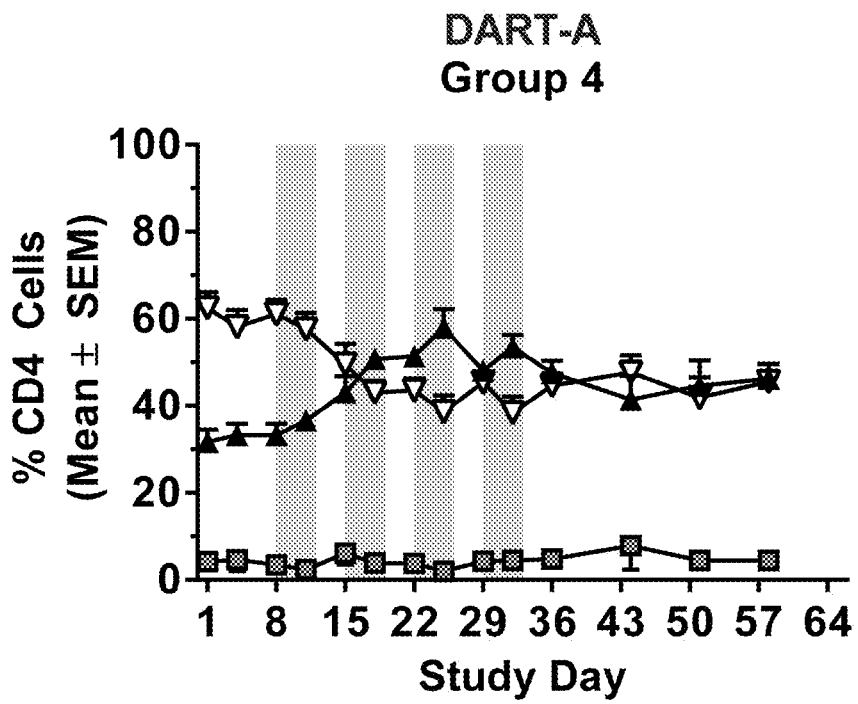
Figure 33D:
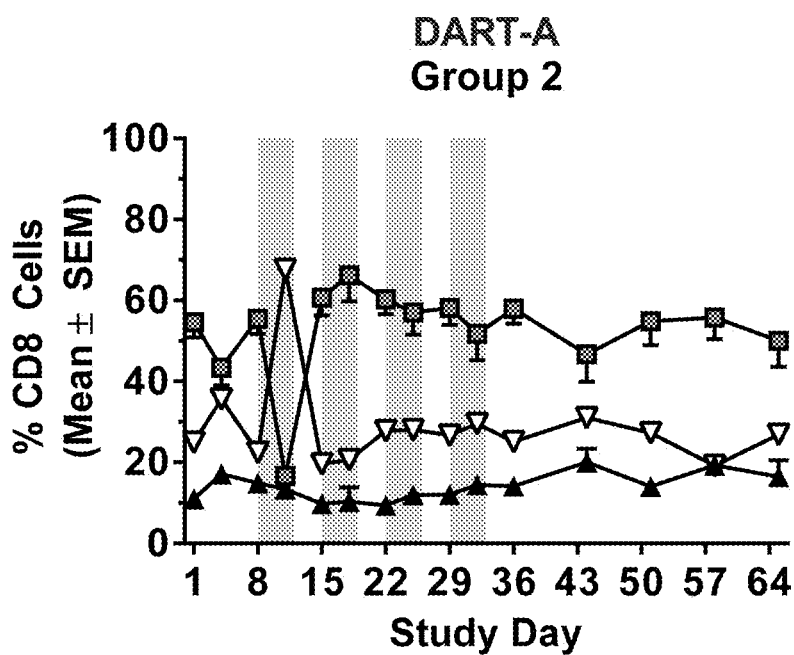
Figure 33E:
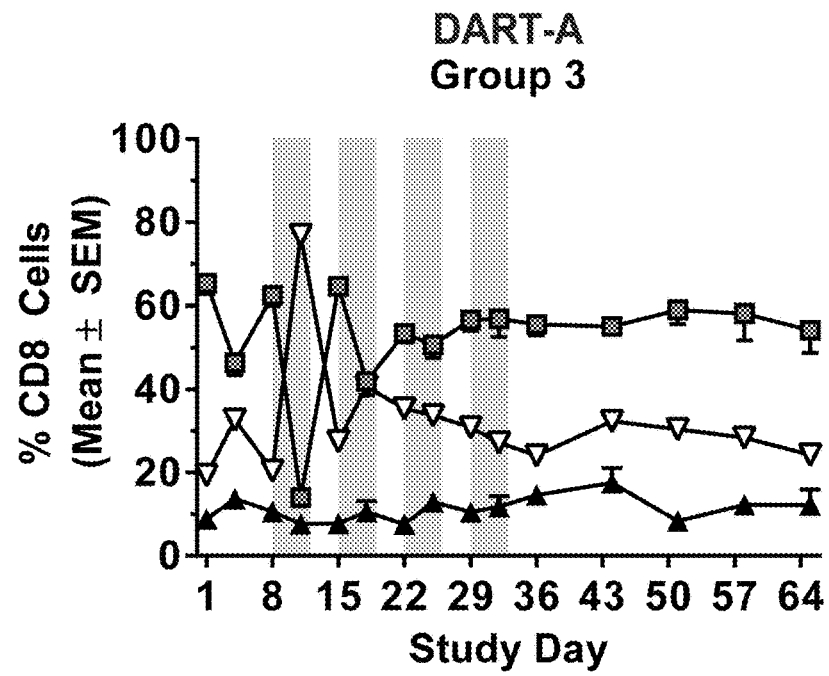
Figure 33F:
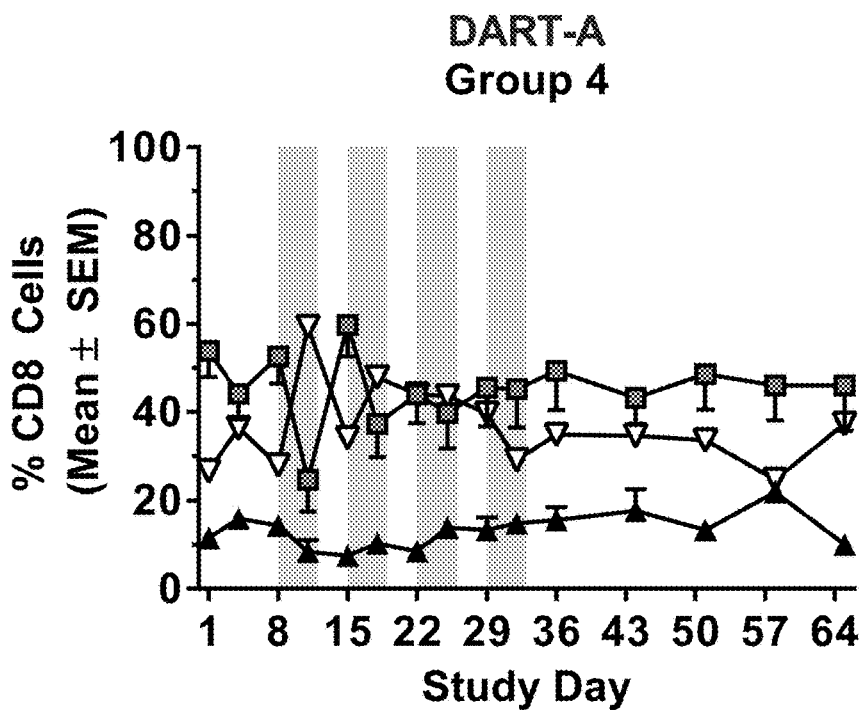

In contrast to the persistent depletion of circulating CD123+ cells, DART-A administered on the 4-day-on/3-day-off schedule (Groups 2-5) were associated with weekly fluctuations in circulating T cells, while administration as continuous 7-day infusions resulted in similarly decreased circulating T cell levels following the first administration that slowly recovered without fluctuation even during the dosing period (FIGS. 31A-31C). The difference between the two dosing strategies indicates that the effect of DART-A on T lymphocytes is consistent with trafficking and/or margination, rather than depletion. Following cessation of dosing, T cells rebounded to levels approximately 2-fold higher than baseline for the duration of the recovery period. Infusion of DART-A was associated with an exposure-dependent, progressive increased frequency of T cells expressing the late activation marker, PD-1, particularly in CD4+ cells, with dose Group 6 displaying the highest overall levels (FIGS. 31D-31I and FIGS. 32A-32F and FIGS. 33A-33F). Tim-3, a marker associated with T cell exhaustion, was not detected on CD4+ T cells and only at low frequency among CD8+ cells (5.5-9.7%) and comprising 20.5-35.5% of the CD8+/PD-1+ double-positive cells. There was no consistent change in the early T cell activation marker, CD69, and only modest variations in CD25 expression among circulating cells.

Figure 34:
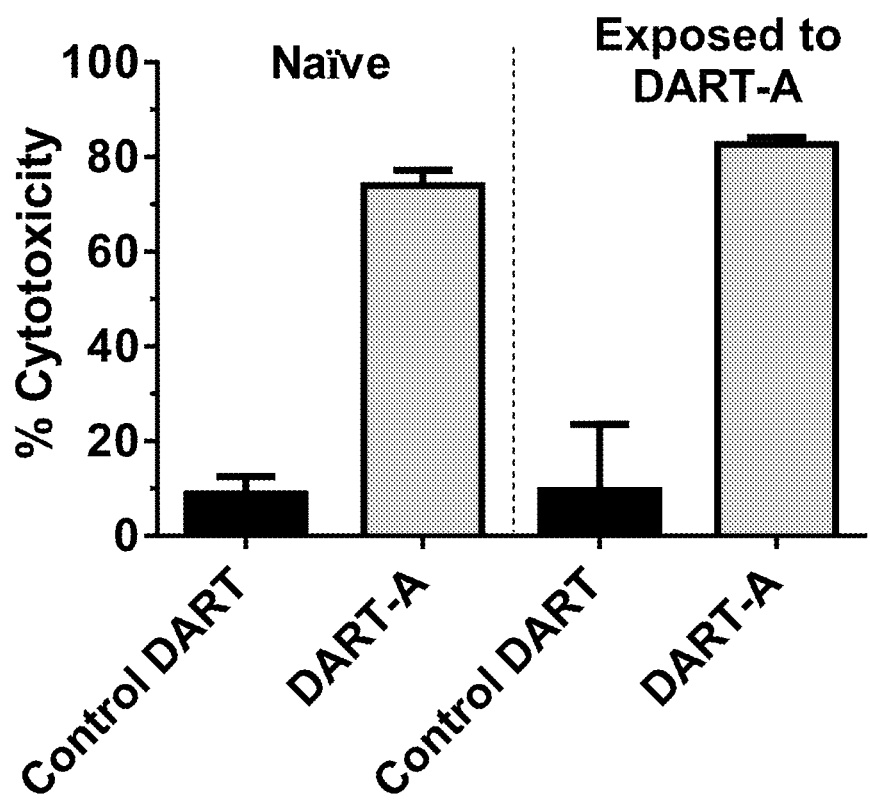
FIG. 34 shows DART-A-mediated cytotoxicity against Kasumi-3 cells with PBMCs from either naïve monkeys or monkeys treated with multiple infusions of DART-A.
Figure 35A:
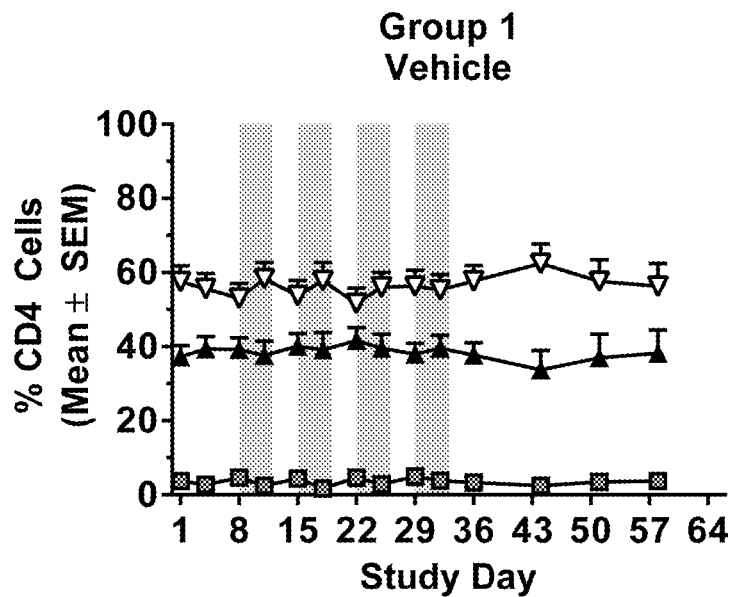
FIGS. 35A-35F show that DART-A exposure increased the relative frequency of central memory CD4 cells and effector memory CD8+ cells at the expense of the corresponding naïve T cell population. The mean±SEM percent of CD4+Naïve (CD95−/CD28+), CMT (CD95+/CD28+), and EMT (CD95+/CD28−) T cells in CD4+ population (FIGS. 35A-35C) or in CD8+ population (FIGS. 35D-35F) by Study Day and by Group is shown. Cynomolgus monkeys were treated with vehicle control on Day 1, followed by 4 weekly infusions of either vehicle (Group 1) or DART-A administered as 4-day weekly infusions starting on Days 8, 15, 22, and 29 (Group 5) or as a 7-day/week infusion for 4 weeks starting on Days 8 (Group 6). Treatment intervals are indicated by the filled gray bars. Legend: Naïve (white triangles); CMT (black triangles), EMT (gray squares).
Figure 35B:
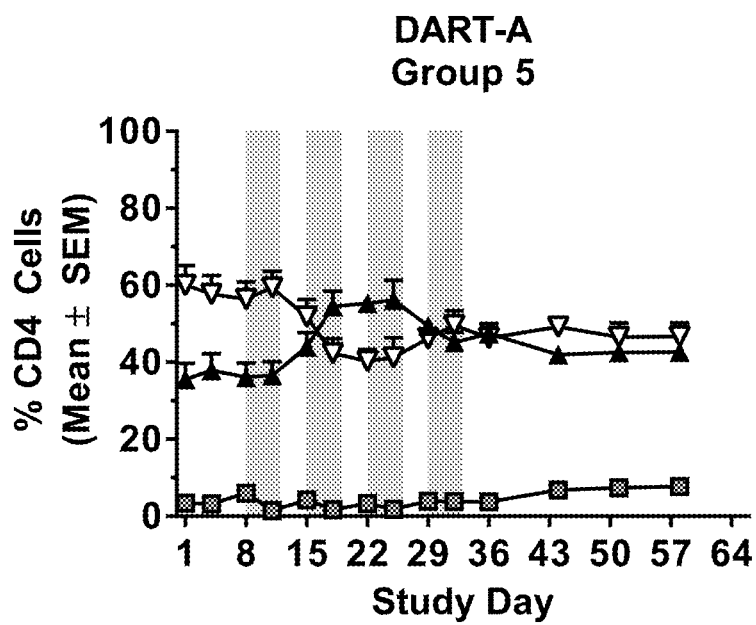
Figure 35C:
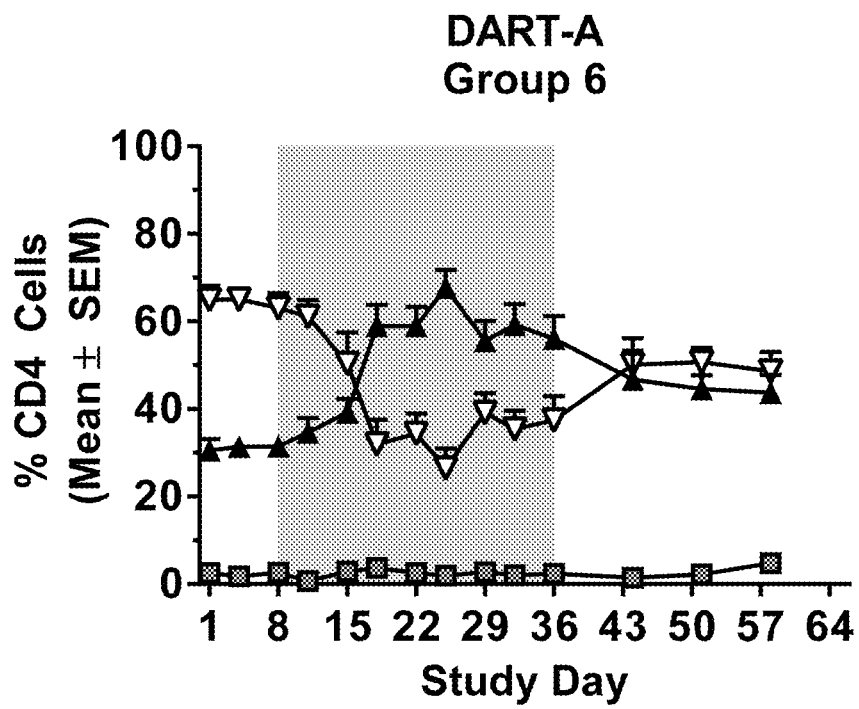
Figure 35D:
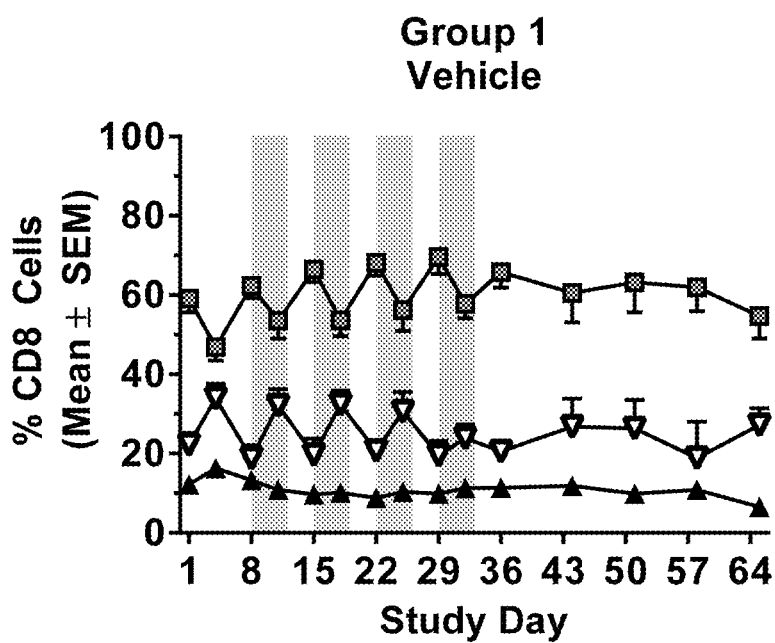
Figure 35E:
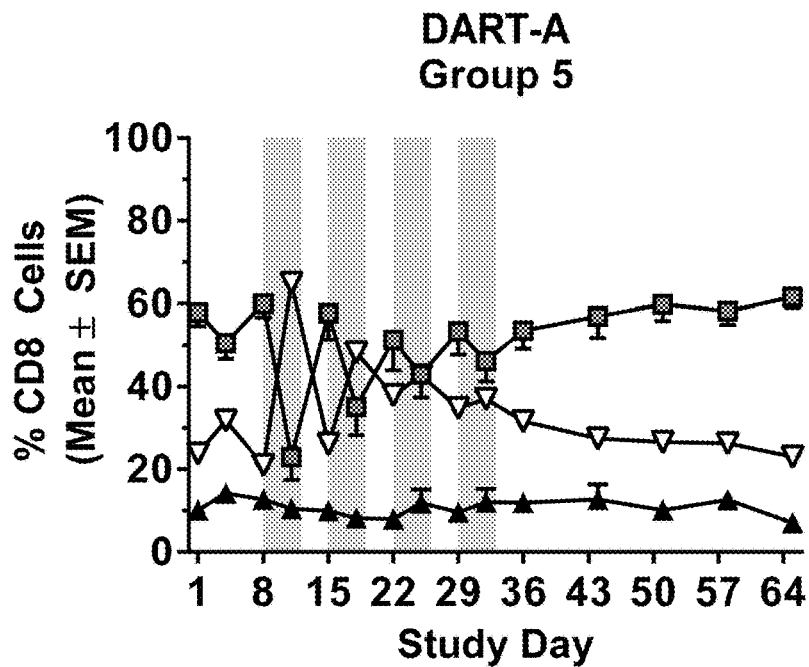
Figure 35F:
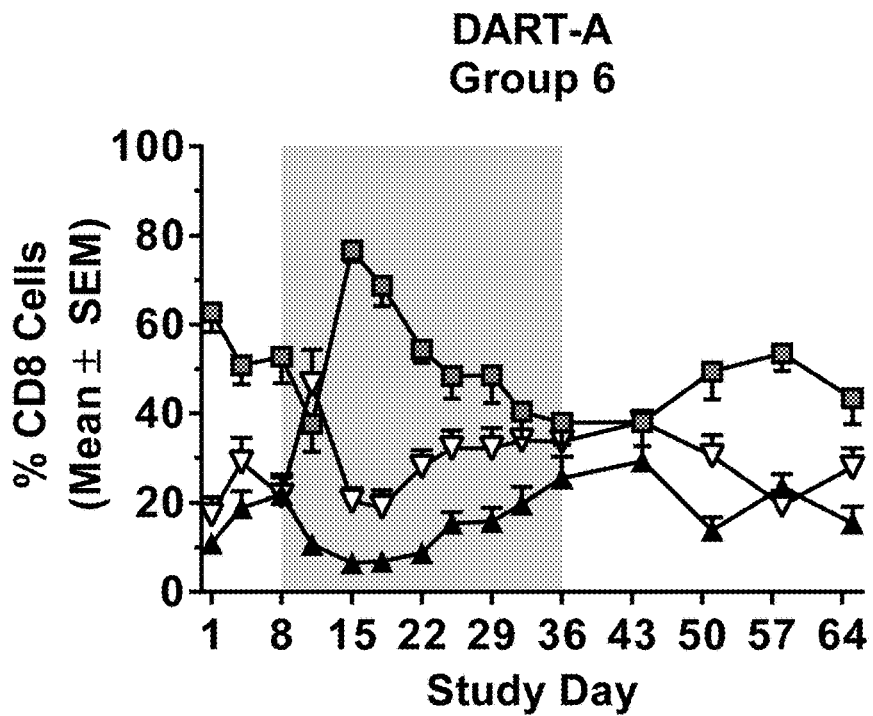

To rule out exhaustion after in vivo exposure, the ex vivo cytotoxic potential of effector cells isolated from cynomolgus monkeys receiving multiple infusions of DART-A was compared to that of cells from naïve monkeys. As shown in FIG. 34, PBMC isolated from DART-A-treated monkeys show cytotoxicity comparable to that of cells isolated from naïve monkeys, indicating that in vivo exposure to DART-A does not negatively impact the ability of T cells to kill target cells.

DART-A exposure increased the relative frequency of central memory CD4 cells and effector memory CD8+ cells at the expense of the corresponding naïve T cell population (FIGS. 35A-35F and FIGS. 32A-32F and FIGS. 33A-33F), indicating that DART-A exposure promoted expansion and/or mobilization of these cells.

Effects on Hematopoiesis and Bone Marrow Precursors

Figure 36A:
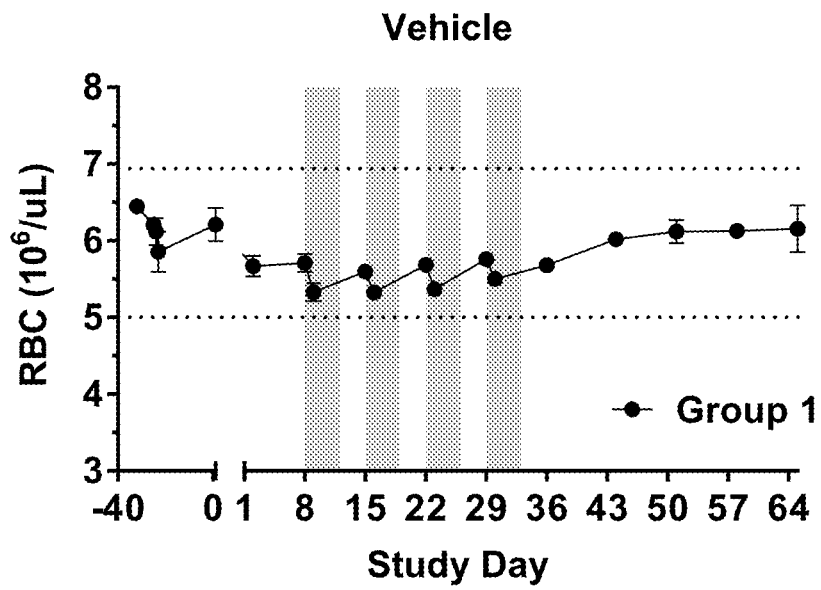
FIGS. 36A-36F show the effect of DART-A on red cell parameters in monkeys that had received infusions of the molecules. Circulating RBCs (FIGS. 36A-36C) or reticulocytes (FIGS. 36D-36F) levels (mean±SEM) in samples collected at the indicated time points from monkeys treated with DART-A are shown.
Figure 36B:
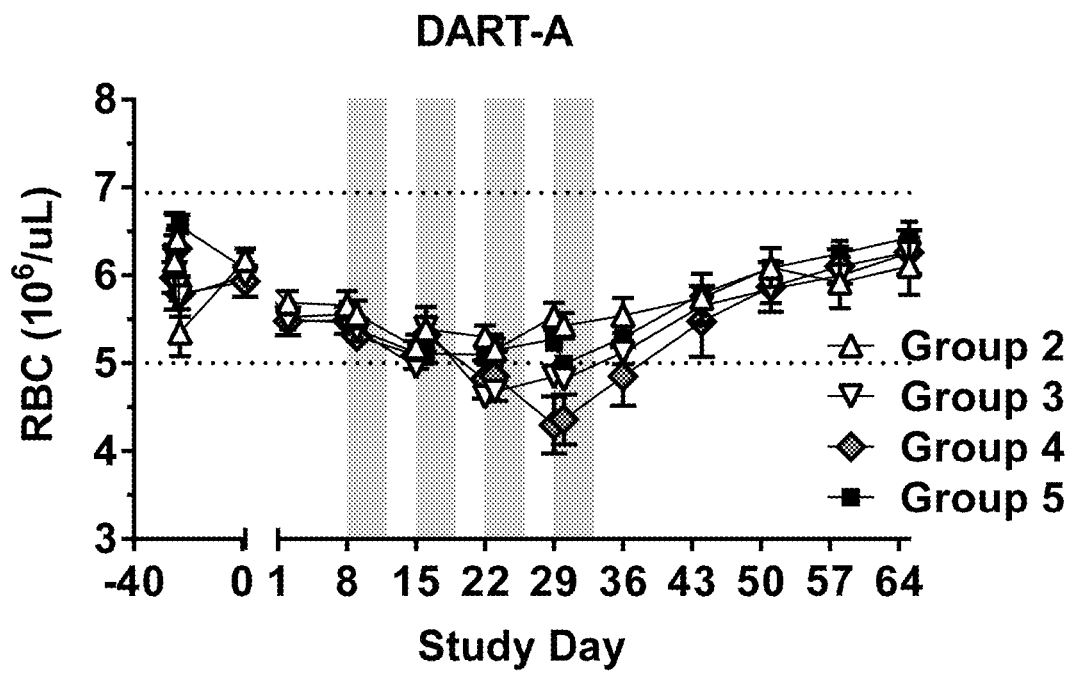
Figure 36C:
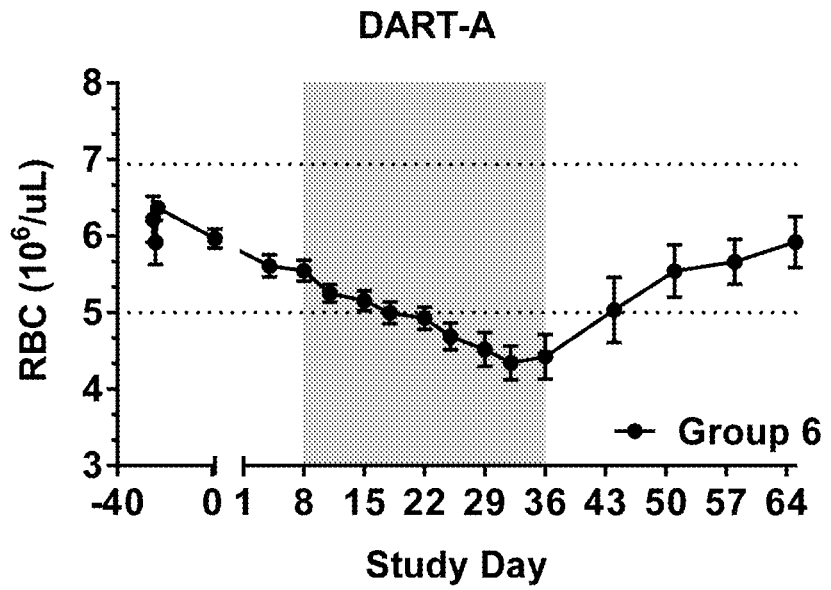
Figure 36D:
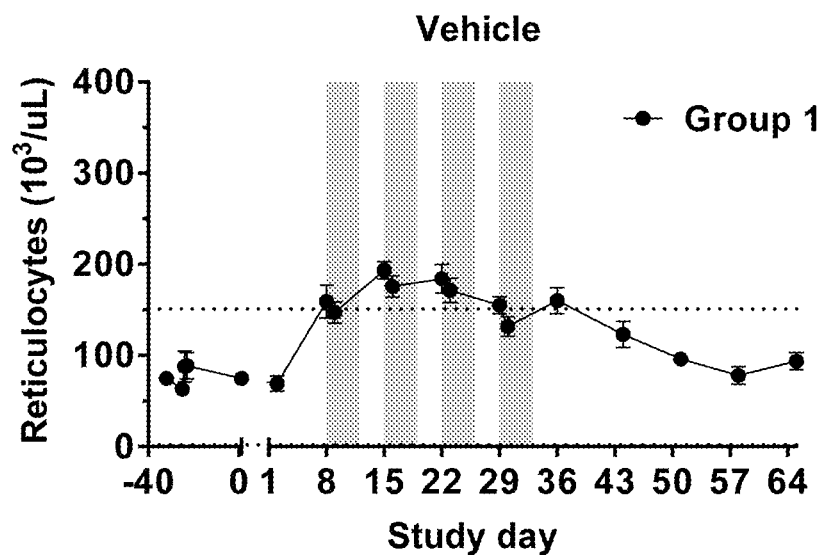
Figure 36E:
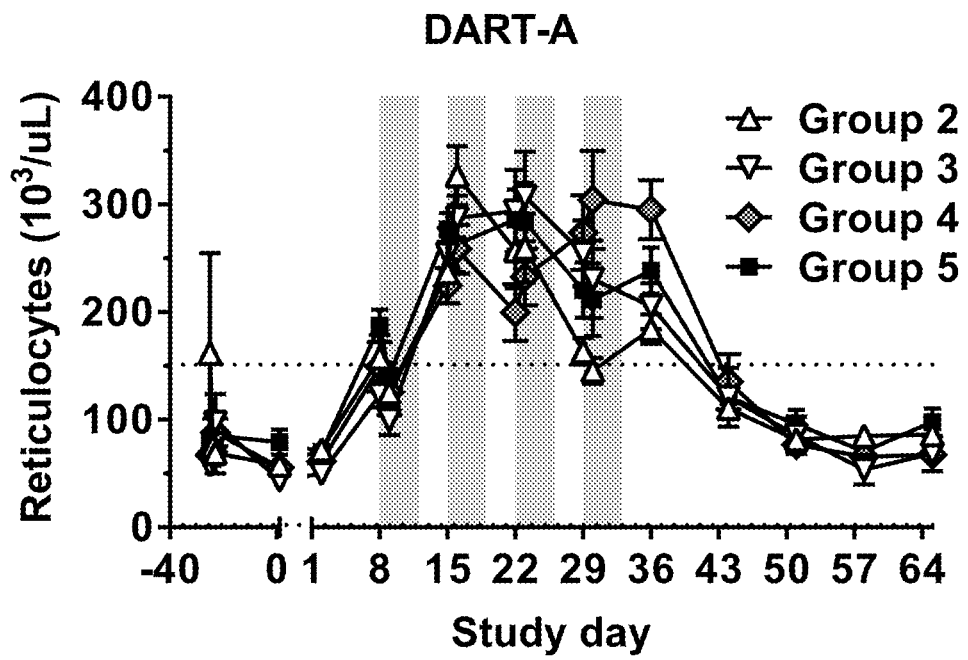
Figure 36F:
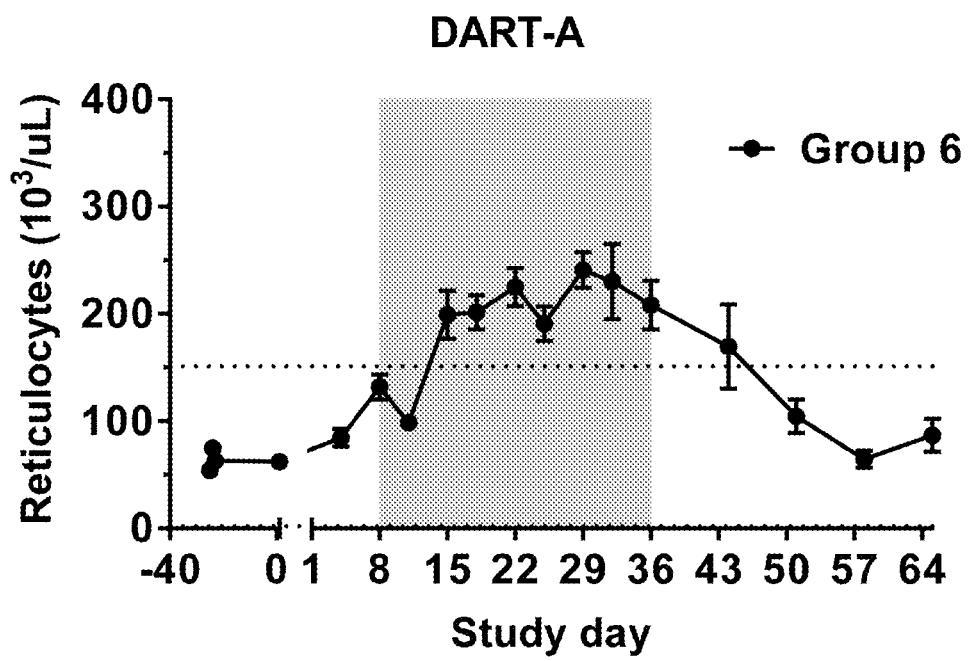
Figure 37A:
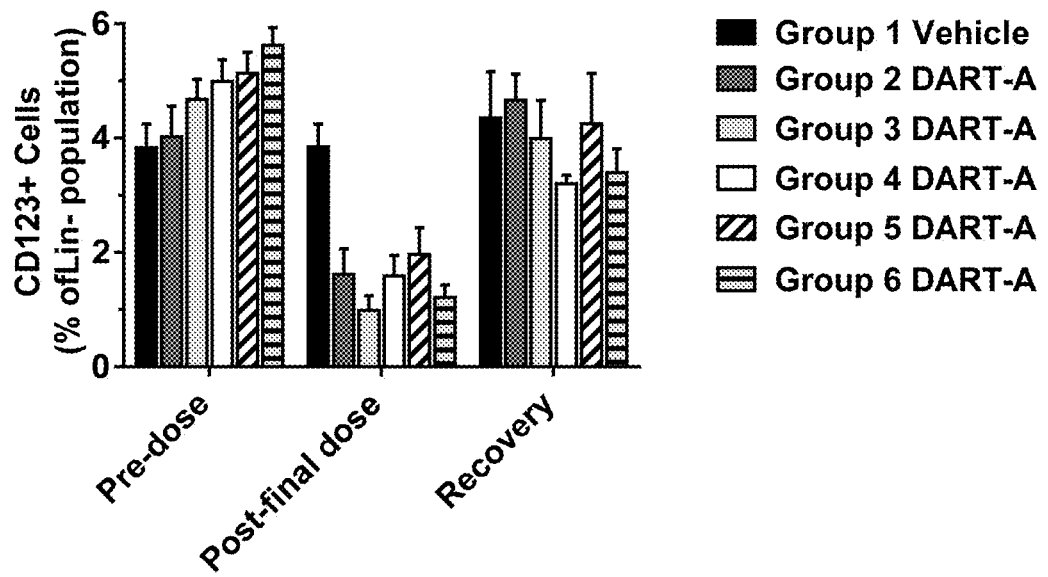
FIGS. 37A-37B show that the frequency (mean percent±SEM) of CD123+ cells (FIG. 37A) or HSC (CD34+/CD38−/CD45−/CD90+ cells) (FIG. 37B) within the Lin−cell population in bone marrow samples collected at the indicated time points from monkeys treated with DART-A. Cynomolgus monkeys were treated with vehicle control on Day 1, followed by 4 weekly infusions of either vehicle (Group 1) or DART-A administered as 4-day weekly infusions starting on Days 8, 15, 22, and 29 (Groups 2-5) or as a 7-day/week infusion for 4 weeks starting on Days 8 (Group 6).
Figure 37B:
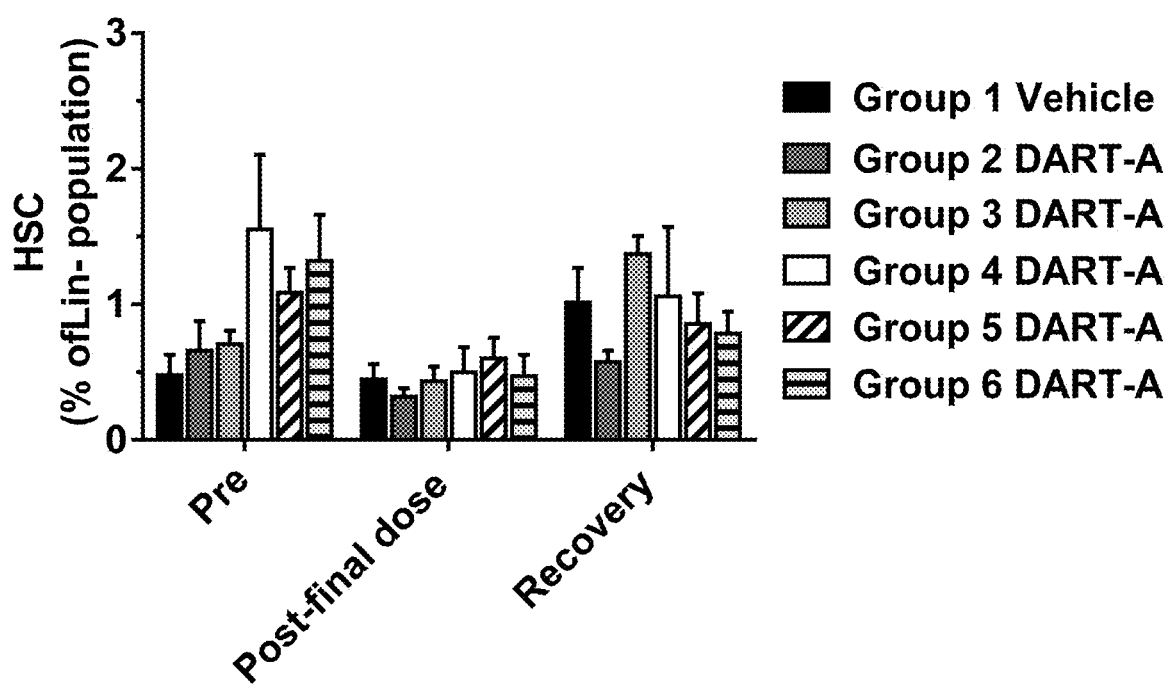

DART-A was well tolerated in monkeys at all doses tested; however, reversible reductions in red cell parameters were observed at the highest doses (FIGS. 36A-36C). Frequent blood sampling could have been a potential contributing factor, since vehicle-treated animals showed a modest decline in red cell mass. Reticulocyte response was observed in all animals; at the highest exposure (Group 6), however, the response appeared slightly less robust for similar decrease in red cell mass (FIGS. 36D-36F). Morphological analysis of bone marrow smears throughout the study was unremarkable. Flow cytometry analysis, however, revealed that the frequency of CD123+ cells within the immature lineage-negative (Lin−) bone marrow populations decreased in DART-A-treated animals at the end of the dosing period, returning to baseline levels by the end of the recovery time (FIG. 37A-37B). HSC (defined as Lin−/CD34+/CD38−/CD45RA−/CD90+ cells (Pang, W. W. et al. (2011) "*Human Bone Marrow Hematopoietic Stem Cells Are Increased In Frequency And Myeloid-Biased With Age*," Proc. Natl. Acad. Sci. (U.S.A.) 108:20012-20017)) showed large inter-group variability; Group 4-6 DART-A-treated monkeys show some apparent reduction compared to the corresponding pre-dose levels, however, no decrease was seen in all treated groups compared to vehicle-treated animals. These data indicate that HSC are less susceptible to targeting by DART-A and are consistent with the observed reversibility of the negative effects of DART-A treatment on hematopoiesis.

As demonstrated above, with respect to infusions for 4 weeks on a 4-day-on/3-day-off weekly schedule or a 7-day-on schedule at starting doses of 100 ng/kg/day that were escalated stepwise weekly to 300, 600, and 1,000 ng/kg/day, the administration of DART-A to cynomolgus monkeys was well tolerated. Depletion of circulating CD123+ cells, including pDCs, was observed after the start of the first administration and persisted throughout the study at all doses and schedules. Reversible reduction in bone marrow CD123+ precursor was also observed. Cytokine release, as significant safety concern with CD3-targeted therapies, appeared manageable and consistent with a first-dose effect. Modest reversible anemia was noted at the highest doses, but no other (on- or off-target) adverse events were noted.

The cynomolgus monkey is an appropriate animal model for the pharmacological assessment of DART-A, given the high homology between the orthologs and the ability of DART-A to bind with similar affinity to the antigens and mediate redirected T cell killing in both species. Furthermore, both antigens are concordantly expressed in monkeys and humans, including similar expression by hematopoietic precursors and in the cytoplasm of the endothelium of multiple tissues. Minor exceptions are the expression in testicular Leydig cells in humans but not monkeys and low-to-absent CD123 in monkey monocytes compared to humans.

A primary concern associated with therapeutic strategies that involve T cell activation includes the release of cytokines and off-target cytotoxic effects. A recent study with a CD3×CD123 bi-specific scFv immunofusion construct with bivalent CD3 recognition demonstrated anti-leukemic activity in vitro, but caused non-specific activation of T cells and IFN-γ secretion (Kuo, S. R. et al. (2012) "*Engineering A CD123×CD3 Bispecific scFv Immunofusion For The Treatment Of Leukemia And Elimination Of Leukemia Stem Cells*," Protein Eng. Des. Sel. 25:561-569). The monovalent nature of each binding arms and the highly homogeneous monomeric form of DART-A ensure that T cell activation depends exclusively upon target cell engagement: no T cell activation was observed in the absence of target cells or by using a Control DART molecule that included only the CD3-targeting arm. Furthermore, high doses (up to 100 ug/kg/day) of the Control DART molecule did not trigger cytokine release in cynomolgus monkeys.

The DART-A molecule starting dose of 100 ng/kg/day was well tolerated, with minimal cytokine release. Cytokine storm, however, did occur with a high starting dose (5 μg/kg/day); however, such dose could be reached safely via stepwise weekly dose escalations, indicating that DART-A-mediated cytokine release appears to be primarily a first-dose effect. Depletion of the CD123+ target cells, thereby eliminating a source of CD3 ligation, may explain the first-dose effect: nearly complete CD123+ cell depletion was observed at doses as low as 3-10 ng/kg/day, indicating that cytokine release in vivo follows a shifted dose-response compared to cytotoxicity. Dose-response profiles for cytotoxicity and cytokine release by human T cells were also consistent with this observation.

T cell desensitization, in which DART-A-induced PD1 upregulation may play a role, appears to also contribute to limit cytokine release after the first infusion of DART-A. Recent studies show that increased PD-1 expression after antigen-induced arrest of T cells at inflammation sites contributes, through interactions with PD-L1, to terminating the stop signal, thus releasing and desensitizing the cells (Honda, T. et al. (2014) "*Tuning Of Antigen Sensitivity By T Cell Receptor-Dependent Negative Feedback Controls T Cell Effector Function In Inflamed Tissues*," Immunity 40:235-247; Wei, F. et al. (2013) "*Strength Of PD-1 Signaling Differentially Affects T-Cell Effector Functions*," Proc. Natl. Acad. Sci. (U.S.A.) 110:E2480-E2489). The PD-1 countering of TCR signaling strength is not uniform: while proliferation and cytokine production appear most sensitive to PD-1 inhibition, cytotoxicity is the least affected (Wei, F. et al. (2013) "*Strength Of PD-1 Signaling Differentially Affects T-Cell Effector Functions*," Proc. Natl. Acad. Sci. (U.S.A.) 110:E2480-E2489). Consistently, the ex vivo cytotoxic potential of T cells from monkeys exposed to multiple infusions of DART-A was comparable to that of T cells from naïve monkeys, despite increased PD-1 levels in the former. Furthermore, PD-1 upregulation was not accompanied by TIM3 expression, a hallmark of T cell exhaustion, as shown for T cells exposed to protracted stimulation with CD3 antibodies or chronic infections (Gebel, H. M. et al. (1989) "*T Cells From Patients Successfully Treated With OKT3 Do Not React With The T-Cell Receptor Antibody*," Hum. Immunol. 26:123-129; Wherry, E. J. (2011) "*T Cell Exhaustion*," Nat. Immunol. 12:492-499).

The depletion of circulating CD123+ cells in DART-A-treated monkeys was rapid and persisted during the weekly dosing holidays in the 4-day-on/3-day-off schedule, consistent with target cell elimination. In contrast, the transient fluctuations in circulating T cells were likely the result of trafficking from/to tissues and lymphoid organs as a function of DART-A. DART-A exposure promotes the expansion and/or mobilization of antigen experienced T lymphocytes, cells that preferentially home to tissues and more readily exert cytotoxic effector function (Mirenda, V. et al. (2007) "*Physiologic And Aberrant Regulation Of Memory T-Cell Trafficking By The Costimulatory Molecule CD28*," Blood 109:2968-2977; Marelli-Berg, F. M. et al. (2010) "*Memory T-Cell Trafficking: New Directions For Busy Commuters*," Immunology 130:158-165).

Depletion of CD123+ normal cells may carry potential liabilities. pDCs and basophils express high levels of CD123, compared to lower levels in monocytes and eosinophils (Lopez, A. F. et al. (1989) "*Reciprocal Inhibition Of Binding Between Interleukin 3 And Granulocyte Macrophage Colony-Stimulating Factor To Human Eosinophils*," Proc. Natl. Acad. Sci. (U.S.A.) 86:7022-7026; Muñoz, L. et al. (2001) "*Interleukin-3 Receptor Alpha Chain (CD123) Is Widely Expressed In Hematologic Malignancies*," Haematologica 86:1261-1269; Masten, B. J. et al. (2006) "*Characterization Of Myeloid And Plasmacytoid Dendritic Cells In Human Lung*," J. Immunol. 177:7784-7793; Korpelainen, E. I. et al. (1995) "*Interferon-Gamma Upregulates Interleukin-3 (IL-3) Receptor Expression In Human Endothelial Cells And Synergizes With IL-3 In Stimulating Major Histocompatibility Complex Class II Expression And Cytokine Production*," Blood 86:176-182). pDCs have been shown to play a role in the control of certain viruses in mouse or monkey models of infection, although they do not appear critical for controlling the immune response to flu (Colonna, M. et al. (1997) "*Specificity And Function Of Immunoglobulin Superfamily NK Cell Inhibitory And Stimulatory Receptors*," Immunol. Rev. 155:127-133; Smit, J. J. et al. (2006) "*Plasmacytoid Dendritic Cells Inhibit Pulmonary Immunopathology And Promote Clearance Of Respiratory Syncytial Virus*," J. Exp. Med. 203:1153-1159). In tumor models, pDCs may promote tumor growth and metastasis, while pDC depletion resulted in tumor inhibition (Sawant, A. et al. (2012) "*Depletion Of Plasmacytoid Dendritic Cells Inhibits Tumor Growth And Prevents Bone Metastasis Of Breast Cancer Cells*," J. Immunol. 189:4258-4265). Transient, modest, dose-independent facial swelling was observed in some monkeys treated with DART-A; however, no increased histamine levels were observed in these monkeys or when human basophils were lysed via DART-A-mediated T cell killing. Monocyte depletion may carry increased risks of infection; the consequence of pDC, basophil or eosinophils depletion in humans should thus be monitored.

Committed hematopoietic precursors that express CD123, such as the common myeloid precursor (CMP) (Jordan, C. T. et al. (2000) "*The Interleukin-3 Receptor Alpha Chain Is A Unique Marker For Human Acute Myelogenous Leukemia Stem Cells*," Leukemia 14:1777-1784; Rieger, M. A. et al. (2012) "*Hematopoiesis*," Cold Spring Harb. Perspect. Biol. 4:a008250), may be targeted by DART-A, a possible explanation for the modest anemia observed following administration of DART-A at the highest dose. The erythropoietic reticulocyte response appeared to function at all DART-A dose levels; however, for commensurate drops in red cell parameters, animals subjected to the greatest DART-A exposure (Group 6, 7-day-on infusion) showed a reduced reticulocyte response, suggesting a possible cytotoxic activity on precursors (e.g., CMP). The effect was reversible following cessation of DART-A treatment, consistent with repopulation from spared CD123low/negative HSC.

Alternate approaches for depletion of CD123+ cells include a second-generation CD123-specific Fc-enhanced monoclonal antibody (Jin, L. et al. (2009) "*Monoclonal Antibody-Mediated Targeting Of CD123, IL-3 Receptor Alpha Chain, Eliminates Human Acute Myeloid Leukemic Stem Cells*," Cell Stem Cell 5:31-42; Roberts, A. W. et al. (2010) "*A Phase I Study Of Anti-CD123 Monoclonal Antibody (mAb) CSL360 Targeting Leukemia Stem Cells (LSC) In AML*," J. Clin. Oncol. 28(Suppl):e13012), IL-3 bound diphtheria toxin (Frankel, A. et al. (2008) "*Phase I Clinical Study Of Diphtheria Toxin-Interleukin 3 Fusion Protein In Patients With Acute Myeloid Leukemia And Myelodysplasia*," Leuk. Lymphoma 49:543-553), cytokine-induced killer (CIK) cells expressing CD123-specific chimeric antigen receptors (CAR) (Tettamanti, S. et al. (2013) "*Targeting Of Acute Myeloid Leukaemia By Cytokine-Induced Killer Cells Redirected With A Novel CD123-Specific Chimeric Antigen Receptor*," Br. J. Haematol. 161:389-401) and CD123 CAR T cells (Gill, S. et al. (2014) "*Efficacy Against Human Acute Myeloid Leukemia And Myeloablation Of Normal Hematopoiesis In A Mouse Model Using Chimeric Antigen Receptor-Modified T Cells*," Blood 123(15): 2343-2354; Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia*," Blood 122:3138-3148). CAR T cells exhibited potent leukemic blast cell killing in vitro and anti-leukemic activity in a xenogeneic model of disseminated AML (Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia*," Blood 122:3138-3148). A recent study reported ablation of normal hematopoiesis in NSG mice engrafted with human CD34+ cells following CD123 CAR T cell transfer (Gill, S. et al. (2014) "*Efficacy Against Human Acute Myeloid Leukemia And Myeloablation Of Normal Hematopoiesis In A Mouse Model Using Chimeric Antigen Receptor Modified T Cells*," Blood 123(15): 2343-2354), although others have not observed similar effects in vitro or in vivo (Tettamanti, S. et al. (2013) "Targeting Of Acute Myeloid Leukaemia By Cytokine-Induced Killer Cells Redirected With A Novel CD123-Specific Chimeric Antigen Receptor," Br. J. Haematol. 161:389-401; Pizzitola, I. et al. (2014) "Chimeric Antigen Receptors Against CD33/CD123 Antigens Efficiently Target Primary Acute Myeloid Leukemia Cells in vivo," Leukemia doi:10.1038/leu.2014.62). In the above-discussed experiments, depletion of CD123+ bone marrow precursor populations was observed, but reversed during recovery; furthermore, depletion of this minority population resulted in no changes in bone marrow cellularity or erythroid to myeloid cell (E:M) ratio at all DART-A dose levels tested. These differences underscore the potential advantages of DART-A over cell therapies, as it provides a titratable system that relies on autologous T cells in contrast to "supercharged" ex vivo transduced cells that may be more difficult to control. CD123 is overexpressed in several hematologic malignancies, including AML, hairy cell leukemia, blastic plasmacytoid dendritic cell neoplasms (BPDCNs), a subset of B-precursor acute lymphoblastic leukemia (B-ALL) and chronic lymphocytic leukemia, Hodgkin's disease Reed-Stemberg cells, as well as in myelodysplastic syndrome and systemic mastocytosis (Kharfan-Dabaja, M. A. et al. (2013) "Diagnostic And Therapeutic Advances In Blastic Plasmacytoid Dendritic Cell Neoplasm: A Focus On Hematopoietic Cell Transplantation," Biol. Blood Marrow Transplant. 19:1006-1012; Florian, S. et al. (2006) "Detection Of Molecular Targets On The Surface Of CD34+/CD38−-Stem Cells In Various Myeloid Malignancies," Leuk. Lymphoma 47:207-222; Muñoz, L. et al. (2001) "Interleukin-3 Receptor Alpha Chain (CD123) Is Widely Expressed In Hematologic Malignancies," Haematologica 86:1261-1269; Fromm, J. R. (2011) "Flow Cytometric Analysis Of CD123 Is Useful For Immunophenotyping Classical Hodgkin Lymphoma," Cytometry B Clin. Cytom. 80:91-99). The predictable pharmacodynamic activity and manageable safety profile observed in non-human primates further supports the clinical utility and efficacy of DART-A as immunotherapy for these disorders.

In sum, DART-A is an antibody-based molecule engaging the CD3ε subunit of the TCR to redirect T lymphocytes against cells expressing CD123, an antigen up-regulated in several hematological malignancies. DART-A binds to both human and cynomolgus monkey's antigens with similar affinities and redirects T cells from both species to kill CD123+ cells. Monkeys infused 4 or 7 days a week with weekly escalating doses of DART-A showed depletion of circulating CD123+ cells 72h after treatment initiation that persisted throughout the 4 weeks of treatment, irrespective of dosing schedules. A decrease in circulating T cells also occurred, but recovered to baseline before the subsequent infusion in monkeys on the 4-day dose schedule, consistent with DART-A-mediated mobilization. DART-A administration increased circulating PD1+, but not TIM-3+, T cells; furthermore, ex vivo analysis of T cells from treated monkeys exhibited unaltered redirected target cell lysis, indicating no exhaustion. Toxicity was limited to a minimal transient release of cytokines following the DART-A first infusion, but not after subsequent administrations even when the dose was escalated, and a minimal reversible decrease in red cell mass with concomitant reduction in CD123+ bone marrow progenitors. Clinical testing of DART-A in hematological malignancies appears warranted.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A CD123 binding molecule comprising:
a VH Domain of a monoclonal antibody capable of binding to CD123 ($VH_{CD123}$) (SEQ ID NO:26); and CDR1 (SEQ ID NO:44), CDR2 (SEQ ID NO:45), and CDR3 (SEQ ID NO:46) of a VL Domain of a monoclonal antibody capable of binding to CD123 ($VL_{CD123}$).

2. A CD123 binding molecule comprising:
a VL Domain of a monoclonal antibody capable of binding to CD123 ($VL_{CD123}$) (SEQ ID NO:25); and CDR1 (SEQ ID NO:47), CDR2 (SEQ ID NO:48), and CDR3 (SEQ ID NO:49) of a VH Domain of a monoclonal antibody capable of binding to CD123 ($VH_{CD123}$).

3. A CD123 binding molecule comprising a VH Domain of a monoclonal antibody capable of binding to CD123 ($VH_{CD123}$) (SEQ ID NO:26) and a VL Domain of a monoclonal antibody capable of binding to CD123 ($VL_{CD123}$) (SEQ ID NO:25).

4. The CD123 binding molecule of claim 3, wherein said molecule further comprises a VH Domain of a monoclonal antibody capable of binding to CD3 ($VH_{CD3}$), and a VL Domain of a monoclonal antibody capable of binding to CD3 ($VL_{CD3}$).

5. The CD123 binding molecule of claim 4, wherein said molecule is a diabody capable of specific binding to an epitope of CD123 and to an epitope of CD3, wherein the diabody comprises a first polypeptide chain and a second polypeptide chain, covalently bonded to one another, wherein:

A. the first polypeptide chain comprises, in the N-terminal to C-terminal direction:
  i. a Domain 1, comprising
    (1) a sub-Domain (1A), which comprises said VL Domain of a monoclonal antibody capable of binding to CD3 ($VL_{CD3}$);
    (2) a sub-Domain (1B), which comprises said VH Domain of a monoclonal antibody capable of binding to CD123 ($VH_{CD123}$) (SEQ ID NO:26);
  ii. a Domain 2, wherein said Domain 2 is an E-coil Domain (SEQ ID NO:34) or a K-coil Domain (SEQ ID NO:35);
B. the second polypeptide chain comprises, in the N-terminal to C-terminal direction:
  i. a Domain 1, comprising
    (1) a sub-Domain (1A), which comprises said VL Domain of a monoclonal antibody capable of binding to CD123 ($VL_{CD123}$) (SEQ ID NO:25); and
    (2) a sub-Domain (1B), which comprises said VH Domain of a monoclonal antibody capable of binding to CD3 ($VH_{CD3}$);
  ii. a Domain 2, wherein said Domain 2 is a K-coil Domain (SEQ ID NO:35) or an E-coil Domain (SEQ ID NO:34), wherein said Domain 2 of said first and said second polypeptide chains are not both E-coil Domains or both K-coil Domains; and
and wherein:
(a) said VL Domain of said first polypeptide chain and said VH Domain of said second polypeptide chain form an Antigen Binding Domain capable of specifically binding to an epitope of CD3; and (b) said VL Domain of said second polypeptide chain and said VH Domain of said first polypeptide chain form an Antigen Binding Domain capable of specifically binding to an epitope of CD123.

6. The CD123 binding molecule of claim 5, wherein said $VL_{CD3}$ comprises SEQ ID NO: 21 and said $VH_{CD3}$ comprises SEQ ID NO: 22.

7. The CD123 binding molecule of claim 5, wherein:
  (i) said first polypeptide chain additionally comprises a Domain 3 comprising a CH2 Domain and/or a CH3 Domain; or
  (ii) said second polypeptide chain additionally comprises a Domain 3 comprising a CH2 Domain and/or a CH3 Domain.

8. The CD123 binding molecule of claim 7, which further comprises a third polypeptide chain comprising a CH2 Domain and/or a CH3 Domain.

9. The CD123 binding molecule of claim 8, wherein:
  (i) said Domain 3 of said first polypeptide chain comprises CH2 and CH3 Domains (SEQ ID NO:56), and said third polypeptide chain comprises CH2 and CH3 Domains (SEQ ID NO:11);
  (ii) said Domain 3 of said first polypeptide chain comprises a CH2 and CH3 Domain (SEQ ID NO:11), and said third polypeptide chain comprises a CH2 and CH3 Domain (SEQ ID NO:56);
  (iii) said Domain 3 of said second polypeptide chain comprises CH2 and CH3 Domains (SEQ ID NO:56), and said third polypeptide chain comprises CH2 and CH3 Domains (SEQ ID NO:11); or
  (iv) said Domain 3 of said second polypeptide chain comprises a CH2 and CH3 Domain (SEQ ID NO:11), and said third polypeptide chain comprises a CH2 and CH3 Domain (SEQ ID NO:56).

10. The CD123 binding molecule of claim 9, further comprising a cysteine-containing peptide (SEQ ID NO:55) N-terminal to SEQ ID NO:11 and SEQ ID NO:56.

11. The CD123 binding molecule of claim 10, wherein said $VL_{CD3}$ comprises SEQ ID NO: 21 and said $VH_{CD3}$ comprises SEQ ID NO: 22.

12. A polynucleotide encoding said first polypeptide chain and/or said second polypeptide chain of the CD123 binding molecule of claim 5.

13. The polynucleotide of claim 12, which comprises SEQ ID NO:2, SEQ ID NO:4, SEQ ID NO: 14 or SEQ ID NO:16.

14. A CD123 binding molecule encoded by:
  (i) SEQ ID NO:2 and SEQ ID NO:4;
  (ii) SEQ ID NO:14, SEQ ID NO:16 and SEQ ID NO:12; or
  (iii) SEQ ID NO:18, SEQ ID NO:2 and SEQ ID NO:12.

15. A pharmaceutical composition comprising the CD123 binding molecule of claim 3 and a physiologically acceptable carrier.

16. A pharmaceutical composition comprising the CD123 binding molecule of claim 5 and a physiologically acceptable carrier.

17. A pharmaceutical composition comprising the CD123 binding molecule of claim 8 and a physiologically acceptable carrier.

18. A pharmaceutical composition comprising the CD123 binding molecule of claim 11 and a physiologically acceptable carrier.

* * * * *

SEQUENCE LISTING

```
<160> NUMBER OF SEQ ID NOS: 59

<210> SEQ ID NO 1
<211> LENGTH: 272
<212> TYPE: PRT
<213> ORGANISM: Artificial Sequence
<220> FEATURE:
<223> OTHER INFORMATION: First Polypeptide Chain of DART-A

<400> SEQUENCE: 1

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95
```

Leu Trp Val Phe Gly Gly Gly Thr Lys Leu Thr Val Leu Gly Gly Gly
                100                 105                 110

Gly Ser Gly Gly Gly Glu Val Gln Leu Val Gln Ser Gly Ala Glu
        115                 120                 125

Leu Lys Lys Pro Gly Ala Ser Val Lys Val Ser Cys Lys Ala Ser Gly
130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
                165                 170                 175

Phe Tyr Asn Gln Lys Phe Lys Gly Arg Val Thr Ile Thr Val Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ser His Leu Leu Arg Ala Ser Trp
210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
            260                 265                 270

<210> SEQ ID NO 2
<211> LENGTH: 816
<212> TYPE: DNA
<213> ORGANISM: Artificial Sequence
<220> FEATURE:
<223> OTHER INFORMATION: Nucleic Acid Molecule Encoding First
      Polypeptide Chain of DART-A

<400> SEQUENCE: 2
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga ggggtggat ccggcggcgg aggcgaggtg     360
cagctggtgc agtccggggc tgagctgaag aaacccggag cttccgtgaa ggtgtcttgc     420
aaagccagtg gctacacctt cacagactac tatatgaagt gggtcaggca ggctccagga     480
cagggactgg aatggatcgg cgatatcatt ccttccaacg gggccacttt ctacaatcag     540
aagtttaaag gcagggtgac tattaccgtg gacaaatcaa caagcactgc ttatatggag     600
ctgagctccc tgcgctctga agatacagcc gtgtactatt gtgctcggtc acacctgctg     660
agagccagct ggtttgctta ttggggacag ggcaccctgg tgacagtgtc ttccggagga     720
tgtggcggtg gagaagtggc cgcactggag aaagaggttg ctgctttgga aggaggtc      780 gctgcacttg aaaaggaggt cgcagccctg gagaaa                               816

<210> SEQ ID NO 3
<211> LENGTH: 280
<212> TYPE: PRT
<213> ORGANISM: Artificial Sequence
<220> FEATURE:

<223> OTHER INFORMATION: Second Polypeptide Chain of DART-A

<400> SEQUENCE: 3

Asp Phe Val Met Thr Gln Ser Pro Asp Ser Leu Ala Val Ser Leu Gly
1               5                   10                  15
Glu Arg Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Ser Tyr Pro Tyr Thr Phe Gly Gln Gly Thr Lys Leu Glu Ile
            100                 105                 110
Lys Gly Gly Gly Ser Gly Gly Gly Gly Glu Val Gln Leu Val Glu Ser
        115                 120                 125
Gly Gly Gly Leu Val Gln Pro Gly Gly Ser Leu Arg Leu Ser Cys Ala
    130                 135                 140
Ala Ser Gly Phe Thr Phe Ser Thr Tyr Ala Met Asn Trp Val Arg Gln
145                 150                 155                 160
Ala Pro Gly Lys Gly Leu Glu Trp Val Gly Arg Ile Arg Ser Lys Tyr
                165                 170                 175
Asn Asn Tyr Ala Thr Tyr Tyr Ala Asp Ser Val Lys Asp Arg Phe Thr
            180                 185                 190
Ile Ser Arg Asp Asp Ser Lys Asn Ser Leu Tyr Leu Gln Met Asn Ser
        195                 200                 205
Leu Lys Thr Glu Asp Thr Ala Val Tyr Tyr Cys Val Arg His Gly Asn
    210                 215                 220
Phe Gly Asn Ser Tyr Val Ser Trp Phe Ala Tyr Trp Gly Gln Gly Thr
225                 230                 235                 240
Leu Val Thr Val Ser Ser Gly Gly Cys Gly Gly Gly Lys Val Ala Ala
                245                 250                 255
Leu Lys Glu Lys Val Ala Ala Leu Lys Glu Lys Val Ala Ala Leu Lys
            260                 265                 270
Glu Lys Val Ala Ala Leu Lys Glu
        275                 280

<210> SEQ ID NO 4
<211> LENGTH: 840
<212> TYPE: DNA
<213> ORGANISM: Artificial Sequence
<220> FEATURE:
<223> OTHER INFORMATION: Nucleic Acid Molecule Encoding Second
      Polypeptide Chain of DART-A

<400> SEQUENCE: 4
gacttcgtga tgacacagtc tcctgatagt ctggccgtga gtctggggga gcgggtgact      60
atgtcttgca agagctccca gtcactgctg aacagcggaa atcagaaaaa ctatctgacc     120
tggtaccagc agaagccagg ccagcccct aaactgctga tctattgggc ttccaccagg      180
gaatctggcg tgcccgacag attcagcggc agcggcagcg gcacagattt taccctgaca     240
atttctagtc tgcaggccga ggacgtggct gtgtactatt gtcagaatga ttacagctat     300

```
ccctacactt tcggccaggg gaccaagctg gaaattaaag gaggcggatc cggcggcgga    360
ggcgaggtgc agctggtgga gtctggggga ggcttggtcc agcctggagg gtccctgaga    420
ctctcctgtg cagcctctgg attcaccttc agcacatacg ctatgaattg ggtccgccag    480
gctccaggga aggggctgga gtgggttgga aggatcaggt ccaagtacaa caattatgca    540
acctactatg ccgactctgt gaaggataga ttcaccatct caagagatga ttcaaagaac    600
tcactgtatc tgcaaatgaa cagcctgaaa accgaggaca cggccgtgta ttactgtgtg    660
agacacggta acttcggcaa ttcttacgtg tcttggtttg cttattgggg acaggggaca    720
ctggtgactg tgtcttccgg aggatgtggc ggtggaaaag tggccgcact gaaggagaaa    780
gttgctgctt tgaaagagaa ggtcgccgca cttaaggaaa aggtcgcagc cctgaaagag    840
```

<210> SEQ ID NO 5
<211> LENGTH: 268
<212> TYPE: PRT
<213> ORGANISM: Artificial Sequence
<220> FEATURE:
<223> OTHER INFORMATION: First Polypeptide Chain of DART-B

<400> SEQUENCE: 5

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Ser Gly Gly
            100                 105                 110

Gly Gly Gln Val Gln Leu Val Gln Ser Gly Ala Glu Leu Lys Lys Pro
        115                 120                 125

Gly Ala Ser Val Lys Val Ser Cys Lys Ala Ser Gly Tyr Thr Phe Thr
    130                 135                 140

Asp Tyr Tyr Met Lys Trp Val Arg Gln Ala Pro Gly Gln Gly Leu Glu
145                 150                 155                 160

Trp Ile Gly Asp Ile Ile Pro Ser Asn Gly Ala Thr Phe Tyr Asn Gln
                165                 170                 175

Lys Phe Lys Gly Arg Val Thr Ile Thr Val Asp Lys Ser Thr Ser Thr
            180                 185                 190

Ala Tyr Met Glu Leu Ser Ser Leu Arg Ser Glu Asp Thr Ala Val Tyr
        195                 200                 205

Tyr Cys Ala Arg Ser His Leu Leu Arg Ala Ser Trp Phe Ala Tyr Trp
    210                 215                 220

Gly Gln Gly Thr Leu Val Thr Val Ser Ser Gly Gly Cys Gly Gly Gly
225                 230                 235                 240

Glu Val Ala Ala Leu Glu Lys Glu Val Ala Ala Leu Glu Lys Glu Val
                245                 250                 255

Ala Ala Leu Glu Lys Glu Val Ala Ala Leu Glu Lys
            260                 265
```

<210> SEQ ID NO 6
<211> LENGTH: 804
<212> TYPE: DNA
<213> ORGANISM: Artificial Sequence
<220> FEATURE:
<223> OTHER INFORMATION: Nucleic Acid Molecule Encoding First
      Polypeptide Chain of DART-B

<400> SEQUENCE: 6

```
gacattcagc tgacccagtc tccagcaatc atgtctgcat ctccagggga gaaggtcacc      60
atgacctgca gagccagttc aagtgtaagt tacatgaact ggtaccagca gaagtcaggc     120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaaagg aggcggatcc ggcggcggag ccaggtgcag ctggtgcag      360
tccggggctg agctgaagaa acccggagct tccgtgaagg tgtcttgcaa agccagtggc     420
tacaccttca cagactacta tatgaagtgg gtcaggcagg ctccaggaca gggactggaa     480
tggatcggcg atatcattcc ttccaacggg gccactttct acaatcagaa gtttaaaggc     540
agggtgacta ttaccgtgga caaatcaaca agcactgctt atatggagct gagctccctg     600
cgctctgaag atacagccgt gtactattgt gctcggtcac acctgctgag agccagctgg     660
tttgcttatt ggggacaggg caccctggtg acagtgtctt ccggaggatg tggcggtgga     720
gaagtggccg cactggagaa agaggttgct gctttggaga aggaggtcgc tgcacttgaa     780
aaggaggtcg cagccctgga gaaa                                            804
```

<210> SEQ ID NO 7
<211> LENGTH: 274
<212> TYPE: PRT
<213> ORGANISM: Artificial Sequence
<220> FEATURE:
<223> OTHER INFORMATION: Second Polypeptide Chain of DART-B

<400> SEQUENCE: 7

```
Asp Phe Val Met Thr Gln Ser Pro Asp Ser Leu Ala Val Ser Leu Gly
1               5                   10                  15
Glu Arg Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Ser Tyr Pro Tyr Thr Phe Gly Gln Gly Thr Lys Leu Glu Ile
            100                 105                 110
Lys Gly Gly Gly Ser Gly Gly Gly Gly Asp Ile Lys Leu Gln Gln Ser
        115                 120                 125
Gly Ala Glu Leu Ala Arg Pro Gly Ala Ser Val Lys Met Ser Cys Lys
    130                 135                 140
Thr Ser Gly Tyr Thr Phe Thr Arg Tyr Thr Met His Trp Val Lys Gln
145                 150                 155                 160
```

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 8
<211> LENGTH: 822
<212> TYPE: DNA
<213> ORGANISM: Artificial Sequence
<220> FEATURE:
<223> OTHER INFORMATION: Nucleic Acid Molecule Encoding Second
      Polypeptide Chain of DART-B

<400> SEQUENCE: 8

```
gacttcgtga tgacacagtc tcctgatagt ctggccgtga gtctggggga gcgggtgact    60
atgtcttgca gagctccca gtcactgctg aacagcggaa atcagaaaaa ctatctgacc   120
tggtaccagc agaagccagg ccagcccct aaactgctga tctattgggc ttccaccagg   180
gaatctggcg tgcccgacag attcagcggc agcggcagcg gcacagattt taccctgaca   240
atttctagtc tgcaggccga ggacgtggct gtgtactatt gtcagaatga ttacagctat   300
ccctacactt tcggccaggg gaccaagctg gaaattaaag gaggcggatc cggcggcgga   360
ggcgatatca aactgcagca gtcaggggct gaactggcaa gacctggggc ctcagtgaag   420
atgtcctgca agacttctgg ctacaccttt actaggtaca cgatgcactg ggtaaaacag   480
aggcctggac agggtctgga atggattgga tacattaatc ctagccgtgg ttatactaat   540
tacaatcaga agttcaagga caaggccaca ttgactacag acaaatcctc agcacagcc   600
tacatgcaac tgagcagcct gacatctgag gactctgcag tctattactg tgcaagatat   660
tatgatgatc attactgcct tgactactgg ggccaaggca ccactctcac agtctcctcc   720
ggaggatgtg gcggtggaaa agtggccgca ctgaaggaga agttgctgc tttgaaagag   780
aaggtcgccg cacttaagga aaaggtcgca gccctgaaag ag                    822
```

<210> SEQ ID NO 9
<211> LENGTH: 322
<212> TYPE: PRT
<213> ORGANISM: Artificial Sequence
<220> FEATURE:
<223> OTHER INFORMATION: CD123 x CD3 Diabody Polypeptide Chain Having
      Albumin Binding Site

<400> SEQUENCE: 9

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Glu Val Gln Leu Val Gln Ser Gly Ala Glu
                115                 120                 125

Leu Lys Lys Pro Gly Ala Ser Val Lys Val Ser Cys Lys Ala Ser Gly
130                 135                 140

Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
                165                 170                 175

Phe Tyr Asn Gln Lys Phe Lys Gly Arg Val Thr Ile Thr Val Asp Lys
                180                 185                 190

Ser Thr Ser Thr Ala Tyr Met Glu Leu Ser Ser Leu Arg Ser Glu Asp
                195                 200                 205

Thr Ala Val Tyr Tyr Cys Ala Arg Ser His Leu Leu Arg Ala Ser Trp
210                 215                 220

Phe Ala Tyr Trp Gly Gln Gly Thr Leu Val Thr Val Ser Ser Gly Gly
225                 230                 235                 240

Cys Gly Gly Gly Glu Val Ala Ala Leu Glu Lys Glu Val Ala Ala Leu
                245                 250                 255

Glu Lys Glu Val Ala Ala Leu Glu Lys Glu Val Ala Ala Leu Glu Lys
                260                 265                 270

Gly Gly Gly Ser Leu Ala Glu Ala Lys Val Leu Ala Asn Arg Glu Leu
                275                 280                 285

Asp Lys Tyr Gly Val Ser Asp Tyr Tyr Lys Asn Leu Ile Asp Asn Ala
290                 295                 300

Lys Ser Ala Glu Gly Val Lys Ala Leu Ile Asp Glu Ile Leu Ala Ala
305                 310                 315                 320

Leu Pro

<210> SEQ ID NO 10
<211> LENGTH: 966
<212> TYPE: DNA
<213> ORGANISM: Artificial Sequence
<220> FEATURE:
<223> OTHER INFORMATION: Polynucleotide Encoding CD123 x CD3 Diabody
      Polypeptide Chain Having Albumin Binding Site

<400> SEQUENCE: 10
caggctgtgg tgactcagga gccttcactg accgtgtccc caggcggaac tgtgaccctg     60
acatgcagat ccagcacagg cgcagtgacc acatctaact acgccaattg ggtgcagcag    120
aagccaggac aggcaccaag gggcctgatc ggggtacaa acaaaaggc tccctggacc      180 cctgcacggt ttctggaag tctgctgggc ggaaaggccg ctctgactat accggggca     240 caggccgagg acgaagccga ttactattgt gctctgtggt atagcaatct gtgggtgttc    300
gggggtggca caaaactgac tgtgctggga gggggtggat ccggcggcgg aggcgaggtg    360

```
cagctggtgc agtccggggc tgagctgaag aaacccggag cttccgtgaa ggtgtcttgc    420
aaagccagtg gctacacctt cacagactac tatatgaagt gggtcaggca ggctccagga    480
cagggactgg aatggatcgg cgatatcatt ccttccaacg gggccacttt ctacaatcag    540
aagtttaaag gcagggtgac tattaccgtg gacaaatcaa caagcactgc ttatatggag    600
ctgagctccc tgcgctctga agatacagcc gtgtactatt gtgctcggtc acacctgctg    660
agagccagct ggtttgctta ttggggacag ggcaccctgg tgacagtgtc ttccggagga    720
tgtggcggtg agaagtggc cgcactggag aaagaggttg ctgctttgga aaggaggtc    780 gctgcacttg aaaaggaggt cgcagccctg gagaaaggcg gcgggtctct ggccgaagca    840
aaagtgctgg ccaaccgcga actggataaa tatggcgtga gcgattatta taagaacctg    900
attgacaacg caaatccgc ggaaggcgtg aaagcactga ttgatgaaat tctggccgcc    960
ctgcct                                                               966
```

<210> SEQ ID NO 11
<211> LENGTH: 217
<212> TYPE: PRT
<213> ORGANISM: Artificial Sequence
<220> FEATURE:
<223> OTHER INFORMATION: CH2-CH3 Domains of a Modified Human Antibody Fc
      Region

<400> SEQUENCE: 11

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215
```

<210> SEQ ID NO 12
<211> LENGTH: 681
<212> TYPE: DNA

<213> ORGANISM: Artificial Sequence
<220> FEATURE:
<223> OTHER INFORMATION: Nucleic Acid Molecule Encoding Peptide 1 and
      the CH2 and CH3 Domains of an IgG Fc region

<400> SEQUENCE: 12

```
gacaaaactc acacatgccc accgtgccca gcacctgaag ccgcgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaaccatctc caaagccaaa     360
gggcagcccc gagaaccaca ggtgtacacc ctgcccccat cccgggagga gatgaccaag     420
aaccaggtca gcctgagttg cgcagtcaaa ggcttctatc ccagcgacat cgccgtggag     480
tgggagagca atgggcagcc ggagaacaac tacaagacca cgcctcccgt gctggactcc     540
gacggctcct tcttcctcgt cagcaagctc accgtggaca agagcaggtg gcagcagggg     600
aacgtcttct catgctccgt gatgcatgag gctctgcaca accgctacac gcagaagagc     660
ctctccctgt ctccgggtaa a                                               681
```

<210> SEQ ID NO 13
<211> LENGTH: 510
<212> TYPE: PRT
<213> ORGANISM: Artificial Sequence
<220> FEATURE:
<223> OTHER INFORMATION: First Polypeptide Chain of DART-A w/Fc Version
      1 Construct

<400> SEQUENCE: 13

```
Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Thr Phe Ser Thr Tyr Ala Met Asn Trp Val Arg Gln
145                 150                 155                 160

Ala Pro Gly Lys Gly Leu Glu Trp Val Gly Arg Ile Arg Ser Lys Tyr
                165                 170                 175

Asn Asn Tyr Ala Thr Tyr Tyr Ala Asp Ser Val Lys Asp Arg Phe Thr
            180                 185                 190

Ile Ser Arg Asp Asp Ser Lys Asn Ser Leu Tyr Leu Gln Met Asn Ser
```

```
              195                 200                 205
Leu Lys Thr Glu Asp Thr Ala Val Tyr Tyr Cys Val Arg His Gly Asn
    210                 215                 220

Phe Gly Asn Ser Tyr Val Ser Trp Phe Ala Tyr Trp Gly Gln Gly Thr
225                 230                 235                 240

Leu Val Thr Val Ser Ser Gly Gly Cys Gly Gly Glu Val Ala Ala
                245                 250                 255

Leu Glu Lys Glu Val Ala Ala Leu Glu Lys Glu Val Ala Ala Leu Glu
                260                 265                 270

Lys Glu Val Ala Ala Leu Glu Lys Gly Gly Asp Lys Thr His Thr
            275                 280                 285

Cys Pro Pro Cys Pro Ala Pro Glu Ala Ala Gly Gly Pro Ser Val Phe
            290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Glu Glu Met Thr Lys Asn Gln Val Ser Leu Trp Cys Leu Val
            420                 425                 430

Lys Gly Phe Tyr Pro Ser Asp Ile Ala Val Glu Trp Glu Ser Asn Gly
            435                 440                 445

Gln Pro Glu Asn Asn Tyr Lys Thr Thr Pro Pro Val Leu Asp Ser Asp
450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510

<210> SEQ ID NO 14
<211> LENGTH: 1530
<212> TYPE: DNA
<213> ORGANISM: Artificial Sequence
<220> FEATURE:
<223> OTHER INFORMATION: Nucleic Acid Molecule Encoding First
      Polypeptide Chain of DART-A w/Fc Version 1 Construct

<400> SEQUENCE: 14
gacttcgtga tgacacagtc tcctgatagt ctggccgtga gtctggggga gcgggtgact      60
atgtcttgca agagctccca gtcactgctg aacagcggaa atcagaaaaa ctatctgacc     120
tggtaccagc agaagccagg ccagcccct aaactgctga tctattgggc ttccaccagg     180
gaatctggcg tgcccgacag attcagcggc agcggcagcg gcacagattt accctgaca      240 atttctagtc tgcaggccga ggacgtggct gtgtactatt gtcagaatga ttacagctat     300
```

```
cctacactt tcggccaggg gaccaagctg gaaattaaag gaggcggatc cggcggcgga    360
ggcgaggtgc agctggtgga gtctggggga ggcttggtcc agcctggagg gtccctgaga    420
ctctcctgtg cagcctctgg attcaccttc agcacatacg ctatgaattg ggtccgccag    480
gctccaggga aggggctgga gtgggttgga aggatcaggt ccaagtacaa caattatgca    540
acctactatg ccgactctgt gaaggataga ttcaccatct caagagatga ttcaaagaac    600
tcactgtatc tgcaaatgaa cagcctgaaa accgaggaca cggccgtgta ttactgtgtg    660
agacacggta acttcggcaa ttcttacgtg tcttggtttg cttattgggg cagggggaca    720
ctggtgactg tgtcttccgg aggatgtggc ggtggagaag tggccgcact ggagaaagag    780
gttgctgctt tggagaagga ggtcgctgca cttgaaaagg aggtcgcagc cctggagaaa    840
ggcggcgggg acaaaactca cacatgccca ccgtgcccag cacctgaagc cgcgggggga    900
ccgtcagtct tcctcttccc cccaaaaccc aaggacaccc tcatgatctc ccggacccct    960
gaggtcacat gcgtggtggt ggacgtgagc cacgaagacc ctgaggtcaa gttcaactgg   1020
tacgtggacg gcgtggaggt gcataatgcc aagacaaagc cgcgggagga gcagtacaac   1080
agcacgtacc gtgtggtcag cgtcctcacc gtcctgcacc aggactggct gaatggcaag   1140
gagtacaagt gcaaggtctc caacaaagcc ctcccagccc ccatcgagaa aaccatctcc   1200
aaagccaaag gcagccccg agaaccacag gtgtacaccc tgcccccatc ccgggaggag   1260
atgaccaaga accaggtcag cctgtggtgc ctggtcaaag gcttctatcc cagcgacatc   1320
gccgtggagt gggagagcaa tgggcagccg gagaacaact acaagaccac gcctcccgtg   1380
ctggactccg acggctcctt cttcctctac agcaagctca ccgtggacaa gagcaggtgg   1440
cagcagggga acgtcttctc atgctccgtg atgcatgagg ctctgcacaa ccactacacg   1500
cagaagagcc tctccctgtc tccgggtaaa                                   1530
```

<210> SEQ ID NO 15
<211> LENGTH: 272
<212> TYPE: PRT
<213> ORGANISM: Artificial Sequence
<220> FEATURE:
<223> OTHER INFORMATION: Second Polypeptide Chain of DART-A w/Fc Version
      1 Construct

<400> SEQUENCE: 15

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Gln Ser Gly Ala Glu
        115                 120                 125

Leu Lys Lys Pro Gly Ala Ser Val Lys Val Ser Cys Lys Ala Ser Gly
```

```
                130             135             140
Tyr Thr Phe Thr Asp Tyr Tyr Met Lys Trp Val Arg Gln Ala Pro Gly
145                 150                 155                 160

Gln Gly Leu Glu Trp Ile Gly Asp Ile Ile Pro Ser Asn Gly Ala Thr
                165                 170                 175

Phe Tyr Asn Gln Lys Phe Lys Gly Arg Val Thr Ile Thr Val Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ser His Leu Leu Arg Ala Ser Trp
    210                 215                 220

Phe Ala Tyr Trp Gly Gln Gly Thr Leu Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 16
<211> LENGTH: 816
<212> TYPE: DNA
<213> ORGANISM: Artificial Sequence
<220> FEATURE:
<223> OTHER INFORMATION: Nucleic Acid Molecule Encoding Second
      Polypeptide Chain of DART-A w/Fc Version 1 Construct

<400> SEQUENCE: 16
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac cgtgctggga ggggtggat ccggcggcgg aggcgaggtg     360
cagctggtgc agtccggggc tgagctgaag aaacccggag cttccgtgaa ggtgtcttgc     420
aaagccagtg gctacacctt cacagactac tatatgaagt gggtcaggca ggctccagga     480
cagggactgg aatggatcgg cgatatcatt ccttccaacg gggccacttt ctacaatcag     540
aagtttaaag gcagggtgac tattaccgtg gacaaatcaa caagcactgc ttatatggag     600
ctgagctccc tgcgctctga agatacagcc gtgtactatt gtgctcggtc acacctgctg     660
agagccagct ggtttgctta ttggggacag ggcaccctgg tgacagtgtc ttccggagga     720
tgtggcggtg aaagtggcc gcactgaag gagaaagttg ctgctttgaa agagaaggtc     780
gccgcactta aggaaaaggt cgcagccctg aaagag                               816

<210> SEQ ID NO 17
<211> LENGTH: 515
<212> TYPE: PRT
<213> ORGANISM: Artificial Sequence
<220> FEATURE:
<223> OTHER INFORMATION: First Polypeptide Chain of DART-A w/Fc Version
      2 Construct

<400> SEQUENCE: 17

Asp Lys Thr His Thr Cys Pro Pro Cys Pro Ala Pro Glu Ala Ala Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Ala Pro Ser Ser Pro Met Glu Asp Phe Val Met Thr
225                 230                 235                 240

Gln Ser Pro Asp Ser Leu Ala Val Ser Leu Gly Glu Arg Val Thr Met
                245                 250                 255

Ser Cys Lys Ser Ser Gln Ser Leu Leu Asn Ser Gly Asn Gln Lys Asn
            260                 265                 270

Tyr Leu Thr Trp Tyr Gln Gln Lys Pro Gly Gln Pro Pro Lys Leu Leu
        275                 280                 285

Ile Tyr Trp Ala Ser Thr Arg Glu Ser Gly Val Pro Asp Arg Phe Ser
290                 295                 300

Gly Ser Gly Ser Gly Thr Asp Phe Thr Leu Thr Ile Ser Ser Leu Gln
305                 310                 315                 320

Ala Glu Asp Val Ala Val Tyr Tyr Cys Gln Asn Asp Tyr Ser Tyr Pro
                325                 330                 335

Tyr Thr Phe Gly Gln Gly Thr Lys Leu Glu Ile Lys Gly Gly Gly Ser
            340                 345                 350

Gly Gly Gly Gly Glu Val Gln Leu Val Glu Ser Gly Gly Gly Leu Val
        355                 360                 365

Gln Pro Gly Gly Ser Leu Arg Leu Ser Cys Ala Ala Ser Gly Phe Thr
370                 375                 380

Phe Ser Thr Tyr Ala Met Asn Trp Val Arg Gln Ala Pro Gly Lys Gly
385                 390                 395                 400

Leu Glu Trp Val Gly Arg Ile Arg Ser Lys Tyr Asn Asn Tyr Ala Thr
                405                 410                 415

Tyr Tyr Ala Asp Ser Val Lys Asp Arg Phe Thr Ile Ser Arg Asp Asp
            420                 425                 430

Ser Lys Asn Ser Leu Tyr Leu Gln Met Asn Ser Leu Lys Thr Glu Asp
```

```
              435                 440                 445
Thr Ala Val Tyr Tyr Cys Val Arg His Gly Asn Phe Gly Asn Ser Tyr
    450                 455                 460
Val Ser Trp Phe Ala Tyr Trp Gly Gln Gly Thr Leu Val Thr Val Ser
465                 470                 475                 480
Ser Gly Gly Cys Gly Gly Gly Lys Val Ala Ala Leu Lys Glu Lys Val
                485                 490                 495
Ala Ala Leu Lys Glu Lys Val Ala Ala Leu Lys Glu Lys Val Ala Ala
        500                 505                 510
Leu Lys Glu
        515

<210> SEQ ID NO 18
<211> LENGTH: 1545
<212> TYPE: DNA
<213> ORGANISM: Artificial Sequence
<220> FEATURE:
<223> OTHER INFORMATION: Nucleic Acid Molecule Encoding First
      Polypeptide Chain of DART-A w/Fc Version 2 Construct

<400> SEQUENCE: 18
gacaaaactc acacatgccc accgtgccca gcacctgaag ccgcgggggg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcccagcc cccatcgaga aaccatctc caaagccaaa      360 gggcagcccc gagaaccaca ggtgtacacc ctgcccccat cccgggagga gatgaccaag     420
aaccaggtca gcctgtggtg cctggtcaaa ggcttctatc ccagcgacat cgccgtggag     480
tgggagagca atgggcagcc ggagaacaac tacaagacca cgcctcccgt gctggactcc     540
gacggctcct tcttcctcta cagcaagctc accgtggaca agagcaggtg gcagcagggg     600
aacgtcttct catgctccgt gatgcatgag gctctgcaca accactacac gcagaagagc     660
ctctccctgt ctccgggtaa agccccttcc agctccccta tggaagactt cgtgatgaca     720
cagtctcctg atagtctggc cgtgagtctg ggggagcggg tgactatgtc ttgcaagagc     780
tcccagtcac tgctgaacag cggaaatcag aaaaactatc tgacctggta ccagcagaag     840
ccaggccagc cccctaaact gctgatctat tgggcttcca cccgggaatc tggcgtgccc     900
gacagattca gcggcagcgg cagcggcaca gattttaccc tgacaatttc tagtctgcag     960
gccgaggacg tggctgtgta ctattgtcag aatgattaca gctatcccta cactttcggc    1020
caggggacca agctggaaat taaggaggcg gatccggcg gcggaggcga ggtgcagctg     1080
gtggagtctg ggggaggctt ggtccagcct ggagggtccc tgagactctc ctgtgcagcc    1140
tctggattca ccttcagcac atacgctatg aattgggtcc gccaggctcc agggaagggg    1200
ctggagtggg ttggaaggat caggtccaag tacaacaatt atgcaaccta ctatgccgac    1260
tctgtgaagg atagattcac catctcaaga gatgattcaa agaactcact gtatctgcaa    1320
atgaacagcc tgaaaaccga ggacacggcc gtgtattact gtgtgagaca cggtaacttc    1380
ggcaattctt acgtgtcttg gtttgcttat tggggacagg gacactggt gactgtgtct    1440 tccggaggat gtggcggtgg aaagtggcc gcactgaagg agaaagttgc tgctttgaaa    1500
gagaaggtcg ccgcacttaa ggaaaaggtc gcagccctga agag                    1545
```

<210> SEQ ID NO 19
<211> LENGTH: 279
<212> TYPE: PRT
<213> ORGANISM: Artificial Sequence
<220> FEATURE:
<223> OTHER INFORMATION: First Polypeptide Chain of Control DART

<400> SEQUENCE: 19

```
Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Asn Thr Tyr Ala Met Asn Trp Val Arg Gln Ala
145                 150                 155                 160

Pro Gly Lys Gly Leu Glu Trp Val Ala Arg Ile Arg Ser Lys Tyr Asn
                165                 170                 175

Asn Tyr Ala Thr Tyr Tyr Ala Asp Ser Val Lys Asp Arg Phe Thr Ile
            180                 185                 190

Ser Arg Asp Asp Ser Lys Asn Ser Leu Tyr Leu Gln Met Asn Ser Leu
        195                 200                 205

Lys Thr Glu Asp Thr Ala Val Tyr Tyr Cys Val Arg His Gly Asn Phe
    210                 215                 220

Gly Asn Ser Tyr Val Ser Trp Phe Ala Tyr Trp Gly Gln Gly Thr Leu
225                 230                 235                 240

Val Thr Val Ser Ser Gly Gly Cys Gly Gly Gly Glu Val Ala Ala Leu
                245                 250                 255

Glu Lys Glu Val Ala Ala Leu Glu Lys Glu Val Ala Ala Leu Glu Lys
            260                 265                 270

Glu Val Ala Ala Leu Glu Lys
        275
```

<210> SEQ ID NO 20
<211> LENGTH: 270
<212> TYPE: PRT
<213> ORGANISM: Artificial Sequence
<220> FEATURE:
<223> OTHER INFORMATION: Second Polypeptide Chain of Control DART

<400> SEQUENCE: 20

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
```

```
                20                  25                  30
Asn Tyr Ala Asn Trp Val Gln Gln Lys Pro Gly Gln Ala Pro Arg Gly
            35                  40                  45
Leu Ile Gly Gly Thr Asn Lys Arg Ala Pro Trp Thr Pro Ala Arg Phe
 50                  55                  60
Ser Gly Ser Leu Leu Gly Gly Lys Ala Ala Leu Thr Ile Thr Gly Ala
 65                  70                  75                  80
Gln Ala Glu Asp Glu Ala Asp Tyr Tyr Cys Ala Leu Trp Tyr Ser Asn
                85                  90                  95
Leu Trp Val Phe Gly Gly Gly Thr Lys Leu Thr Val Leu Gly Gly Gly
            100                 105                 110
Gly Ser Gly Gly Gly Gly Glu Val Lys Leu Asp Glu Thr Gly Gly Gly
            115                 120                 125
Leu Val Gln Pro Gly Arg Pro Met Lys Leu Ser Cys Val Ala Ser Gly
        130                 135                 140
Phe Thr Phe Ser Asp Tyr Trp Met Asn Trp Val Arg Gln Ser Pro Glu
145                 150                 155                 160
Lys Gly Leu Glu Trp Val Ala Gln Ile Arg Asn Lys Pro Tyr Asn Tyr
                165                 170                 175
Glu Thr Tyr Tyr Ser Asp Ser Val Lys Gly Arg Phe Thr Ile Ser Arg
            180                 185                 190
Asp Asp Ser Lys Ser Ser Val Tyr Leu Gln Met Asn Asn Leu Arg Val
        195                 200                 205
Glu Asp Met Gly Ile Tyr Tyr Cys Thr Gly Ser Tyr Tyr Gly Met Asp
    210                 215                 220
Tyr Trp Gly Gln Gly Thr Ser Val Thr Val Ser Ser Gly Gly Cys Gly
225                 230                 235                 240
Gly Gly Lys Val Ala Ala Leu Lys Glu Lys Val Ala Ala Leu Lys Glu
                245                 250                 255
Lys Val Ala Ala Leu Lys Glu Lys Val Ala Ala Leu Lys Glu
            260                 265                 270

<210> SEQ ID NO 21
<211> LENGTH: 110
<212> TYPE: PRT
<213> ORGANISM: Artificial Sequence
<220> FEATURE:
<223> OTHER INFORMATION: Light Chain CD3-Binding Domain of DART-A

<400> SEQUENCE: 21

Gln Ala Val Val Thr Gln Glu Pro Ser Leu Thr Val Ser Pro Gly Gly
 1                   5                  10                  15
Thr Val Thr Leu Thr Cys Arg Ser Ser Thr Gly Ala Val Thr Thr Ser
                20                  25                  30
Asn Tyr Ala Asn Trp Val Gln Gln Lys Pro Gly Gln Ala Pro Arg Gly
            35                  40                  45
Leu Ile Gly Gly Thr Asn Lys Arg Ala Pro Trp Thr Pro Ala Arg Phe
 50                  55                  60
Ser Gly Ser Leu Leu Gly Gly Lys Ala Ala Leu Thr Ile Thr Gly Ala
 65                  70                  75                  80
Gln Ala Glu Asp Glu Ala Asp Tyr Tyr Cys Ala Leu Trp Tyr Ser Asn
                85                  90                  95
Leu Trp Val Phe Gly Gly Gly Thr Lys Leu Thr Val Leu Gly
            100                 105                 110
```

```
<210> SEQ ID NO 22
<211> LENGTH: 125
<212> TYPE: PRT
<213> ORGANISM: Artificial Sequence
<220> FEATURE:
<223> OTHER INFORMATION: Heavy Chain CD3-Binding Domain of DART-A

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 23
<211> LENGTH: 106
<212> TYPE: PRT
<213> ORGANISM: Artificial Sequence
<220> FEATURE:
<223> OTHER INFORMATION: Light Chain CD3-Binding Domain of DART-B

<400> SEQUENCE: 23

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 24
<211> LENGTH: 119
<212> TYPE: PRT
<213> ORGANISM: Artificial Sequence
<220> FEATURE:
<223> OTHER INFORMATION: Heavy Chain CD3-Binding Domain of DART-B

<400> SEQUENCE: 24

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30
```

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 25
<211> LENGTH: 113
<212> TYPE: PRT
<213> ORGANISM: Artificial Sequence
<220> FEATURE:
<223> OTHER INFORMATION: Light Chain CD123-Binding Domain of DART-A

<400> SEQUENCE: 25

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 26
<211> LENGTH: 120
<212> TYPE: PRT
<213> ORGANISM: Artificial Sequence
<220> FEATURE:
<223> OTHER INFORMATION: Heavy Chain CD123-Binding Domain of DART-A

<400> SEQUENCE: 26

Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 27
<211> LENGTH: 113
<212> TYPE: PRT
<213> ORGANISM: Artificial Sequence
<220> FEATURE:
<223> OTHER INFORMATION: Light Chain CD123-Binding Domain of DART-B

<400> SEQUENCE: 27

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 28
<211> LENGTH: 120
<212> TYPE: PRT
<213> ORGANISM: Artificial Sequence
<220> FEATURE:
<223> OTHER INFORMATION: Heavy Chain CD123-Binding Domain of DART-B

<400> SEQUENCE: 28

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Arg Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 29
<211> LENGTH: 8
<212> TYPE: PRT
<213> ORGANISM: Artificial Sequence
```

```
<220> FEATURE:
<223> OTHER INFORMATION: Linker 1 Polypeptide

<400> SEQUENCE: 29

Gly Gly Gly Ser Gly Gly Gly Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Linker 2 Polypeptide

<400> SEQUENCE: 30

Gly Gly Cys Gly Gly Gly
1               5

<210> SEQ ID NO 31
<211> LENGTH: 4
<212> TYPE: PRT
<213> ORGANISM: Artificial Sequence
<220> FEATURE:
<223> OTHER INFORMATION: Linker 3 Polypeptide

<400> SEQUENCE: 31

Gly Gly Gly Ser
1

<210> SEQ ID NO 32

<400> SEQUENCE: 32

000

<210> SEQ ID NO 33
<211> LENGTH: 8
<212> TYPE: PRT
<213> ORGANISM: Artificial Sequence
<220> FEATURE:
<223> OTHER INFORMATION: Linker 4 Polypeptide

<400> SEQUENCE: 33

Ala Pro Ser Ser Ser Pro Met Glu
1               5

<210> SEQ ID NO 34
<211> LENGTH: 28
<212> TYPE: PRT
<213> ORGANISM: Artificial Sequence
<220> FEATURE:
<223> OTHER INFORMATION: E-Coil Domain

<400> SEQUENCE: 34

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 35
<211> LENGTH: 28
<212> TYPE: PRT
<213> ORGANISM: Artificial Sequence
<220> FEATURE:
<223> OTHER INFORMATION: K-Coil Domain

<400> SEQUENCE: 35
```

```
Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25
```

<210> SEQ ID NO 36
<211> LENGTH: 46
<212> TYPE: PRT
<213> ORGANISM: Artificial Sequence
<220> FEATURE:
<223> OTHER INFORMATION: Preferred Albumin Binding Domain

<400> SEQUENCE: 36

```
Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
                20                  25                  30

Gly Val Lys Ala Leu Ile Asp Glu Ile Leu Ala Ala Leu Pro
                35                  40                  45
```

<210> SEQ ID NO 37
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domains of Human Fc Region

<400> SEQUENCE: 37

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

```
<210> SEQ ID NO 38
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDR1 of Light Chain Variable Domain of Anti-CD3
      Antibody

<400> SEQUENCE: 38

Arg Ser Ser Thr Gly Ala Val Thr Thr Ser Asn Tyr Ala Asn
1               5                   10

<210> SEQ ID NO 39
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR2 of Light Chain Variable Domain of Anti-CD3
      Antibody

<400> SEQUENCE: 39

Gly Thr Asn Lys Arg Ala Pro
1               5

<210> SEQ ID NO 40
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain Variable Domain of Anti-CD3
      Antibody

<400> SEQUENCE: 40

Ala Leu Trp Tyr Ser Asn Leu Trp Val
1               5

<210> SEQ ID NO 41
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR1 of Heavy Chain Variable Domain of Anti-CD3
      Antibody

<400> SEQUENCE: 41

Thr Tyr Ala Met Asn
1               5

<210> SEQ ID NO 42
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: CDR2 of Heavy Chain Variable Domain of Anti-CD3
      Antibody

<400> SEQUENCE: 42

Arg Ile Arg Ser Lys Tyr Asn Asn Tyr Ala Thr Tyr Tyr Ala Asp Ser
```

```
1               5                   10                  15
Val Lys Asp

<210> SEQ ID NO 43
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDR3 of Heavy Chain Variable Domain of Anti-CD3
      Antibody

<400> SEQUENCE: 43

His Gly Asn Phe Gly Asn Ser Tyr Val Ser Trp Phe Ala Tyr
1               5                   10

<210> SEQ ID NO 44
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR1 of Light Chain Variable Domain of Anti-
      CD123 Antibody

<400> SEQUENCE: 44

Lys Ser Ser Gln Ser Leu Leu Asn Ser Gly Asn Gln Lys Asn Tyr Leu
1               5                   10                  15

Thr

<210> SEQ ID NO 45
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR2 of Light Chain Variable Domain of Anti-
      CD123 Antibody

<400> SEQUENCE: 45

Trp Ala Ser Thr Arg Glu Ser
1               5

<210> SEQ ID NO 46
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain Variable Domain of Anti-
      CD123 Antibody

<400> SEQUENCE: 46

Gln Asn Asp Tyr Ser Tyr Pro Tyr Thr
1               5

<210> SEQ ID NO 47
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR1 of Heavy Chain Variable Domain of Anti-
```

```
                      CD123 Antibody

<400> SEQUENCE: 47

Asp Tyr Tyr Met Lys
1               5

<210> SEQ ID NO 48
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR2 of Heavy Chain Variable Domain of Anti-
      CD123 Antibody

<400> SEQUENCE: 48

Asp Ile Ile Pro Ser Asn Gly Ala Thr Phe Tyr Asn Gln Lys Phe Lys
1               5                   10                  15

Gly

<210> SEQ ID NO 49
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR3 of Heavy Chain Variable Domain of Anti-
      CD123 Antibody

<400> SEQUENCE: 49

Ser His Leu Leu Arg Ala Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Heterodimerization Domain

<400> SEQUENCE: 50

Gly Val Glu Pro Lys Ser Cys
1               5

<210> SEQ ID NO 51
<211> LENGTH: 6
<212> TYPE: PRT
<213> ORGANISM: Artificial Sequence
<220> FEATURE:
<223> OTHER INFORMATION: Heterodimerization Domain

<400> SEQUENCE: 51

Val Glu Pro Lys Ser Cys
1               5

<210> SEQ ID NO 52
<211> LENGTH: 7
<212> TYPE: PRT
<213> ORGANISM: Artificial Sequence
<220> FEATURE:
<223> OTHER INFORMATION: Heterodimerization Domain

<400> SEQUENCE: 52

Gly Phe Asn Arg Gly Glu Cys
1               5
```

<210> SEQ ID NO 53
<211> LENGTH: 6
<212> TYPE: PRT
<213> ORGANISM: Artificial Sequence
<220> FEATURE:
<223> OTHER INFORMATION: Heterodimerization Domain

<400> SEQUENCE: 53

Phe Asn Arg Gly Glu Cys
1               5

<210> SEQ ID NO 54
<211> LENGTH: 227
<212> TYPE: PRT
<213> ORGANISM: Artificial Sequence
<220> FEATURE:
<223> OTHER INFORMATION: Third Polypeptide Chain of DART-A w/Fc Version
      1 Construct

<400> SEQUENCE: 54

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 55
<211> LENGTH: 10
<212> TYPE: PRT
<213> ORGANISM: Artificial Sequence
<220> FEATURE:
<223> OTHER INFORMATION: Peptide 1

<400> SEQUENCE: 55

```
Asp Lys Thr His Thr Cys Pro Pro Cys Pro
1               5                  10
```

<210> SEQ ID NO 56
<211> LENGTH: 217
<212> TYPE: PRT
<213> ORGANISM: Artificial Sequence
<220> FEATURE:
<223> OTHER INFORMATION: Preferred CH2 and CH3 Domains of Fc Region

<400> SEQUENCE: 56

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 57
<211> LENGTH: 5
<212> TYPE: PRT
<213> ORGANISM: Artificial Sequence
<220> FEATURE:
<223> OTHER INFORMATION: Linker 4 Polypeptide

<400> SEQUENCE: 57

```
Ala Pro Ser Ser Ser
1               5
```

<210> SEQ ID NO 58
<211> LENGTH: 273
<212> TYPE: PRT
<213> ORGANISM: Artificial Sequence
<220> FEATURE:
<223> OTHER INFORMATION: Amino Acid Sequence of First Polypeptide Chain
      of "Control DART-2"

<400> SEQUENCE: 58

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Gly Gly Gly Ser Gly Gly Gly Gly Glu Val Lys Leu Asp Glu Thr
            115                 120                 125

Gly Gly Gly Leu Val Gln Pro Gly Arg Pro Met Lys Leu Ser Cys Val
        130                 135                 140

Ala Ser Gly Phe Thr Phe Ser Asp Tyr Trp Met Asn Trp Val Arg Gln
145                 150                 155                 160

Ser Pro Glu Lys Gly Leu Glu Trp Val Ala Gln Ile Arg Asn Lys Pro
                165                 170                 175

Tyr Asn Tyr Glu Thr Tyr Tyr Ser Asp Ser Val Lys Gly Arg Phe Thr
            180                 185                 190

Ile Ser Arg Asp Asp Ser Lys Ser Ser Val Tyr Leu Gln Met Asn Asn
        195                 200                 205

Leu Arg Val Glu Asp Met Gly Ile Tyr Tyr Cys Thr Gly Ser Tyr Tyr
210                 215                 220

Gly Met Asp Tyr Trp Gly Gln Gly Thr Ser Val Thr Val Ser Ser Gly
225                 230                 235                 240

Gly Cys Gly Gly Gly Glu Val Ala Ala Leu Glu Lys Glu Val Ala Ala
            245                 250                 255

Leu Glu Lys Glu Val Ala Ala Leu Glu Lys Glu Val Ala Ala Leu Glu
        260                 265                 270

Lys

<210> SEQ ID NO 59
<211> LENGTH: 274
<212> TYPE: PRT
<213> ORGANISM: Artificial Sequence
<220> FEATURE:
<223> OTHER INFORMATION: Amino Acid Sequence of Second Polypeptide Chain
      of "Control DART-2"

<400> SEQUENCE: 59

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Leu Gly Val Tyr Phe Cys Ser Gln Ser
            85                  90                  95
Thr His Val Pro Trp Thr Phe Gly Gly Gly Thr Lys Leu Glu Ile Lys
            100                 105                 110
Gly Gly Gly Ser Gly Gly Gly Gly Glu Val Gln Leu Val Gln Ser Gly
            115                 120                 125
Ala Glu Leu Lys Lys Pro Gly Ala Ser Val Lys Val Ser Cys Lys Ala
            130                 135                 140
Ser Gly Tyr Thr Phe Thr Asp Tyr Tyr Met Lys Trp Val Arg Gln Ala
145                 150                 155                 160
Pro Gly Gln Gly Leu Glu Trp Ile Gly Asp Ile Ile Pro Ser Asn Gly
                165                 170                 175
Ala Thr Phe Tyr Asn Gln Lys Phe Lys Gly Arg Val Thr Ile Thr Val
                180                 185                 190
Asp Lys Ser Thr Ser Thr Ala Tyr Met Glu Leu Ser Ser Leu Arg Ser
            195                 200                 205
Glu Asp Thr Ala Val Tyr Tyr Cys Ala Arg Ser His Leu Leu Arg Ala
            210                 215                 220
Ser Trp Phe Ala Tyr Trp Gly Gln Gly Thr Leu Val Thr Val Ser Ser
225                 230                 235                 240
Gly Gly Cys Gly Gly Lys Val Ala Ala Leu Lys Glu Lys Val Ala
            245                 250                 255
Ala Leu Lys Glu Lys Val Ala Ala Leu Lys Glu Lys Val Ala Ala Leu
            260                 265                 270
Lys Glu
```